US012753161B2

(12) United States Patent
Fleming et al.

(10) Patent No.: US 12,753,161 B2
(45) Date of Patent: Oct. 6, 2026

(54) PHD INHIBITOR COMPOUNDS, COMPOSITIONS, AND USE

(71) Applicant: Akebia Therapeutics, Inc., Cambridge, MA (US)

(72) Inventors: Paul E. Fleming, Cambridge, MA (US); Thomas P. Blaisdell, Cambridge, MA (US); Senkara Rao Allu, Cambridge, MA (US)

(73) Assignee: Akebia Therapeutics, Inc., Cambridge, MA (US)

( * ) Notice: Subject to any disclaimer, the term of this patent is extended or adjusted under 35 U.S.C. 154(b) by 868 days.

(21) Appl. No.: 17/906,652

(22) PCT Filed: Mar. 19, 2021

(86) PCT No.: PCT/US2021/023222
§ 371 (c)(1),
(2) Date: Sep. 19, 2022

(87) PCT Pub. No.: WO2021/188938
PCT Pub. Date: Sep. 23, 2021

(65) Prior Publication Data

US 2023/0159489 A1 May 25, 2023

Related U.S. Application Data

(60) Provisional application No. 62/992,606, filed on Mar. 20, 2020.

(51) Int. Cl.

| | |
|---|---|
| ***C07D 401/04*** | (2006.01) |
| ***A61K 31/4439*** | (2006.01) |
| ***A61K 31/444*** | (2006.01) |
| ***A61K 31/496*** | (2006.01) |
| ***A61K 31/5377*** | (2006.01) |
| ***A61P 1/00*** | (2006.01) |
| ***A61P 1/04*** | (2006.01) |
| ***A61P 1/16*** | (2006.01) |
| ***A61P 9/10*** | (2006.01) |
| ***A61P 13/12*** | (2006.01) |
| ***A61P 29/00*** | (2006.01) |
| ***A61P 35/00*** | (2006.01) |
| ***C07D 401/14*** | (2006.01) |
| ***C07D 403/04*** | (2006.01) |
| ***C07D 403/14*** | (2006.01) |
| ***C07D 413/14*** | (2006.01) |
| ***C07D 417/14*** | (2006.01) |
| ***C07F 9/6558*** | (2006.01) |

(52) U.S. Cl.
CPC ........ *C07D 401/04* (2013.01); *A61K 31/4439* (2013.01); *A61K 31/444* (2013.01); *A61K 31/496* (2013.01); *A61K 31/5377* (2013.01); *A61P 1/00* (2018.01); *A61P 1/04* (2018.01); *A61P 1/16* (2018.01); *A61P 9/10* (2018.01); *A61P 13/12* (2018.01); *A61P 29/00* (2018.01); *A61P 35/00* (2018.01); *C07D 401/14* (2013.01); *C07D 403/04* (2013.01); *C07D 403/14* (2013.01); *C07D 413/14* (2013.01); *C07D 417/14* (2013.01); *C07F 9/65583* (2013.01); *C07B 2200/05* (2013.01)

(58) Field of Classification Search
None
See application file for complete search history.

(56) References Cited

U.S. PATENT DOCUMENTS 4,663,327 A 5/1987 Sasse et al.
4,698,344 A 10/1987 Sasse et al.
4,772,608 A 9/1988 Sasse et al.
(Continued)

FOREIGN PATENT DOCUMENTS

CN 101213189 A 7/2008
CN 101541785 A 9/2009
(Continued)

OTHER PUBLICATIONS

Patani et. al. (1996) Bioisosterism A rational approach in drug design, Chem. Rev., 96, 3147-3176 (Year: 1996).*
(Continued)

*Primary Examiner* — Juliet C Switzer
*Assistant Examiner* — Dawanna Shar-Day White
(74) *Attorney, Agent, or Firm* — Proskauer Rose LLP

(57) ABSTRACT

The present invention provides, in part, novel small molecule inhibitors of PHD, having a structure according to Formula (A), and sub-formulas thereof: or a pharmaceutically acceptable salt thereof. The compounds provided herein can be useful for treatment of diseases including heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

(I)

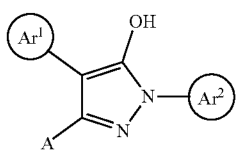

(A)

21 Claims, 1 Drawing Sheet

(56) References Cited

U.S. PATENT DOCUMENTS

| | | | |
|---|---|---|---|
| 5,175,176 | A | 12/1992 | Sasse et al. |
| 5,620,995 | A | 4/1997 | Weidmann et al. |
| 7,811,595 | B2 | 10/2010 | Kawamoto et al. |
| 8,323,671 | B2 | 12/2012 | Wu et al. |
| 8,343,952 | B2 | 1/2013 | Wu et al. |
| 8,524,699 | B2 | 9/2013 | Thede et al. |
| 8,598,210 | B2 | 12/2013 | Kawamoto et al. |
| 8,609,698 | B2 | 12/2013 | Thede et al. |
| 8,722,895 | B2 | 5/2014 | Kawamoto et al. |
| 8,940,773 | B2 | 1/2015 | Kawamoto et al. |
| 9,040,522 | B2 | 5/2015 | Brown et al. |
| 9,168,249 | B2 | 10/2015 | Thede et al. |
| 9,598,370 | B2 | 3/2017 | Kawamoto et al. |
| 10,729,681 | B2 | 8/2020 | Kawamoto et al. |
| 11,426,393 | B2 | 8/2022 | Kawamoto et al. |
| 11,883,386 | B2 | 1/2024 | Kawamoto et al. |
| 2012/0309977 | A1 | 12/2012 | Lanthier et al. |
| 2012/0322772 | A1 | 12/2012 | Flamme et al. |
| 2023/0212138 | A1 | 7/2023 | Fleming et al. |
| 2023/0227426 | A1 | 7/2023 | Fleming et al. |
| 2024/0358691 | A1 | 10/2024 | Kawamoto et al. |

FOREIGN PATENT DOCUMENTS

| | | | |
|---|---|---|---|
| CN | 101600710 | A | 12/2009 |
| CN | 101631785 | A | 1/2010 |
| CN | 105492433 | A | 4/2016 |
| CN | 106831735 | A | 6/2017 |
| CN | 109879804 | A | 6/2019 |
| DE | 3443308 | A1 | 5/1986 |
| DE | 102006050512 | A1 | 4/2008 |
| DE | 102007044032 | A1 | 3/2009 |
| EP | 3336084 | A1 | 6/2018 |
| IN | 201621021801 | A | 12/2017 |
| JP | S60255788 | A | 12/1985 |
| JP | S61137878 | A | 6/1986 |
| JP | 2008539180 | A | 11/2008 |
| JP | 2010507602 | A | 3/2010 |
| JP | 2010507605 | A | 3/2010 |
| JP | 2012513976 | A | 6/2012 |
| JP | 2016501882 | A | 1/2016 |
| JP | 2016515582 | A | 5/2016 |
| KR | 20080007482 | A | 1/2008 |
| KR | 20090081000 | A | 7/2009 |
| KR | 20110099786 | A | 9/2011 |
| KR | 20150135794 | A | 12/2015 |
| RU | 2469031 | C2 | 12/2012 |
| TM | 2021188936 | A1 | 9/2021 |
| TW | 200833330 | A | 8/2008 |
| WO | WO 2006/114213 | A1 | 11/2006 |
| WO | WO 2007/090068 | A2 | 8/2007 |
| WO | WO 2008/002576 | A2 | 1/2008 |
| WO | WO 2008/040002 | A2 | 4/2008 |
| WO | WO 2008/067874 | A1 | 6/2008 |
| WO | WO 2008/121861 | A2 | 10/2008 |
| WO | 2010005851 | A1 | 1/2010 |
| WO | 2010076524 | A3 | 7/2010 |
| WO | WO 2013/134660 | A1 | 9/2013 |
| WO | WO 2014/089364 | A1 | 6/2014 |
| WO | WO 2014/160810 | A1 | 10/2014 |
| WO | WO 2016/148306 | A1 | 9/2016 |
| WO | WO 2017/143131 | A1 | 8/2017 |
| WO | WO 2021/188936 | A1 | 9/2021 |
| WO | WO 2021/188938 | A1 | 9/2021 |
| WO | WO 2021/188944 | A1 | 9/2021 |
| WO | WO 2021/216530 | A1 | 10/2021 |
| WO | WO 2022/036188 | A1 | 2/2022 |

OTHER PUBLICATIONS

International Search Report for PCT/US2021/023219 dated Jul. 6, 2021 (6 pages).

International Search Report for PCT/US2021/023222 dated Jul. 6, 2021 (5 pages).

International Search Report for PCT/US2021/023228 dated Jun. 28, 2021 (10 pages).

"4-[2-(5-acetylpyridin-2-yl)-3-oxo-1H-pyrazol-4-yl]benzonitrile", PubChem, National Center for Biotechnology Information, CID 135129723, Dec. 15, 2018 from URL: https://pubchem.ncbi.nlm.nih.gov/compound/135129723 (10 pages).

Büchi, et al., "Synthesis and pharmacological properties of certain pyridylpyrazol-5-one", Helvetica Chimica Acta, vol. 49 (pp. 272-280) (10 pages).

Lee, et al., "Hypoxia signaling in human diseases and therapeutic targets", Experimental & Molecular Medicine, vol. 51, Jun. 20, 2019, pp. 1-13, DOI: 10.1038/s12276-019-0235-1, (13 pages).

U.S. Appl. No. 17/906,650, filed Sep. 19, 2022, Fleming et al.

U.S. Appl. No. 17/906,653, filed Sep. 19, 2022, Fleming et al.

U.S. Appl. No. 18/041,490, filed Feb. 13, 2023, Blaisdell et al.

Beck et al., "Discovery of Molidustat (BAY 85-3934): A Small-Molecule Oral HIF-Prolyl Hydroxylase (HIF-PH) Inhibitor for the Treatment of Renal Anemia", ChemMedChem, vol. 13, No. 10, Feb. 28, 2018, pp. 988-1003, DOI: 10.1002/cmdc.201700783, (16 pages).

Cadieux et al., "Synthesis and biological evaluation of substituted pyrazoles as blockers of divalent metal transporter 1 (DMT1)", Bioorganic & Medicinal Chemistry Letters, vol. 22. No. 1, Nov. 25, 2011, pp. 90-95, DOI: 10.1016/j.bmcl.2011.11.069, (6 pages).

Markham, Anthony, "Vadadustat: First Approval", Drugs, vol. 80, Aug. 27, 2020, pp. 1365-1371, DOI: 10.1007/s40265-020-01383-z, (7 pages).

Xue et al., "Prolyl Hydroxylase-3 is down regulated in colorectal cancer cells and inhibits IKKβ independent of hydroxylase activity", Gastroenterology, vol. 138, No. 2, Feb. 2010, pp. 606-615, DOI: 10.1053/j.gastro.2009.09.049, (5 pages).

Compound with CAS Registry No. 5575-24-6. 2-(6-Chloro-2-pyridinyl)-1,2-dihydro-5-methyl-4-phenyl-3H-pyrazol-3-one. Nov. 16, 1984 (1 page).

Guillo, Sandrine , et al., "N-arylation of 3-alkoxypyrazoles, the case of the pyridines", Tetrahedron, Apr. 3, 2010, vol. 66, No. 14 (pp. 2654-2663).

Laskaris, Paris , et al., "A Novel Polyaminocarboxylate Compound To Treat Murine Pulmonary Aspergillosis by Interfering with Zinc Metabolism", Antimicrobial Agents and Chemotherapy, Jun. 1, 2018, vol. 62, No. 6 (11 pages).

Tsuganezawa, Keiko, et al., "Identification of Small Molecule Inhibitors of Human COQ7", Bioorganic & Medicinal Chemistry, vol. 28, No. 1, 2020, 115182, DOI:10.1016/j.bmc.2019.115182 (7 pages).

* cited by examiner

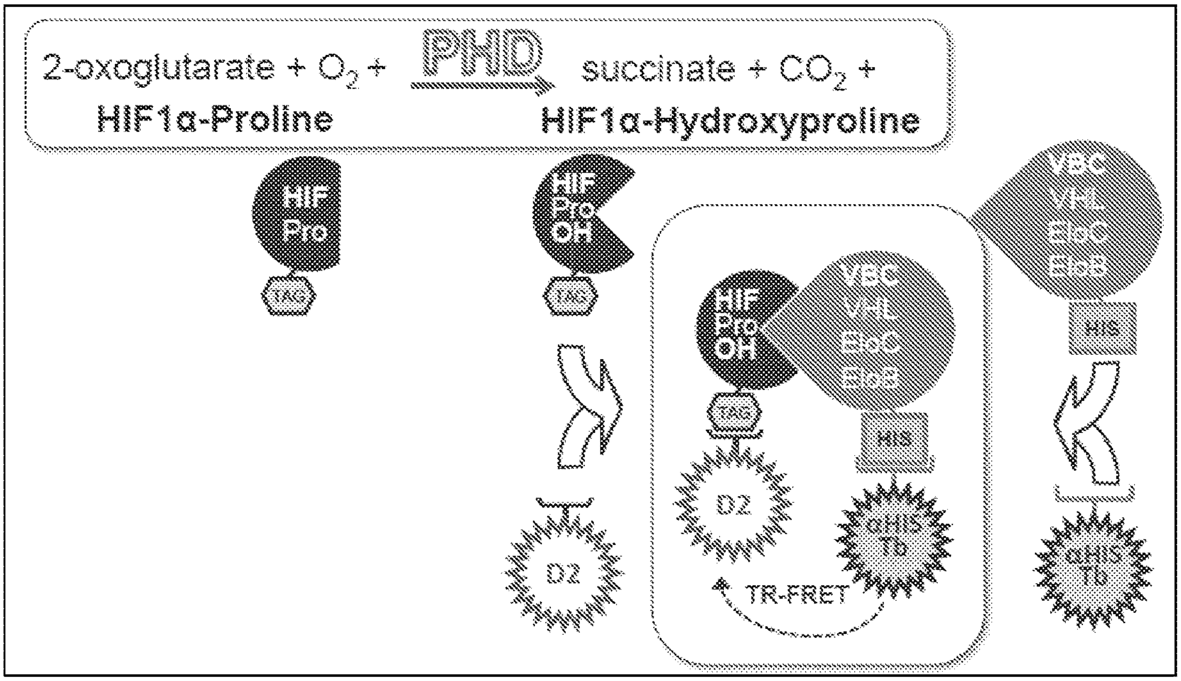

αHis-Tb: monoclonal antibody anti-6His-Terbium-cryptate Gold; $CO_2$: carbon dioxide; D2: streptavidin (SA)-D2 Acceptor; EloB: elongin B; EloC: elongin C; HIF-Pro: proline 564 of HIF; HIF-Pro-OH: HIF-1α-hydroxyproline 564; HIF-1α: hypoxia inducible factor 1 alpha; $O_2$: oxygen; PHD: prolyl-4-hydroxylase domain; PHD1: prolyl-4-hydroxylase domain 1; PHD2: prolyl-4-hydroxylase domain 2; PHD3: prolyl-4-hydroxylase domain 3; TR-FRET: time-resolved fluorescence resonance energy transfer; VBC: Von Hippel–Lindau protein, elongin B, elongin C complex; VHL: Von Hippel–Lindau

PHD INHIBITOR COMPOUNDS, COMPOSITIONS, AND USE

CROSS-REFERENCE TO RELATED APPLICATIONS

This application is a 35 U.S.C. § 371 National Stage Application of International Application No. PCT/US2021/023222, filed on Mar. 19, 2021, which claims priority to U.S. Provisional Patent Application No. 62/992,606, filed Mar. 20, 2020, which is are hereby incorporated by reference in its entirety their entireties.

BACKGROUND

Hypoxia is a condition or state in which the supply of oxygen is insufficient for normal life function, for example, where there is low arterial oxygen supply. Hypoxia can lead to functional impairment of cells and structural tissue damage. The activation of cellular defense mechanisms during hypoxia is mediated by HIF (Hypoxia-inducible factor) protein. In response to hypoxic conditions, levels of HIFα are elevated in most cells because of a decrease in HIFα prolyl hydroxylation. Prolyl hydroxylation of HIFα is accomplished by a family of proteins variously termed the prolyl hydroxylase domain-containing proteins (PHD1, 2, and 3), also known as HIF prolyl hydroxylases (HPH-3, 2, and 1) or EGLN-2, 1, and 3. The PHD proteins are oxygen sensors and regulate the stability of HIF in an oxygen dependent manner. The three PHD isoforms function differently in their regulation of HIF and may have other non-HIF related regulatory roles.

In fact, many studies demonstrate that stabilization of HIF can dampen tissue inflammation and promote its repair. Accordingly, compounds that can inhibit the activity of PHD proteins may be particular beneficial in new therapies (Lee et al. (2019) Exp. Mol. Med. 51:68)

Described herein are novel small molecule PHD inhibitors that have utility for the treatment of disease including heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

SUMMARY

The present invention provides, among other things, novel small molecule inhibitors of PHD and have utility for the treatment of diseases, including but not limited to heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

In an aspect, provided herein are compounds having a structure according to Formula (A), (A)

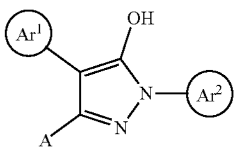

or a pharmaceutically acceptable salt thereof, wherein:

A is $C_{1-3}$ alkyl, or $C_{3-6}$ cycloalkyl;

$Ar^1$ is aryl or heteroaryl, optionally substituted with one or more groups selected from halogen, CN, OH, $C_{1-3}$ alkyl optionally substituted with CN or one or more halogens, and $C_{1-3}$ alkoxy; and $Ar^2$ is pyrid-2-yl, optionally substituted with one or more groups selected from halogen; amino; amide; OH; a sulfonyl group; a sulfinyl group; a carbonyl group; a phosphoryl group; $C_{3-6}$ cycloalkyl; $C_{3-6}$ heterocycloalkyl optionally substituted with a sulfonyl group or ═O; $C_{1-3}$ alkyl optionally substituted with carbonyl or one or more halogens; and heteroaryl optionally substituted with $C_{1-3}$ alkyl or phenyl.

In embodiments, A is $C_{1-3}$ alkyl.

In embodiments, A is $C_{3-6}$ cycloalkyl.

In embodiments, $Ar^1$ is

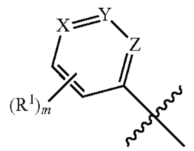

, wherein

X is N or $CR^{1a}$;

Y and Z are independently CH or N;

$R^{1a}$ is H, CN, halogen, $C_{1-3}$ alkoxy, OH, or $C_{1-3}$ alkyl optionally substituted with CN;

$R^1$, each time taken, is independently selected from the group consisting of hydrogen, halogen, CN, OH, $C_{1-3}$ alkyl optionally substituted with one or more halogens, and $C_{1-3}$ alkoxy; and m is 1, 2, 3 or 4.

In embodiments, $Ar^1$ is

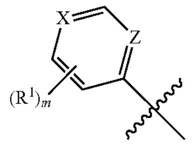

.

In embodiments, $Ar^1$ is

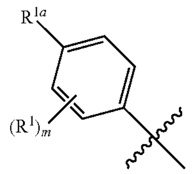

, wherein $R^{1a}$ is H, CN, halogen, $C_{1-3}$ alkoxy, OH, or $C_{1-3}$ alkyl optionally substituted with CN.

In embodiments, $R^{1a}$ is H, CN, halogen, $C_{1-3}$ alkoxy, OH, or $C_{1-3}$ alkyl optionally substituted with CN.

In embodiments, $R^1$, each time taken, is independently selected from the group consisting of hydrogen, halogen, CN, OH, $C_{1-3}$ alkyl optionally substituted with one or more halogens, and $C_{1-3}$ alkoxy.

In embodiments, $Ar^2$ is

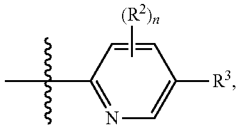

wherein $R^2$, each time taken, is independently selected from the group consisting of hydrogen, halogen, $NR^4R^5$, OH, $C_{1-3}$ alkyl, and $C_{3-6}$ cycloalkyl;

$R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens;

$R^6$ is $C_{1-3}$ alkyl, $NHCOR^{15}$, $NR^{16}R^{17}$, or phenyl;

$R^7$ is $C_{1-3}$ alkyl, $C_{3-5}$ cycloalkyl, phenyl, or $NR^{18}R^{19}$.

$R^8$ is NH, NCN, or $NCH_3$;

$R^{10}$ is $C_{1-3}$ alkyl or $NHSO_2R^{20}$;

$R^{11}$ is $COR^{21}$ or $SO_2R^{22}$;

$R^9$, $R^{12}$, $R^{13}$ $R^{14}$, $R^{15}$, and $R^{20}$ are each independently $C_{1-3}$ alkyl;

$R^{21}$ is heterocycloalkyl, cycloalkyl, or $C_{1-3}$ alkyl;

$R^{22}$ is $NR^{23}R^{24}$ or $C_{1-3}$ alkyl optionally substituted with carboxyl;

$R^4$, $R^5$, $R^{18}$, $R^{19}$, $R^{23}$ and $R^{24}$ are each independently H or $C_{1-3}$ alkyl;

$R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl;

p is 1, 2, or 3; and n is 0, 1, 2 or 3.

In embodiments, $Ar^2$ is

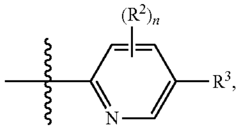

wherein $R^3$ is selected from the group consisting of F, Cl, Br, and I.

In embodiments, $Ar^2$ is

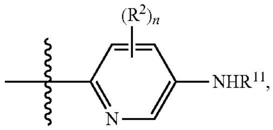

wherein $R^{11}$ is $COR^{21}$ or $SO_2R^{22}$; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; and $R^{23}$ and $R^{24}$ are independently H or $C_{1-3}$ alkyl.

In embodiments, $Ar^2$ is

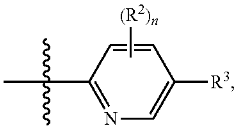

wherein $R^3$ is cycloalkyl or heterocycloalkyl optionally substituted with $SO_2R^{14}$ or =O; and $R^{14}$ is $C_{1-3}$ alkyl.

In embodiments, $Ar^2$ is

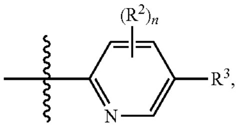

wherein $R^3$ is heteroaryl optionally substituted with $C_{1-3}$ alkyl or phenyl.

In embodiments, cycloalkyl or optionally substituted heterocycloalkyl is selected from the group consisting of

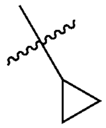,
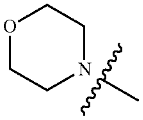,
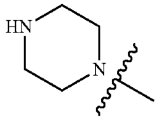,
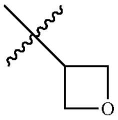,
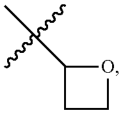,
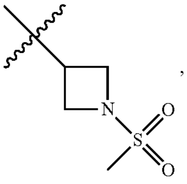, and
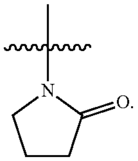

In embodiments, an optionally substituted heteroaryl is selected from the group consisting of

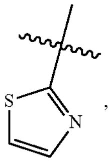,
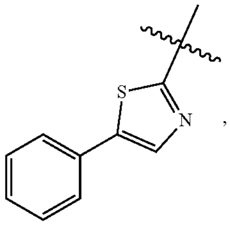,
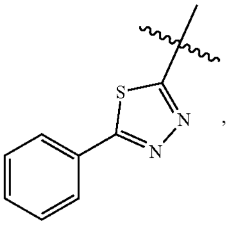,

-continued

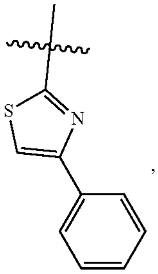

,

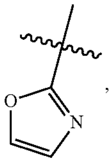

,

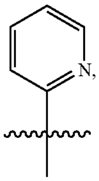

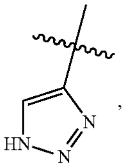

,

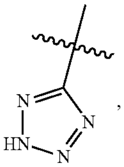

,

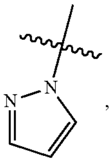

,

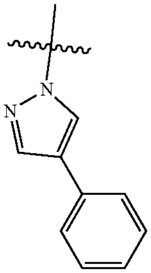

,

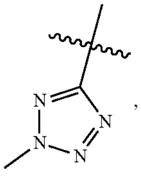

,

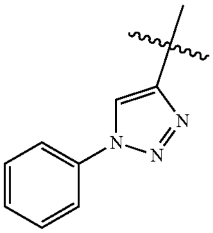

, and

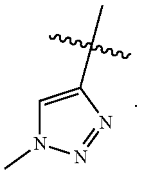

.

In embodiments, $R^2$, each time taken, is independently selected from the group consisting of hydrogen, halogen, $NR^4R^5$, OH, $C_{1-3}$ alkyl, and $C_{3-6}$ cycloalkyl, wherein $R^4$ and $R^5$ are each independently H or $C_{1-3}$ alkyl.

In embodiments, $R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens, wherein $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{18}R^{19}$; $R^8$ is NH, NCN, or $NCH_3$; $R^{10}$ is $C_{1-3}$ alkyl or $NHSO_2R^{20}$; $R^{11}$ is $COR^{21}$ or $SO_2R^{22}$; $R^9$, $R^{12}$, $R^{13}$ $R^{14}$, $R^{15}$, and $R^{20}$ are each independently $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^4$, $R^5$, $R^{18}$, $R^{19}$, $R^{23}$ and $R^{24}$ are each independently H or $C_{1-3}$ alkyl; $R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl; and p is 1, 2, or 3.

In embodiments, a compound of Formula (A) has the following structure, (I)

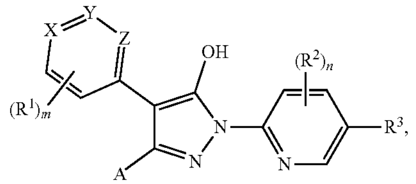

or a pharmaceutically acceptable salt thereof.

In embodiments of Formula (I), X is N or $CR^{1a}$; Y and Z are independently CH or N; A is $C_{1-3}$ alkyl, or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens; $R^4$ and $R^5$ are each independently H or $C_{1-3}$ alkyl; $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{18}R^{19}$; $R^8$ is NH, NCN, or $NCH_3$; $R^9$ is $C_{1-3}$ alkyl; $R^{10}$ is $C_{1-3}$ alkyl or $NHSO_2R^{20}$; $R^{11}$ is $COR^{21}$ or $SO_2R^{22}$; $R^{12}$ and $R^{13}$ are each independently $C_{1-3}$ alkyl; $R^{14}$ is $C_{1-3}$ alkyl; $R^{15}$ is $C_{1-3}$ alkyl; $R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl; $R^{18}$ and $R^{19}$ are each independently H or $C_{1-3}$ alkyl; $R^{20}$ is $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are each independently H or $C_{1-3}$ alkyl; m is 1, 2, 3, or 4; n is 0, 1, 2 or 3; and p is 1, 2, or 3.

In embodiments, a compound of Formula (A) or Formula (I) has the following structure, (II)

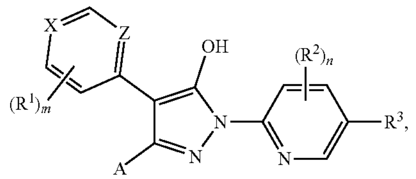

or a pharmaceutically acceptable salt thereof.

In embodiments of Formula (II), X is N or $CR^{1a}$; Z is CH or N; A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens; $R^4$ and $R^5$ are each independently H or $C_{1-3}$ alkyl; $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{18}R^{19}$; $R^8$ is NH, NCN, or $NCH_3$; $R^9$ is $C_{1-3}$ alkyl; $R^{10}$ is $C_{1-3}$ alkyl or $NHSO_2R^{20}$; $R^{11}$ is $COR^{21}$ or $SO_2R^{22}$; $R^{12}$ and $R^{13}$ are each independently $C_{1-3}$ alkyl; $R^{14}$ is $C_{1-3}$ alkyl; $R^{15}$ is $C_{1-3}$ alkyl; $R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl; $R^{18}$ and $R^{19}$ are independently H or $C_{1-3}$ alkyl; $R^{20}$ is $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are independently H or $C_{1-3}$ alkyl; m is 1, 2, 3, or 4; n is 0, 1, 2 or 3; and p is 1, 2, or 3.

In embodiments, a compound of Formula (A), Formula (I), or Formula (II) has the following structure, (III)

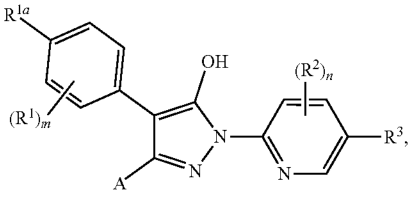

or a pharmaceutically acceptable salt thereof.

In embodiments of Formula (III), A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens; $R^4$ and $R^5$ are each independently H or $C_{1-3}$ alkyl; $R^6$ is $C_{1-3}$ alkyl, $NHCOR^{15}$, $NR^{16}R^{17}$, or phenyl; $R^7$ is $C_{1-3}$ alkyl, $C_{3-5}$ cycloalkyl, phenyl, or $NR^{18}R^{19}$; $R^8$ is NH, NCN, or $NCH_3$; $R^9$ is $C_{1-3}$ alkyl; $R^{10}$ is $C_{1-3}$ alkyl or $NHSO_2R^{20}$; $R^{11}$ is $COR^{21}$ or $SO_2R^{22}$; $R^{12}$ and $R^{13}$ are each independently $C_{1-3}$ alkyl; $R^{14}$ is $C_{1-3}$ alkyl; $R^{15}$ is $C_{1-3}$ alkyl; $R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl; $R^{18}$ and $R^{19}$ are independently H or $C_{1-3}$ alkyl; $R^{20}$ is $C_{1-3}$ alkyl; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are independently H or $C_{1-3}$ alkyl; m is 1, 2, 3, or 4; n is 0, 1, 2 or 3; and p is 1, 2, or 3.

In embodiments, a compound of Formula (A), Formula (I), Formula (II) or Formula (III) has the following structure, (IV)

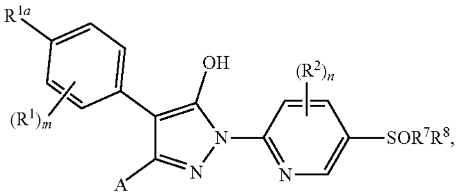

or a pharmaceutically acceptable salt thereof.

In embodiments of Formula (IV), A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^7$ is $C_{1-3}$ alkyl, $C_{3-5}$ cycloalkyl, phenyl, or $NR^{18}R^{19}$; $R^8$ is NH, NCN or $NCH_3$; $R^{18}$ is and $R^{19}$ are each independently H or $C_{1-3}$ alkyl; m is 1, 2, 3, or 4; and n is 0, 1, 2 or 3.

In embodiments, $R^1$ is $C_{1-3}$ alkyl. In embodiments, $R^1$ is $CH_3$.

In embodiments, a compound of Formula (A), Formula (I), Formula (II), Formula (III) or Formula (IV) has the following structure, (IVa)

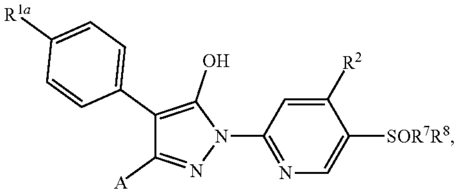

or a pharmaceutically acceptable salt thereof.

In embodiments, A is $C_{1-3}$ alkyl; $R^{1a}$ is CN or halogen; $R^2$ is selected from the group consisting of hydrogen or $C_{1-3}$ alkyl; $R^7$ is $C_{1-3}$ alkyl, $C_{3-5}$ cycloalkyl, phenyl, or $NR^{18}R^{19}$; $R^8$ is NH, NCN, or $NCH_3$; and $R^{18}$ and $R^{19}$ are each independently H or $C_{1-3}$ alkyl.

In embodiments, $R^{1a}$ is CN.

In embodiments, $R^{1a}$ is halogen. In embodiments, $R^{1a}$ is Cl.

In embodiments, A is $C_{1-3}$ alkyl. In embodiments, A is $CH_3$.

In embodiments, $R^2$ is $C_{1-3}$ alkyl.

In embodiments, $R^2$ is $CH_3$.

In embodiments, $R^7$ is $C_{1-3}$ alkyl. In embodiments, $R^7$ is $CH_3$. In embodiments, $R^7$ is $CH_2CH_3$. In embodiments, $R^7$ is $CH(CH_3)_2$. In embodiments, $R^7$ is $C_{3-5}$ cycloalkyl. In embodiments, $R^7$ is cyclopropyl. In embodiments, $R^7$ is cyclopentyl. In embodiments, $R^7$ is phenyl. In embodiments, $R^7$ is $NR^{18}R^{19}$, and wherein $R^{18}$ and $R^{19}$ are each independently H or $C_{1-3}$ alkyl.

In embodiments, $R^{18}$ and $R^{19}$ are independently H. In embodiments, $R^{18}$ is H and $R^{19}$ is $C_{1-3}$ alkyl. In embodiments, $R^{19}$ is $CH_3$. In embodiments, $R^{18}$ and $R^{19}$ are independently $CH_3$.

In embodiments, $R^8$ is NH. In embodiments, $R^8$ is NCN. In embodiments, $R^8$ is $NCH_3$.

In embodiments, a compound of Formula (A), Formula (I), or Formula (II) has the following structure, (V)

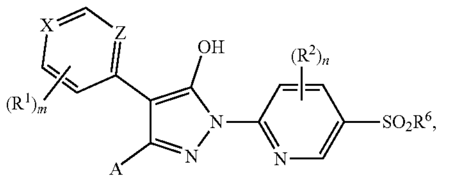

or a pharmaceutically acceptable salt thereof.

In embodiments of Formula (V), X is N or $CR^{1a}$; Z is N or CH; A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^6$ is $C_{1-3}$ alkyl, $NHCOR^{15}$, $NR^{16}R^{17}$, or phenyl; and $R^{15}$ is $C_{1-3}$ alkyl; $R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl; m is 1, 2, 3, or 4; and n is 0, 1, 2 or 3.

In embodiments, X is N. In embodiments, X is $CR^{1a}$.

In embodiments, A is $C_{1-3}$ alkyl. In embodiments, A is $CH_3$. In embodiments, A is $CH_2CH_3$. In embodiments, A is cycloalkyl. In embodiments, A is cyclopropyl.

In embodiments, $R^{1a}$ is CN. In embodiments, $R^{1a}$ is halogen. In embodiments, $R^{1a}$ is $C_1$. In embodiments, $R^{1a}$ is F. In embodiments, $R^{1a}$ is Br. In embodiments, $R^{1a}$ is $C_{1-3}$ alkoxy.

In embodiments, $R^{1a}$ is methoxy. In embodiments, $R^{1a}$ is H. In embodiments, Ria is $C_{1-3}$ alkyl optionally substituted with CN. In embodiments, $R^{1a}$ is $CH_2CN$. In embodiments, $R^{1a}$ is OH.

In embodiments, Z is CH. In embodiments, Z is N.

In embodiments, $R^1$ is H. In embodiments, $R^1$ is $C_{1-3}$ alkyl. In embodiments, $R^1$ is $CH_3$. In embodiments, $R^1$ is $C_{1-3}$ alkoxy. In embodiments, $R^1$ is methoxy. In embodiments, $R^1$ is CN.

In embodiments, $R^2$ is H. In embodiments, $R^2$ is $C_{1-3}$ alkyl. In embodiments, $R^2$ is $CH_3$.

In embodiments, $R^6$ is $C_{1-3}$ alkyl. In embodiments, $R^6$ is $CH_3$. In embodiments, $R^6$ is $NHCOR^{15}$, and wherein $R^{15}$ is $C_{1-3}$ alkyl. In embodiments, $R^{15}$ is $CH_3$. In embodiments, $R^6$ is $NR^{16}R^{17}$, and wherein $R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl. In embodiments, $R^6$ is $NH_2$. In embodiments, P is phenyl.

In embodiments, a compound of Formula (A), Formula (I), Formula (II) or Formula (III) has the following structure, (VI)

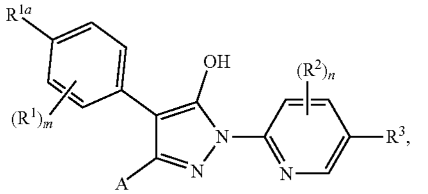

or a pharmaceutically acceptable salt thereof, wherein $R^3$ is cycloalkyl or heterocycloalkyl optionally substituted with $SO_2R^{14}$ or =O.

In embodiments of Formula (VI), A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^{14}$ is $C_{1-3}$ alkyl; m is 1, 2, 3, or 4; and n is 0, 1, 2 or 3.

In embodiments, a compound of Formula (A), Formula (I), Formula (II), Formula (III) or Formula (VI) has the following structure, (VIa)

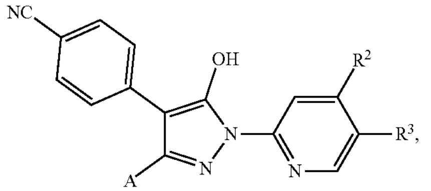

or a pharmaceutically acceptable salt thereof, wherein $R^3$ is cycloalkyl or heterocycloalkyl optionally substituted with $SO_2R^{14}$ or =O.

In embodiments, A is $C_{1-3}$ alkyl; $R^2$ is hydrogen or $C_{1-3}$ alkyl; and $R^{14}$ is $C_{1-3}$ alkyl.

In embodiments, A is $C_{1-3}$ alkyl. In embodiments, A is $CH_3$.

In embodiments, $R^2$ is H. In embodiments, $R^2$ is $C_{1-3}$ alkyl. In embodiments, $R^2$ is $CH_3$.

In embodiments, $R^3$ is cycloalkyl.

In embodiments, $R^3$ is cyclopropyl.

In embodiments, $R^3$ is heterocycloalkyl optionally substituted with $SO_2R^{14}$ or =O, and wherein $R^{14}$ is $C_{1-3}$ alkyl.

In embodiments, $R^3$ is

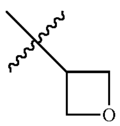

or

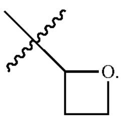

In embodiments, $R^3$ is

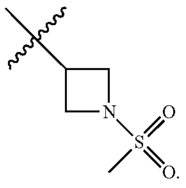 [SMILES: *C1CN(S(C)(=O)=O)C1]

In embodiments, $R^3$ is

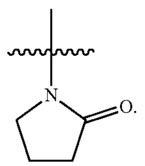 [SMILES: *N1CCCC1=O]

In embodiments, a compound of Formula (A), Formula (I), Formula (II), or Formula (III) has the following structure, (VII)

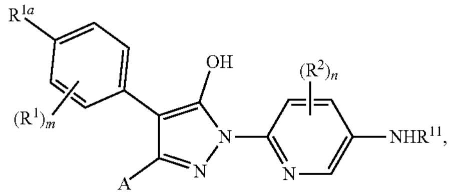

or a pharmaceutically acceptable salt thereof.

In embodiments of Formula (VII), A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^{11}$ is $COR^{21}$ or $SO_2R^{22}$; $R^{21}$ is heterocycloalkyl, cycloalkyl, or $C_{1-3}$ alkyl; $R^{22}$ is $NR^{23}R^{24}$ or $C_{1-3}$ alkyl optionally substituted with carboxyl; $R^{23}$ and $R^{24}$ are independently H or $C_{1-3}$ alkyl; m is 1, 2, 3, or 4; and n is 0, 1, 2 or 3.

In embodiments, a compound of Formula (A), Formula (I), Formula (II), Formula (III) or Formula (VII) has the following structure, (VIIa)

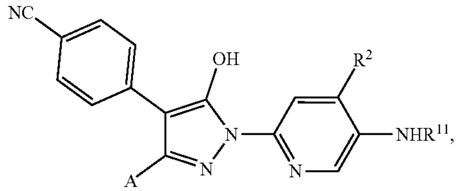

or a pharmaceutically acceptable salt thereof.

In embodiments, A is $C_{1-3}$ alkyl or cycloalkyl; $R^2$ is hydrogen or $C_{3-6}$ cycloalkyl; $R^{11}$ is $COR^{21}$ or $SO_2R^{22}$; $R^{21}$ is heterocycloalkyl, cycloalkyl, or $C_{1-3}$ alkyl; and $R^{22}$ is $NR^{23}R^{24}$ or $C_{1-3}$ alkyl optionally substituted with carboxyl, and wherein $R^{23}$ and $R^{24}$ are independently H or $C_{1-3}$ alkyl.

In embodiments, A is $C_{1-3}$ alkyl. In embodiments, A is $CH_3$.

In embodiments, $R^2$ is H. In embodiments, $R^2$ is $C_{1-3}$ alkyl. In embodiments, $R^2$ is $CH_3$.

In embodiments, $R^{11}$ is $COR^{21}$, and wherein $R^{21}$ is heterocycloalkyl, cycloalkyl, or $C_{1-3}$ alkyl.

In embodiments, $R^{21}$ is heterocycloalkyl. In embodiments, $R^{21}$ is

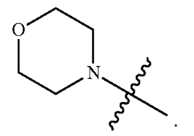 [SMILES: *N1CCOCC1]

In embodiments, $R^{21}$ is

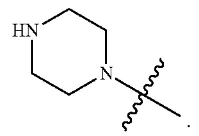 [SMILES: *N1CCNCC1]

In embodiments, $R^{21}$ is cycloalkyl. In embodiments, $R^{21}$ is cyclopropyl. In embodiments, $R^{21}$ is $C_{1-3}$ alkyl. In embodiments, $R^{21}$ is $CH_2CH_3$.

In embodiments, $R^{11}$ is $SO_2R^{22}$, wherein $R^{22}$ is $NR^{23}R^{24}$ or $C_{1-3}$ alkyl optionally substituted with carboxyl, and wherein $R^{23}$ and $R^{24}$ are independently H or $C_{1-3}$ alkyl.

In embodiments, $R^{22}$ is $C_{1-3}$ alkyl optionally substituted with carboxyl. In embodiments, $R^{22}$ is $CH_3$. In embodiments, $R^{22}$ is $CH_2CH_3$. In embodiments, $R^{22}$ is $CH_2COOH$. In embodiments, $R^{22}$ is $NR^{23}R^{24}$, and wherein $R^{23}$ and $R^{24}$ are independently H or $C_{1-3}$ alkyl. In embodiments, $R^{22}$ is $NHCH_3$. In embodiments, $R^{22}$ is $N(CH_3)_2$.

In embodiments, a compound of Formula (A), Formula (I), Formula (II), or Formula (III) has the following structure, (VIII)

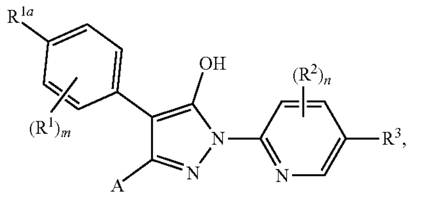

or a pharmaceutically acceptable salt thereof, wherein $R^3$ is heteroaryl optionally substituted with $C_{1-3}$ alkyl or phenyl.

In embodiments, A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, C1-3 alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; m is 1, 2, 3, or 4; and n is 0, 1, 2 or 3.

In embodiments, a compound of Formula (A), Formula (I), Formula (II) or Formula (III) or Formula (VIII) has the following structure, (VIIIa)

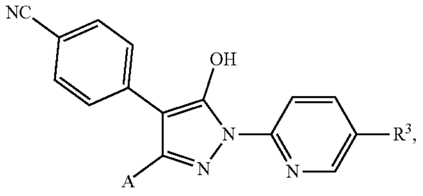

or a pharmaceutically acceptable salt thereof, wherein $R^3$ is heteroaryl optionally substituted with $C_{1-3}$ alkyl or phenyl.

In embodiments, A is $C_{1-3}$ alkyl or cycloalkyl.

In embodiments, A is $C_{1-3}$ alkyl.

In embodiments, A is $CH_3$.

In embodiments, $R^3$ is heteroaryl. In embodiments, $R^3$ is

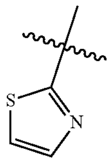

.

In embodiments, $R^3$ is

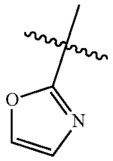

.

In embodiments, $R^3$ is

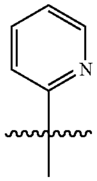

.

In embodiments, $R^3$ is

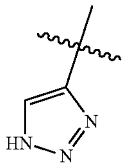

.

In embodiments, $R^3$ is

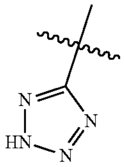

.

In embodiments, $R^3$ is

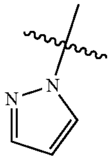

.

In embodiments, $R^3$ is heteroaryl optionally substituted with $C_{1-3}$ alkyl or phenyl. In embodiments, $R^3$ is

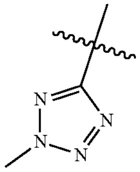

.

In embodiments, $R^3$ is

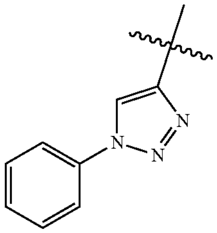

.

In embodiments, $R^3$ is

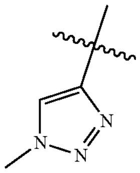

.

In embodiments, $R^3$ is

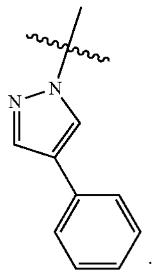 [SMILES: *n1cc(-c2ccccc2)cn1]

In embodiments, $R^3$ is

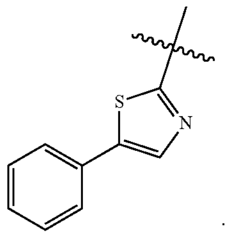 [SMILES: *c1ncc(-c2ccccc2)s1]

In embodiments, $R^3$ is

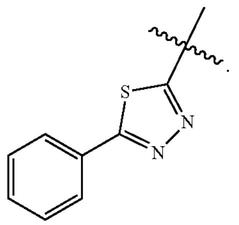 [SMILES: *c1nnc(-c2ccccc2)s1]

In embodiments, $R^3$ is

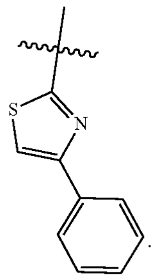 [SMILES: *c1nc(-c2ccccc2)cs1]

In embodiments, a compound of Formula (A), Formula (I), Formula (II) or Formula (III) has the following structure, (IX)

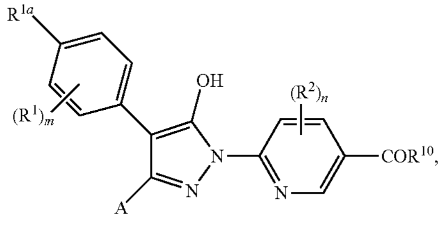

or a pharmaceutically acceptable salt thereof.

In embodiments, A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; Ria is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^{10}$ is $C_{1-3}$ alkyl or $NHSO_2R^{20}$; $R^{20}$ is $C_{1-3}$ alkyl; m is 1, 2, 3, or 4; and n is 0, 1, 2 or 3.

In embodiments, a compound of Formula (A), Formula (I), Formula (II), Formula (III) or Formula (IX) has the following structure, (IXa)

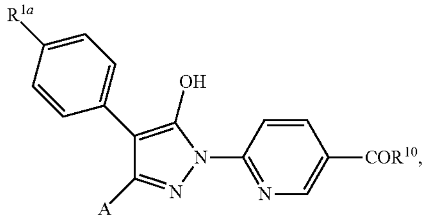

or a pharmaceutically acceptable salt thereof.

In embodiments of Formula (IXa), A is $C_{1-3}$ alkyl; Ria is CN or halogen; $R^{10}$ is $C_{1-3}$ alkyl or $NHSO_2R^{20}$; and $R^{20}$ is $C_{1-3}$ alkyl.

In embodiments, $R^{1a}$ is CN. In embodiments, $R^{1a}$ is halogen. In embodiments, $R^{1a}$ is Cl.

In embodiments, $R^{10}$ is $C_{1-3}$ alkyl. In embodiments, $R^{10}$ is $CH_3$. In embodiments, $R^{10}$ is $CH(CH_3)_2$. In embodiments, $R^{10}$ is $CH_2CH_3$. In embodiments, $R^{10}$ is $NHSO_2R^{20}$, and wherein $R^{20}$ is $C_{1-3}$ alkyl. In embodiments, $R^{20}$ is $CH_3$.

In embodiments, a compound of Formula (A), Formula (I), Formula (II) or Formula (III) has the following structure, (X)

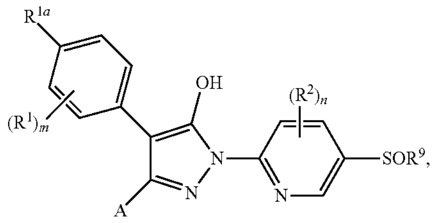

or a pharmaceutically acceptable salt thereof.

In embodiments, A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^9$ is $C_{1-3}$ alkyl; m is 1, 2, 3, or 4; and n is 0, 1, 2 or 3.

In embodiments, $R^{1a}$ is CN.

In embodiments, $R^1$ is H.

In embodiments, A is $C_{1-3}$ alkyl. In embodiments, A is $CH_3$.

In embodiments, $R^2$ is H.

In embodiments, $R^9$ is $C_{1-3}$ alkyl. In embodiments, $R^9$ is $CH_3$.

In embodiments, a compound of Formula (A), Formula (I), Formula (II) or Formula (III) has the following structure, (XI)

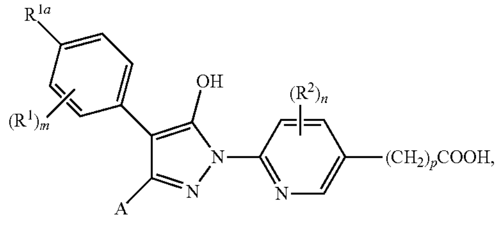

or a pharmaceutically acceptable salt thereof.

In embodiments of Formula (XI), A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; m is 1, 2, 3, or 4; n is 0, 1, 2 or 3; and p is 1, 2, or 3.

In embodiments, $R^{1a}$ is CN.

In embodiments, $R^1$ is H.

In embodiments, A is $C_{1-3}$ alkyl. In embodiments, A is $CH_3$.

In embodiments, $R^2$ is H.

In embodiments, p is 1.

In embodiments, a compound of Formula (A), Formula (I), Formula (II) or Formula (III) has the following structure, (XII)

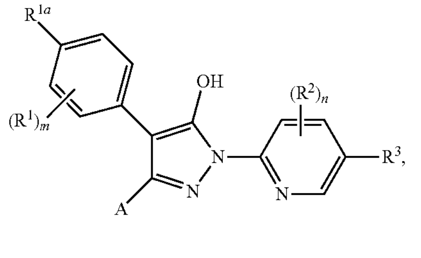

or a pharmaceutically acceptable salt thereof, wherein $R^3$ is halogen.

In embodiments of Formula (XII), A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; m is 1, 2, 3, or 4; and n is 0, 1, 2 or 3.

In embodiments, $R^{1a}$ is CN.

In embodiments, $R^1$ is H.

In embodiments, $R^2$ is H.

In embodiments, $R^3$ is Cl. In embodiments, $R^3$ is Br. In embodiments, $R^3$ is F.

In embodiments, a compound of Formula (A), Formula (I), Formula (II), or Formula (III) has the following structure, (XIII)

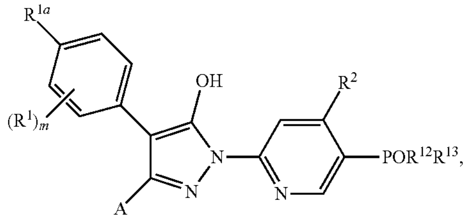

or a pharmaceutically acceptable salt thereof.

In embodiments, A is $C_{1-3}$ alkyl or cycloalkyl; $R^1$, each time taken, is independently selected from the group consisting of hydrogen, halogen, CN, OH, $C_{1-3}$ alkyl optionally substituted one or more halogens, and $C_{1-3}$ alkoxy; $R^{1a}$ is H, CN, halogen, $C_{1-3}$ alkoxy, OH, or $C_{1-3}$ alkyl optionally substituted with CN; and $R^2$, each time taken, is independently selected from the group consisting of hydrogen, halogen, $NR^4R^5$, OH, $C_{1-3}$ alkyl, and $C_{3-6}$ cycloalkyl; $R^4$ and $R^5$ are each independently H or $C_{1-3}$ alkyl; $R^{12}$ is $C_{1-3}$ alkyl; $R^{13}$ is $C_{1-3}$ alkyl; and m is 1, 2, 3, or 4.

In embodiments, $R^{1a}$ is CN.

In embodiments, $R^1$ is H.

In embodiments, A is $C_{1-3}$ alkyl. In embodiments, A is $CH_3$.

In embodiments, $R^2$ is $C_{1-3}$ alkyl. In embodiments, $R^2$ is $CH_3$.

In embodiments, $R^{12}$ is $C_{1-3}$ alkyl. In embodiments, $R^{12}$ is $CH_3$.

In embodiments, $R^{13}$ is $C_{1-3}$ alkyl. In embodiments, $R^{13}$ is $CH_3$.

In embodiments, a compound is any one of Compounds 1-83:

| Cmpd No. | Structure |
|---|---|
| 1 | 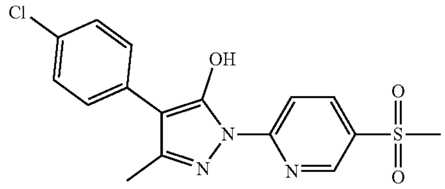 [SMILES: Cc1nn(-c2ccc(S(C)(=O)=O)cn2)c(O)c1-c1ccc(Cl)cc1] |
| 2 | 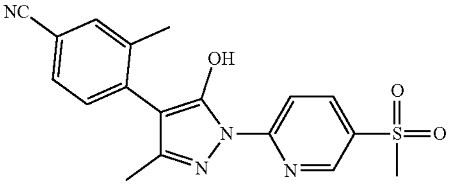 [SMILES: Cc1cc(C#N)ccc1-c1c(C)nn(-c2ccc(S(C)(=O)=O)cn2)c1O] |
| 3 | 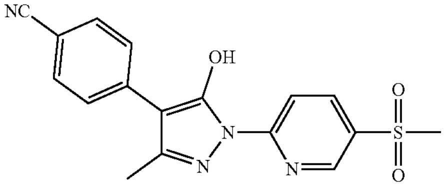 [SMILES: Cc1nn(-c2ccc(S(C)(=O)=O)cn2)c(O)c1-c1ccc(C#N)cc1] |
| 4 | 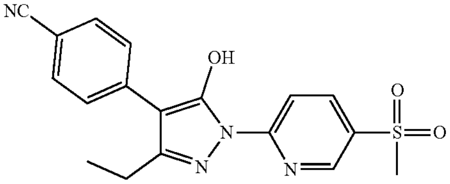 [SMILES: CCc1nn(-c2ccc(S(C)(=O)=O)cn2)c(O)c1-c1ccc(C#N)cc1] |
| 5 | 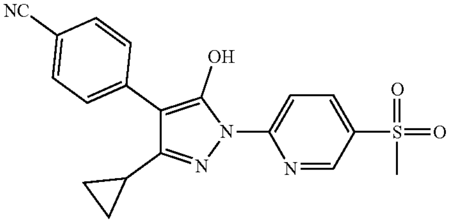 [SMILES: CS(=O)(=O)c1ccc(-n2nc(C3CC3)c(-c3ccc(C#N)cc3)c2O)nc1] |
| 6 | 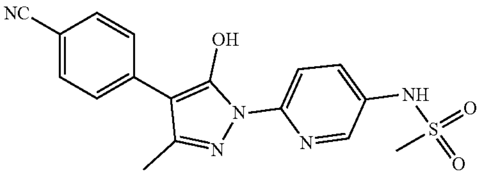 [SMILES: Cc1nn(-c2ccc(NS(C)(=O)=O)cn2)c(O)c1-c1ccc(C#N)cc1] |
| 7 | 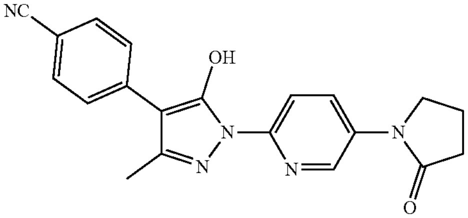 [SMILES: Cc1nn(-c2ccc(N3CCCC3=O)cn2)c(O)c1-c1ccc(C#N)cc1] |
| 8 | 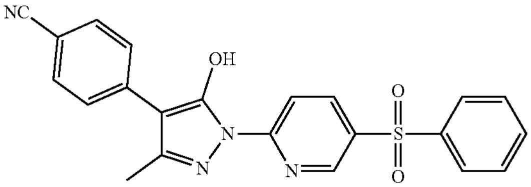 [SMILES: Cc1nn(-c2ccc(S(=O)(=O)c3ccccc3)cn2)c(O)c1-c1ccc(C#N)cc1] |

-continued
| Cmpd No. | Structure |
| --- | --- |
| 9 | 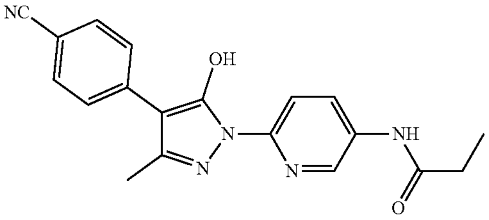 [SMILES: CCC(=O)Nc1ccc(-n2nc(C)c(-c3ccc(C#N)cc3)c2O)nc1] |
| 10 | 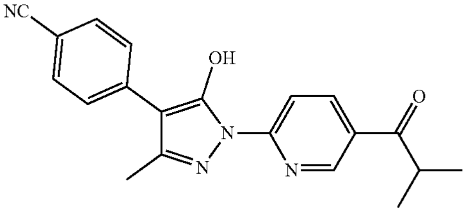 [SMILES: Cc1nn(-c2ccc(C(=O)C(C)C)cn2)c(O)c1-c1ccc(C#N)cc1] |
| 11 | 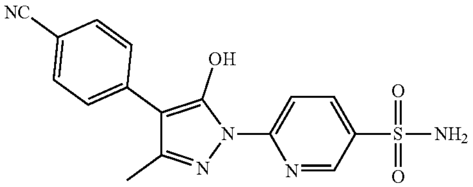 [SMILES: Cc1nn(-c2ccc(S(N)(=O)=O)cn2)c(O)c1-c1ccc(C#N)cc1] |
| 12 | 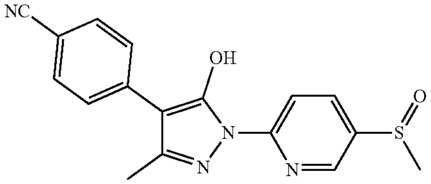 |
| 13 | 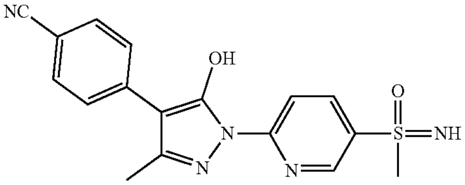 [SMILES: Cc1nn(-c2ccc(S(C)(=N)=O)cn2)c(O)c1-c1ccc(C#N)cc1] |
| 14 | 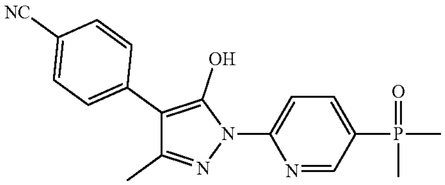 [SMILES: Cc1nn(-c2ccc(P(C)(C)=O)cn2)c(O)c1-c1ccc(C#N)cc1] |
| 15 | 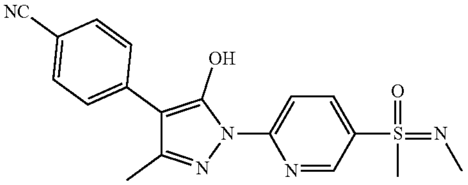 [SMILES: CN=S(C)(=O)c1ccc(-n2nc(C)c(-c3ccc(C#N)cc3)c2O)nc1] |

-continued
| Cmpd No. | Structure |
|---|---|
| 16 | 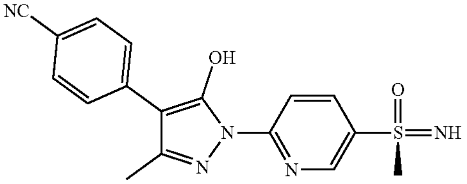 [SMILES: Cc1nn(-c2ccc([S@@](C)(=N)=O)cn2)c(O)c1-c1ccc(C#N)cc1] |
| 17 | 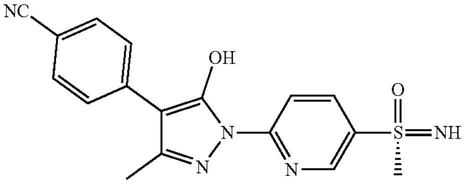 |
| 18 | 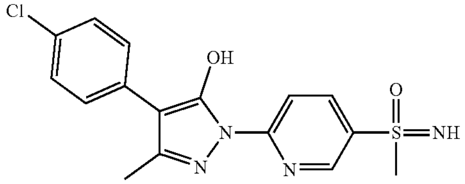 [SMILES: Cc1nn(-c2ccc(S(C)(=N)=O)cn2)c(O)c1-c1ccc(Cl)cc1] |
| 19 | 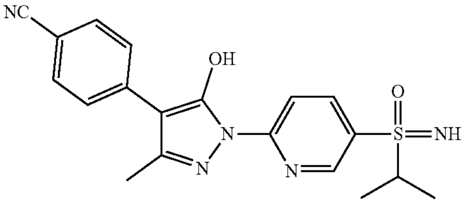 [SMILES: Cc1nn(-c2ccc(S(=N)(=O)C(C)C)cn2)c(O)c1-c1ccc(C#N)cc1] |
| 20 | 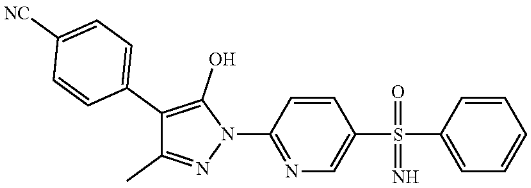 [SMILES: Cc1nn(-c2ccc(S(=N)(=O)c3ccccc3)cn2)c(O)c1-c1ccc(C#N)cc1] |
| 21 | 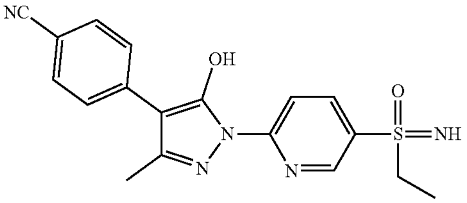 [SMILES: CCS(=N)(=O)c1ccc(-n2nc(C)c(-c3ccc(C#N)cc3)c2O)nc1] |
| 22 | 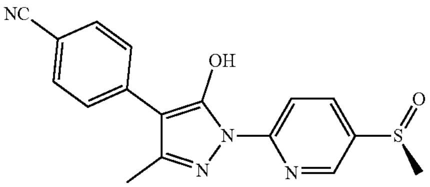 [SMILES: Cc1nn(-c2ccc([S@](C)=O)cn2)c(O)c1-c1ccc(C#N)cc1] |
| 23 | 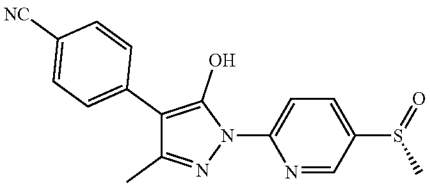 |

-continued
| Cmpd No. | Structure |
| --- | --- |
| 24 | 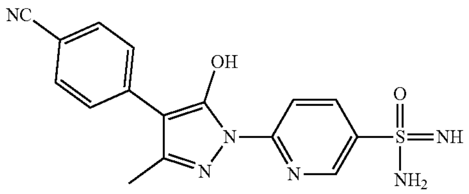 [SMILES: Cc1nn(-c2ccc(S(=N)(N)=O)cn2)c(O)c1-c1ccc(C#N)cc1] |
| 25 | 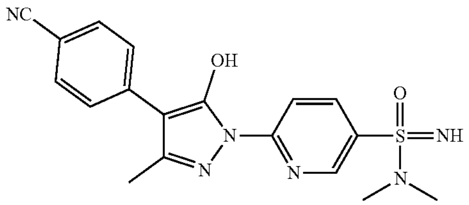 [SMILES: Cc1nn(-c2ccc(S(=N)(=O)N(C)C)cn2)c(O)c1-c1ccc(C#N)cc1] |
| 26 | 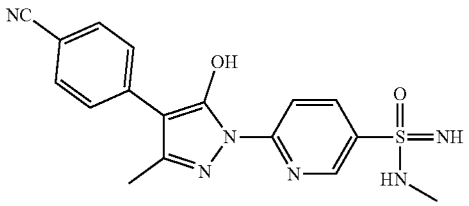 [SMILES: CNS(=N)(=O)c1ccc(-n2nc(C)c(-c3ccc(C#N)cc3)c2O)nc1] |
| 27 | 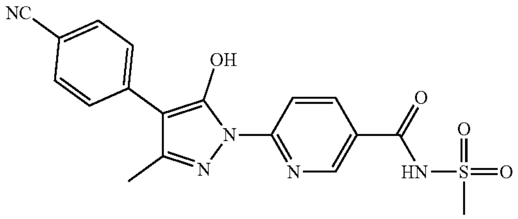 [SMILES: Cc1nn(-c2ccc(C(=O)NS(C)(=O)=O)cn2)c(O)c1-c1ccc(C#N)cc1] |
| 28 | 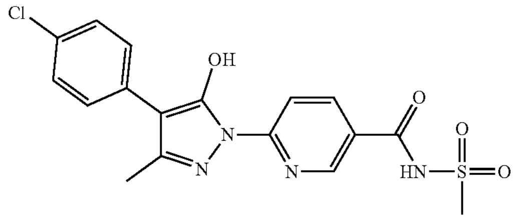 [SMILES: Cc1nn(-c2ccc(C(=O)NS(C)(=O)=O)cn2)c(O)c1-c1ccc(Cl)cc1] |
| 29 | 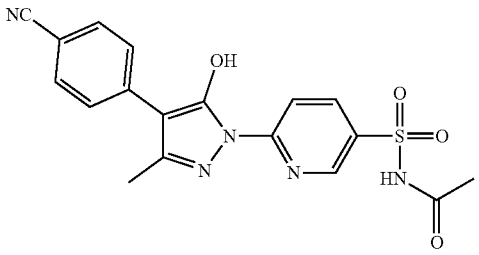 [SMILES: CC(=O)NS(=O)(=O)c1ccc(-n2nc(C)c(-c3ccc(C#N)cc3)c2O)nc1] |
| 30 | 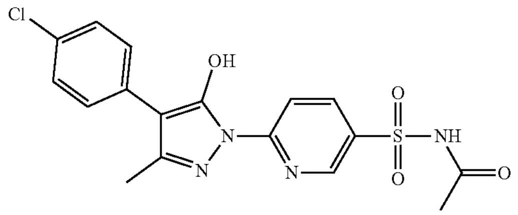 [SMILES: CC(=O)NS(=O)(=O)c1ccc(-n2nc(C)c(-c3ccc(Cl)cc3)c2O)nc1] |

-continued
| Cmpd No. | Structure |
|---|---|
| 31 | 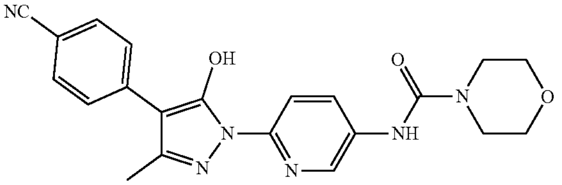 [SMILES: Cc1nn(-c2ccc(NC(=O)N3CCOCC3)cn2)c(O)c1-c1ccc(C#N)cc1] |
| 32 | 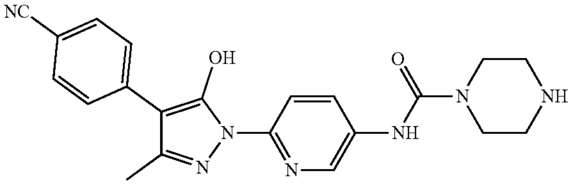 [SMILES: Cc1nn(-c2ccc(NC(=O)N3CCNCC3)cn2)c(O)c1-c1ccc(C#N)cc1] |
| 33 | 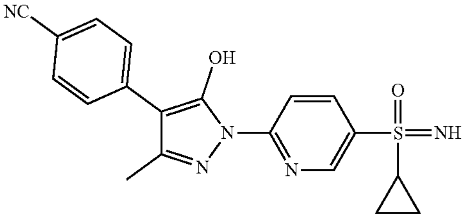 [SMILES: Cc1nn(-c2ccc(S(=N)(=O)C3CC3)cn2)c(O)c1-c1ccc(C#N)cc1] |
| 34 | 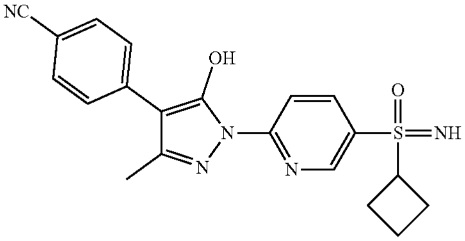 [SMILES: Cc1nn(-c2ccc(S(=N)(=O)C3CCC3)cn2)c(O)c1-c1ccc(C#N)cc1] |
| 35 | 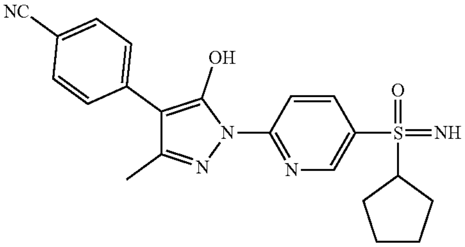 [SMILES: Cc1nn(-c2ccc(S(=N)(=O)C3CCCC3)cn2)c(O)c1-c1ccc(C#N)cc1] |
| 36 | 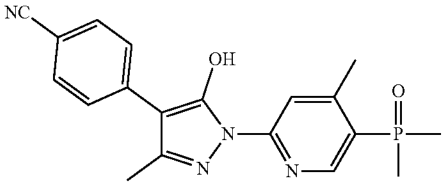 [SMILES: Cc1cc(-n2nc(C)c(-c3ccc(C#N)cc3)c2O)ncc1P(C)(C)=O] |
| 37 | 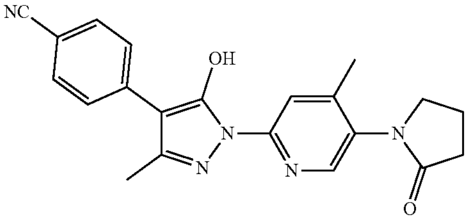 [SMILES: Cc1cc(-n2nc(C)c(-c3ccc(C#N)cc3)c2O)ncc1N1CCCC1=O] |

-continued
| Cmpd No. | Structure |
|---|---|
| 38 | 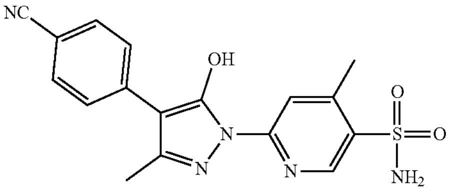 |
| 39 | 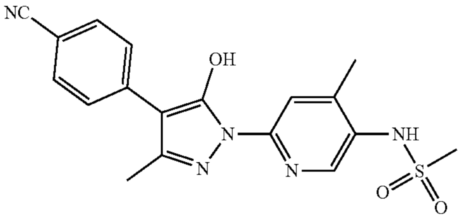 [SMILES: Cc1cc(-n2nc(C)c(-c3ccc(C#N)cc3)c2O)ncc1NS(C)(=O)=O] |
| 40 | 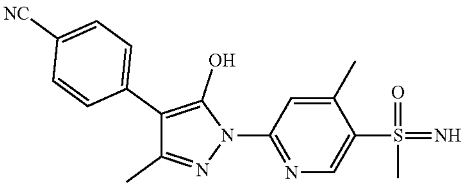 [SMILES: Cc1cc(-n2nc(C)c(-c3ccc(C#N)cc3)c2O)ncc1S(C)(=N)=O] |
| 41 | 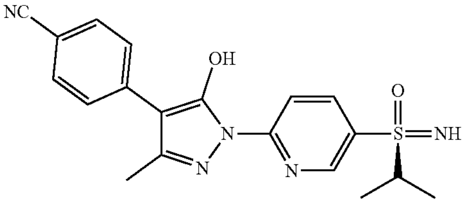 [SMILES: Cc1nn(-c2ccc([S@@](=N)(=O)C(C)C)cn2)c(O)c1-c1ccc(C#N)cc1] |
| 42 | 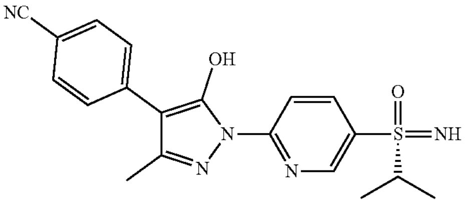 [SMILES: Cc1nn(-c2ccc([S@](=N)(=O)C(C)C)cn2)c(O)c1-c1ccc(C#N)cc1] |
| 43 | 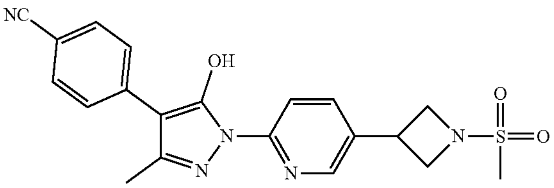 |
| 44 | 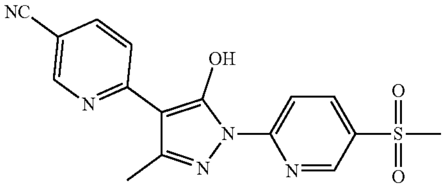 [SMILES: Cc1nn(-c2ccc(S(C)(=O)=O)cn2)c(O)c1-c1ccc(C#N)cn1] |

-continued
| Cmpd No. | Structure |
|---|---|
| 45 | 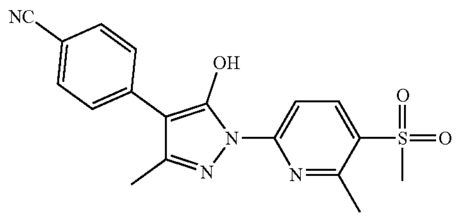 [SMILES: Cc1nc(-n2nc(C)c(-c3ccc(C#N)cc3)c2O)ccc1S(C)(=O)=O] |
| 46 | 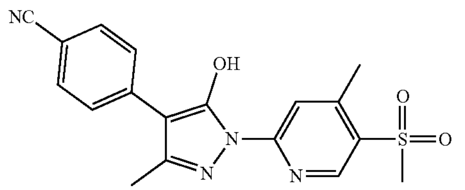 [SMILES: Cc1cc(-n2nc(C)c(-c3ccc(C#N)cc3)c2O)ncc1S(C)(=O)=O] |
| 47 | 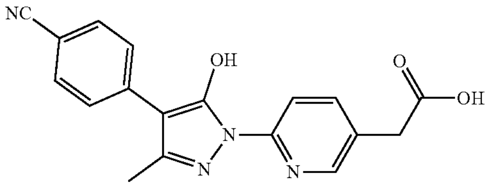 [SMILES: Cc1nn(-c2ccc(CC(=O)O)cn2)c(O)c1-c1ccc(C#N)cc1] |
| 48 | 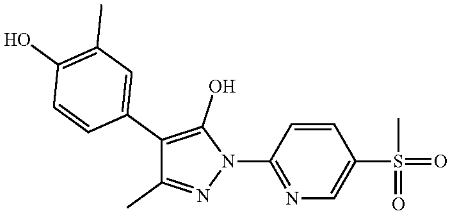 [SMILES: Cc1cc(-c2c(C)nn(-c3ccc(S(C)(=O)=O)cn3)c2O)ccc1O] |
| 49 | 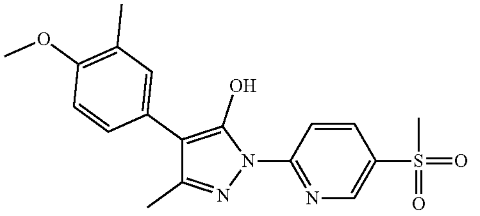 [SMILES: COc1ccc(-c2c(C)nn(-c3ccc(S(C)(=O)=O)cn3)c2O)cc1C] |
| 50 | 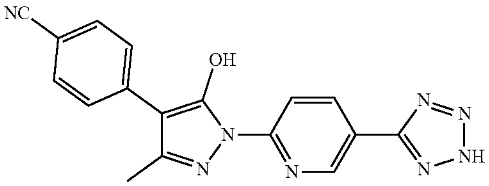 [SMILES: Cc1nn(-c2ccc(-c3nn[nH]n3)cn2)c(O)c1-c1ccc(C#N)cc1] |
| 51 | 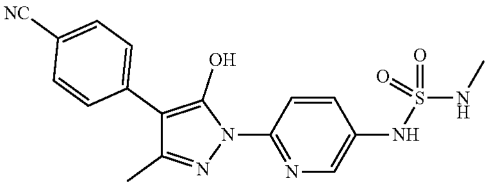 [SMILES: CNS(=O)(=O)Nc1ccc(-n2nc(C)c(-c3ccc(C#N)cc3)c2O)nc1] |

-continued
| Cmpd No. | Structure |
| --- | --- |
| 52 | 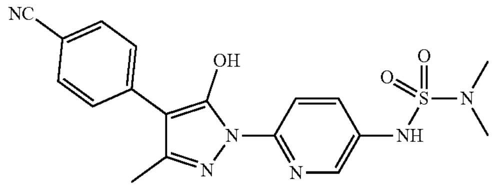 [SMILES: Cc1nn(-c2ccc(NS(=O)(=O)N(C)C)cn2)c(O)c1-c1ccc(C#N)cc1] |
| 53 | 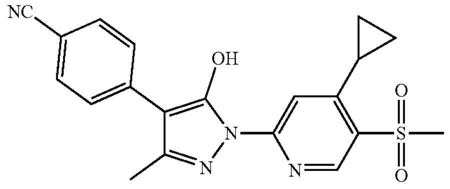 [SMILES: Cc1nn(-c2cc(C3CC3)c(S(C)(=O)=O)cn2)c(O)c1-c1ccc(C#N)cc1] |
| 54 | 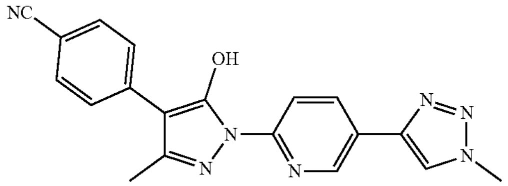 [SMILES: Cc1nn(-c2ccc(-c3cn(C)nn3)cn2)c(O)c1-c1ccc(C#N)cc1] |
| 55 | 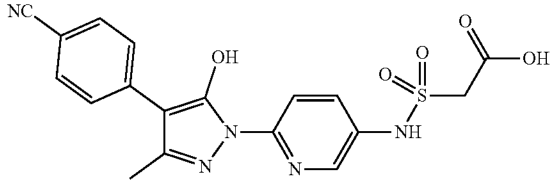 [SMILES: Cc1nn(-c2ccc(NS(=O)(=O)CC(=O)O)cn2)c(O)c1-c1ccc(C#N)cc1] |
| 56 | 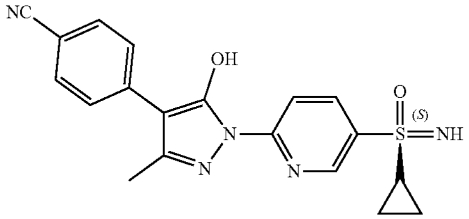 |
| 57 | 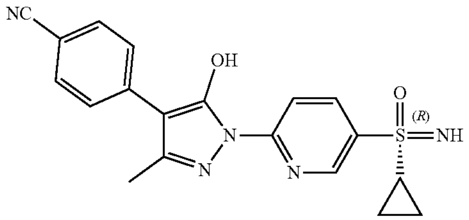 |
| 58 | 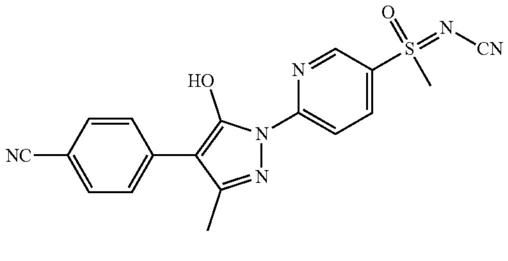 [SMILES: Cc1nn(-c2ccc(S(C)(=O)=NC#N)cn2)c(O)c1-c1ccc(C#N)cc1] |

-continued
| Cmpd No. | Structure |
| --- | --- |
| 59 | 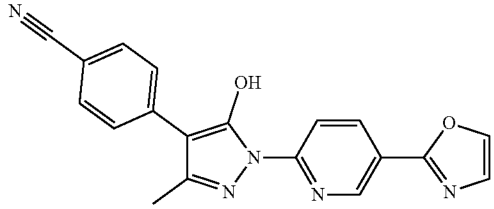 |
| 60 | 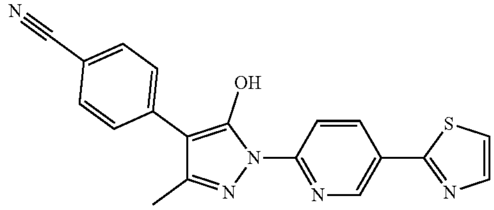 |
| 61 | 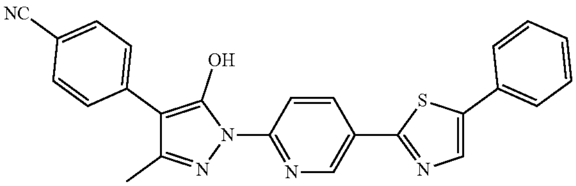 [SMILES: Cc1nn(-c2ccc(-c3ncc(-c4ccccc4)s3)cn2)c(O)c1-c1ccc(C#N)cc1] |
| 62 | 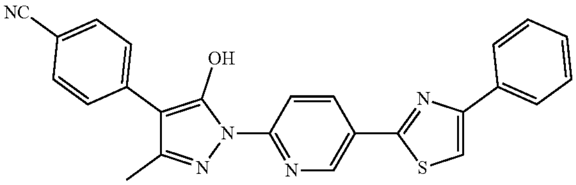 |
| 63 | 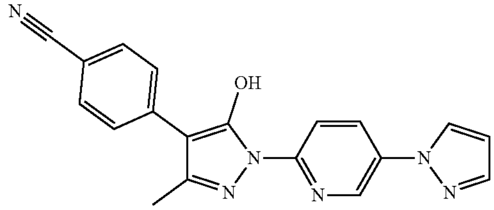 [SMILES: Cc1nn(-c2ccc(-n3cccn3)cn2)c(O)c1-c1ccc(C#N)cc1] |
| 64 | 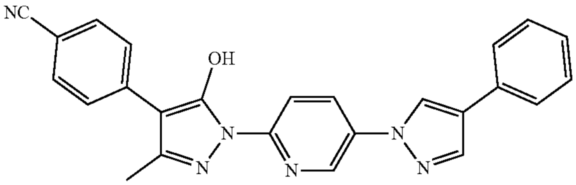 [SMILES: Cc1nn(-c2ccc(-n3cc(-c4ccccc4)cn3)cn2)c(O)c1-c1ccc(C#N)cc1] |
| 65 | 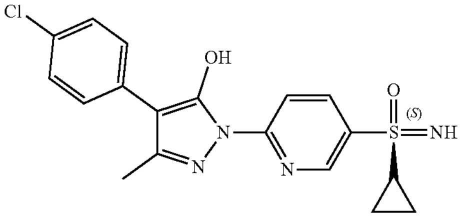 |

-continued
| Cmpd No. | Structure |
|---|---|
| 66 | 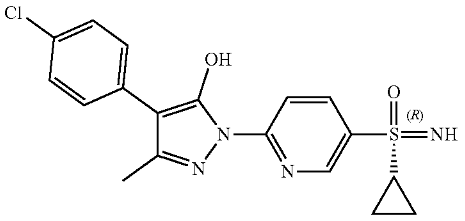 |
| 67 | 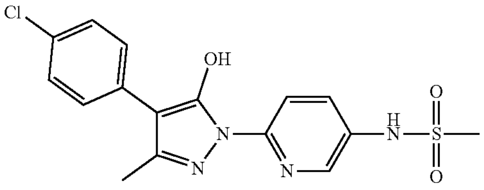 [SMILES: Cc1nn(-c2ccc(NS(C)(=O)=O)cn2)c(O)c1-c1ccc(Cl)cc1] |
| 68 | 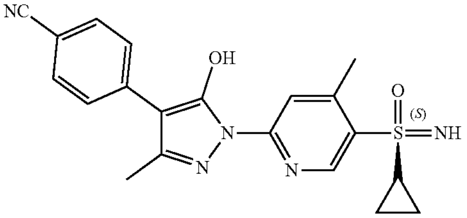 |
| 69 | 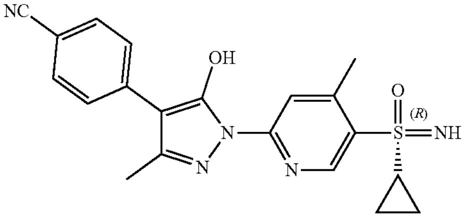 |
| 70 | 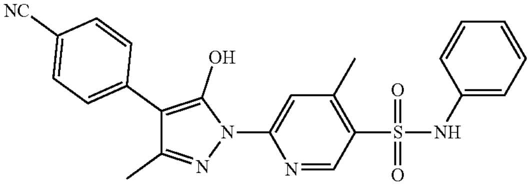 [SMILES: Cc1cc(-n2nc(C)c(-c3ccc(C#N)cc3)c2O)ncc1S(=O)(=O)Nc1ccccc1] |
| 71 | 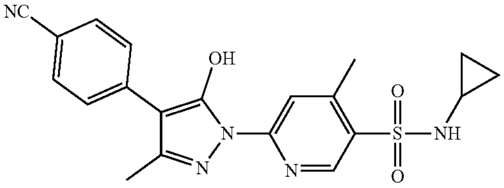 [SMILES: Cc1cc(-n2nc(C)c(-c3ccc(C#N)cc3)c2O)ncc1S(=O)(=O)NC1CC1] |
| 72 | 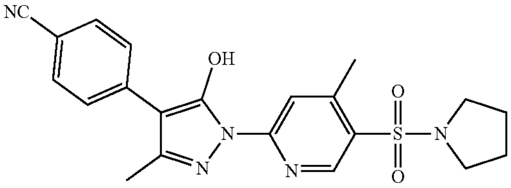 [SMILES: Cc1cc(-n2nc(C)c(-c3ccc(C#N)cc3)c2O)ncc1S(=O)(=O)N1CCCC1] |

-continued
| Cmpd No. | Structure |
| --- | --- |
| 73 | 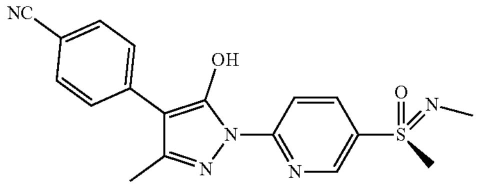 [SMILES: CN=[S@@](C)(=O)c1ccc(-n2nc(C)c(-c3ccc(C#N)cc3)c2O)nc1] |
| 74 | 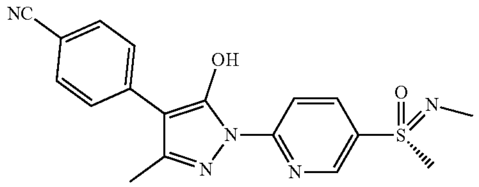 [SMILES: CN=[S@](C)(=O)c1ccc(-n2nc(C)c(-c3ccc(C#N)cc3)c2O)nc1] |
| 75 | 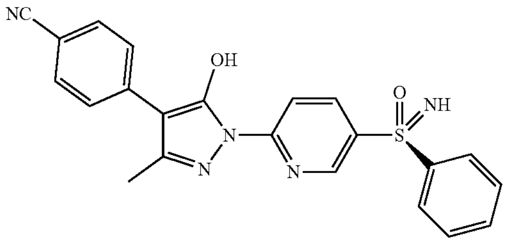 [SMILES: Cc1nn(-c2ccc([S@@](=N)(=O)c3ccccc3)cn2)c(O)c1-c1ccc(C#N)cc1] |
| 76 | 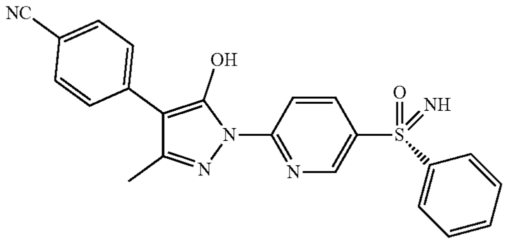 [SMILES: Cc1nn(-c2ccc([S@](=N)(=O)c3ccccc3)cn2)c(O)c1-c1ccc(C#N)cc1] |
| 77 | 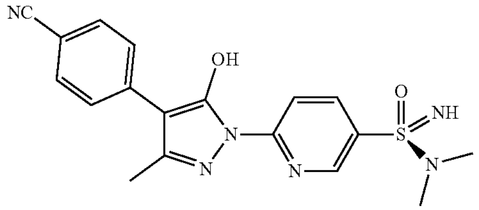 [SMILES: Cc1nn(-c2ccc([S@@](=N)(=O)N(C)C)cn2)c(O)c1-c1ccc(C#N)cc1] |
| 78 | 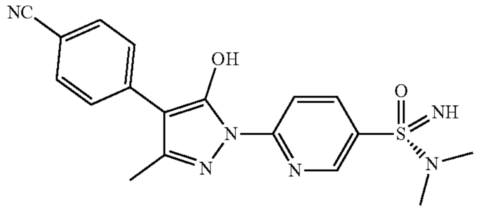 [SMILES: Cc1nn(-c2ccc([S@](=N)(=O)N(C)C)cn2)c(O)c1-c1ccc(C#N)cc1] |
| 79 | 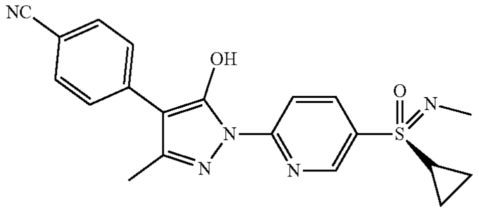 [SMILES: CN=[S@@](=O)(c1ccc(-n2nc(C)c(-c3ccc(C#N)cc3)c2O)nc1)C1CC1] |

-continued

| Cmpd No. | Structure |
|---|---|
| 80 | 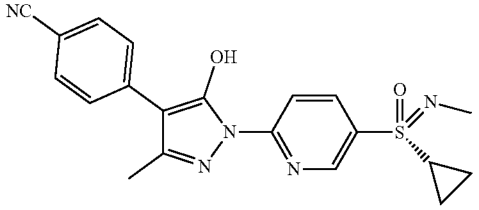 [SMILES: CN=[S@](=O)(c1ccc(-n2nc(C)c(-c3ccc(C#N)cc3)c2O)nc1)C1CC1] |
| 81 | 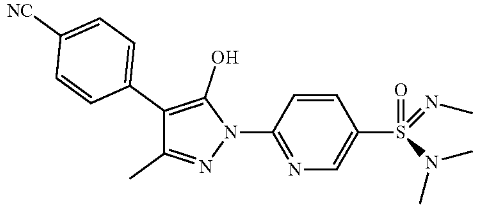 [SMILES: CN=[S@@](=O)(c1ccc(-n2nc(C)c(-c3ccc(C#N)cc3)c2O)nc1)N(C)C] |
| 82 | 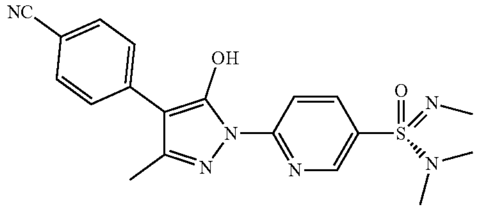 [SMILES: CN=[S@](=O)(c1ccc(-n2nc(C)c(-c3ccc(C#N)cc3)c2O)nc1)N(C)C] |
| 83 | 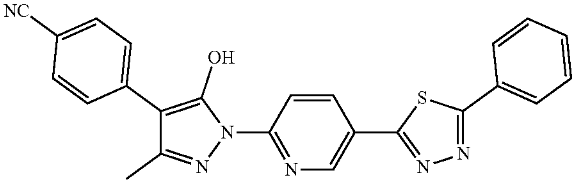 [SMILES: Cc1nn(-c2ccc(-c3nnc(-c4ccccc4)s3)cn2)c(O)c1-c1ccc(C#N)cc1] |

In embodiments, a compound of Formulas (A) and (I)-(XIII) such as any one of Compounds 1-83, at least one hydrogen atom is replaced with a deuterium atom.

In another aspect, the invention features a pharmaceutical composition comprising any compound described herein (e.g., a compound of Formulas (A) and (I)-(XIII) such as any one of Compounds 1-83), or a pharmaceutically acceptable salt thereof, and a pharmaceutically acceptable excipient.

In another aspect, the invention features a method for treating a disease mediated by PHD activity comprising administering to a subject any compound described herein (e.g., a compound of Formulas (A) and (I)-(XIII) such as any one of Compounds 1-83), or a pharmaceutically acceptable salt thereof.

In embodiments, a disease mediated by PHD activity is an ischemic reperfusion injury. (e.g., stroke, myocardial infarction, or acute kidney injury).

In embodiments, a disease mediated by PHD activity is inflammatory bowel disease (e.g., ulcerative colitis or Crohn's disease).

In embodiments, a disease mediated by PHD activity is cancer (e.g., colorectal cancer).

In embodiments, a disease mediated by PHD activity is liver disease.

In embodiments, a disease mediated by PHD activity is atherosclerosis.

In embodiments, a disease mediated by PHD activity is cardiovascular disease.

In embodiments, a disease mediated by PHD activity is a disease or condition of the eye (e.g., radiation retinopathy, retinopathy of prematurity, diabetic retinopathy, age-related macular degeneration, and ocular ischemia).

In embodiments, a disease mediated by PHD activity is anemia (e.g., anemia associated with chronic kidney disease).

In embodiments, a disease mediated by PHD activity is associated with hyperoxia.

In embodiments, a disease mediated by PHD activity is retinopathy of prematurity.

In embodiments, a disease mediated by PHD activity is bronchopulmonary dysplasia (BPD).

In embodiments, a disease mediated by PHD activity is ischemic heart disease, valvular heart disease, congestive heart failure, acute lung injury, pulmonary fibrosis, pulmonary hypertension, chronic obstructive pulmonary disease (COPD), acute liver failure, liver fibrosis, or cirrhosis.

BRIEF DESCRIPTION OF DRAWINGS

FIG. 1 is an exemplary schematic illustration demonstrating the principle of the TR-FRET Assay for PHD enzymes (PHD1, PHD2, and PHD3). In the presence of 2-oxoglutarate and $O_2$, PHD enzyme hydroxylates proline 564 of biotin-tagged HIF-1α peptide resulting in generation of biotin-tagged HIF-1α-hydroxyproline, succinate and $CO_2$. The resulting proximity of the donor fluorophore complex, monoclonal antibody anti-6His-Terbium (Tb)-cryptate Gold, bound to the His-tagged VHL protein, EloB, EloC complex (His-VBC) and the acceptor fluorophore, SA-D2 complex, bound to HIF-1α-hydroxyproline results in a fluorescence resonance energy transfer signal that can be detected and quantified.

DETAILED DESCRIPTION OF THE DISCLOSURE

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, a bovine, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used in the description and the appended claims, the singular forms "a," "an," and "the" include plural referents unless the context clearly dictates otherwise. Thus, for example, reference to "a composition" includes mixtures of two or more such compositions.

Throughout the description and claims of this specification the word "comprise" and other forms of the word, such as "comprising" and "comprises," means including but not limited to, and is not intended to exclude, for example, other additives, components, integers, or steps.

"Optional" or "optionally" means that the subsequently described event or circumstance may or may not occur, and that the description includes instances where the event or circumstance occurs and instances where it does not.

Improve, increase, or reduce: As used herein, the terms "improve," "increase," or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable," as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4 alkyl)4 salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate, and aryl sulfonate. Further pharmaceutically acceptable salts include salts formed from the quarternization of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Aliphatic: As used herein, the term aliphatic refers to $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ alkyls (e.g., linear or branched $C_1$-$C_{20}$ saturated alkyls), $C_2$-$C_{20}$ alkenyls (e.g., linear or branched $C_4$-$C_{20}$ dienyls, linear, or branched $C_6$-$C_{20}$ trienyls, and the like), and $C_2$-$C_{20}$ alkynyls (e.g., linear or branched $C_2$-$C_{20}$ alkynyls). $C_1$-$C_{20}$ aliphatics can include $C_3$-$C_{20}$ cyclic aliphatics (e.g., $C_3$-$C_{20}$ cycloalkyls, $C_4$-$C_{20}$ cycloalkenyls, or $C_5$-$C_{20}$ cycloalkynyls). In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. An aliphatic group is unsubstituted or substituted with one or more substituent groups as described herein. For example, an aliphatic may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —N(R')$_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the aliphatic is unsubstituted. In some embodiments, the aliphatic does not include any heteroatoms.

Alkyl: As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, isohexyl, etc. The term "lower alkyl" means an alkyl group straight chain or branched alkyl having 1 to 6 carbon atoms. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —N(R')$_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the alkyl is substituted (e.g., with 1, 2, 3, 4, 5, or 6 substituent groups as described herein). In some embodiments, an alkyl group is substituted with a-OH group and may also be referred to herein as a "hydroxyalkyl" group, where the prefix denotes the —OH group and "alkyl" is as described herein. In some embodiments, the alkyl is substituted with a —OR' group and may also be referred to herein as "alkoxy" group.

Affixing the suffix "-ene" to a group indicates the group is a divalent moiety, e.g., arylene is the divalent moiety of aryl, and heteroarylene is the divalent moiety of heteroaryl.

Alkylene: The term "alkylene," as used herein, represents a saturated divalent straight or branched chain hydrocarbon group and is exemplified by methylene, ethylene, isopropylene and the like. Likewise, the term "alkenylene" as used herein represents an unsaturated divalent straight or branched chain hydrocarbon group having one or more unsaturated carbon-carbon double bonds that may occur in any stable point along the chain, and the term "alkynylene" herein represents an unsaturated divalent straight or branched chain hydrocarbon group having one or more unsaturated carbon-carbon triple bonds that may occur in any stable point along the chain. In certain embodiments, an alkylene, alkenylene, or alkynylene group may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. For example, an alkylene, alkenylene, or alkynylene may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —N(R')$_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In certain embodiments, an alkylene, alkenylene, or alkynylene is unsubstituted. In certain embodiments, an alkylene, alkenylene, or alkynylene does not include any heteroatoms.

Alkenyl: As used herein, "alkenyl" means any linear or branched hydrocarbon chains having one or more unsaturated carbon-carbon double bonds that may occur in any stable point along the chain, e.g. "$C_2$-$C_{20}$ alkenyl" refers to an alkenyl group having 2-20 carbons. For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. In some embodiments, the alkenyl comprises 1, 2, or 3 carbon-carbon double bond. In some embodiments, the alkenyl comprises a single carbon-carbon double bond. In some embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the alkenyl is unsubstituted. In some embodiments, the alkenyl is substituted (e.g., with 1, 2, 3, 4, 5, or 6 substituent groups as described herein). In some embodiments, an alkenyl group is substituted with a-OH group and may also be referred to herein as a "hydroxyalkenyl" group, where the prefix denotes the —OH group and "alkenyl" is as described herein.

Alkynyl: As used herein, "alkynyl" means any hydrocarbon chain of either linear or branched configuration, having one or more carbon-carbon triple bonds occurring in any stable point along the chain, e.g. "$C_2$-$C_{20}$ alkynyl" refers to an alkynyl group having 2-20 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, etc. In some embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In some embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In some embodiments, R' independently is unsubstituted $C_1$-$C_3$ alkyl. In some embodiments, the alkynyl is unsubstituted. In some embodiments, the alkynyl is substituted (e.g., with 1, 2, 3, 4, 5, or 6 substituent groups as described herein).

Aryl: The term "aryl" used alone or as part of a larger moiety as in "aralkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. In some embodiments, an aryl group has 6 ring carbon atoms ("$C_6$ aryl," e.g., phenyl). In some embodiments, an aryl group has 10 ring carbon atoms ("$C_{10}$ aryl," e.g., naphthyl such as 1-naphthyl and 2-naphthyl). In some embodiments, an aryl group has 14 ring carbon atoms ("$C_{14}$ aryl," e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Exemplary aryls include phenyl, naphthyl, and anthracene.

Arylene: The term "arylene" as used herein refers to an aryl group that is divalent (that is, having two points of attachment to the molecule). Exemplary arylenes include phenylene (e.g., unsubstituted phenylene or substituted phenylene).

Halogen or Halo: As used herein, the term "halogen" or "halo" means fluorine, chlorine, bromine, or iodine.

Amide: The term "amide" or "amido" refers to a chemical moiety with formula —C(O)$N(R')_2$, —C(O)N(R')—, —NR'C(O)R', —NR'C(O)$N(R')_2$—, or —NR'C(O)—, where each R' is independently selected from hydrogen, alkyl, alkenyl, alkynyl, heteroalkyl (bonded through a chain carbon), cycloalkyl, aryl, arylalkyl, heteroaryl (bonded through a ring carbon), heteroarylalkyl, or heterocycloalkyl (bonded through a ring carbon), unless stated other-wise in the specification, each of which moiety can itself be optionally substituted as described herein, or two R' can combine with the nitrogen atom to form a 3-, 4-, 5-, 6-, or 7-membered ring.

Amino: The term "amino" or "amine" refers to a —$N(R')_2$ group, where each R' is independently selected from hydrogen, alkyl, alkenyl, alkynyl, heteroalkyl (bonded through a chain carbon), cycloalkyl, aryl, arylalkyl, heteroaryl (bonded through a ring carbon), heteroarylalkyl, heterocycloalkyl (bonded through a ring carbon), sulfonyl, amide, or carbonyl group, unless stated other-wise in the specification, each of which moiety can itself be optionally substituted as described herein, or two R' can combine with the nitrogen atom to form a 3-, 4-, 5-, 6-, or 7-membered ring. In embodiments, an amino group is —NHR', where R' is aryl ("arylamino"), heteroaryl ("heteroarylamino"), amide, or alkyl ("alkylamino").

Sulfonyl: The term "sulfonyl" refers to a —S(═O)$_2$R', or —S(═O)$_2$— group, where R' is selected from hydrogen, alkyl, alkenyl, alkynyl, heteroalkyl (bonded through a chain carbon), amino, cycloalkyl, aryl, arylalkyl, heteroaryl (bonded through a ring carbon), heteroarylalkyl, heterocycloalkyl (bonded through a ring carbon), unless stated otherwise in the specification, each of which moiety can itself be optionally substituted as described herein. For example, in one embodiment, the sulfonyl group is —$SO_2$R', wherein R' is alkyl substituted with a carbonyl group Sulfinyl: The term "sulfinyl" refers to a chemical moiety with formula —S(═O)R', —S(═O)—, or —S(═O)(═NR')—, where R' is selected from hydrogen, alkyl, alkenyl, alkynyl, heteroalkyl (bonded through a chain carbon), cycloalkyl, aryl, arylalkyl, heteroaryl (bonded through a ring carbon), heteroarylalkyl, heterocycloalkyl (bonded through a ring carbon), unless stated other-wise in the specification, each of which moiety can itself be optionally substituted as described herein.

Carbonyl: The term "carbonyl" refers to a —C(═O)R', or —C(═O)— group, where R' is selected from hydrogen, alkyl, alkenyl, alkynyl, heteroalkyl (bonded through a chain carbon), cycloalkyl, aryl, arylalkyl, amino, hydroxyl, heteroaryl (bonded through a ring carbon), heteroarylalkyl, heterocycloalkyl (bonded through a ring carbon), unless stated other-wise in the specification, each of which moiety can itself be optionally substituted as described herein.

Phosphoryl: The term "phosphoryl" refers to a —P(═O)$(R')_2$, or —P(═O)(R')— group, where R' is selected from hydrogen, alkyl, alkenyl, alkynyl, heteroalkyl (bonded through a chain carbon or through the heteroatom), cycloalkyl, aryl, arylalkyl, heteroaryl (bonded through a ring carbon), heteroarylalkyl, or heterocycloalkyl (bonded through a ring carbon) group, unless stated other-wise in the specification, each of which moiety can itself be optionally substituted as described herein, or two R' can combine with the nitrogen atom to form a 3-, 4-, 5-, 6-, or 7-membered ring.

Heteroalkyl: The term "heteroalkyl" is meant a branched or unbranched alkyl, alkenyl, or alkynyl group having from 1 to 14 carbon atoms in addition to 1, 2, 3 or 4 heteroatoms independently selected from the group consisting of N, O, S, and P. Heteroalkyls include tertiary amines, secondary amines, ethers, thioethers, amides, thioamides, carbamates, thiocarbamates, hydrazones, imines, phosphodiesters, phosphoramidates, sulfonamides, and disulfides. A heteroalkyl group may optionally include monocyclic, bicyclic, or tricyclic rings, in which each ring desirably has three to six members. Examples of heteroalkyls include polyethers, such as methoxymethyl and ethoxyethyl.

Heteroalkylene: The term "heteroalkylene," as used herein, represents a divalent form of a heteroalkyl group as described herein.

Heteroaryl: The term "heteroaryl," as used herein, refers to a monocyclic, bicyclic, or tricyclic carbocyclic ring system having a total of six to fourteen ring members, wherein said ring system has a single point of attachment to the rest of the molecule, wherein at least one ring in the system is aromatic, wherein each ring in the system contains 4 to 7 ring members, and wherein at least one ring atom is a heteroatom such as, but not limited to, nitrogen and oxygen.

Heterocycloalkyl: The term "heterocycloalkyl," as used herein, is a non-aromatic ring wherein at least one atom is a heteroatom such as, but not limited to, nitrogen, oxygen, sulfur, or phosphorus, and the remaining atoms are carbon. The heterocycloalkyl group can be substituted or unsubstituted.

Deuterium: The term "deuterium" ("D" or "$^2$H") is also called heavy hydrogen. Deuterium is isotope of hydrogen with a nucleus consisting of one proton and one neutron, which is double the mass of the nucleus of ordinary hydrogen (one proton).

Isotope: The term "isotope" refers to a variant of a particular chemical element which differs in neutron number, and consequently in nucleon number. All isotopes of a given element have the same number of protons but different numbers of neutrons in each atom.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system, e.g., the substitution results in a stable compound (e.g., a compound which does not spontaneously undergo transformation such as by rearrangement, cyclization, elimination, or other reaction). In cases where a specified moiety or group is not expressly noted as being optionally substituted or substituted with any specified substituent, it is understood that such a moiety or group is intended to be unsubstituted.

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. It is also understood that hydrogen atoms are presumed present to fill the remaining valence of a ring system. The substituted group encompasses only those combinations of substituents and variables that result in a stable or chemically feasible compound. A stable compound or chemically feasible compound is one that, among other factors, has stability sufficient to permit its preparation and detection.

A wide variety of substituents are well known, and methods for their formation and introduction into a variety of parent groups are also well known. Representative substituents include but are not limited to alkyl, cycloalkyl, alkenyl, cycloalkenyl, alkynyl, arylalkyl, alkylaryl, aryl, arylalkoxy, arylamino, heteroarylamino, heteroaryl, heteroarylalkoxy, heterocycloalkyl, hydroxyalkyl, aminoalkyl, haloalkyl, thioalkyl, alkylthioalkyl, carboxyalkyl, imidazolylalkyl, indolylalkyl, mono-, di- and trihaloalkyl, mono-, di- and trihaloalkoxy, amino, alkylamino, dialkylamino, amide, cyano, alkoxy, hydroxy, sulfonamide, halo (e.g., —Cl and —Br), nitro, oximino, $—COOR^{50}$, $—COR^{50}$, $—SO_{0-2}R^{50}$, $—SO_2NR^{50}R^{51}$, $NR^{52}SO_2R^{50}$, $═C(R^{50}R^{51})$, $═N—OR^{50}$, ═N—CN, $═C(halo)_2$, ═S, ═O, $—CON(R^{50}R^{51})$, $—OCOR^{50}$, $—OCON(R^{50}R^{51})$, $—N(R^{52})CO(R^{50})$, $—N(R^{52})COOR^{50}$ and $—N(R^{52})CON(R^{50}(R^{51})$, wherein $R^{50}$, $R^{51}$ and $R^{52}$ may be independently selected from the following: a hydrogen atom and a branched or straight-chain, $C_{1-6}$-alkyl, $C_{3-6}$-cycloalkyl, $C_{4-6}$-heterocycloalkyl, heteroaryl and aryl group, with or without substituents. When permissible, $R^{50}$ and $R^{51}$ can be joined together to form a carbocyclic or heterocyclic ring system.

In preferred embodiments, the substituent is selected from halogen, —COR', $—CO_2H$, $—CO_2R'$, —CN, —OH, —OR', —OCOR', $—OCO_2R'$, $—NH_2$, —NHR', $—N(R')_2$, —SR', and $—SO_2R'$, wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In certain embodiments thereof, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). Preferably, R' independently is unsubstituted $C_1$-$C_3$ alkyl.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Compound of the Invention

Disclosed herein are compounds that are potent inhibitors of PHD. In some embodiments, the compounds of the present invention have enzymatic half maximal inhibitory concentration ($IC_{50}$) values of less than 100 μM against any one of PHD1, PHD2, and PHD3. In some embodiments, the compounds of the present invention have an $IC_{50}$ value of less than 50 μM against any one of PHD1, PHD2, and PHD3. In some embodiments, the compounds of the present invention have an $IC_{50}$ value of less than 25 μM against any one of PHD1, PHD2, and PHD3. In some embodiments, the compounds of the present invention have an $IC_{50}$ value of less than 20 μM against any one of PHD1, PHD2, and PHD3. In some embodiments, the compounds of the present invention have an $IC_{50}$ value of less than 15 μM against any one of PHD1, PHD2, and PHD3. In some embodiments, the compounds of the present invention have an $IC_{50}$ value of less than 10 μM against any one of PHD1, PHD2, and PHD3. In some embodiments, the compounds of the present invention have an $IC_{50}$ value of less than 5 μM against any one of PHD1, PHD2, and PHD3. In some embodiments, the compounds of the present invention have an $IC_{50}$ value of less than 1 μM against any one of PHD1, PHD2, and PHD3. In some embodiments, the compounds of the present invention have an $IC_{50}$ value of about 3 nM to about 5 nM against any one of PHD1, PHD2, and PHD3. In some embodiments, the compounds of the present invention have an $IC_{50}$ value of about 5 nM to about 10 nM against any one of PHD1, PHD2, and PHD3. In some embodiments, the compounds of the present invention have an $IC_{50}$ value of about 10 nM to about 20 nM against any one of PHD1, PHD2, and PHD3. In some embodiments, the compounds of the present invention have an $IC_{50}$ value of about 20 nM to about 50 nM against any one of PHD1, PHD2, and PHD3. In some embodiments, the compounds of the present invention have an $IC_{50}$ value of about 50 nM to about 100 nM against any one of PHD1, PHD2, and PHD3. In some embodiments, the compounds of the present invention have an $IC_{50}$ value of about 100 nM to about 200 nM against any one of PHD1, PHD2, and PHD3. In some embodiments, the compounds of the present invention have an $IC_{50}$ value of about 200 nM to about 500 nM against any one of PHD1, PHD2, and PHD3. In some embodiments, the compounds of the present invention have an $IC_{50}$ value of about 500 nM to about 1000 nM against any one of PHD1, PHD2, and PHD3.

Representative examples from this class show inhibitory activity for PHD1, PHD2 and PHD3 in vitro.

Exemplary compounds are described herein. In particular, these selective inhibitors can feature a pyrazole moiety (e.g., a 5-hydroxy substituted pyrazole) linking the two aromatic moieties.

Compounds of Formulas (A) and (I)-(XIII)

In an aspect, provided herein are compounds having a structure according to Formula (A):

(A)

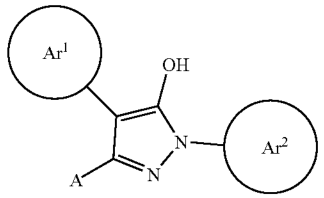

or a pharmaceutically acceptable salt thereof, wherein:

A is $C_{1-3}$ alkyl, or $C_{3-6}$ cycloalkyl;

$Ar^1$ is aryl or heteroaryl, optionally substituted with one or more groups selected from halogen, CN, OH, $C_{1-3}$ alkyl optionally substituted with CN or one or more halogens, and $C_{1-3}$ alkoxy; and $Ar^2$ is pyrid-2-yl, optionally substituted with one or more groups selected from halogen; amino; amide; OH; a sulfonyl group; a sulfinyl group; a carbonyl group; a phosphoryl group; $C_{3-6}$ cycloalkyl; $C_{3-6}$ heterocycloalkyl optionally substituted with a sulfonyl group or =O; $C_{1-3}$ alkyl optionally substituted with carbonyl or one or more halogens; and heteroaryl optionally substituted with $C_{1-3}$ alkyl or phenyl.

In embodiments, A is $C_{1-3}$ alkyl. In embodiments, A is $CH_3$. In embodiments, A is $CH_2CH_3$. In embodiments, A is $CH_2CH_2CH_3$. In embodiments, A is $CH(CH_3)_2$.

In embodiments, A is $C_{3-6}$ cycloalkyl. In embodiments, A is cyclopropyl. In embodiments, A is cyclobutyl. In embodiments, A is cyclopentyl. In embodiments, A is cyclohexyl.

In embodiments, $Ar^1$ is an unsubstituted aryl. In embodiments, $Ar^1$ is a substituted aryl. In embodiments, $Ar^1$ is a substituted phenyl.

In embodiments, $Ar^1$ is an unsubstituted 6-membered heteroaryl. In embodiments, $Ar^1$ is a substituted 6-membered heteroaryl.

In embodiments, $Ar^1$ is substituted with one or more groups selected from halogen, CN, OH, $C_{1-3}$ alkyl optionally substituted with CN or one or more halogens, and $C_{1-3}$ alkoxy. In some embodiments, $Ar^1$ is substituted with 1 substituent group. In some embodiments, $Ar^1$ is substituted with 2 substituent groups. In some embodiments, $Ar^1$ is substituted with 3 substituent groups. In some embodiments, $Ar^1$ is substituted with 4 substituent groups.

In embodiments, $Ar^1$ comprises one or more $R^1$ groups, wherein each $R^1$ is selected independently from hydrogen, halogen, CN, OH, $C_{1-3}$ alkyl optionally substituted with one or more halogens, and $C_{1-3}$ alkoxy. In embodiments, $Ar^1$ comprises a quantity of $R^1$ groups that is represented by m, wherein m is 1, 2, 3, or 4. When $R^1$ is present, $R^1$ can replace a hydrogen in the parent molecular structure. In embodiments, when $R^1$ is present and is a non-hydrogen moiety, $R^1$ represents a substituent group. In embodiments, $R^1$ is selected independently from halogen, CN, OH, $C_{1-3}$ alkyl optionally substituted with one or more halogens, and $C_{1-3}$ alkoxy.

Accordingly, it is also understood that for any value of m described herein, hydrogens are present as appropriate in order to complete valency requirements at constituent atoms of $Ar^1$ such that the molecule is a stable compound (e.g., the molecule is a compound which does not spontaneously undergo transformation such as by rearrangement, cyclization, elimination, or other reaction). Exemplary embodiments of $Ar^1$, $R^1$, and m are described herein.

In embodiments, $Ar^1$ is

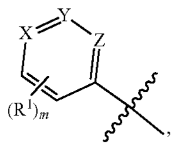

, wherein

X is N or $CR^{1a}$;

Y and Z are independently CH or N; and m is 1, 2, 3 or 4.

In embodiments, $R^1$ is not a hydrogen. In embodiments, when $R^1$ is present and is a non-hydrogen moiety, $R^1$ represents a substituent group.

In embodiments, the value of m is based on the number of nitrogen atoms present in the ring. In embodiments, when one and only one of Y and Z is N, m is 1, 2, or 3. In embodiments, when each of Y and Z are N, m is 1 or 2.

In embodiments, X is N. In embodiments, X is $CR^{1a}$.

In embodiments, Y is CH. In embodiments, Z is N.

In embodiments, m is 1. In embodiments, m is 2. In embodiments, m is 3. In embodiments, m is 4.

In embodiments, Y and Z are both N, and m is 1 or 2. In embodiments, m is 1, and any remaining unsubstituted carbon ring atoms are assumed bonded to hydrogen in order to fill the valence. In embodiments, m is 2.

In embodiments, Y and Z are both CH, and m is 1, 2, 3, or 4. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3, and any remaining unsubstituted carbon ring atoms are assumed bonded to hydrogen in order to fill the valence. In embodiments, m is 4.

In embodiments, one of Y and Z is CH and the other is N, and m is 1, 2, or 3. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3.

In embodiments, $Ar^1$ is

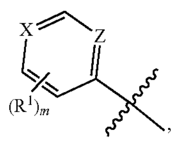

wherein

X is N or $CR^{1a}$;

Z is CH or N; and m is 1, 2, 3 or 4.

In embodiments, Z is N, and m is 1, 2 or 3. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3.

In embodiments, Z is CH, and m is 1, 2, 3, or 4. In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3, and any remaining unsubstituted carbon ring atoms are assumed bonded to hydrogen in order to fill the valence. In embodiments, m is 4.

In embodiments, X is N. In embodiments, X is $CR^{1a}$.

In embodiments, $Ar^1$ is

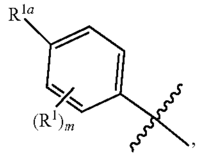

wherein m is 1, 2, 3 or 4.

In embodiments, m is 1, and any remaining unsubstituted carbon ring atoms are assumed bonded to hydrogen in order to fill the valence. In embodiments, m is 2, and any remaining unsubstituted carbon ring atoms are assumed bonded to hydrogen in order to fill the valence. In embodiments, m is 3, and any remaining unsubstituted carbon ring atoms are assumed bonded to hydrogen in order to fill the valence. In embodiments, m is 4.

In embodiments, $R^{1a}$ is H.

In embodiments, $R^{1a}$ is CN.

In embodiments, $R^{1a}$ is OH.

In embodiments, $R^{1a}$ is halogen. In embodiments, $R^{1a}$ is F. In embodiments, $R^{1a}$ is Cl.

In embodiments, $R^{1a}$ is Br. In embodiments, $R^{1a}$ is I.

In embodiments, $R^{1a}$ is $C_{1-3}$ alkoxy. In embodiments, $R^{1a}$ is methoxy. In embodiments, $R^{1a}$ is ethoxy. In embodiments, $R^{1a}$ is propoxy.

In embodiments, $R^{1a}$ is $C_{1-3}$ alkyl.

In embodiments, $R^{1a}$ is unsubstituted $C_{1-3}$ alkyl. In embodiments, $R^{1a}$ is $CH_3$.

In embodiments, $R^{1a}$ is substituted $C_{1-3}$ alkyl. In embodiments, $R^{1a}$ is $C_{1-3}$ alkyl substituted with CN group. In embodiments, $R^{1a}$ is $CH_2CN$.

In embodiments, $R^1$, each time taken, is hydrogen.

In embodiments, $R^1$, each time taken, is CN.

In embodiments, $R^1$, each time taken, is OH.

In embodiments, $R^1$, each time taken, is halogen. In embodiments, a halogen is Cl. In embodiments, a halogen is Br. In embodiments, a halogen is I.

In embodiments, $R^1$, each time taken, is $C_{1-3}$ alkyl.

In embodiments, $R^1$, each time taken, is unsubstituted $C_{1-3}$ alkyl. In embodiments, $R^1$, each time taken, is $CH_3$.

In embodiments, $R^1$, each time taken, is substituted $C_{1-3}$ alkyl. In embodiments, $R^1$, each time taken, is $C_{1-3}$ alkyl substituted with one or more halogens. In embodiments, the halogen is F. In embodiments, the halogen is Cl. In embodiments, the halogen is Br. In embodiments, the halogen is I.

In embodiments, $R^1$, each time taken, is $CF_3$.

In embodiments, $R^1$, each time taken, is $C_{1-3}$ alkoxy. In embodiments, $R^1$, each time taken, is OMe.

In embodiments, $Ar^2$ is pyrid-2-yl, optionally substituted with one or more groups selected from halogen; amino; amide; OH; a sulfonyl group (e.g. $SO_2R^6$); a sulfinyl group (e.g. $SOR^7R^8$ or $SOR^9$); a carbonyl group (e.g. $COR^{10}$); a phosphoryl group (e.g. $POR^{12}R^{13}$); $C_{3-6}$ cycloalkyl; $C_{3-6}$ heterocycloalkyl optionally substituted with a sulfonyl group or =O; $C_{1-3}$ alkyl optionally substituted with carbonyl or one or more halogens; and heteroaryl optionally substituted with $C_{1-3}$ alkyl or phenyl. In embodiments, $Ar^2$ is unsubstituted pyrid-2-yl. In embodiments, $Ar^2$ is substituted pyrid-2-yl. In embodiments, $Ar^2$ is pyrid-2-yl substituted by 1 or 2 substituents as described herein. In embodiments, $Ar^2$ is pyrid-2-yl substituted by 3 substituents as described herein.

In embodiments, $Ar^2$ is

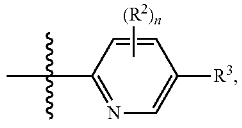

wherein $R^2$, each time taken, is independently selected from the group consisting of hydrogen, halogen, $NR^4R^5$, OH, $C_{1-3}$ alkyl, and $C_{3-6}$ cycloalkyl;

$R^3$ is $SO_2R^6$, $SOR^7R^8$, $SOR^9$, $COR^{10}$, $(CH_2)_pCOOH$, $NHR^{11}$, $POR^{12}R^{13}$, halogen, cycloalkyl, heterocycloalkyl optionally substituted with $SO_2R^{14}$ or =O, heteroaryl optionally substituted with $C_{1-3}$ alkyl or phenyl, or $C_{1-3}$ alkyl optionally substituted with one or more halogens;

$R^6$ is $C_{1-3}$ alkyl, $NHCOR^{15}$, $NR^{16}R^{17}$, or phenyl;

$R^7$ is $C_{1-3}$ alkyl, $C_{3-5}$ cycloalkyl, phenyl, or $NR^{18}R^{19}$;

$R^8$ is NH, NCN, or $NCH_3$;

$R^{10}$ is $C_{1-3}$ alkyl or $NHSO_2R^{20}$;

$R^{11}$ is $COR^{21}$ or $SO_2R^{22}$;

$R^9$, $R^{12}$, $R^{13}$ $R^{14}$, $R^{15}$, and $R^{20}$ are each independently $C_{1-3}$ alkyl;

$R^{21}$ is heterocycloalkyl, cycloalkyl, or $C_{1-3}$ alkyl;

$R^{22}$ is $NR^{23}R^{24}$ or $C_{1-3}$ alkyl optionally substituted with carboxyl;

$R^4$, $R^5$, $R^{18}$, $R^{19}$, $R^{23}$ and $R^{24}$ are each independently H or $C_{1-3}$ alkyl;

$R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl;

p is 1, 2, or 3; and n is 0, 1, 2 or 3.

In embodiments, n is 0. In embodiments, n is 1. In embodiments, n is 2. In embodiments, n is 3.

In embodiments, n is 0, and any remaining unsubstituted carbon ring atoms are assumed bonded to hydrogen in order to fill the valence. In embodiments, n is 1, and any remaining unsubstituted carbon ring atoms are assumed bonded to hydrogen in order to fill the valence. In embodiments, n is 2, and any remaining unsubstituted carbon ring atoms are assumed bonded to hydrogen in order to fill the valence. In embodiments, n is 3.

In embodiments, $R^2$, each time taken, is hydrogen.

In embodiments, $R^2$, each time taken, is OH.

In embodiments, $R^2$, each time taken, is halogen. In embodiments, the halogen is Cl.

In embodiments, the halogen is Br. In embodiments, the halogen is I.

In embodiments, $R^2$, each time taken, is $NR^4R^5$, wherein $R^4$ and $R^5$ are each independently H or $C_{1-3}$ alkyl.

In embodiments, $R^4$ and $R^5$ are both H.

In embodiments, one of $R^4$ and $R^5$ is H, and the other is $C_{1-3}$ alkyl. In embodiments, the $C_{1-3}$ alkyl is $CH_3$.

In embodiments, $R^2$, each time taken, is $C_{1-3}$ alkyl.

In embodiments, $R^2$, each time taken, is $C_{3-6}$ cycloalkyl.

In embodiments, $R^3$ is $SO_2R^6$, wherein $R^6$ is $C_{1-3}$ alkyl, $NHCOR^{15}$, $NR^{16}R^{17}$, or phenyl.

In embodiments, $R^3$ is $SOR^7R^8$, wherein $R^7$ is $C_{1-3}$ alkyl, $C_{3-5}$ cycloalkyl, phenyl, or $NR^{18}R^{19}$, and wherein $R^8$ is NH, NCN, or $NCH_3$.

In embodiments, $R^3$ is $SOR^9$, wherein $R^9$ is $C_{1-3}$ alkyl.

In embodiments, $R^3$ is $COR^{10}$, wherein $R^{10}$ is $C_{1-3}$ alkyl or $NHSO_2R^{20}$.

In embodiments, $R^3$ is $(CH_2)_pCOOH$.

In embodiments, p is 1, 2, or 3. In embodiments, p is 1. In embodiments, p is 2. In embodiments, p is 3.

In embodiments, $R^3$ is $NHR^{11}$, wherein $R^{11}$ is $COR^{21}$ or $SO_2R^{22}$.

In embodiments, $R^3$ is $POR^{12}R^{13}$, wherein $R^{12}$ and $R^{13}$ are each independently $C_{1-3}$ alkyl.

In embodiments, $R^3$ is halogen.

In embodiments, $R^3$ is cycloalkyl or heterocycloalkyl. In embodiments, the cycloalkyl or heterocycloalkyl is unsubstituted. In embodiments, the cycloalkyl or heterocycloalkyl is substituted.

In embodiments, $R^3$ is heteroaryl. In embodiments, the heteroaryl is unsubstituted. In embodiments, the heteroaryl is substituted.

In embodiments, $R^3$ is $C_{1-3}$ alkyl. In embodiments, the $C_{1-3}$ alkyl is unsubstituted. In embodiments, the $C_{1-3}$ alkyl is substituted with one or more halogens.

In embodiments, a compound of Formula (A) has the following structure, (I)

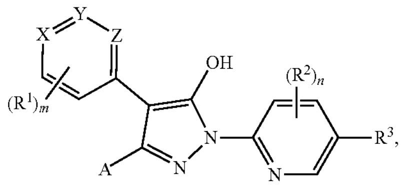

or a pharmaceutically acceptable salt thereof, wherein A, X, Y, Z, $R^1$, $R^2$, and $R^3$ are as defined anywhere herein.

In embodiments, a compound of Formula (A) or Formula (I) has the following structure, (II)

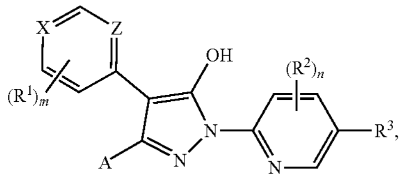

or a pharmaceutically acceptable salt thereof, wherein A, X, Z, $R^1$, $R^2$, and $R^3$ are as defined anywhere herein.

In embodiments, a compound of Formula (A), Formula (I), or Formula (II) has the following structure, (III)

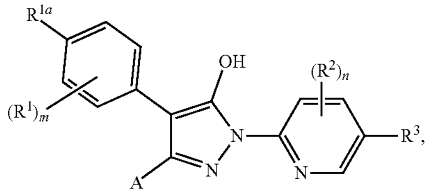

or a pharmaceutically acceptable salt thereof, wherein A, $R^{1a}$, $R^1$, $R^2$, and $R^3$ are as defined anywhere herein.

In embodiments, a compound of Formula (A), Formula (I), Formula (II) or Formula (III) has the following structure, (IV)

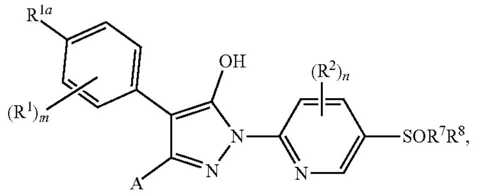

or a pharmaceutically acceptable salt thereof, wherein A, $R^{1a}$, $R^1$, and $R^2$ are as defined anywhere herein.

In embodiments, a compound of Formula (A), Formula (I), Formula (II), Formula (III) or Formula (IV) has the following structure, (IVa)

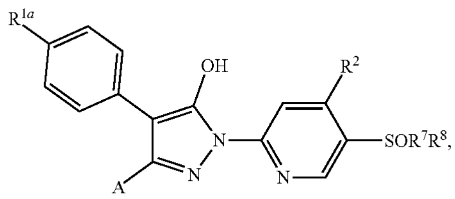

or a pharmaceutically acceptable salt thereof, wherein A, $R^{1a}$, and $R^2$ are as defined anywhere herein.

In embodiments, $R^7$ is $C_{1-3}$ alkyl.

In embodiments, $R^7$ is $C_{3-5}$ cycloalkyl.

In embodiments, $R^7$ is phenyl.

In embodiments, $R^7$ is $NR^{18}R^{19}$, wherein $R^{18}$ and $R^{19}$ are each independently H or $C_{1-3}$ alkyl.

In embodiments, $R^{18}$ and $R^{19}$ are both H.

In embodiments, $R^{18}$ and $R^{19}$ are both $C_{1-3}$ alkyl. In embodiments, $R^{18}$ and $R^{19}$ are both $CH_3$.

In embodiments, $R^{18}$ is H and $R^{19}$ is $C_{1-3}$ alkyl. In embodiments, $R^{19}$ is $CH_3$.

In embodiments, $R^8$ is NH.

In embodiments, $R^8$ is NCN.

In embodiments, $R^8$ is $NCH_3$.

In embodiments, a compound of Formula (A), Formula (I), or Formula (II) has the following structure, (V)

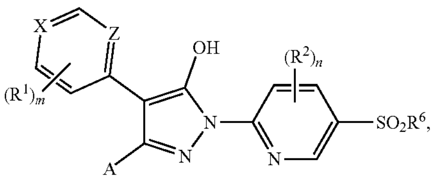

or a pharmaceutically acceptable salt thereof, wherein A, X, Z, $R^1$, and $R^2$ are as defined anywhere herein.

In embodiments, $R^6$ is $C_{1-3}$ alkyl. In embodiments, $R^6$ is $CH_3$.

In embodiments, $R^6$ is $NHCOR^{15}$, and wherein $R^{15}$ is $C_{1-3}$ alkyl. In embodiments, $R^6$ is $NHCOCH_3$.

In embodiments, $R^6$ is $NR^{16}R^{17}$, and wherein $R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl.

In embodiments, $R^{16}$ and $R^{17}$ are both H.

In embodiments, $R^{16}$ and $R^{17}$ are both $C_{1-3}$ alkyl. In embodiments, $R^{16}$ and $R^{17}$ are both $CH_3$.

In embodiments, $R^{16}$ is H and $R^{17}$ is $C_{1-3}$ alkyl. In embodiments, $R^{17}$ is $CH_3$.

In embodiments, $R^{16}$ is H and $R^{17}$ is aryl. In embodiments, $R^{17}$ is phenyl.

In embodiments, $R^{16}$ is H and $R^{17}$ is cycloalkyl. In embodiments, $R^{17}$ is cyclopropyl.

In embodiments, $R^{16}$ and $R^{17}$ together with the carbon to which they are attached form a heterocycloalkyl. In embodiments, $R^{16}$ and $R^{17}$ together with the carbon to which they are attached form

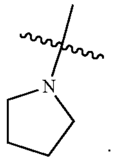

In embodiments, $R^6$ is phenyl.

In embodiments, a compound of Formula (A), Formula (I), Formula (II) or Formula (III) has the following structure, (VI)

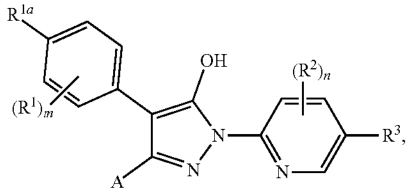

or a pharmaceutically acceptable salt thereof, wherein A, $R^{1a}$, $R^1$, and $R^2$ are as defined anywhere herein.

In embodiments, a compound of Formula (A), Formula (I), Formula (II), Formula (III) or Formula (VI) has the following structure, (VIa)

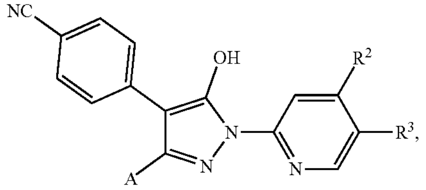

or a pharmaceutically acceptable salt thereof, wherein A and $R^2$ are as defined anywhere herein.

In embodiments, $R^3$ is cycloalkyl.

In embodiments, $R^3$ is unsubstituted cycloalkyl. In embodiments, $R^3$ is

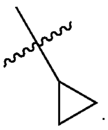 [SMILES: *C1CC1]

In embodiments, $R^3$ is substituted cycloalkyl. In embodiments, $R^3$ is cycloalkyl substituted with $SO_2R^{14}$ or =O, and wherein $R^{14}$ is $C_{1-3}$ alkyl.

In embodiments, $R^3$ is heterocycloalkyl.

In embodiments, $R^3$ is unsubstituted heterocycloalkyl. In embodiments, $R^3$ is

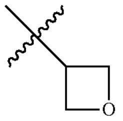
or
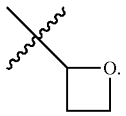

In embodiments, $R^3$ is substituted heterocycloalkyl. In embodiments, $R^3$ is heterocycloalkyl substituted with $SO_2R^{14}$ or $=O$, and wherein $R^{14}$ is $C_{1-3}$ alkyl. In embodiments, $R^3$ is

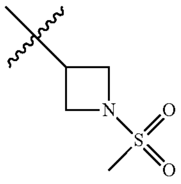
or
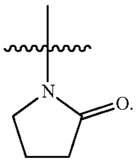

In embodiments, a compound of Formula (A), Formula (I), Formula (II) or Formula (III) has the following structure, (VII)

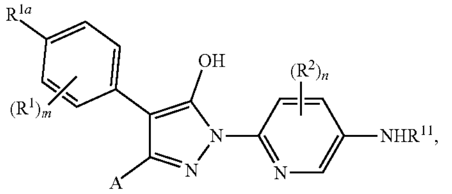

or a pharmaceutically acceptable salt thereof, wherein A, $R^{1a}$, $R^1$, and $R^2$ are as defined anywhere herein.

In embodiments, a compound of Formula (A), Formula (I), Formula (II), Formula (III) or Formula (VII) has the following structure, (VIIa)

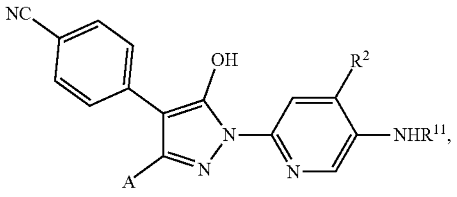

or a pharmaceutically acceptable salt thereof, wherein A and $R^2$ are as defined anywhere herein.

In embodiments, $R^{11}$ is $COR^{21}$.

In embodiments, $R^{21}$ is cycloalkyl. In embodiments, $R^{21}$ is

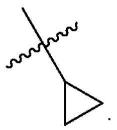 [SMILES: *C1CC1]

In embodiments, $R^{21}$ is heterocycloalkyl. In embodiments, $R^{21}$ is

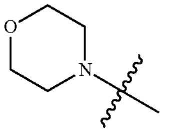
or
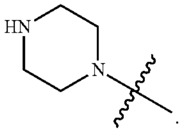

In embodiments, $R^{21}$ is $C_{1-3}$ alkyl. In embodiments, $R^{21}$ is $CH_2CH_3$.

In embodiments, $R^{11}$ is $SO_2R^{22}$.

In embodiments, $R^{22}$ is $C_{1-3}$ alkyl. In embodiments, $R^{22}$ is unsubstituted $C_{1-3}$ alkyl. In embodiments, $R^{22}$ is $C_{1-3}$ alkyl substituted with carboxyl group. In embodiments, $R^{22}$ is $CH_2COOH$.

In embodiments, $R^{22}$ is $NR^{23}R^{24}$, and wherein $R^{23}$ and $R^{24}$ are independently H or $C_{1-3}$ alkyl.

In embodiments, $R^{23}$ and $R^{24}$ are both H.

In embodiments, $R^{23}$ and $R^{24}$ are both $C_{1-3}$ alkyl. In embodiments, $R^{23}$ and $R^{24}$ are both $CH_3$.

In embodiments, $R^{23}$ is H and $R^{24}$ is $C_{1-3}$ alkyl. In embodiments, $R^{24}$ is $CH_3$.

In embodiments, a compound of Formula (A), Formula (I), Formula (II) or Formula (III) has the following structure, (VIII)

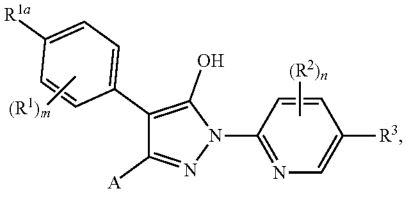

or a pharmaceutically acceptable salt thereof, wherein A, $R^{1a}$, $R^1$, and $R^2$ are as defined anywhere herein.

In embodiments, a compound of Formula (A), Formula (I), Formula (II), Formula (III) or Formula (VIII) has the following structure, (VIIIa)

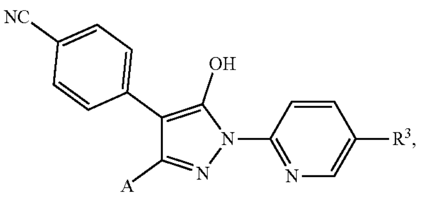

or a pharmaceutically acceptable salt thereof, wherein A is as defined anywhere herein.

In embodiments, $R^3$ is heteroaryl. In embodiments, the heteroaryl is thiazole, oxazole, pyridine, triazole, tetrazole, or pyrazole.

In embodiments, $R^3$ is unsubstituted heteroaryl. In embodiments, $R^3$ is

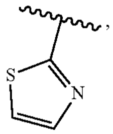, 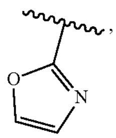, 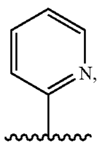, 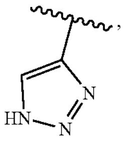, 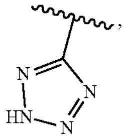, or 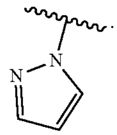.

In embodiments, $R^3$ is heteroaryl substituted with $C_{1-3}$ alkyl or phenyl. In embodiments, $R^3$ is

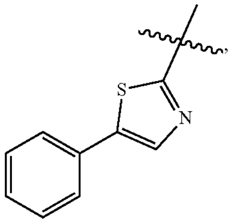, 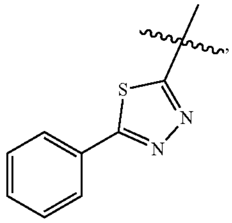, 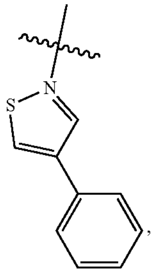, 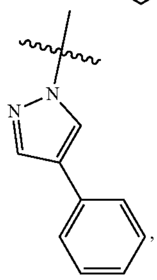, 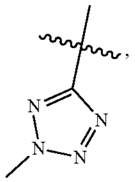, 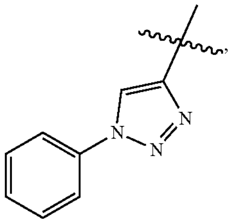, or 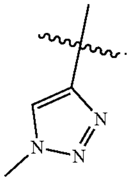.

In embodiments, a compound of Formula (A), Formula (I), Formula (II) or Formula (III) has the following structure, (IX)

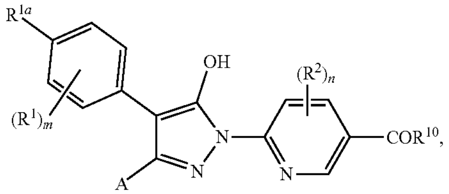

or a pharmaceutically acceptable salt thereof, wherein A, $R^{1a}$, $R^1$, and $R^2$ are as defined anywhere herein.

In embodiments, a compound of Formula (A), Formula (I), Formula (II), Formula (III) or Formula (IX) has the following structure, (IXa)

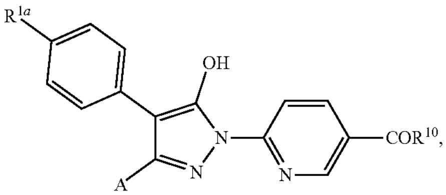

or a pharmaceutically acceptable salt thereof, wherein A and $R^{1a}$ are as defined anywhere herein.

In embodiments, $R^{10}$ is $C_{1-3}$ alkyl.

In embodiments, $R^{10}$ is $NHSO_2R^{20}$, and wherein $R^{20}$ is $C_{1-3}$ alkyl. In embodiments, $R^{10}$ is $NHSO_2CH_3$.

In embodiments, a compound of Formula (A), Formula (I), Formula (II) or Formula (III) has the following structure, (X)

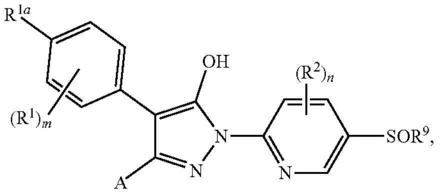

or a pharmaceutically acceptable salt thereof, wherein A, $R^{1a}$, $R^1$, and $R^2$ are as defined anywhere herein.

In embodiments, $R^9$ is $C_{1-3}$ alkyl.

In embodiments, a compound of Formula (A), Formula (I), Formula (II) or Formula (III) has the following structure, (XI)

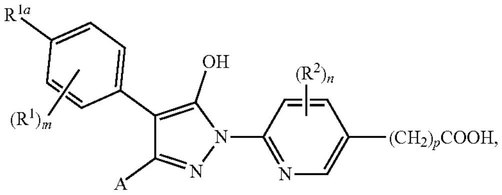

or a pharmaceutically acceptable salt thereof, wherein A, $R^{1a}$, $R^1$, and $R^2$ are as defined anywhere herein.

In embodiments, p is 1. In embodiments, p is 2. In embodiments, p is 3.

In embodiments, a compound of Formula (A), Formula (I), Formula (II) or Formula (III) has the following structure, (XII)

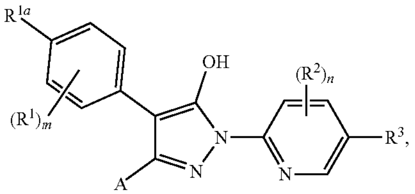

or a pharmaceutically acceptable salt thereof, wherein A, $R^{1a}$, $R^1$, and $R^2$ are as defined anywhere herein.

In embodiments, $R^3$ is halogen. In embodiments, $R^3$ is F. In embodiments, $R^3$ is Cl. In embodiments, $R^3$ is Br. In embodiments, $R^3$ is I.

In embodiments, a compound of Formula (A), Formula (I), Formula (II) or Formula (III) has the following structure, (XIII)

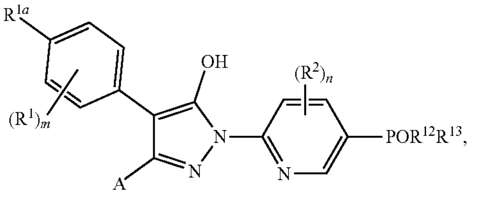

or a pharmaceutically acceptable salt thereof, wherein A, $R^{1a}$, $R^1$, and $R^2$ are as defined anywhere herein.

In embodiments, $R^{12}$ and $R^{13}$ are both $C_{1-3}$ alkyl. In embodiments, $R^{12}$ and $R^{13}$ are both $CH_3$.

Exemplary Compounds

In some embodiments, the PHD inhibitor compounds is any one of Compounds 1-83 or a pharmaceutically acceptable salt thereof.

| Cmpd No. | Structure |
|---|---|
| 1 | 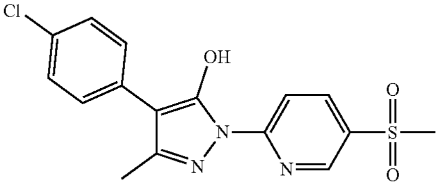 [SMILES: Cc1nn(-c2ccc(S(C)(=O)=O)cn2)c(O)c1-c1ccc(Cl)cc1] |
| 2 | 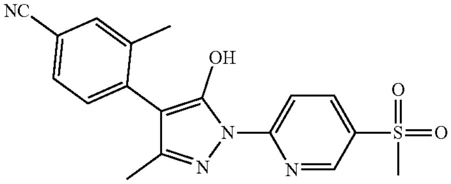 [SMILES: Cc1cc(C#N)ccc1-c1c(C)nn(-c2ccc(S(C)(=O)=O)cn2)c1O] |
| 3 | 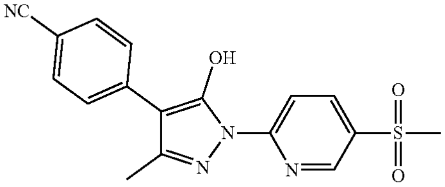 [SMILES: Cc1nn(-c2ccc(S(C)(=O)=O)cn2)c(O)c1-c1ccc(C#N)cc1] |
| 4 | 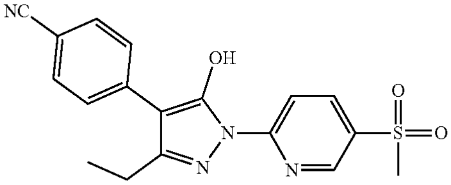 [SMILES: CCc1nn(-c2ccc(S(C)(=O)=O)cn2)c(O)c1-c1ccc(C#N)cc1] |

-continued

| Cmpd No. | Structure |
|---|---|
| 5 | 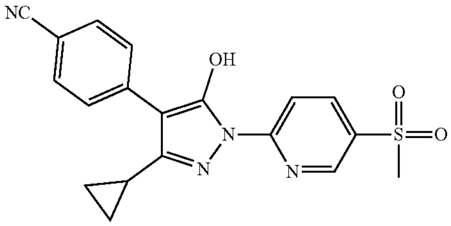 [SMILES: CS(=O)(=O)c1ccc(-n2nc(C3CC3)c(-c3ccc(C#N)cc3)c2O)nc1] |
| 6 | 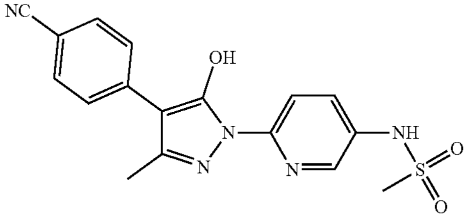 [SMILES: Cc1nn(-c2ccc(NS(C)(=O)=O)cn2)c(O)c1-c1ccc(C#N)cc1] |
| 7 | 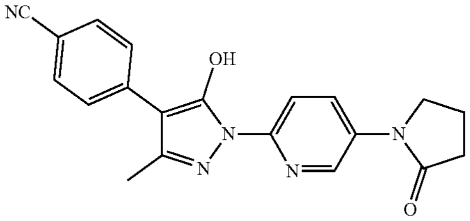 [SMILES: Cc1nn(-c2ccc(N3CCCC3=O)cn2)c(O)c1-c1ccc(C#N)cc1] |
| 8 | 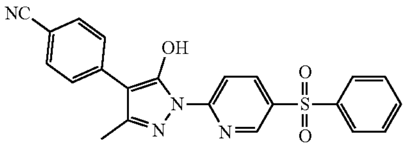 [SMILES: Cc1nn(-c2ccc(S(=O)(=O)c3ccccc3)cn2)c(O)c1-c1ccc(C#N)cc1] |
| 9 | 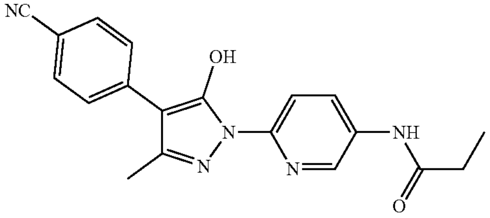 [SMILES: CCC(=O)Nc1ccc(-n2nc(C)c(-c3ccc(C#N)cc3)c2O)nc1] |
| 10 | 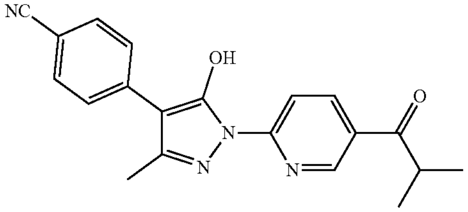 [SMILES: Cc1nn(-c2ccc(C(=O)C(C)C)cn2)c(O)c1-c1ccc(C#N)cc1] |
| 11 | 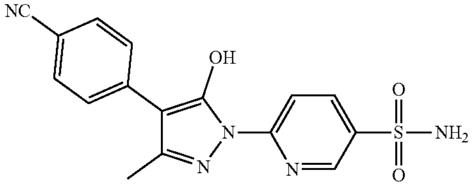 [SMILES: Cc1nn(-c2ccc(S(N)(=O)=O)cn2)c(O)c1-c1ccc(C#N)cc1] |

-continued
| Cmpd No. | Structure |
|---|---|
| 12 | 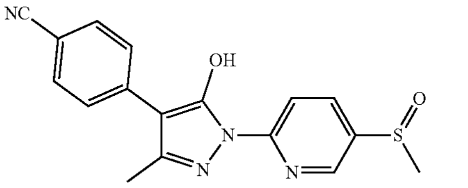 |
| 13 | 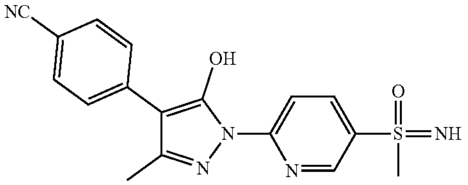 [SMILES: Cc1nn(-c2ccc(S(C)(=N)=O)cn2)c(O)c1-c1ccc(C#N)cc1] |
| 14 | 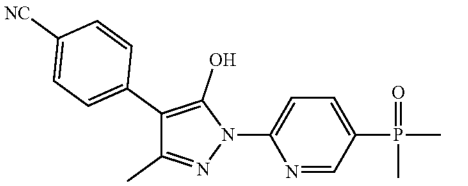 [SMILES: Cc1nn(-c2ccc(P(C)(C)=O)cn2)c(O)c1-c1ccc(C#N)cc1] |
| 15 | 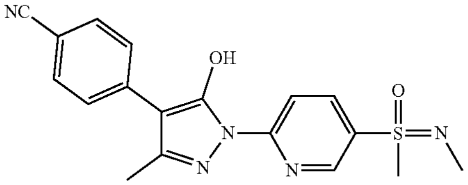 [SMILES: CN=S(C)(=O)c1ccc(-n2nc(C)c(-c3ccc(C#N)cc3)c2O)nc1] |
| 16 | 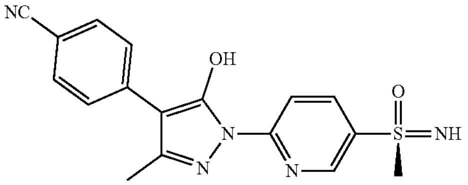 [SMILES: Cc1nn(-c2ccc([S@@](C)(=N)=O)cn2)c(O)c1-c1ccc(C#N)cc1] |
| 17 | 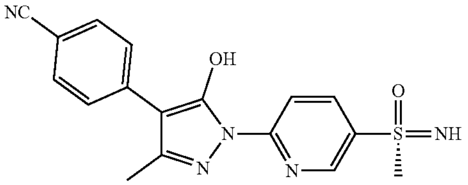 [SMILES: Cc1nn(-c2ccc([S@](C)(=N)=O)cn2)c(O)c1-c1ccc(C#N)cc1] |
| 18 | 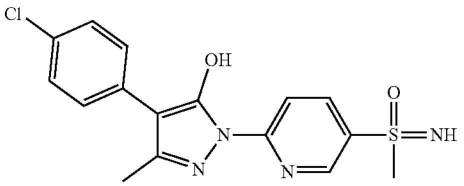 [SMILES: Cc1nn(-c2ccc(S(C)(=N)=O)cn2)c(O)c1-c1ccc(Cl)cc1] |
| 19 | 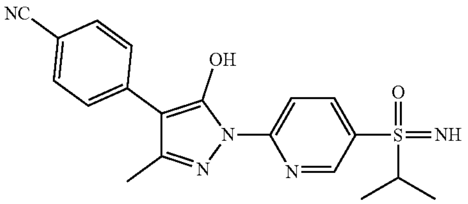 [SMILES: Cc1nn(-c2ccc(S(=N)(=O)C(C)C)cn2)c(O)c1-c1ccc(C#N)cc1] |
-continued
| Cmpd No. | Structure |
|---|---|
| 20 | 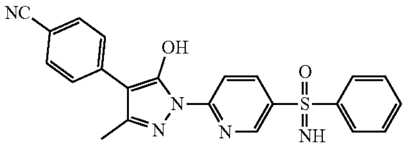 [SMILES: Cc1nn(-c2ccc(S(=N)(=O)c3ccccc3)cn2)c(O)c1-c1ccc(C#N)cc1] |
| 21 | 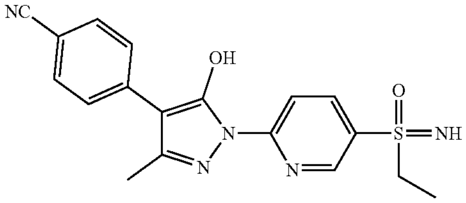 [SMILES: CCS(=N)(=O)c1ccc(-n2nc(C)c(-c3ccc(C#N)cc3)c2O)nc1] |
| 22 | 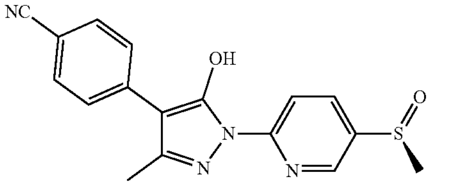 |
| 23 | 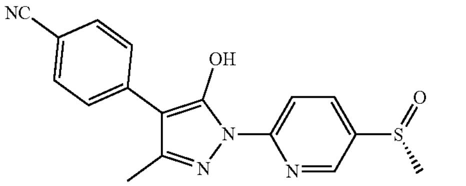 |
| 24 | 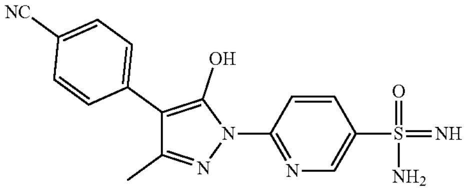 [SMILES: Cc1nn(-c2ccc(S(=N)(N)=O)cn2)c(O)c1-c1ccc(C#N)cc1] |
| 25 | 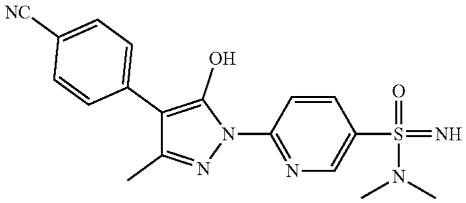 |
| 26 | 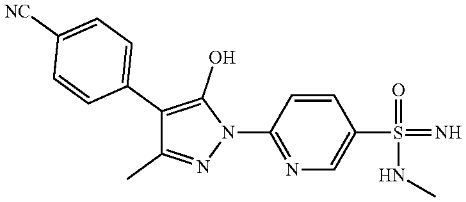 |
| 27 | 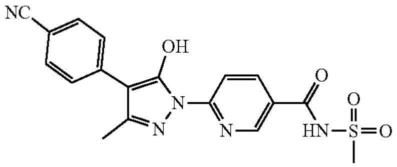 [SMILES: Cc1nn(-c2ccc(C(=O)NS(C)(=O)=O)cn2)c(O)c1-c1ccc(C#N)cc1] |

-continued
| Cmpd No. | Structure |
|---|---|
| 28 | 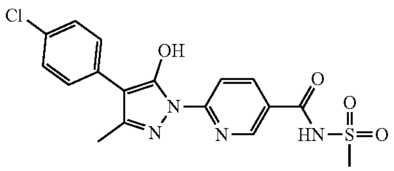 [SMILES: Cc1nn(-c2ccc(C(=O)NS(C)(=O)=O)cn2)c(O)c1-c1ccc(Cl)cc1] |
| 29 | 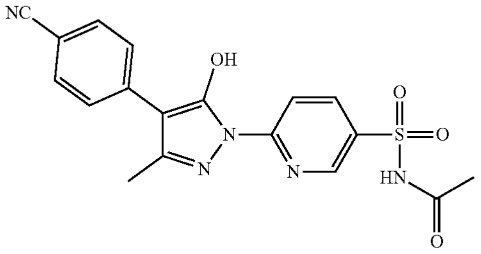 [SMILES: CC(=O)NS(=O)(=O)c1ccc(-n2nc(C)c(-c3ccc(C#N)cc3)c2O)nc1] |
| 30 | 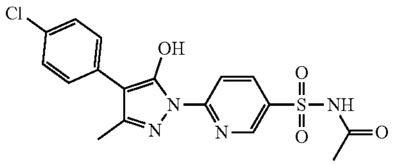 [SMILES: CC(=O)NS(=O)(=O)c1ccc(-n2nc(C)c(-c3ccc(Cl)cc3)c2O)nc1] |
| 31 | 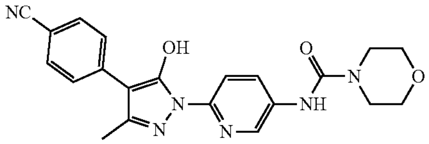 [SMILES: Cc1nn(-c2ccc(NC(=O)N3CCOCC3)cn2)c(O)c1-c1ccc(C#N)cc1] |
| 32 | 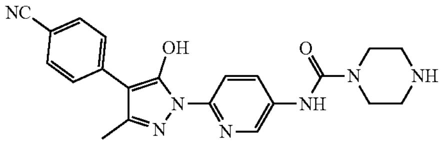 [SMILES: Cc1nn(-c2ccc(NC(=O)N3CCNCC3)cn2)c(O)c1-c1ccc(C#N)cc1] |
| 33 | 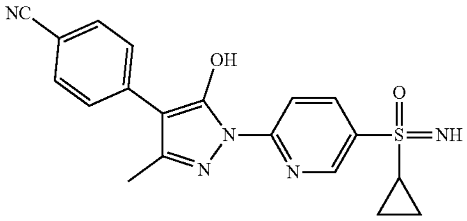 [SMILES: Cc1nn(-c2ccc(S(=N)(=O)C3CC3)cn2)c(O)c1-c1ccc(C#N)cc1] |
| 34 | 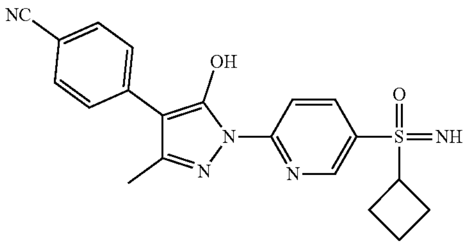 [SMILES: Cc1nn(-c2ccc(S(=N)(=O)C3CCC3)cn2)c(O)c1-c1ccc(C#N)cc1] |
-continued
| Cmpd No. | Structure |
|---|---|
| 35 | 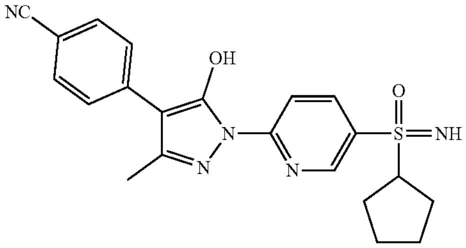 [SMILES: Cc1nn(-c2ccc(S(=N)(=O)C3CCCC3)cn2)c(O)c1-c1ccc(C#N)cc1] |
| 36 | 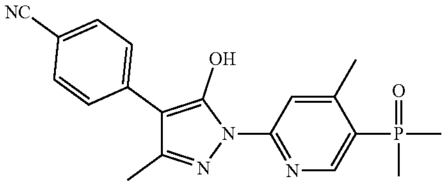 [SMILES: Cc1cc(-n2nc(C)c(-c3ccc(C#N)cc3)c2O)ncc1P(C)(C)=O] |
| 37 | 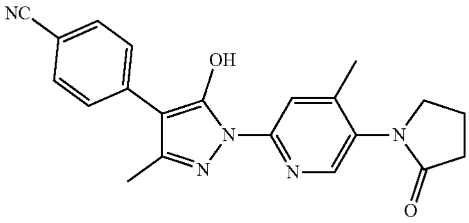 [SMILES: Cc1cc(-n2nc(C)c(-c3ccc(C#N)cc3)c2O)ncc1N1CCCC1=O] |
| 38 | 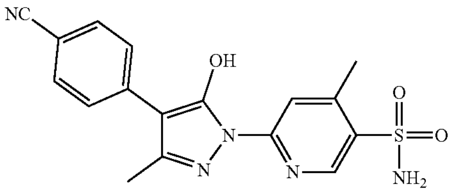 [SMILES: Cc1cc(-n2nc(C)c(-c3ccc(C#N)cc3)c2O)ncc1S(N)(=O)=O] |
| 39 | 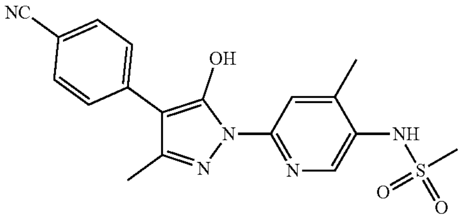 [SMILES: Cc1cc(-n2nc(C)c(-c3ccc(C#N)cc3)c2O)ncc1NS(C)(=O)=O] |
| 40 | 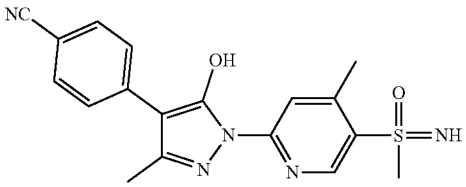 [SMILES: Cc1cc(-n2nc(C)c(-c3ccc(C#N)cc3)c2O)ncc1S(C)(=N)=O] |
| 41 | 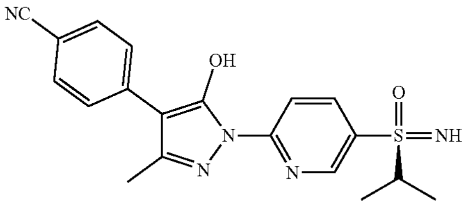 |

-continued
| Cmpd No. | Structure |
|---|---|
| 42 | 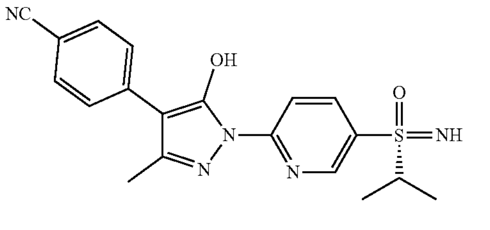 |
| 43 | 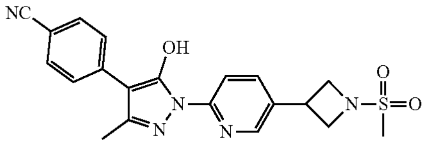 [SMILES: Cc1nn(-c2ccc(C3CN(S(C)(=O)=O)C3)cn2)c(O)c1-c1ccc(C#N)cc1] |
| 44 | 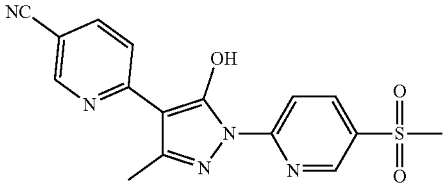 |
| 45 | 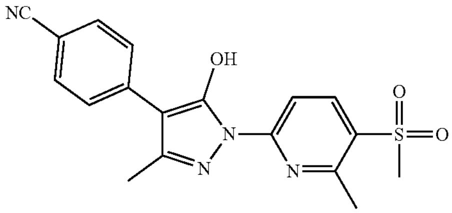 [SMILES: Cc1nc(-n2nc(C)c(-c3ccc(C#N)cc3)c2O)ccc1S(C)(=O)=O] |
| 46 | 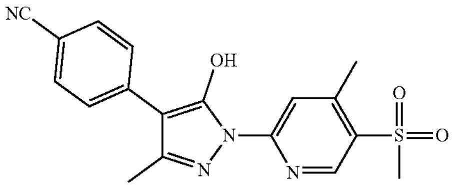 [SMILES: Cc1cc(-n2nc(C)c(-c3ccc(C#N)cc3)c2O)ncc1S(C)(=O)=O] |
| 47 | 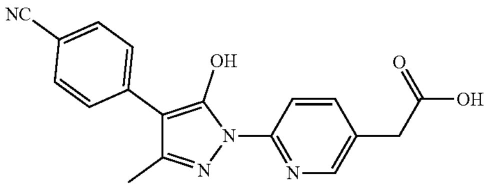 [SMILES: Cc1nn(-c2ccc(CC(=O)O)cn2)c(O)c1-c1ccc(C#N)cc1] |
| 48 | 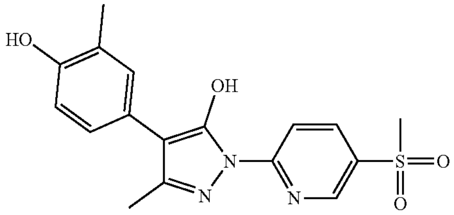 [SMILES: Cc1cc(-c2c(C)nn(-c3ccc(S(C)(=O)=O)cn3)c2O)ccc1O] |
-continued
| Cmpd No. | Structure |
|---|---|
| 49 | 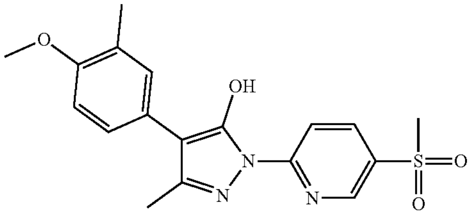 [SMILES: COc1ccc(-c2c(C)nn(-c3ccc(S(C)(=O)=O)cn3)c2O)cc1C] |
| 50 | 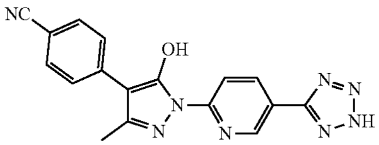 [SMILES: Cc1nn(-c2ccc(-c3nn[nH]n3)cn2)c(O)c1-c1ccc(C#N)cc1] |
| 51 | 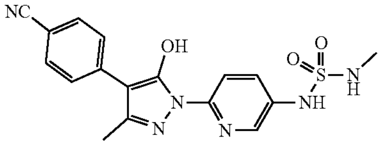 [SMILES: CNS(=O)(=O)Nc1ccc(-n2nc(C)c(-c3ccc(C#N)cc3)c2O)nc1] |
| 52 | 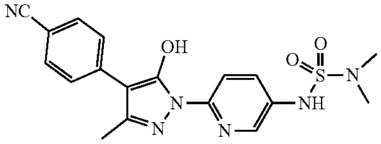 [SMILES: Cc1nn(-c2ccc(NS(=O)(=O)N(C)C)cn2)c(O)c1-c1ccc(C#N)cc1] |
| 53 | 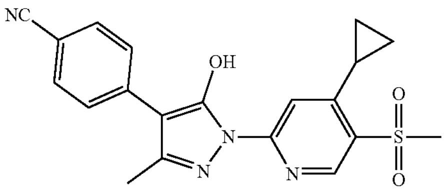 [SMILES: Cc1nn(-c2cc(C3CC3)c(S(C)(=O)=O)cn2)c(O)c1-c1ccc(C#N)cc1] |
| 54 | 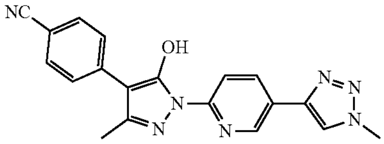 [SMILES: Cc1nn(-c2ccc(-c3cn(C)nn3)cn2)c(O)c1-c1ccc(C#N)cc1] |
| 55 | 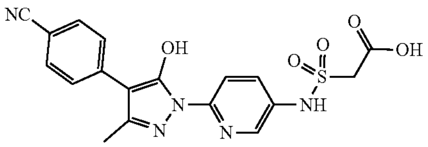 [SMILES: Cc1nn(-c2ccc(NS(=O)(=O)CC(=O)O)cn2)c(O)c1-c1ccc(C#N)cc1] |
| 56 | 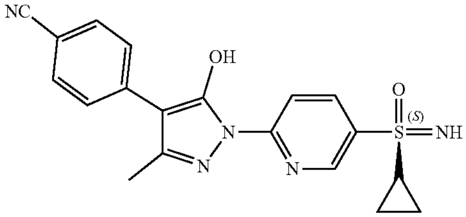 |

-continued
| Cmpd No. | Structure |
| --- | --- |
| 57 | 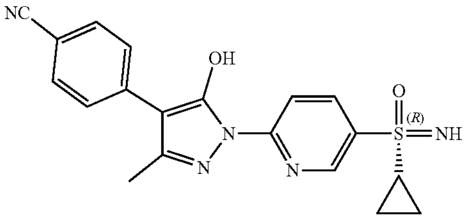 |
| 58 | 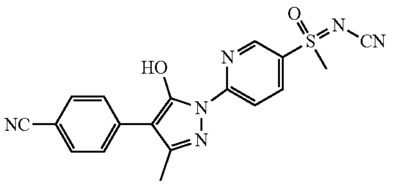 [SMILES: Cc1nn(-c2ccc(S(C)(=O)=NC#N)cn2)c(O)c1-c1ccc(C#N)cc1] |
| 59 | 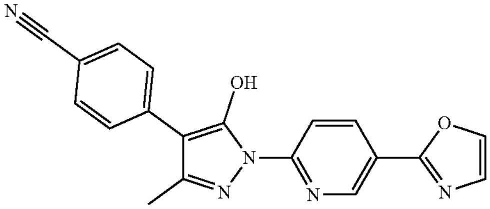 |
| 60 | 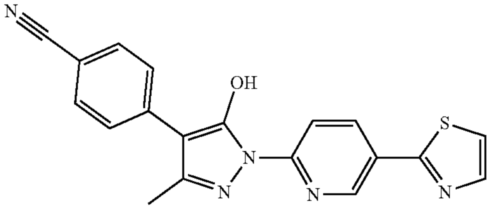 |
| 61 | 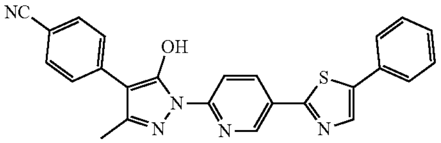 [SMILES: Cc1nn(-c2ccc(-c3ncc(-c4ccccc4)s3)cn2)c(O)c1-c1ccc(C#N)cc1] |
| 62 | 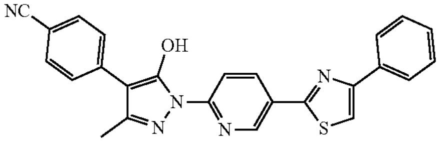 [SMILES: Cc1nn(-c2ccc(-c3nc(-c4ccccc4)cs3)cn2)c(O)c1-c1ccc(C#N)cc1] |
| 63 | 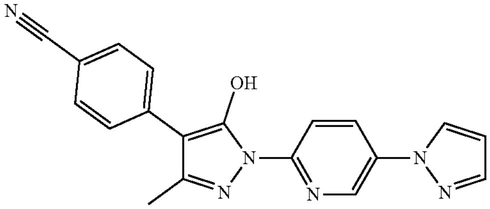 [SMILES: Cc1nn(-c2ccc(-n3cccn3)cn2)c(O)c1-c1ccc(C#N)cc1] |
| 64 | 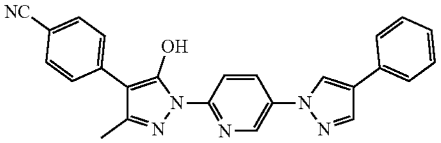 |
| 65 | 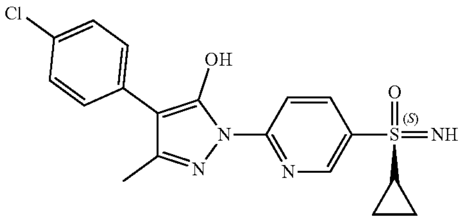 |
| 66 | 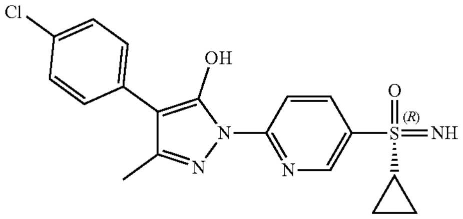 |
| 67 | 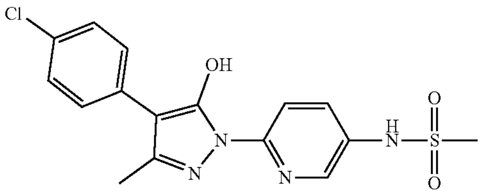 [SMILES: Cc1nn(-c2ccc(NS(C)(=O)=O)cn2)c(O)c1-c1ccc(Cl)cc1] |
| 68 | 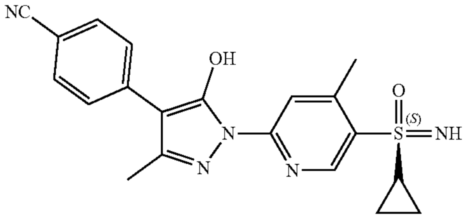 |
| 69 | 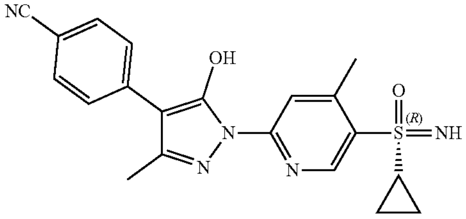 |
| 70 | 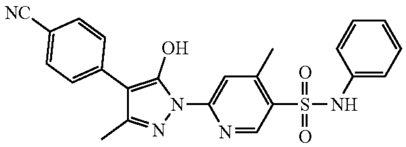 [SMILES: Cc1cc(-n2nc(C)c(-c3ccc(C#N)cc3)c2O)ncc1S(=O)(=O)Nc1ccccc1] |
| 71 | 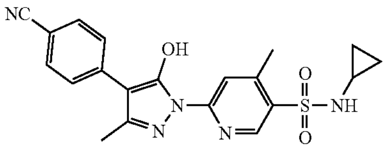 [SMILES: Cc1cc(-n2nc(C)c(-c3ccc(C#N)cc3)c2O)ncc1S(=O)(=O)NC1CC1] |
| 72 | 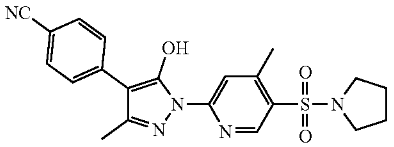 [SMILES: Cc1cc(-n2nc(C)c(-c3ccc(C#N)cc3)c2O)ncc1S(=O)(=O)N1CCCC1] |

-continued

| Cmpd No. | Structure |
|---|---|
| 73 | 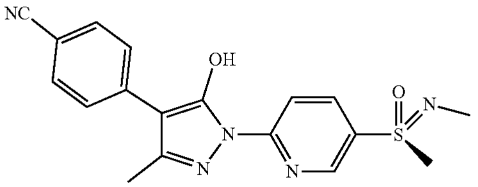 [SMILES: CN=[S@@](C)(=O)c1ccc(-n2nc(C)c(-c3ccc(C#N)cc3)c2O)nc1] |
| 74 | 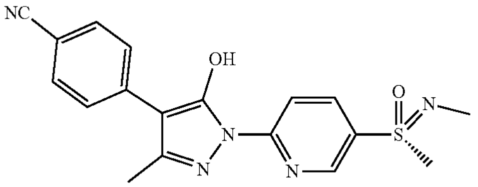 [SMILES: CN=[S@](C)(=O)c1ccc(-n2nc(C)c(-c3ccc(C#N)cc3)c2O)nc1] |
| 75 | 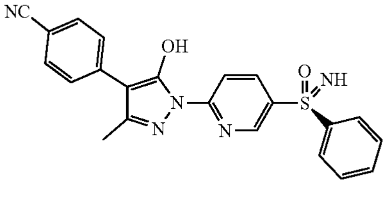 [SMILES: Cc1nn(-c2ccc([S@@](=N)(=O)c3ccccc3)cn2)c(O)c1-c1ccc(C#N)cc1] |
| 76 | 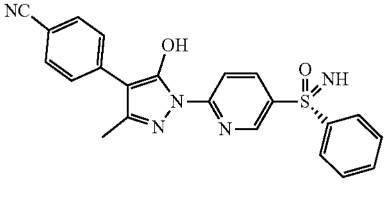 [SMILES: Cc1nn(-c2ccc([S@](=N)(=O)c3ccccc3)cn2)c(O)c1-c1ccc(C#N)cc1] |
| 77 | 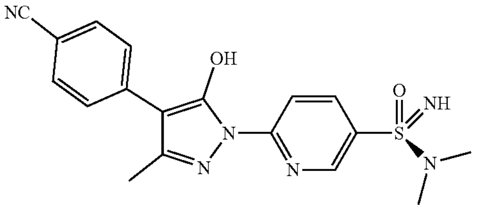 |
| 78 | 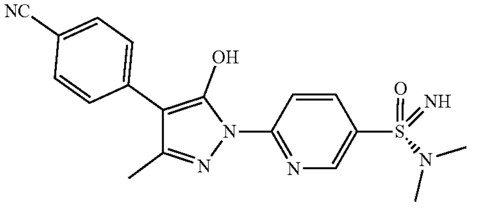 |
| 79 | 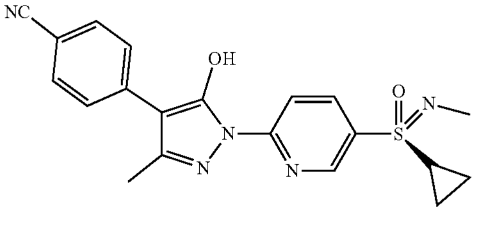 [SMILES: CN=[S@@](=O)(c1ccc(-n2nc(C)c(-c3ccc(C#N)cc3)c2O)nc1)C1CC1] |

-continued

| Cmpd No. | Structure |
|---|---|
| 80 | 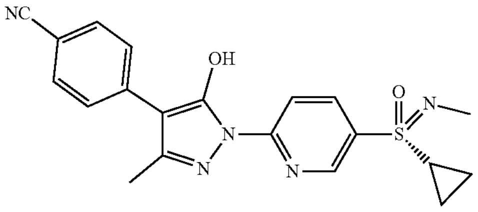 [SMILES: CN=[S@](=O)(c1ccc(-n2nc(C)c(-c3ccc(C#N)cc3)c2O)nc1)C1CC1] |
| 81 | 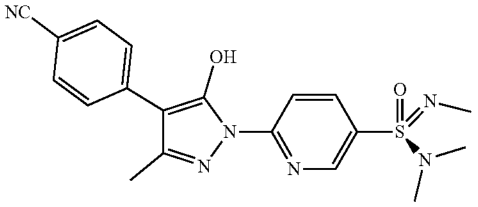 |
| 82 | 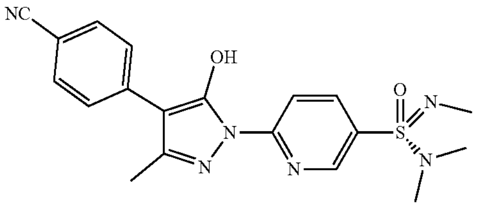 |
| 83 | 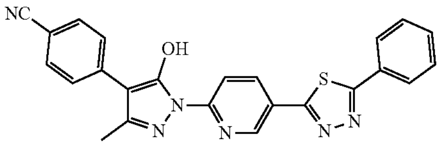 [SMILES: Cc1nn(-c2ccc(-c3nnc(-c4ccccc4)s3)cn2)c(O)c1-c1ccc(C#N)cc1] |

Isotopologues

It should be understood that in the compounds described herein (e.g., a compound of any one of Formulas (A) and (I)-(XIII) such as any one of compounds 1-83), the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of the compounds described herein (e.g., a compound of any one of Formulas (A) and (I)-(XIII) such as any one of compounds 1-83). For example, different isotopic forms of hydrogen (H) include protium ($^1$H), deuterium ($^2$H), and tritium ($^3$H). Protium is the predominant hydrogen isotope found in nature.

In some embodiments, one or more of the hydrogens of the compounds described herein (e.g., a compound of any one of Formulas (A) and (I)-(XIII) such as any one of compounds 1-83) is replaced by a deuterium. Enriching for deuterium may afford certain therapeutic advantages, such as increasing in vivo half-life or reducing dosage requirements, or may provide a compound useful as a standard for characterization of biological samples. In some embodiments, one or more of the hydrogens of the compounds described herein (e.g., a compound of any one of Formulas (A) and (I)-(XIII) such as any one of compounds 1-83) is replaced by tritium. Tritium is radioactive and may therefore provide for a radiolabeled compound, useful as a tracer in metabolic or kinetic studies.

Isotopic-enrichment of compounds disclosed herein (e.g., a compound of any one of Formulas (A) and (I)-(XIII) such as any one of compounds 1-83), may be achieved without undue experimentation by conventional techniques well known to those skilled in the art or by processes analogous to those described in the Schemes and Examples herein using appropriate isotopically-enriched reagents and/or intermediates.

The term "isotopologue" refers to a species that has the same chemical structure and formula as a specific compound provided herein, with the exception of the positions of isotopic substitution and/or level of isotopic enrichment at one or more positions, e.g., hydrogen vs. deuterium. Thus, the term "compound," as used herein, encompasses a collection of molecules having identical chemical structure, but also having isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound provided depends upon a number of factors including, but not limited to, the isotopic purity of deuterated reagents used to make the compound and the efficiency of incorporation of deuterium in the various synthesis steps used to prepare the compound.

When a position is designated as "H" or "hydrogen", the position is understood to have hydrogen at its natural abundance isotopic composition. When a position is designated as "D" or "deuterium", the position is understood to have deuterium at an abundance that is at least 3340 times greater than the natural abundance of deuterium, which is 0.015% (i.e., the term "D" or "deuterium" indicates at least 50.1% incorporation of deuterium).

In embodiments, a compound provided herein may have an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Synthesis of Compounds of the Inventions

The compounds described herein (e.g., a compound of any one of Formulas (A) and (I)-(XIII) such as any one of compounds 1-83) can be prepared according to methods known in the art, including the exemplary syntheses of the Examples provided herein.

Abbreviations and acronyms used herein including the following:

| Term | Acronym |
|---|---|
| 4-Dimethylaminopyridine | DMAP |
| Acetyl | Ac |
| Aqueous | aq. |
| Benzyl | Bn |
| tert-Butyloxycarbonyl | Boc |
| Broad singlet | brs |
| Dichloromethane | DCM |
| Dimethylsulfoxide | DMSO |
| Doublet | d |

-continued

| Term | Acronym |
|---|---|
| Electrospray ionization | ESI |
| Equivalent | eq |
| Ethyl acetate | EtOAc |
| Gram | g |
| Hexanes | Hex |
| High performance liquid chromatography | HPLC |
| Hour | hr |
| Isopropyl | i-Pr |
| Liquid chromatography-mass spectrometry | LCMS |
| Megahertz | MHz |
| meta-Chloroperoxybenzoic acid | m-CPBA |
| Methanol | MeOH |
| Milligram | mg |
| Milliliter | mL |
| Minute | min |
| Molarity | M |
| Multiplet | m |
| N,N-Diisopropylethylamine | DIPEA |
| N,N-Dimethylformamide | DMF |
| N,N-dimethylformamide dimethyl acetal | DMF-DMA |
| Normal | N |
| Nuclear magnetic resonance | NMR |
| Palladium on carbon | Pd/C |
| Pentet | P |
| Petroleum ether | PE |
| Phenyl | Ph |
| Quartet | q |
| Room temperature | RT |
| Singlet | s |
| Tetrahydrofuran | THF |
| Thin layer chromatography | TLC |
| Triethylamine | TEA |
| Trifluoroacetic acid | TFA |
| Triplet | t |

Compositions and Methods

The invention provides for use of a compound of any one of Formulas (A) and (I)-(XIII), or a pharmaceutically acceptable salt thereof, for the manufacture of a medicament for use in treating various conditions or disorders as described herein. In one embodiment, a pharmaceutical composition is provided comprising at least one compound of any one of Formulas (A) and (I)-(XIII), or a pharmaceutically acceptable salt thereof, and a pharmaceutically acceptable excipient or carrier. In various embodiments, the medicament or pharmaceutical composition can further comprise or be used in combination with at least one additional therapeutic agent.

The compounds of the present invention, or medicaments or compositions comprising the compounds, can be used to inhibit the activity of PHD. Inhibition of PHD may be of particular benefit in treating diseases including heart (e.g. ischemic heart disease, congestive heart failure, and valvular heart disease), lung (e.g., acute lung injury, pulmonary hypertension, pulmonary fibrosis, and chronic obstructive pulmonary disease), liver (e.g. acute liver failure and liver fibrosis and cirrhosis), and kidney (e.g. acute kidney injury and chronic kidney disease) disease.

In one embodiment, the method of the invention comprises administering to a patient in need a therapeutically effective amount of a compound of any one of Formulas (A) and (I)-(XIII), or a pharmaceutically acceptable salt thereof, or a pharmaceutical composition comprising one or more compounds of any one of Formulas (A) and (I)-(XIII).

The invention is also directed to a method of inhibiting the activity of PHD. In one embodiment, the method comprises contacting PHD with an effective amount of one or more compounds selected from the group comprising compounds of any one of Formulas (A) and (I)-(XIII), or a pharmaceutically acceptable salt thereof.

In still other embodiments, the compounds disclosed herein (e.g., a compound of any one of Formulas (A) and (I)-(XIII) such as any one of compounds 1-83), or a pharmaceutically acceptable salt thereof, are useful for the treatment or prevention of anemia comprising treatment of anemic conditions associated with chronic kidney disease, polycystic kidney disease, aplastic anemia, autoimmune hemolytic anemia, bone marrow transplantation anemia, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, refractory anemia with excess of blasts, rheumatoid arthritis, Shwachman syndrome, sickle cell disease, thalassemia major, thalassemia minor, thrombocytopenic purpura, anemic or non-anemic patients undergoing surgery, anemia associated with or secondary to trauma, sideroblastic anemia, anemic secondary to other treatment including: reverse transcriptase inhibitors to treat HIV, corticosteroid hormones, cyclic cisplatin or non-cisplatin-containing chemotherapeutics, vinca alkaloids, mitotic inhibitors, topoisomerase II inhibitors, anthracyclines, alkylating agents, particularly anemia secondary to inflammatory, aging and/or chronic diseases. PHD1 inhibition may also be used to treat symptoms of anemia including chronic fatigue, pallor, and dizziness.

In other embodiments, the compounds disclosed herein (e.g., a compound of Formulas (A) and (I)-(XIII) such as any one of compounds 1-83), or a pharmaceutically acceptable salt thereof, are useful for the treatment or prevention of diseases of metabolic disorders, including but not limited to diabetes and obesity.

In yet other embodiments, the compounds disclosed herein (e.g., a compound of Formulas (A) and (I)-(XIII) such as any one of compounds 1-83), or a pharmaceutically acceptable salt thereof, are useful for the treatment or prevention of vascular disorders. These include but are not limited to hypoxic or wound healing related diseases requiring pro-angiogenic mediators for vasculogenesis, angiogenesis, and arteriogenesis.

In still other embodiments, the compounds disclosed herein (e.g., a compound of Formulas (A) and (I)-(XIII) such as any one of compounds 1-83), or a pharmaceutically acceptable salt thereof, are useful for the treatment or prevention of ischemia reperfusion injury. These include but are not limited to stroke, myocardial infarction, and acute kidney injury).

In other embodiments, the compounds disclosed herein (e.g., a compound of Formulas (A) and (I)-(XIII) such as any one of compounds 1-83), or a pharmaceutically acceptable salt thereof, are useful in the treatment of inflammatory bowel disease. These include but are not limited to ulcerative colitis, and Crohn's disease.

In other embodiments, the compounds disclosed herein (e.g., a compound of Formulas (A) and (I)-(XIII) such as any one of compounds 1-83), or a pharmaceutically acceptable salt thereof, are useful in the treatment of cancers, such as colorectal cancer.

In other embodiments, the compounds disclosed herein (e.g., a compound of Formulas (A) and (I)-(XIII) such as any one of compounds 1-83), or a pharmaceutically acceptable salt thereof, are useful in the treatment of atherosclerosis.

In other embodiments, the compounds disclosed herein (e.g., a compound of Formulas (A) and (I)-(XIII) such as any one of compounds 1-83), or a pharmaceutically acceptable salt thereof, are useful in the treatment of cardiovascular disease.

In other embodiments, the compounds disclosed herein (e.g., a compound of Formulas (A) and (I)-(XIII) such as any one of compounds 1-83), or a pharmaceutically acceptable salt thereof, are useful in the treatment of a disease or condition of the eye. These include but are not limited to radiation retinopathy, retinopathy of prematurity, diabetic retinopathy, age-related macular degeneration, and ocular ischemia.

In other embodiments, the compounds disclosed herein (e.g., a compound of Formulas (A) and (I)-(XIII) such as any one of compounds 1-83), or a pharmaceutically acceptable salt thereof, are useful in the treatment of a disease that is associated with hyperoxia.

In other embodiments, the compounds disclosed herein (e.g., a compound of Formulas (A) and (I)-(XIII) such as any one of compounds 1-83), or a pharmaceutically acceptable salt thereof, are useful in the treatment of bronchopulmonary dysplasia (BPD).

In yet other embodiments, the compounds disclosed herein (e.g., a compound of Formulas (A) and (I)-(XIII) such as any one of compounds 1-83), or a pharmaceutically acceptable salt thereof, are useful in the treatment of heart diseases. The conditions include but are not limited to postoperative myocardial ischemia in pancreatic surgery, myocardial injury after percutaneous coronary intervention (PCI), myocardial injury after non-cardiac surgery, perioperative myocardial ischemia in elective operation of abdominal aortic aneurysm, myocardial injury after PCI, myocardial damage in patients undergoing coronary artery bypass graft (CABG) surgery, minimally invasive mitral valve (MIMV) repair or replacement, adult patient undergoing open heart surgery, chronic heart failure, NYHA class II-IV.

In other embodiments, the compounds disclosed herein (e.g., a compound of Formulas (A) and (I)-(XIII) such as any one of compounds 1-83), or a pharmaceutically acceptable salt thereof, are useful in the treatment of lung diseases. The conditions include but are not limited to lung injury during elective lung lobectomy, lung injury during CABG surgery, lung transplantation.

In other embodiments, the compounds disclosed herein (e.g., a compound of Formulas (A) and (I)-(XIII) such as any one of compounds 1-83), or a pharmaceutically acceptable salt thereof, are useful in the treatment of liver disease. The conditions include but are not limited to non-alcoholic steatohepatitis (NASH).

In other embodiments, the compounds disclosed herein (e.g., a compound of Formulas (A) and (I)-(XIII) such as any one of compounds 1-83), or a pharmaceutically acceptable salt thereof, are useful in the treatment of kidney disease. The conditions include but are not limited to contrast-induced acute kidney injury, stage III-IV chronic kidney disease undergoing planned coronary angiography, acute kidney injury in patients undergoing valvular heart surgery, non-dialysis dependent chronic kidney disease, chronic kidney disease patients initiating dialysis, non-dialysis dependent chronic kidney disease.

In addition, the compounds disclosed herein (e.g., a compound of any one of Formulas (A) and (I)-(XIII) such as any one of compounds 1-83), or a pharmaceutically acceptable salt thereof, may be used in combination with additional active ingredients in the treatment of the above conditions. The additional compounds may be co-administered separately with the compounds disclosed herein (e.g., a compound of any one of Formulas (A) and (I)-(XIII) such as any one of compounds 1-83), or a pharmaceutically acceptable salt thereof, or included with an additional active ingredient in a pharmaceutical composition according to the invention. In an exemplary embodiment, additional active ingredients are those that are known or discovered to be effective in the treatment of conditions, disorders, or diseases mediated by PHD enzyme or that are active against another targets associated with the particular condition, disorder, or disease, such as an alternate PHD modulator. The combination may serve to increase efficacy (e.g., by including in the combination a compound potentiating the potency or effectiveness of a compound according to the invention), decrease one or more side effects, or decrease the required dose of the compound according to the invention.

The compounds of the invention are used, alone or in combination with one or more other active ingredients, to formulate pharmaceutical compositions of the invention. A pharmaceutical composition of the invention comprises: (a) an effective amount of the compounds disclosed herein (e.g., a compound of any one of Formulas (A) and (I)-(XIII) such as any one of compounds 1-83), or a pharmaceutically acceptable salt, pharmaceutically acceptable prodrug, or pharmaceutically active metabolite thereof, and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable excipients may also include antioxidants. Such antioxidants may be used in a pharmaceutical composition or in a storage medium to prolong the shelf-life of the drug product.

Pharmaceutical Formulations and Routes of Administration

The compounds and compositions of the present invention can be delivered directly or in pharmaceutical compositions or medicaments along with suitable carriers or excipients, as is well known in the art. Present methods of treatment can comprise administration of an effective amount of a compound of the invention to a subject in need. In a preferred embodiment, the subject is a mammalian subject, and in a most preferred embodiment, the subject is a human subject.

An effective amount of such compound, composition, or medicament can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. See, e.g., the U.S. Pharmacopeia (USP), Japanese Pharmacopoeia (JP), European Pharmacopoeia (EP), and British pharmacopeia (BP); the U.S. Food and Drug.

Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott NY; etc.) [0149] Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc., talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compounds and compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays. In certain some embodiments, a compound of the disclosure is formulated for oral administration. An exemplary dose of a compound of the disclosure in a pharmaceutical formulation for oral administration is from about 0.5 to about 10 mg/kg body weight of subject. In some embodiments, a pharmaceutical formulation comprises from about 0.7 to about 5.0 mg/kg body weight of subject, or alternatively, from about 1.0 to about 2.5 mg/kg body weight of subject. A typical dosing regimen for oral administration would be administration of the pharmaceutical formulation for oral administration three times per week, two times per week, once per week or daily.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compounds and compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXEMPLIFICATION

Purity Determination with HPLC

Purity of the compounds and their synthetic intermediates were determined with reverse phase HPLC using either one of the methods described below:

Method A: Mobile Phase: A: Water (0.01% TFA) B: Acetonitrile (0.01% TFA); Gradient Phase: 5% B increase to 95% B within 1.4 min, 95% B with 1.6 min (total run time: 3 min); Flow Rate: 2.3 mL/min. Column: SunFire C18, 4.6*50 mm, 3.5 μm; Column Temperature: 50° C. Detectors: ADC ELSD, DAD (214 nm and 254 nm), ES-API.

Method B: Mobile Phase: A: Water (10 mM NH4HCO3) B: Acetonitrile; Gradient Phase: 5% to 95% B within 1.5 min, 95% B with 1.5 min (total run time: 3 min); Flow Rate: 2.0 mL/min; Column: XBridge C18, 4.6*50 mm, 3.5 um; Column Temperature: 40° C. Detectors: ADC ELSD, DAD (214 nm and 254 nm), MSD (ES-API).

Synthesis for Exemplary Compounds

Example 1: Preparation of Compound 1 ethyl 2-(4-chlorophenyl)-3-oxobutanoate

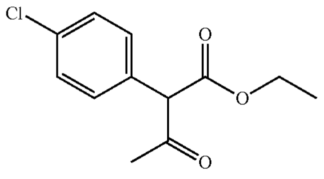 [SMILES: CCOC(=O)C(C(C)=O)c1ccc(Cl)cc1]

To a solution of ethyl 2-(4-chlorophenyl)acetate (1.98 g, 10.0 mmol) in anhydrous tetrahydrofuran (15.0 mL) was added lithium bis(trimethylsilyl)amide (25.0 mL, 25.0 mmol, 1.0 M in tetrahydrofuran) at −78° C. under nitrogen. The mixture was stirred at −78° C. for 10 min and acetyl chloride (1.17 g, 15.0 mmol) in anhydrous tetrahydrofuran (5.0 mL) was added. The mixture was allowed to warm up to 0° C. and stirred for another one hour. The reaction was quenched with water and extracted twice with ethyl acetate. The organic layer was separated, washed with brine, dried over sodium sulfate and concentrated under reduced pressure. The crude product was purified by flash chromatography (petroleum ether/ethyl acetate=10/1) to obtain ethyl 2-(4-chlorophenyl)-3-oxobutanoate (800 mg, 3.3 mmol, 33.3% yield) as yellow solid. LCMS: m/z=241.1 $(M+H)^+$, retention time 2.12 min (Method A).

2-bromo-5-(methylsulfonyl)pyridine

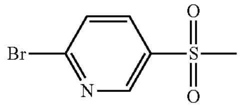

To a solution of 3,6-dibromopyridine (2.5 g, 12.7 mmol) in anhydrous tetrahydrofuran (10.0 mL) was added isopropylmagnesium chloride (8.25 mL, 16.5 mmol, 2.0 M in hexane) at 0° C. under nitrogen. The mixture was stirred at 0° C. for 45 min and then a solution of methanesulfonyl chloride (1.89 g, 16.5 mmol) in anhydrous tetrahydrofuran (5.0 mL) was added. The mixture was allowed to warm up to room temperature and left stirring for another one hour. The reaction was quenched with water and extracted twice with ethyl acetate. The organic layer was separated, washed with brine, dried over sodium sulfate and concentrated under reduced pressure. The crude product was purified by flash chromatography (petroleum ether/ethyl acetate=3/1) to obtain 2-bromo-5-(methylsulfonyl)pyridine (1.4 g, 5.98 mmol, 47.1% yield) as yellow solid. LC-MS: m/z=236.0 $(M+H)^+$, retention time 1.54 min (Method A).

2-hydrazinyl-5-(methylsulfonyl)pyridine

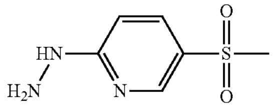

To a solution of 2-bromo-5-(methanesulfonyl)-pyridine (1.0 g, 4.25 mmol) in ethanol (10.0 mL) was added hydrazine hydrate (1.0 g, 17.0 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford 2-hydrazinyl-5-(methylsulfonyl)pyridine (1.2 g, 6.4 mmol, 75% yield) as white solid. LC-MS: m/z=188.0 (M+H)+, retention time 0.43 min (Method A).

4-(4-chlorophenyl)-3-methyl-1-(5-(methylsulfonyl)pyridin-2-yl)-1H-pyrazol-5-ol

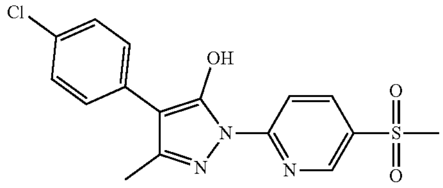 [SMILES: Cc1nn(-c2ccc(S(C)(=O)=O)cn2)c(O)c1-c1ccc(Cl)cc1]

To a solution of ethyl 2-(4-chlorophenyl)-3-oxobutanoate (0.24 g, 1.0 mmol) and 2-hydrazinyl-5-(methylsulfonyl)pyridine (0.20 g, 1.0 mmol) in ethanol (3.0 mL) was added p-toluenesulfonic acid monohydrate (0.19 g, 1.0 mmol). The mixture was stirred at reflux for 12 hr and cooled. The insoluble solid was filtered and the filtrate was concentrated to dryness. The residue was purified by reverse prep-HPLC to provide 4-(4-chlorophenyl)-3-methyl-1-(5-(methylsulfonyl)pyridin-2-yl)-1H-pyrazol-5-ol (45 mg, 0.12 mmol, 12.3% yield) as white solid. LCMS: m/z=364.0 $[M+H]^+$, retention time 4.49 min (Method A). $^1H$ NMR (400 MHz, DMSO-$d_6$) δ 12.81 (s, 1H), 8.91 (s, 1H), 8.72 (m, 1H), 8.43-8.46 (d, J=7.5 Hz, 1H), 7.65-7.67 (d, J=7.5 Hz, 1H), 7.44-7.49 (m, 2H), 3.25 (s, 3H), 2.54 (s, 3H).

Example 2: Preparation of Compound 2 ethyl 2-(4-cyano-2-methylphenyl) acetate

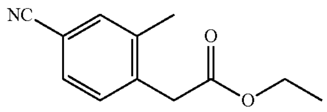

A mixture of 4-bromo-3-methylbenzonitrile (5.0 g, 25.6 mmol), tris(dibenzylidene acetone)dipalladium(0) (0.24 g, 0.26 mmol), tri-tert-butylphosphine tetrafluoroborate (0.08 g, 0.26 mmol), potassium carbonate (5.3 g, 38.4 mmol) and potassium hydrogen carbonate (3.84 g, 38.4 mmol) in diethyl malonate (27 g 168 mmol) was stirred at 160° C. for 12 h. The mixture was cooled and concentrated to dryness. The residue was partitioned with ethyl acetate and water. The organic layer was washed with brine, dried over sodium sulfate and concentrated. The crude product was purified by flash chromatography (petroleum ether/ethyl acetate=1/1) to afford ethyl 2-(4-cyano-2-methylphenyl)acetate (2.0 g, 8.11 mmol, 31.7% yield) as yellow oil. LCMS: m/z=204.1 $(M+H)^+$, retention time 1.87 min (Method A).

ethyl 2-(4-cyano-2-methylphenyl)-3-oxobutanoate

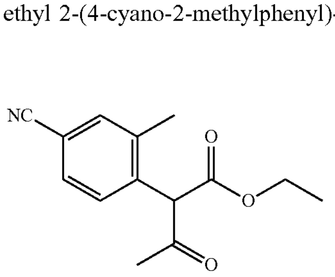

To a solution of ethyl 2-(4-cyano-2-methylphenyl)acetate (0.2 g, 1.0 mmol) in anhydrous tetrahydrofuran (10.0 mL) was added lithium bis(trimethylsilyl)amide (2.5 mL, 2.5 mmol, 1.0 M in tetrahydrofuran) at −78° C. under nitrogen. The mixture was stirred at −78° C. for 10 min and acetyl chloride (0.11 g, 1.5 mmol) in anhydrous tetrahydrofuran (2.0 mL) was added. The mixture was allowed to warm up to 0° C. and left stirring for another one hour. The reaction was quenched with water and extracted twice with ethyl acetate. The organic layer was separated, washed with brine, dried over sodium sulfate and concentrated under reduced pressure. The crude product was purified by flash chromatography (petroleum ether/ethyl acetate=10/1) to obtain ethyl 2-(4-cyano-2-methylphenyl)-3-oxobutanoate (0.1 g, 0.4 mmol, 40% yield) as white solid. LCMS: m/z=246.1 $(M+H)^+$, retention time 2.11 min (Method A).

4-(5-hydroxy-3-methyl-1-(5-(methylsulfonyl)pyridin-2-yl)-1H-pyrazol-4-yl)-3-methylbenzonitrile

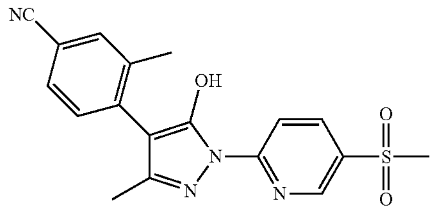 [SMILES: Cc1cc(C#N)ccc1-c1c(C)nn(-c2ccc(S(C)(=O)=O)cn2)c1O]

To a solution of 2-hydrazineyl-5-(methylsulfonyl)pyridine (0.18 g, 1.0 mmol) and ethyl 2-(4-cyano-2-methylphenyl)-3-oxobutanoate (0.25 g, 1.0 mmol) in ethanol (3.0 mL) was added p-toluenesulfonic acid monohydrate (38 mg, 0.2 mmol). The mixture was stirred at reflux for 12 hr and cooled. The insoluble solid was filtered and the filtrate was concentrated to dryness. The residue was purified by reverse prep-HPLC to provide 4-(5-hydroxy-3-methyl-1-(5-(methylsulfonyl)pyridin-2-yl)-1H-pyrazol-4-yl)-3-methylbenzonitrile (11.3 mg, 0.03 mmol, 1.98% yield) as white solid. LCMS: m/z=369.0 $[M+H]^+$, retention time 3.83 min (Method A). $^1H$ NMR (400 MHz, DMSO-$d_6$) δ 12.58 (s, 1H), 8.88 (s, 1H), 8.62-8.64 (d, J=8.5 Hz, 1H), 8.37-8.39 (d, J=8.5 Hz, 1H), 8.14 (s, 1H), 7.72 (s, 1H), 7.37-7.48 (d, J=8.5 Hz, 1H), 7.10-7.12 (d, J=7.5 Hz, 1H), 3.52 (s, 3H), 2.38 (s, 3H), 2.08 (s, 3H).

Example 3: Preparation of Compound 3 methyl 2-(4-cyanophenyl)acetate

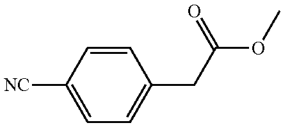

To a mixture of 2-(4-cyanophenyl)acetic acid (5.0 g, 31.0 mmol) in methanol (10.0 mL) was added hydrochloric acid in methanol (20.0 mL, 3.0 M) at 0° C. The mixture was stirred at 70° C. for 3.0 h and cooled to precipitate solid. The solid was filtered, washed with methanol and dried to give methyl 2-(4-cyanophenyl)acetate (5.0 g, 28.4 mmol, 92% yield) as yellow solid. LC-MS: m/z=176.0 $[M+H]^+$, retention time 1.54 min (Method A).

methyl 2-(4-cyanophenyl)-3-oxobutanoate

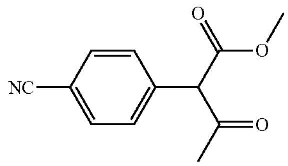 [SMILES: COC(=O)C(C(C)=O)c1ccc(C#N)cc1]

To a solution of methyl 2-(4-cyanophenyl)acetate (300 mg, 1.71 mmol) in anhydrous tetrahydrofuran (10.0 mL) was added lithium bis(trimethylsilyl)amide (4.29 mL, 4.29 mmol, 1.0 M in tetrahydrofuran) at −78° C. under nitrogen. The mixture was stirred at −78° C. for 10 min and acetyl chloride (200 mg, 2.57 mmol) in anhydrous tetrahydrofuran (2.0 mL) was added. The mixture was allowed to warm up to 0° C. and left stirring for another one hour. The reaction was quenched with water and extracted twice with ethyl acetate. The organic layer was washed with brine, dried over sodium sulfate and concentrated under reduced pressure. The crude product was purified by flash chromatography (petroleum ether/ethyl acetate=10/1) to obtain methyl 2-(4-cyanophenyl)-3-oxobutanoate (300 mg, 1.37 mmol, 80% yield) as yellow solid. LC-MS: m/z=218.1 $(M+H)^+$, retention time 2.08 min (Method A).

4-(5-hydroxy-3-methyl-1-(5-(methylsulfonyl)pyridin-2-yl)-1H-pyrazol-4-yl)benzonitrile

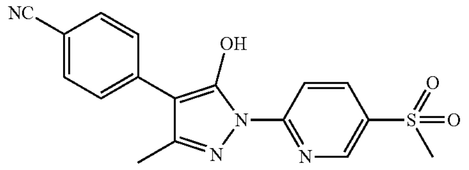 [SMILES: Cc1nn(-c2ccc(S(C)(=O)=O)cn2)c(O)c1-c1ccc(C#N)cc1]

To a suspension of methyl 2-(4-cyanophenyl)-3-oxobutanoate (0.26 g, 1.11 mmol) in acetic acid (10 ml) was added 2-hydrazinyl-5-(methylsulfonyl)pyridine (0.21 g, 1.11 mmol) in one portion. The suspension became a clear solution after the reaction was stirred at 110° C. for 2 h. After the reaction was completed by TLC analysis, the reaction was quenched with ice water (100 mL) and a large amount of solid was precipitated. After filtration, the solid was slurried in methanol (2 mL), filtered to give the desired product (35 mg) as solid. LCMS (ESI+): m/z 355 $(M+H^+)$; 1H NMR (300 MHz, DMSO-d6) δ 8.90 (d, J=1.5 Hz, 1H), 8.66 (d, J=8.7 Hz, 1H), 8.44 (dd, J=9.0 Hz, 2.1 Hz, 1H), 7.88 (d, J=8.4 Hz, 2H), 7.80 (d, J=8.4 Hz, 2H), 3.32 (s, 3H), 2.48 (s, 3H).

Example 4: Preparation of Compound 4 methyl 2-(4-cyanophenyl)-3-oxopentanoate

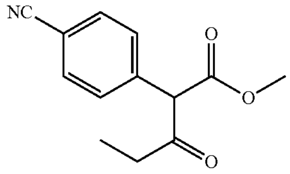 [SMILES: CCC(=O)C(C(=O)OC)c1ccc(C#N)cc1]

To a solution of methyl 2-(4-cyanophenyl)acetate (300 mg, 1.71 mmol) in anhydrous tetrahydrofuran (10.0 mL) was added lithium bis(trimethylsilyl)amide (4.29 mL, 4.29 mmol, 1.0 M in tetrahydrofuran) at −78° C. under nitrogen. The mixture was stirred at −78° C. for 10 min and propionyl chloride (236.5 mg, 2.57 mmol) in anhydrous tetrahydrofuran (2.0 mL) was added. The mixture was allowed to warm up to 0° C. and left stirring for another one hour. The reaction was quenched with water and extracted twice with ethyl acetate. The organic layer was separated, washed with brine, dried over sodium sulfate and concentrated under reduced pressure. The crude product was purified by flash chromatography (petroleum ether/ethyl acetate=10/1) to obtain methyl 2-(4-cyanophenyl)-3-oxopentanoate (300 mg, 1.29 mmol, 75.9% yield) as yellow solid. LCMS: m/z=232.1 $(M+H)^+$, retention time 2.08 min (Method A).

4-(3-ethyl-5-hydroxy-1-(5-(methylsulfonyl)pyridin-2-yl)-1H-pyrazol-4-yl)benzonitrile

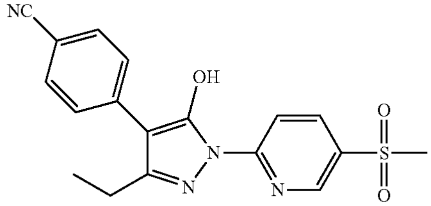 [SMILES: CCc1nn(-c2ccc(S(C)(=O)=O)cn2)c(O)c1-c1ccc(C#N)cc1]

To a solution of methyl 2-(4-cyanophenyl)-3-oxopentanoate (350.0 mg, 1.52 mmol) and 2-hydrazinyl-5-(methylsulfonyl)pyridine (283.3 mg, 1.52 mmol) in ethanol (5.0 mL) was added p-toluenesulfonic acid monohydrate (52.1 mg, 0.30 mmol). The mixture was stirred at reflux for 12 hr and cooled. The insoluble solid was filtered and the filtrate was concentrated to dryness. The residue was purified by reverse prep-HPLC to provide 4-(3-ethyl-5-hydroxy-1-(5-(methylsulfonyl)pyridin-2-yl)-1H-pyrazol-4-yl)benzonitrile (29.8 mg, 0.08 mmol, 5.33%) as white solid. LCMS: m/z=369.0 $[M+H]^+$, retention time 4.12 min (Method A). $^1H$ NMR (400 MHz, DMSO-$d_6$) δ 8.91 (d, J=1.2 Hz, 1H), 8.67 (d, J=4.4 Hz, 1H), 8.45-8.42 (m, 1H), 8.14 (s, 1H), 7.86-7.80 (m, 4H), 3.34 (s, 3H), 2.88-2.82 (m, 2H), 1.22 (t, J=7.2 Hz, 3H).

Example 5: Preparation of Compound 5 methyl 2-(4-cyanophenyl)-3-cyclopropyl-3-oxopropanoate

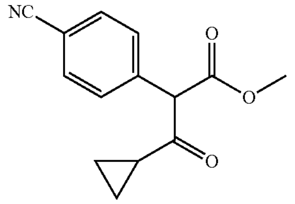 [SMILES: COC(=O)C(C(=O)C1CC1)c1ccc(C#N)cc1]

To a solution of methyl 2-(4-cyanophenyl)acetate (400 mg, 2.29 mmol) in anhydrous tetrahydrofuran (10.0 mL) was added lithium bis(trimethylsilyl)amide (5.71 mL, 5.71 mmol, 1.0 M in tetrahydrofuran)) at −78° C. under nitrogen. The mixture was stirred at −78° C. for 10 min and cyclopropanecarbonyl chloride (356.5 mg, 3.43 mmol) in anhydrous tetrahydrofuran (2.0 mL) was added. The mixture was allowed to warm up to 0° C. and stirred for another one hour. The reaction was quenched with water and extracted twice with ethyl acetate. The organic layer was separated, washed with brine, dried over sodium sulfate and concentrated under reduced pressure. The crude product was purified by flash chromatography (petroleum ether/ethyl acetate=10/1) to obtain methyl 2-(4-cyanophenyl)-3-cyclopropyl-3-oxopropanoate (500 mg, 2.04 mmol, 89.9% yield) as white solid. LCMS: m/z=244.1 $(M+H)^+$, retention time 2.12 min (Method A).

4-(3-cyclopropyl-5-hydroxy-1-(5-(methylsulfonyl) pyridin-2-yl)-1H-pyrazol-4-yl) benzonitrile

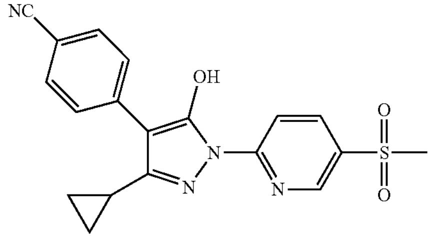 [SMILES: CS(=O)(=O)c1ccc(-n2nc(C3CC3)c(-c3ccc(C#N)cc3)c2O)nc1]

To a solution of 2-(4-cyanophenyl)-3-cyclopropyl-3-oxopropanoate (350.0 mg, 1.44 mmol) and 2-hydrazinyl-5-(methylsulfonyl)pyridine (269.34 mg, 1.44 mmol) in ethanol (5.0 mL) was added p-toluenesulfonic acid monohydrate (49.5 mg, 0.29 mmol). The mixture was stirred at reflux for 12 hr and cooled. The insoluble solid was filtered and the filtrate was concentrated to dryness. The residue was purified by reverse prep-HPLC to obtain 4-(3-cyclopropyl-5-hydroxy-1-(5-(methylsulfonyl)pyridin-2-yl)-1H-pyrazol-4-yl) benzonitrile (59.7 mg, 0.16 mmol, 10.9%) as white solid. LCMS: m/z=369.0 $[M+H]^+$, retention time 4.12 min (Method A). $^1H$ NMR (400 MHz, DMSO-$d_6$) δ 8.91 (d, J=1.2 Hz, 1H), 8.67 (d, J=4.4 Hz, 1H), 8.45-8.42 (m, 1H), 8.14 (s, 1H), 7.86-7.80 (m, 4H), 3.34 (s, 3H), 2.88-2.82 (m, 2H), 1.22 (t, J=7.2 Hz, 3H).

Example 6: Preparation of Compound 6

N-(6-fluoropyridin-3-yl)methanesulfonamide

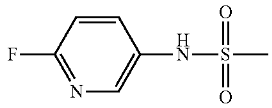

To a solution of 6-fluoropyridin-3-amine (500 mg, 4.46 mmol) in pyridine (5.0 mL) was added methanesulfonyl chloride (600 mg, 5.36 mmol) at 0° C. The mixture was allowed to warm up to room temperature and left stirring for another one hour. The reaction was diluted with water and extracted twice with ethyl acetate. The organic layer was washed with brine, dried over sodium sulfate and concentrated to give N-(6-fluoropyridin-3-yl) methanesulfonamide (420 mg, 2.20 mmol, 49.3% yield) as white solid. LCMS: m/z=191.1 $[M+H]^+$, retention time 1.32 min (Method A). The product was pure enough and used directly to the next step.

N-(6-hydrazineylpyridin-3-yl)methanesulfonamide

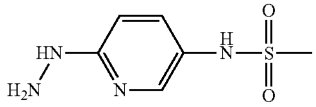

To a solution of N-(6-fluoropyridin-3-yl)methanesulfonamide (420 mg, 2.20 mmol) in ethanol (5.0 mL) was added hydrazine hydrate (5.0 mL, 85% in water). The mixture was stirred at 100° C. for 4 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford N-(6-hydrazineylpyridin-3-yl) ethanesulfonamide (210 mg, 1.03 mmol, 46.8% yield) as yellow solid. LCMS: m/z=203.0 $(M+H)^+$, retention time 0.34 min (Method A).

N-(6-(4-(4-cyanophenyl)-5-hydroxy-3-methyl-1H-pyrazol-1-yl)pyridin-3-yl) methanesulfonamide

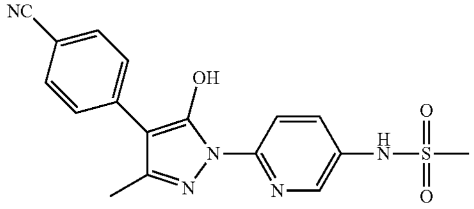 [SMILES: Cc1nn(-c2ccc(NS(C)(=O)=O)cn2)c(O)c1-c1ccc(C#N)cc1]

To a solution of methyl 2-(4-cyanophenyl)-3-oxobutanoate (217 mg, 1.0 mmol) and N-(6-hydrazineylpyridin-3-yl) methanesulfonamide (202 mg, 1.0 mmol) in ethanol (5.0 mL) was added p-toluenesulfonic acid monohydrate (38 mg, 0.2 mmol). The mixture was stirred at reflux for 12 hr and cooled to precipitate solid. The solid was purified by reverse prep-HPLC to give N-(6-(4-(4-cyanophenyl)-5-hydroxy-3-methyl-1H-pyrazol-1-yl) pyridin-3-yl)methanesulfonamid (11.3 mg, 0.03 mmol, 3.05% yield) as white solid. LCMS: m/z=370.0 $(M+H)^+$, retention time 4.75 min (Method A). $^1H$ NMR (400 MHz, DMSO-$d_6$) δ 12.85 (s, 1H), 9.91 (s, 1H), 8.31-8.38 (m, 2H), 8.15 (s, 1H), 7.90-7.493 (d, J=8.7 Hz, 1H), 7.76-7.81 (m, 3H), 3.05 (s, 3H), 2.45 (s, 3H).

Example 7: Preparation of Compound 7

1-(6-bromopyridin-3-yl)pyrrolidin-2-one

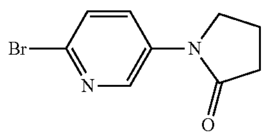 [SMILES: O=C1CCCN1c1ccc(Br)nc1]

A mixture of 2-bromo-5-iodopyridine (2.0 g, 7.07 mmol), pyrrolidin-2-one (3.0 g, 35.3 mmol), cuprous iodide (133 mg, 0.7 mmol), potassium phosphate (4.5 g, 21.2 mmol), ethylene glycol (62 mg, 1.0 mmol) in dry isopropanol (10.0 mL) was stirred at 110° C. in a sealed tube for 12.0 h. After cooling to room temperature, the reaction mixture was diluted with ethyl acetate and water. The organic layer was washed with brine, dried over sodium sulfate and concentrated. The residue was purified by flash chromatography (dichloromethane ether/methanol=20/1) to afford 1-(6-bromopyridin-3-yl)pyrrolidin-2-one (820 mg, 3.40 mmol, 48.1% yield) as yellow solid. LC-MS: m/z=241.0 $(M+H)^+$, retention time 1.65 min (Method A).

1-(6-hydrazineylpyridin-3-yl)pyrrolidin-2-one

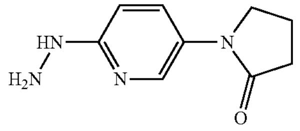 [SMILES: NNc1ccc(N2CCCC2=O)cn1]

To a solution of 1-(6-bromopyridin-3-yl)pyrrolidin-2-one (400 mg, 1.66 mmol) in ethanol (5.0 mL) was added hydrazine hydrate (5.0 mL, 85% in water). The mixture was stirred at 130° C. in a sealed tube overnight. The mixture was cooled and concentrated to give dryness. The residue was partitioned between ethyl acetate and water. The organic layer was washed with brine, dried over sodium sulfate and concentrated to give 1-(6-hydrazineylpyridin-3-yl)pyrrolidin-2-one (160 mg, 0.83 mmol, 50.2% yield) as yellow oil. LC-MS: m/z=193.2 $[M+H]^+$, retention time 0.69 min (Method B).

4-(5-hydroxy-3-methyl-1-(5-(2-oxopyrrolidin-1-yl) pyridin-2-yl)-1H-pyrazol-4-yl)benzonitrile

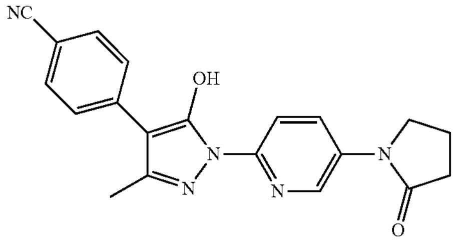 [SMILES: Cc1nn(-c2ccc(N3CCCC3=O)cn2)c(O)c1-c1ccc(C#N)cc1]

To a solution of methyl 2-(4-cyanophenyl)-3-oxobutanoate (50 mg, 0.23 mmol) and 1-(6-hydrazineylpyridin-3-yl) pyrrolidin-2-one (44 mg, 0.23 mmol) in ethanol (3.0 mL) was added p-toluenesulfonic acid monohydrate (4.0 mg, 0.02 mmol). The mixture was stirred at 90° C. in a sealed tube for 12.0 h and cooled to precipitate solid. The solid was purified by reverse prep-HPLC to give 4-(5-hydroxy-3-methyl-1-(5-(2-oxopyrrolidin-1-yl)pyridin-2-yl)-1H-pyrazol-4-yl)benzonitrile (Formate salt) (8.0 mg, 0.022 mmol, 9.7% yield) as white solid. LC-MS: m/z=360.1 $(M+H)^+$, retention time 4.06 min (Method A). $^1$HNMR (400 MHz, DMSO-$d_6$) δ 8.79 (s, 1H), 8.37 (s, 1H), 8.21-8.19 (m, 1H), 7.92-7.90 (m, 2H), 7.78-7.76 (m, 2H), 3.90-3.87 (m, 2H), 2.54-2.52 (m, 2H), 2.50 (s, 3H), 2.12-2.09 (m, 2H).

Example 8: Preparation of Compound 8

2-chloro-5-(phenylsulfonyl)pyridine

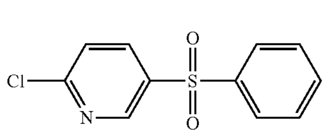 [SMILES: O=S(=O)(c1ccccc1)c1ccc(Cl)nc1]

A mixture of 2-chloro-5-iodopyridine (2.38 g, 10.0 mmol), copper(I) iodide (0.19 g, 1.0 mmol) and benzenesulfinate (978 mg, 6.0 mmol) in dimethyl sulfoxide (20.0 mL) was stirred at 60° C. for 2 h. The reaction mixture was cooled and diluted with ethyl acetate. The organic layer was washed with brine, dried over sodium sulfate and concentrated. The residue was purified by flash chromatography (petroleum ether/ethyl acetate=10/1) to afford 2-chloro-5-(phenylsulfonyl)pyridine (400 mg, 1.58 mmol, 15.8% yield) as yellow oil. LCMS: m/z=254.0 $(M+H)^+$, retention time 1.92 min (Method A).

2-hydrazineyl-5-(phenylsulfonyl)pyridine

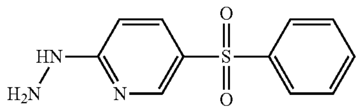 [SMILES: NNc1ccc(S(=O)(=O)c2ccccc2)cn1]

To a solution of 2-chloro-5-(phenylsulfonyl)pyridine (0.4 g, 1.58 mmol) in ethanol (5.0 mL) was added hydrazine hydrate (5.0 mL, 85% in water). The mixture was stirred at 100° C. for 4 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford 2-hydrazineyl-5-(phenylsulfonyl)pyridine (150 mg, 0.6 mmol, 37.9% yield) as yellow solid. LCMS: m/z=250.0 $(M+H)^+$, retention time 1.38 min (Method A).

4-(5-hydroxy-3-methyl-1-(5-(phenylsulfonyl)pyridin-2-yl)-1H-pyrazol-4-yl) benzonitrile

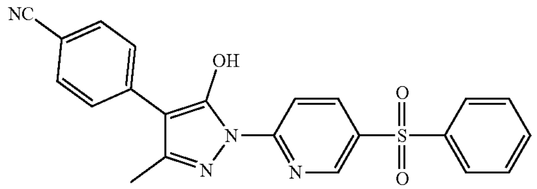 [SMILES: Cc1nn(-c2ccc(S(=O)(=O)c3ccccc3)cn2)c(O)c1-c1ccc(C#N)cc1]

To a solution of methyl 2-(4-cyanophenyl)-3-oxobutanoate (217.0 mg, 1.0 mmol) and 2-hydrazineyl-5-(phenylsulfonyl)pyridine (249.0 mg, 1.0 mmol) in ethanol (5.0 mL) was added p-toluenesulfonic acid monohydrate (38.0 mg, 0.2 mmol). The mixture was stirred at reflux for 12 hr and cooled to precipitate solid. The solid was purified by reverse prep-HPLC to give 4-(5-hydroxy-3-methyl-1-(5-(phenylsulfonyl)pyridin-2-yl)-1H-pyrazol-4-yl)benzonitrile (4.5 mg, 0.01 mmol, 1.1% yield) as white solid. LCMS: m/z=417.0 $(M+H)^+$, retention time 4.75 min (Method A). $^1H$ NMR (400 MHz, DMSO-$d_6$) δ 2.45 (s, 1H), 8.94 (s, 1H), 8.63-8.65 (d, J=8.9 Hz, 1H), 8.37-8.63 (d, J=8.9 Hz, 1H), 8.13 (s, 1H), 8.00-8.02 (d, J=8.9 Hz, 2H), 7.89-7.91 (d, J=7.5 Hz, 2H), 7.63-7.72 (m, 5H), 2.41 (s, 3H).

Example 9: Preparation of Compound 9

N-(6-fluoropyridin-3-yl)propionamide

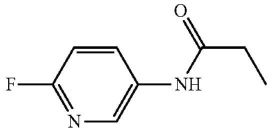

To a solution of 6-fluoropyridin-3-amine (0.5 g, 4.5 mmol) and triethylamine (0.91 g, 9.0 mmol) in dichloromethane (20.0 mL) was added propionyl chloride (0.41 g, 4.5 mmol) at 0° C. The mixture was allowed to warm up to room temperature and stirred for another one hour. The reaction was quenched with water and extracted twice with dichloromethane. The organic layer was washed with brine, dried over sodium sulfate and concentrated. The residue was purified by flash chromatography (petroleum ether/ethyl acetate=2/1) to obtain N-(6-fluoropyridin-3-yl)propionamide (0.6 g, 3.57 mmol, 79.3% yield) as yellow solid. LCMS: m/z=169.0 $(M+H)^+$, retention time 1.50 min (Method A).

N-(6-hydrazineylpyridin-3-yl)propionamide

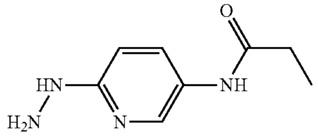

To a solution of N-(6-fluoropyridin-3-yl)propionamide (0.17 g, 1.0 mmol) in ethanol (5.0 mL) was added hydrazine hydrate (5.0 mL, 85% in water). The mixture was stirred at 100° C. for 4 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford N-(6-hydrazineylpyridin-3-yl)propionamide (147 mg, 0.82 mmol, 82.8% yield) as yellow solid. LCMS: m/z=181.0 $(M+H)^+$, retention time 0.34 min (Method A).

N-(6-(4-(4-cyanophenyl)-5-hydroxy-3-methyl-1H-pyrazol-1-yl)pyridin-3 yl)propionamide

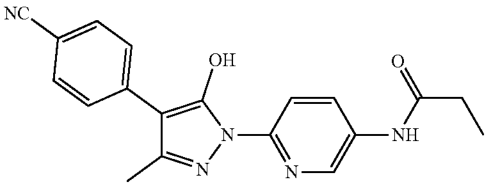 [SMILES: CCC(=O)Nc1ccc(-n2nc(C)c(-c3ccc(C#N)cc3)c2O)nc1]

To a solution of methyl 2-(4-cyanophenyl)-3-oxobutanoate (217 mg, 1.0 mmol) and N-(6-hydrazineylpyridin-3-yl) propionamide (180 mg, 1.0 mmol) in ethanol (5.0 mL) was added p-toluenesulfonic acid monohydrate (38 mg, 0.2 mmol). The mixture was stirred at reflux for 12 hr and cooled to precipitate solid. The solid was purified by reverse prep-HPLC to give N-(6-(4-(4-cyanophenyl)-5-hydroxy-3-methyl-1H-pyrazol-1-yl)pyridin-3-yl)propionamide (4.6 mg, 0.01 mmol, 1.3% yield) as white solid. LCMS: m/z=348.0 $(M+H)^+$, retention time 4.10 min (Method A). $^1H$ NMR (400 MHz, DMSO-$d_6$) δ 12.00 (s, 1H), 8.21 (s, 2H), 7.83-8.00 (m, 3H), 7.54-7.57 (m, 2H), 2.32-2.43 (m, 5H), 1.04-1.12 (m, 3H).

Example 10: Preparation of Compound 10 tert-butyl 6-chloronicotinate

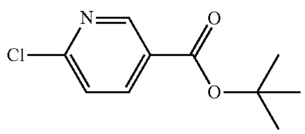

To a solution of 6-chloronicotinic acid (5.0 g, 6.37 mmol) and 4-dimethylaminopyridine (0.39 g, 0.64 mmol) in tetrahydrofuran (50.0 mL) was added di-tert-butyl dicarbonate (10.41 g, 47.77 mmol). The reaction mixture was refluxed for 4.0 h and concentrated. The residue was purified by flash chromatography (petroleum ether/ethyl acetate=10/1) to afford tert-butyl 6-chloronicotinate (5.5 g, 5.17 mmol, 81.12% yield) as yellow solid. LC-MS: m/z=214.0 $(M+H)^+$, retention time 1.83 min (Method A).

tert-butyl 6-hydrazineylnicotinate

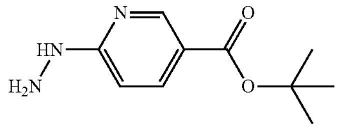

To a solution of tert-butyl 6-chloronicotinate (5.5 g, 25.82 mmol) in ethanol (25.0 mL) was added hydrazine hydrate (6.46 g, 129.11 mmol, 85% in water). The mixture was stirred at 100° C. for 2.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford tert-butyl 6-hydrazineylnicotinate (5.0 g, 23.9 mmol, 92.76% yield) as yellow solid. LC-MS: m/z=210.0 $(M+H)^+$, retention time 1.19 min (Method A).

tert-butyl 6-(4-(4-cyanophenyl)-5-hydroxy-3-methyl-1H-pyrazol-1-yl)nicotinate

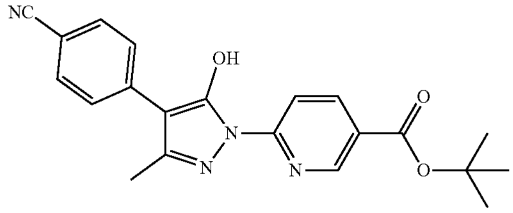 [SMILES: Cc1nn(-c2ccc(C(=O)OC(C)(C)C)cn2)c(O)c1-c1ccc(C#N)cc1]

A solution of methyl 2-(4-cyanophenyl)-3-oxobutanoate (600 mg, 2.76 mmol) and tert-butyl 6-hydrazineylnicotinate (577 mg, 2.76 mmol) in acetic acid (5.0 mL) was stirred at 120° C. for 1.0 h and concentrated to give dryness. The residue was purified by flash chromatography (methanol/dichloromethane=1/10) to afford tert-butyl 6-(4-(4-cyanophenyl)-5-hydroxy-3-methyl-1H-pyrazol-1-yl)nicotinate (610 mg, 1.62 mmol, 58.7% yield) as yellow solid. LC-MS: m/z=377.1 $(M+H)^+$, retention time 2.24 min (Method A).

6-(4-(4-cyanophenyl)-5-hydroxy-3-methyl-1H-pyrazol-1-yl)nicotinic acid

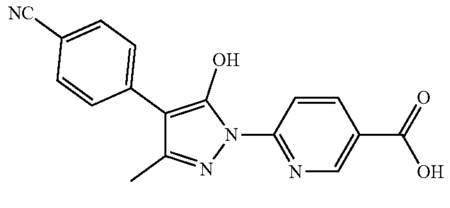 [SMILES: Cc1nn(-c2ccc(C(=O)O)cn2)c(O)c1-c1ccc(C#N)cc1]

To a solution of tert-butyl 6-(4-(4-cyanophenyl)-5-hydroxy-3-methyl-1H-pyrazol-1-yl)nicotinate (610 mg 1.62 mmol) in dichloromethane (10.0 mL) was added trifluoroacetic acid (5.0 mL). The mixture was stirred at 40° C. for 2.0 h and concentrated. The residue was triturated with ethyl acetate and filtered to afford 6-(4-(4-cyanophenyl)-5-hydroxy-3-methyl-1H-pyrazol-1-yl)nicotinic acid (500 mg, 1.56 mmol, 96.4% yield) as yellow solid. LC-MS: m/z=321.0 $(M+H)^+$, retention time 3.38 min (Method A).

6-(4-(4-cyanophenyl)-5-hydroxy-3-methyl-1H-pyrazol-1-yl)nicotinoyl chloride

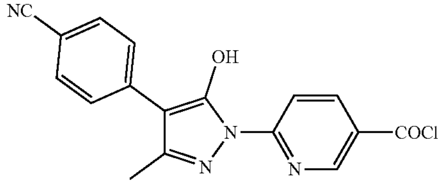 [SMILES: Cc1nn(-c2ccc(C(=O)Cl)cn2)c(O)c1-c1ccc(C#N)cc1]

To a solution of 6-(4-(4-cyanophenyl)-5-hydroxy-3-methyl-1H-pyrazol-1-yl)nicotinic acid (500 mg, 1.56 mmol) in dichloromethane (15.0 mL) was added thionyl chloride (15.0 mL). The mixture was stirred at 40° C. for 3.0 h and concentrated to give dryness. The crude product (500 mg) was obtained and directly used to the next step. LC-MS: m/z=335.1 $(M+H)^+$, retention time 1.99 min (Method A).

6-(4-(4-cyanophenyl)-5-hydroxy-3-methyl-1H-pyrazol-1-yl)-N-methoxy-N-methylnicotinamide

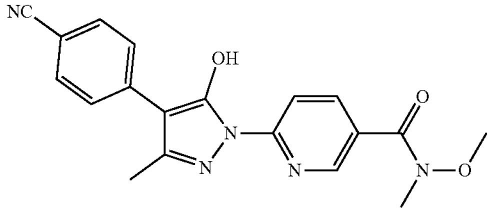 [SMILES: CON(C)C(=O)c1ccc(-n2nc(C)c(-c3ccc(C#N)cc3)c2O)nc1]

To a solution of N, O-dimethylhydroxylamine hydrochloride (230 mg, 2.33 mmol) and N,N-diisopropylethylamine (0.60 g, 4.65 mmol) in dichloromethane (5.0 mL) was added 6-(4-(4-cyanophenyl)-5-hydroxy-3-methyl-1H-pyrazol-1-yl)nicotinoyl chloride (500 mg, crude) at 0° C. The mixture was stirred at 0° C. for 3.0 h and concentrated to give dryness. The residue was purified by flash chromatography (dichloromethane/methanol=10/1) to obtain 6-(4-(4-cyano-phenyl)-5-hydroxy-3-methyl-1H-pyrazol-1-yl)-N-methoxy-N-methylnicotinamide (450 mg, 1.24 mmol, 79.5% yield) as yellow solid. LC-MS: m/z=364.0 $[M+H]^+$, retention time 4.08 min (Method A).

4-(5-hydroxy-1-(5-isobutyrylpyridin-2-yl)-3-methyl-1H-pyrazol-4-yl)benzonitrile

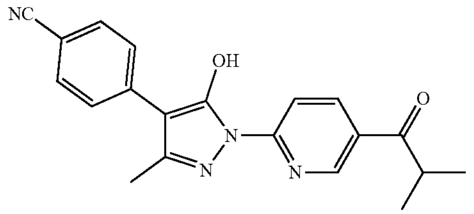 [SMILES: Cc1nn(-c2ccc(C(=O)C(C)C)cn2)c(O)c1-c1ccc(C#N)cc1]

To a solution of isopropylmagnesium chloride (3.40 mL, 3.40 mmol, 1M in tetrahydrofuran) in anhydrous tetrahydrofuran (8.0 mL) was added 6-(4-(4-cyanophenyl)-5-hydroxy-3-methyl-1H-pyrazol-1-yl)-N-methoxy-N-methylnicotinamide (300 mg, 0.82 mmol) at −20° C. The mixture was allowed to warm up to 0° C. and left stirring for another one hour. The reaction was quenched with water and extracted twice with ethyl acetate. The organic layer was washed with brine, dried over sodium sulfate and concentrated under reduced pressure. The crude product was purified by reverse Prep-HPLC to give 4-(5-hydroxy-1-(5-isobutyrylpyridin-2-yl)-3-methyl-1H-pyrazol-4-yl)benzonitrile (Formate salt) (17.3 mg, 0.044 mmol, 5.38% yield) as white solid. LC-MS: m/z=347.1 $(M+H)^+$, retention time 5.05 min (Method A). $^1$HNMR (400 MHz, DMSO-$d_6$) δ 9.01 (d, J=0.8 Hz, 1H), 8.59-8.48 (m, 2H), 8.14 (s, 1H), 7.91-7.81 (m, 4H), 3.72-3.65 (m, 1H), 2.49 (s, 3H), 1.14 (d, J=3.4 Hz, 6H).

Example 11: Preparation of Compound 11

6-hydrazineylpyridine-3-sulfonamide

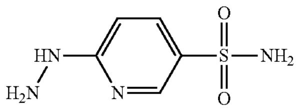 [SMILES: NNc1ccc(S(N)(=O)=O)cn1]

To a solution of 6-chloropyridine-3-sulfonamide (1.63 g, 8.5 mmol) in ethanol (5.0 mL) was added hydrazine hydrate (5.0 mL, 85% in water). The mixture was stirred at 100° C. for 4 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford 6-hydrazineylpyridine-3-sulfonamide (600 mg, 3.20 mmol, 37.7% yield) as yellow solid. LCMS: m/z=189.0 $(M+H)^+$, retention time 0.32 min (Method A).

6-(4-(4-cyanophenyl)-5-hydroxy-3-methyl-1H-pyrazol-1-yl)pyridine-3-sulfonamide

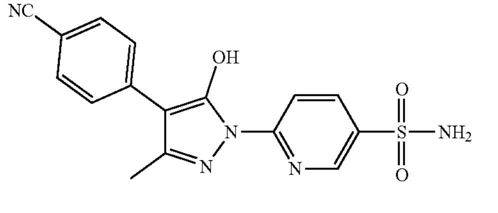 [SMILES: Cc1nn(-c2ccc(S(N)(=O)=O)cn2)c(O)c1-c1ccc(C#N)cc1]

To a solution of methyl 2-(4-cyanophenyl)-3-oxobutanoate (217 mg, 1.0 mmol) and 6-hydrazineylpyridine-3-sulfonamide (188 mg, 1.0 mmol) in ethanol (5.0 mL) was added p-toluenesulfonic acid monohydrate (38 mg, 0.2 mmol). The mixture was stirred at reflux for 12 hr and cooled to precipitate solid. The solid was purified by reverse prep-HPLC to give 6-(4-(4-cyanophenyl)-5-hydroxy-3-methyl-1H-pyrazol-1-yl)pyridine-3-sulfonamide (8.8 mg, 0.24 mmol, 2.4% yield) as white solid. LCMS: m/z=356.0 $(M+H)^+$, retention time 3.50 min (Method A). $^1$H NMR (400 MHz, DMSO-$d_6$) δ 12.95 (s, 1H), 8.80 (s, 1H), 8.60-8.62 (d, J=7.9 Hz, 2H), 8.24-8.26 (d, J=7.9 Hz, 1H), 8.14 (s, 1H), 7.92-7.94 (d, J=7.9 Hz, 2H), 7.71-7.73 (d, J=7.3 Hz, 2H), 7.51 (s, 2H), 2.43 (s, 3H).

Example 12: Preparation of Compound 12

2-chloro-5-(methylthio)pyridine

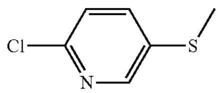

To a solution of 5-bromo-2-chloropyridine (1.92 g, 10.0 mmol) and N,N,N',N'-tetramethylethylenediamine (1.51 g, 13.0 mmol) in anhydrous tetrahydrofuran (15.0 mL) was added n-butyllithium (7.5 mL, 12.0 mmol, 1.6M in hexane) at −78° C. under nitrogen. The mixture was stirred at −78° C. for 50 min and dimethyldisulfide (1.13 g, 12.0 mmol) was added. The mixture was allowed to warm up to 20° C. and left stirring for another one hour. The reaction was quenched with saturated ammonium chloride solution and extracted twice with ethyl acetate. The organic layer was separated, washed with brine, dried over sodium sulfate and concentrated under reduced pressure. The crude product was purified by flash chromatography (petroleum ether/ethyl acetate=50/1) to obtain 2-chloro-5-(methylthio)pyridine (1.0 g, 6.29 mmol, 62.9% yield) as yellow oil. LC-MS: m/z=160 $(M+H)^+$, retention time 0.85 min (Method A).

2-chloro-5-(methylsulfinyl)pyridine

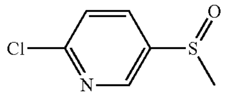

To a solution of 2-chloro-5-(methylthio)pyridine (900 mg, 5.66 mmol) in dichloromethane (10.0 mL) was added 3-chloroperoxybenzoic acid (1.26 g, 6.22 mmol, 85%) at 0° C. The mixture was stirred at this temperature for 1 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-5-(methylsulfinyl)pyridine (700 mg, 4.0 mmol, 70.6% yield) as white solid. LC-MS: m/z=176.1 $(M+H)^+$, retention time 0.55 min (Method A).

2-hydrazineyl-5-(methylsulfinyl)pyridine

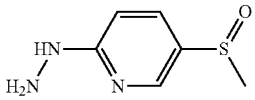

To a solution of 2-chloro-5-(methylsulfinyl)pyridine (700 mg, 4.0 mmol) in ethanol (10.0 mL) was added hydrazine hydrate (1.23 g, 20.0 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford 2-hydrazineyl-5-(methylsulfinyl)pyridine (400 mg, 2.34 mmol, 58.5% yield) as yellow solid. LC-MS: m/z=172.0 $(M+H)^+$, retention time 0.38 min (Method A).

4-(5-hydroxy-3-methyl-1-(5-(methylsulfinyl)pyridin-2-yl)-1H-pyrazol-4-yl)benzonitrile

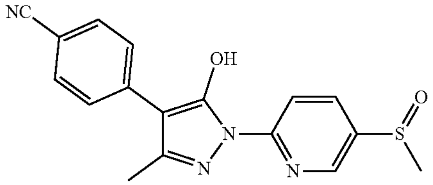 [SMILES: Cc1nn(-c2ccc(S(C)=O)cn2)c(O)c1-c1ccc(C#N)cc1]

A mixture of methyl 2-(4-cyanophenyl)-3-oxobutanoate (400 mg, 2.34 mmol) and 2-hydrazineyl-5-(methylsulfinyl)pyridine (400 mg, 2.34 mmol) in acetic acid (8.0 mL) was stirred at 120° C. for 1 h and cooled to precipitate solid. The solid was purified by reverse prep-HPLC to give 4-(5-hydroxy-3-methyl-1-(5-(methylsulfinyl)pyridin-2-yl)-1H-pyrazol-4-yl)benzonitrile (94 mg, 0.28 mmol, 11.8% yield) as white solid. LC-MS: m/z=339.0 $(M+H)^+$, retention time 3.32 min (Method A). $^1$HNMR (400 MHz, DMSO-$d_6$) δ 13.08 (s, 1H), 8.66-8.73 (m, 2H), 8.29-8.31 (d, J=10.4 Hz, 1H), 7.89-7.91 (d, J=8.3 Hz, 2H), 7.81-7.83 (d, J=8.4 Hz, 2H), 2.88 (s, 3H), 2.50 (s, 3H).

Example 13: Preparation of Compound 13

(6-chloropyridin-3-yl)(imino)(methyl)-$\lambda^6$-sulfanone

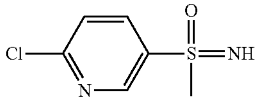

To a mixture of 2-chloro-5-(methylsulfinyl)pyridine (200 mg, 1.14 mmol) (Intermediate for Example 12) and sodium azide (223 mg, 3.43 mmol) in chloroform (5.0 mL) was added concentrated sulfuric acid (1.0 mL) at 0° C. The mixture was stirred at 55° C. for 16.0 h and cooled. The reaction was diluted with ice-water and the organic layer removed. The aqueous phase was made basic by addition of ammonium hydroxide solution whereupon an oil separated, which was extracted with dichloromethane. The organic layer was separated, washed with brine, dried over sodium sulfate and concentrated to afford (6-chloropyridin-3-yl)(imino)(methyl)-$\lambda^6$-sulfanone (120 mg, 0.63 mmol, 55.4% yield) as yellow solid. LC-MS: m/z=191.0 $(M+H)^+$, retention time 1.3 min (Method A).

(6-hydrazineylpyridin-3-yl)(imino)(methyl)-$\lambda^6$-sulfanone

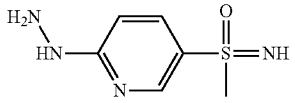

To a solution of (6-chloropyridin-3-yl)(imino)(methyl)-$\lambda^6$-sulfanone (120 mg, 0.63 mmol) in ethanol (10.0 mL) was added hydrazine hydrate (200 mg, 3.15 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (6-hydrazineylpyridin-3-yl)(imino)(methyl)-$\lambda^6$-sulfanone (100 mg, 0.54 mmol, 85.3% yield) as yellow solid. LC-MS: m/z=187.0 (M+H)+, retention time 0.36 min (Method A).

4-(5-hydroxy-3-methyl-1-(5-(S-methylsulfonimidoyl)pyridin-2-yl)-1H-pyrazol-4-yl)benzonitrile

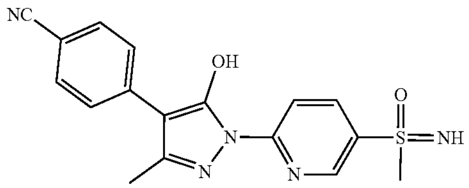 [SMILES: Cc1nn(-c2ccc(S(C)(=N)=O)cn2)c(O)c1-c1ccc(C#N)cc1]

A mixture of methyl 2-(4-cyanophenyl)-3-oxobutanoate (117 mg, 0.54 mmol) and (6-hydrazineylpyridin-3-yl)(imino)(methyl)-$\lambda^6$-sulfanone (100 mg, 0.54 mmol) in acetic acid (8.0 mL) was stirred at 120° C. for 1 h and concentrated. The resulting residue was purified by reverse prep-HPLC to give 4-(5-hydroxy-3-methyl-1-(5-(S-methylsulfonimidoyl)pyridin-2-yl)-1H-pyrazol-4-yl)benzonitrile (37 mg, 0.10 mmol, 19.4% yield) as white solid. LC-MS: m/z=354.0 $(M+H)^+$, retention time 3.19 min (Method A). $^1$HNMR (400 MHz, DMSO-$d_6$) δ 13.15 (s, 1H), 8.90 (s, 1H), 8.63-8.66 (d, J=8.7 Hz, 1H), 8.41-8.44 (d, J=8.7 Hz, 1H), 7.89-7.92 (d, J=8.7 Hz, 2H), 7.81-7.83 (d, J=8.7 Hz, 2H), 3.18 (s, 3H), 2.54 (s, 3H).

Example 14: Preparation of Compound 14

(6-bromopyridin-3-yl)dimethylphosphine oxide

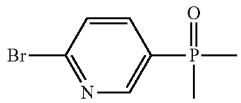

A mixture of 2-bromo-5-iodopyridine (500 mg, 1.76 mmol), dimethylphosphine oxide (275 mg 3.53 mmol), potassium phosphate (1.12 g, 5.28 mmol), 4,5-bis(diphenylphosphino)-9,9-dimethylxanthene (203 mg, 0.35 mmol) and palladium acetate (156 mg, 0.7 mmol) in 1,4-dioxane (15.0 mL) was stirred at 100° C. overnight under nitrogen. The reaction mixture was filtered with celite, and the filtrate was concentrated under reduced pressure. The obtained residue was purified by flash chromatography (petroleum ether/ethyl acetate=1/1) to afford (6-bromopyridin-3-yl)dimethylphosphine oxide (50 mg, 0.21 mmol, 12.1% yield) as yellow oil. LC-MS: m/z=234 $[M+H]^+$, retention time=1.36 min (Method A).

(6-hydrazineylpyridin-3-yl)dimethylphosphine oxide

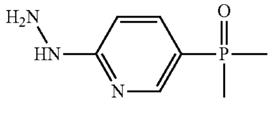

To a solution of (6-bromopyridin-3-yl)dimethylphosphine oxide (120 mg, 0.51 mmol) in ethanol (5.0 mL) was added hydrazine hydrate (160 mg, 2.55 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (6-hydrazineylpyridin-3-yl)dimethylphosphine oxide (80 mg, 0.43 mmol, 80% yield) as yellow solid. LC-MS: m/z=186.0 $(M+H)^+$, retention time 0.36 min (Method A).

4-(1-(5-(dimethylphosphoryl)pyridin-2-yl)-5-hydroxy-3-methyl-1H-pyrazol-4-yl)benzonitrile

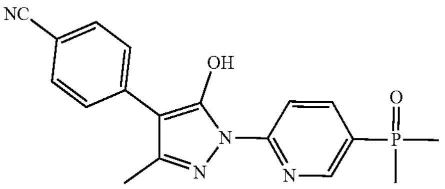 [SMILES: Cc1nn(-c2ccc(P(C)(C)=O)cn2)c(O)c1-c1ccc(C#N)cc1]

A mixture of methyl 2-(4-cyanophenyl)-3-oxobutanoate (93 mg, 0.43 mmol) and (6-hydrazineylpyridin-3-yl)dimethylphosphine oxide (80 mg, 0.43 mmol) in acetic acid (5.0 mL) was stirred at 120° C. for 1.0 h and concentrated. The resulting residue was purified by reverse prep-HPLC to give 4-(1-(5-(dimethylphosphoryl)pyridin-2-yl)-5-hydroxy-3-methyl-1H-pyrazol-4-yl)benzonitrile (68 mg, 0.19 mmol, 44.9% yield) as white solid. LC-MS: m/z=353.1.0 $(M+H)^+$, retention time 3.17 min (Method A). $^1$HNMR (400 MHz, DMSO-$d_6$) δ 13.07 (s, 1H), 8.76 (s, 1H), 8.59 (s, 1H), 8.29-8.33 (m, 1H), 7.81-7.91 (m, 4H), 2.50 (s, 3H), 1.72-1.76 (d, J=12.9 Hz, 6H).

Example 15: Preparation of Compound 15

(6-chloropyridin-3-yl)(methyl)(methylimino)-$\lambda^6$-sulfanone

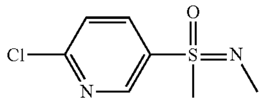

To a solution of (6-chloropyridin-3-yl)(imino)(methyl)-$\lambda^6$-sulfanone (330 mg, 1.73 mmol) (Intermediate for Example 13) in anhydrous tetrahydrofuran (10.0 mL) was added sodium hydride (83 mg, 2.08 mmol, 60 percent in oil) at 0° C. The mixture was stirred at 0° C. for 20 min and iodomethane (487 mg, 3.46 mmol) was added. The mixture was allowed to warm up to room temperature and left stirring for another 3.0 h. The reaction was quenched with ice-water and extracted twice with ethyl acetate. The organic layer was separated, washed with brine, dried over sodium sulfate and concentrated under reduced pressure. The crude product was purified by flash chromatography (petroleum ether/ethyl acetate=3/1) to obtain (6-chloropyridin-3-yl)(methyl)(methylimino)-$\lambda^6$-sulfanone (300 mg, 1.47 mmol, 85.1% yield) as yellow oil. LC-MS: m/z=205.0 $(M+H)^+$, retention time 1.45 min (Method A).

(6-hydrazineylpyridin-3-yl)(methyl)(methylimino)-$\lambda^6$-sulfanone

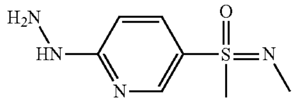

To a solution of (6-chloropyridin-3-yl)(methyl)(methylimino)-$\lambda^6$-sulfanone (300 mg, 1.47 mmol) in ethanol (8.0 mL) was added hydrazine hydrate (460 mg, 7.35 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (6-hydrazineylpyridin-3-yl)(methyl)(methylimino)-$\lambda^6$-sulfanone (200 mg, 1.0 mmol, 68% yield) as yellow solid. LC-MS: m/z=201.0 $(M+H)^+$, retention time 0.49 min (Method A).

4-(1-(5-(N,S-dimethylsulfonimidoyl)pyridin-2-yl)-5-hydroxy-3-methyl-1H-pyrazol-4-yl)benzonitrile

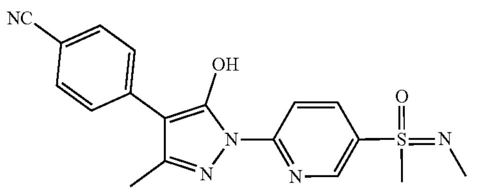 [SMILES: CN=S(C)(=O)c1ccc(-n2nc(C)c(-c3ccc(C#N)cc3)c2O)nc1]

A mixture of methyl 2-(4-cyanophenyl)-3-oxobutanoate (217 mg, 1.0 mmol) and (6-hydrazineylpyridin-3-yl)(methyl)(methylimino)-λ$^6$-sulfanone (200 mg, 1.0 mmol) in acetic acid (8.0 mL) was stirred at 120° C. for 1.0 h and concentrated. The resulting residue was purified by reverse prep-HPLC to give 4-(1-(5-(N,S-dimethylsulfonimidoyl)pyridin-2-yl)-5-hydroxy-3-methyl-1H-pyrazol-4-yl)benzonitrile (93.7 mg, 0.25 mmol, 25.5% yield) as white solid. LC-MS: m/z=368.1.0 (M+H)$^+$, retention time 4.23 min (Method A). $^1$HNMR (400 MHz, DMSO-d$_6$) δ 13.15 (s, 1H), 8.80 (s, 1H), 8.68 (s, 1H), 8.32-8.35 (d, J=8.8 Hz, 1H), 7.89-7.91 (d, J=7.9 Hz, 2H), 7.81-7.83 (d, J=7.9 Hz, 2H), 3.24 (s, 3H), 3.51 (s, 3H).

Example 16: Preparation of Compound 16

(S)-(6-chloropyridin-3-yl)(imino)(methyl)-λ$^6$-sulfanone

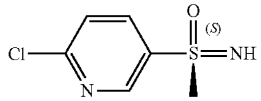

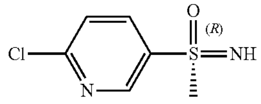

To a mixture of 2-chloro-5-(methylsulfinyl)pyridine (2.0 g, 11.4 mmol) (Intermediate for Example 12) and sodium azide (2.23 g, 34.3 mmol) in chloroform (50.0 mL) was added concentrated sulfuric acid (5.0 mL) at 0° C. The mixture was stirred at 55° C. for 16 h and cooled. The reaction was diluted with ice-water and the organic layer removed. The aqueous phase was made basic by addition of ammonium hydroxide solution whereupon an oil separated, which was extracted with dichloromethane. The organic layer was separated, washed with brine, dried over sodium sulfate and concentrated to afford (6-chloropyridin-3-yl)(imino)(methyl)-λ$^6$-sulfanone (1.0 g, 5.26 mmol, 46.1% yield) as yellow solid. LC-MS: m/z=191.0 (M+H)$^+$, retention time 0.55 min (Method A).

The two chiral isomers were separated by Chiral Prep-HPLC. (Chiralpak AD-H column; Mobile Phase: A: Hexane, B: MeOH (0.2% Methanolamine); Gradient Phase: B %=25%; Flow Rate: 1.0 mL/min; Column Temperature: 40° C. Wavelength: 254 nm.)

(S)-(6-chloropyridin-3-yl)(imino)(methyl)-λ$^6$-sulfanone (247 mg, 1.30 mmol) as yellow solid.

(R)-(6-chloropyridin-3-yl)(imino)(methyl)-λ$^6$-sulfanone (211 mg, 1.11 mmol) as yellow solid.

(S)-(6-hydrazineylpyridin-3-yl)(imino)(methyl)-λ$^6$-sulfanone

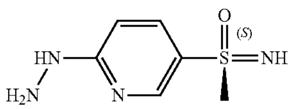

To a solution of (S)-(6-chloropyridin-3-yl)(imino)(methyl)-λ$^6$-sulfanone (100 mg, 0.53 mmol) in ethanol (5.0 mL) was added hydrazine hydrate (200 mg, 3.15 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (S)-(6-hydrazineylpyridin-3-yl)(imino)(methyl)-λ$^6$-sulfanone (100 mg, crude) as yellow solid. LC-MS: m/z=187.0 (M+H)$^+$, retention time 0.37 min (Method A).

(S)-4-(5-hydroxy-3-methyl-1-(5-(S-methylsulfonimidoyl)pyridin-2-yl)-1H-pyrazol-4-yl)benzonitrile

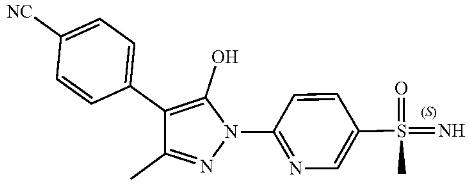

A mixture of methyl 2-(4-cyanophenyl)-3-oxobutanoate (117 mg, 0.54 mmol) and (S)-(6-hydrazineylpyridin-3-yl)(imino)(methyl)-λ$^6$-sulfanone (100 mg, crude) in acetic acid (8.0 mL) was stirred at 120° C. for 1 h and concentrated. The resulting residue was purified by reverse prep-HPLC to give (S)-4-(5-hydroxy-3-methyl-1-(5-(S-methylsulfonimidoyl)pyridin-2-yl)-1H-pyrazol-4-yl)benzonitrile (36.7 mg, 0.103 mmol, 19.2% yield) as white solid. LC-MS: m/z=354.0 (M+H)$^+$, retention time 3.10 min (Method A). $^1$HNMR (400 MHz, DMSO-d$_6$) δ 13.15 (s, 1H), 8.90 (s, 1H), 8.65 (s, 1H), 8.42-8.44 (dd, J=8.8 Hz, 1H), 7.89-7.91 (d, J=7.8 Hz, 2H), 7.82-7.83 (d, J=7.8 Hz, 2H), 3.18 (s, 3H), 2.50 (s, 3H).

Example 17: Preparation of Compound 17

(R)-(6-hydrazineylpyridin-3-yl)(imino)(methyl)-λ$^6$-sulfanone

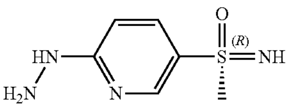

To a solution of (R)-(6-chloropyridin-3-yl)(imino)(methyl)-λ$^6$-sulfanone (100 mg, 0.53 mmol) (Intermediate for Example 16) in ethanol (5.0 mL) was added hydrazine hydrate (200 mg, 3.15 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (R)-(6-hydrazineylpyridin-3-yl)(imino)(methyl)-λ$^6$-sulfanone (100 mg, crude) as yellow solid. LC-MS: m/z=187.0 (M+H)+, retention time 0.37 min (Method A).

(R)-4-(5-hydroxy-3-methyl-1-(5-(S-methylsulfonimidoyl)pyridin-2-yl)-1H-pyrazol-4-yl)benzonitrile

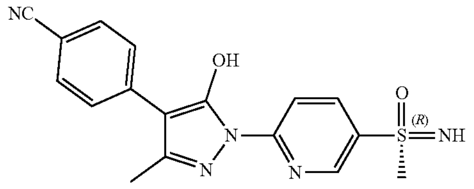

A mixture of methyl 2-(4-cyanophenyl)-3-oxobutanoate (117 mg, 0.54 mmol) and (R)-(6-hydrazineylpyridin-3-yl)(imino)(methyl)-$\lambda^6$-sulfanone (100 mg, crude) in acetic acid (8.0 mL) was stirred at 120° C. for 1 h and concentrated. The resulting residue was purified by reverse prep-HPLC to give (R)-4-(5-hydroxy-3-methyl-1-(5-(S-methylsulfonimidoyl)pyridin-2-yl)-1H-pyrazol-4-yl)benzonitrile (47.5 mg, 0.134 mmol, 24.8% yield) as white solid. LC-MS: m/z=354.0 $(M+H)^+$, retention time 3.10 min (Method A). $^1$HNMR (400 MHz, DMSO-$d_6$) δ 13.15 (s, 1H), 8.90 (s, 1H), 8.64 (m, 1H), 8.42-8.45 (dd, J=8.7 Hz, 1H), 7.89-7.91 (d, J=8.7 Hz, 2H), 7.82-7.84 (d, J=8.7 Hz, 2H), 3.18 (s, 3H), 2.51 (s, 3H).

Example 18: Preparation of Compound 18

(6-(4-(4-chlorophenyl)-5-hydroxy-3-methyl-1H-pyrazol-1-yl)pyridin-3-yl)(imino)-(methyl)-$\lambda^6$-sulfanone

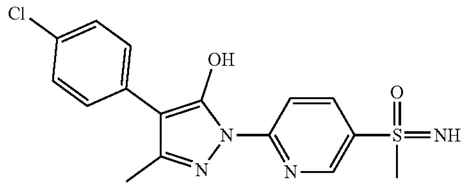 [SMILES: Cc1nn(-c2ccc(S(C)(=N)=O)cn2)c(O)c1-c1ccc(Cl)cc1]

A mixture of ethyl 2-(4-chlorophenyl)-3-oxobutanoate (250 mg, 1.04 mmol) (Intermediate for Example 1) and (6-hydrazineylpyridin-3-yl)(imino)(methyl)-_$^6$-sulfanone (190 mg, 1.04 mmol) (Intermediate for Example 13) in acetic acid (8.0 mL) was stirred at 120° C. for 1.0 h and concentrated. The resulting residue was purified by reverse prep-HPLC to give (6-(4-(4-chlorophenyl)-5-hydroxy-3-methyl-1H-pyrazol-1-yl)pyridin-3-yl)(imino)(methyl)-$\lambda^6$-sulfanone (Formate salt) (27 mg, 0.07 mmol, 7.17% yield) as white solid. LC-MS: m/z=363.0 $(M+H)^+$, retention time 3.82 min (Method A). $^1$HNMR (400 MHz, DMSO-$d_6$) δ 12.73 (s, 1H), 8.88 (s, 1H), 8.61-8.64 (d, J=10.7 Hz, 1H), 8.39-8.41 (d, J=10.7 Hz, 1H), 7.67-7.68 (d, J=8.2 Hz, 2H), 7.42-7.44 (d, J=8.2 Hz, 2H), 4.49 (s, 1H), 3.17 (s, 3H), 2.42 (s, 3H).

Example 19: Preparation of Compound 19

2-chloro-5-(isopropylthio)pyridine

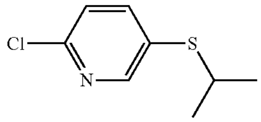

To a solution of 5-bromo-2-chloropyridine (1.92 g, 10.0 mmol) in anhydrous diethyl ether (15.0 mL) was added n-butyllithium (7.5 mL, 12.0 mmol, 1.6M in hexane) at −78° C. under nitrogen. The mixture was stirred at −78° C. for 30 min and 1,2-diisopropyldisulfane (1.80 g, 12.0 mmol) was added. The mixture was allowed to warm up to 20° C. and left stirring for another one hour. The reaction was quenched with saturated ammonium chloride solution and extracted twice with ethyl acetate. The organic layer was separated, washed with brine, dried over sodium sulfate and concentrated under reduced pressure. The crude product was purified by flash chromatography (petroleum ether/ethyl acetate=50/1) to obtain 2-chloro-5-(isopropylthio)pyridine (1.2 g, 6.42 mmol, 64.2% yield) as yellow oil. LC-MS: m/z=188.0 $(M+H)^+$, retention time 2.05 min (Method A).

2-chloro-5-(isopropylsulfinyl)pyridine

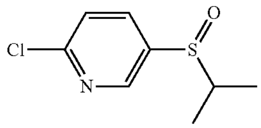

To a solution of 2-chloro-5-(isopropylthio)pyridine (1.2 g, 6.42 mmol) in dichloromethane (20.0 mL) was added 3-chloroperoxybenzoic acid (1.43 g, 7.06 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-5-(isopropylsulfinyl)pyridine (1.1 g, 5.42 mmol, 84.4% yield) as white solid. LC-MS: m/z=204.1 $(M+H)^+$, retention time 0.55 min (Method A).

(6-chloropyridin-3-yl)(imino)(isopropyl)-$\lambda^6$-sulfanone

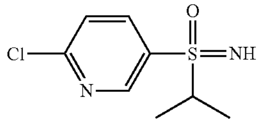

To a mixture of 2-chloro-5-(isopropylsulfinyl)pyridine (200 mg, 0.91 mmol) and ammonium carbamate (286 mg, 3.67 mmol) in methanol (5.0 mL) was added (diacetoxyiodo)benzene (880 mg, 2.73 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-chloropyridin-3-yl)(imino)(isopropyl)-λ$^6$-sulfanone (150 mg, 0.69 mmol, 75.6% yield) as yellow solid. LC-MS: m/z=219.1 $(M+H)^+$, retention time 1.50 min (Method A).

(6-hydrazineylpyridin-3-yl)(imino)(isopropyl)-λ$^6$-sulfanone

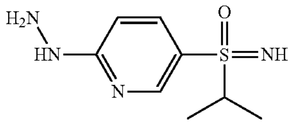

To a solution of (6-chloropyridin-3-yl)(imino)(isopropyl)-λ$^6$-sulfanone (200 mg, 0.92 mmol) in ethanol (8.0 mL) was added hydrazine hydrate (280 mg, 4.6 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The crude (6-hydrazineylpyridin-3-yl)(imino)(isopropyl)-λ$^6$-sulfanone (200 mg, crude) was obtained as yellow syrup. LC-MS: m/z=215.0 (M+H)+, retention time 0.56 min (Method A). The crude product was used to the next step.

4-(5-hydroxy-3-methyl-1-(5-(propan-2-ylsulfonimidoyl)pyridin-2-yl)-1H-pyrazol-4-yl)benzonitrile

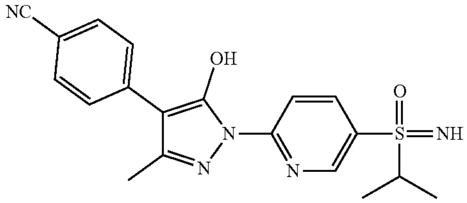

A mixture of methyl 2-(4-cyanophenyl)-3-oxobutanoate (195 mg, 0.90 mmol) and (6-hydrazineylpyridin-3-yl)(imino)(isopropyl)-λ$^6$-sulfanone (200 mg, 2.34 mmol) in acetic acid (8.0 mL) was stirred at 120° C. for 1.0 h and evaporated to give dryness. The residue was purified by reverse prep-HPLC to give 4-(5-hydroxy-3-methyl-1-(5-(propan-2-ylsulfonimidoyl)pyridin-2-yl)-1H-pyrazol-4-yl)benzonitrile (28.8 mg, 0.08 mmol, 8.4% yield) as white solid. LC-MS: m/z=382.0 $(M+H)^+$, retention time 3.51 min (Method A). $^1$HNMR (400 MHz, DMSO-$d_6$) δ 13.17 (s, 1H), 8.80 (s, 1H), 8.65-8.67 (d, J=8.6 Hz, 1H), 8.32-8.35 (dd, J=8.7 Hz, 4H), 4.48 (s, 1H), 2.51 (s, 3H), 1.17-1.23 (m, 6H).

Example 20: Preparation of Compound 20

2-chloro-5-(phenylthio)pyridine

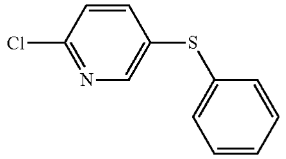 [SMILES: Clc1ccc(Sc2ccccc2)cn1]

A mixture of 2-chloro-5-iodopyridine (2.3 g, 10 mmol), thiophenol (1.32 g, 12 mmol), sodium methoxide (648 mg, 12 mmol), copper (320 mg, 5.0 mmol) in methanol (10.0 mL) was stirred at 80° C. for 12.0 h under nitrogen. The reaction mixture was filtered with celite, and the filtrate was concentrated under reduced pressure. The obtained residue was purified by flash chromatography (petroleum ether/ethyl acetate=4/1) to afford 2-chloro-5-(phenylthio)pyridine (1.5 g, 6.79 mmol, 67.9% yield) as white solid. LC-MS: m/z=222 $[M+H]^+$, retention time=2.10 min (Method A).

2-chloro-5-(phenylsulfinyl)pyridine

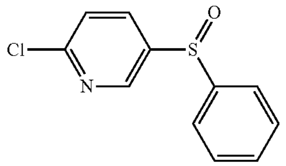 [SMILES: O=S(c1ccccc1)c1ccc(Cl)nc1]

To a solution of 2-chloro-5-(phenylthio)pyridine (1.5 g, 6.79 mmol) in dichloromethane (20.0 mL) was added 3-chloroperoxybenzoic acid (1.65 g, 8.15 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=3/1) to obtain 2-chloro-5-(phenylsulfinyl)pyridine (1.0 g, 4.22 mmol, 62.1% yield) as white solid. LC-MS: m/z=238.1 $(M+H)^+$, retention time 1.75 min (Method A).

(6-chloropyridin-3-yl)(imino)(phenyl)-λ$^6$-sulfanone

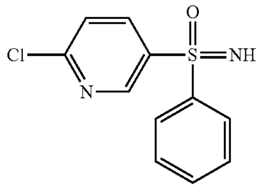 [SMILES: N=S(=O)(c1ccccc1)c1ccc(Cl)nc1]

To a mixture of 2-chloro-5-(phenylsulfinyl)pyridine (300 mg, 1.26 mmol) and ammonium carbamate (393 mg, 5.04 mmol) in methanol (8.0 mL) was added (diacetoxyiodo)benzene (1.22 g, 3.78 mmol). The mixture was stirred at room temperature for 30 min and cooled. The reaction was diluted with ice-water and extracted twice with ethyl acetate.

The organic layer was separated, washed with brine, dried over sodium sulfate and concentrated under reduced pressure. The crude product was purified by flash chromatography (petroleum ether/ethyl acetate=1/1) to obtain (6-chloropyridin-3-yl)(imino)(phenyl)-λ$^6$-sulfanone (150 mg, 0.59 mmol, 47.2% yield) as yellow solid. LC-MS: m/z=253.0 $(M+H)^+$, retention time 1.69 min (Method A).

(6-hydrazineylpyridin-3-yl)(imino)(phenyl)-λ$^6$-sulfanone

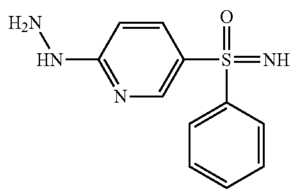 [SMILES: N=S(=O)(c1ccccc1)c1ccc(NN)nc1]

To a solution of (6-chloropyridin-3-yl)(imino)(phenyl)-λ$^6$-sulfanone (150 mg, 0.59 mmol) in ethanol (3.0 mL) was added hydrazine hydrate (180 mg, 2.95 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The crude (6-hydrazineylpyridin-3-yl)(imino)(isopropyl)-λ$^6$-sulfanone (75 mg, 0.30 mmol, 51.2% yield) was obtained as yellow syrup. LC-MS: m/z=249.0 $(M+H)^+$, retention time 1.22 min (Method A). The crude product was used to the next step.

4-(5-hydroxy-3-methyl-1-(5-(phenylsulfonimidoyl)pyridin-2-yl)-1H-pyrazol-4-yl)benzonitrile

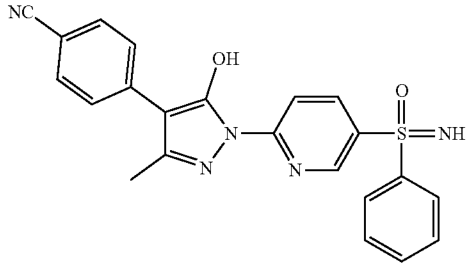 [SMILES: Cc1nn(-c2ccc(S(=N)(=O)c3ccccc3)cn2)c(O)c1-c1ccc(C#N)cc1]

A mixture of methyl 2-(4-cyanophenyl)-3-oxobutanoate (65.1 mg, 0.30 mmol) and (6-hydrazineylpyridin-3-yl)(imino)(isopropyl)-λ$^6$-sulfanone (75 mg, 0.30 mmol) in acetic acid (8.0 mL) was stirred at 120° C. for 1.0 h and evaporated to give dryness. The residue was purified by reverse prep-HPLC to give 4-(5-hydroxy-3-methyl-1-(5-(phenylsulfonimidoyl)pyridin-2-yl)-1H-pyrazol-4-yl)benzonitrile (Formate salt) (28.8 mg, 0.08 mmol, 8.4% yield) as white solid. LC-MS: m/z=416.0 $(M+H)^+$, retention time 4.05 min (Method A). $^1$HNMR (400 MHz, DMSO-$d_6$) δ 8.95 (s, 1H), 8.58 (s, 1H), 8.37-8.40 (d, J=8.3 Hz, 1H), 8.14 (s, 1H), 8.00-8.02 (d, J=7.3 Hz, 2H), 7.88-7.90 (d, J=8.3 Hz, 2H), 7.72-7.74 (d, J=8.3 Hz, 2H), 7.58-7.62 (m, 3H), 5.26 (s, 1H), 2.43 (s, 3H).

Example 21: Preparation of Compound 21

2-chloro-5-(ethylthio)pyridine

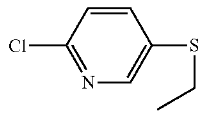

To a solution of 5-bromo-2-chloropyridine (3.0 g, 15.6 mmol) in anhydrous diethyl ether (30.0 mL) was added n-butyllithium (11.7 mL, 18.7 mmol, 1.6M in hexane) at −78° C. under nitrogen. The mixture was stirred at −78° C. for 30 min and 1,2-diethyldisulfane (2.28 g, 18.7 mmol) was added. The mixture was allowed to warm up to 20° C. and left stirring for another one hour. The reaction was quenched with saturated ammonium chloride solution and extracted twice with ethyl acetate. The organic layer was separated, washed with brine, dried over sodium sulfate and concentrated under reduced pressure. The crude product was purified by flash chromatography (petroleum ether/ethyl acetate=20/1) to obtain 2-chloro-5-(ethylthio)pyridine (2.5 g, 14.45 mmol, 92.6% yield) as yellow oil. LC-MS: m/z=174.1 $(M+H)^+$, retention time 2.01 min (Method A).

2-chloro-5-(ethylsulfinyl)pyridine

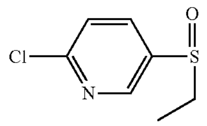

To a solution of 2-chloro-5-(ethylthio)pyridine (2.5 g, 14.45 mmol) in dichloromethane (20.0 mL) was added 3-chloroperoxybenzoic acid (3.51 g, 17.34 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=3/1) to obtain 2-chloro-5-(ethylsulfinyl)pyridine (2.0 g, 9.80 mmol, 67.8% yield) as white solid. LC-MS: m/z=190.1 $(M+H)^+$, retention time 1.47 min (Method A).

(6-chloropyridin-3-yl)(imino)(ethyl)-λ$^6$-sulfanone

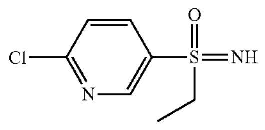

To a mixture of 2-chloro-5-(ethylsulfinyl)pyridine (2.0 g, 9.80 mmol) and sodium azide (1.91 g, 29.4 mmol) in chloroform (15.0 mL) was added concentrated sulfuric acid (2.0 mL) at 0° C. The mixture was stirred at 55° C. for 16.0 h and cooled. The reaction was diluted with ice-water and the organic layer removed. The aqueous phase was made basic by addition of ammonium hydroxide solution whereupon an oil separated, which was extracted with dichloromethane. The organic layer was separated, washed with brine, dried over sodium sulfate and concentrated to afford (6-chloropyridin-3-yl)(imino)(ethyl)-$\lambda^6$-sulfanone (1.82 g, 9.1 mmol, 92.8% yield) as yellow solid. LC-MS: m/z=205.1 $(M+H)^+$, retention time 1.40 min (Method A).

(6-hydrazineylpyridin-3-yl)(imino)(ethyl)-$\lambda^6$-sulfanone

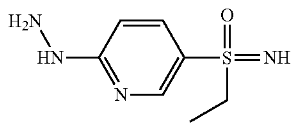

To a solution of 6-chloropyridin-3-yl)(imino)(ethyl)-$\lambda^6$-sulfanone (1.82 g, 9.1 mmol) in ethanol (10.0 mL) was added hydrazine hydrate (2.89 g, 45.5 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (6-hydrazineylpyridin-3-yl)(imino)(ethyl)-$\lambda^6$-sulfanone (2.0 g, crude) as yellow solid. LC-MS: m/z=201.1 $(M+H)^+$, retention time 0.39 min (Method A). The crude product was used to the next step.

4-(5-hydroxy-3-methyl-1-(5-(S-ethylsulfonimidoyl)pyridin-2-yl)-1H-pyrazol-4-yl)benzonitrile

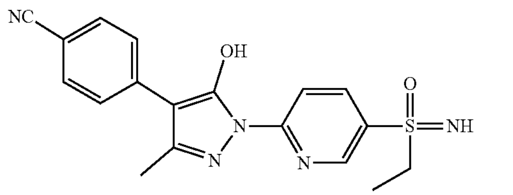 [SMILES: CCS(=N)(=O)c1ccc(-n2nc(C)c(-c3ccc(C#N)cc3)c2O)nc1]

A mixture of methyl 2-(4-cyanophenyl)-3-oxobutanoate (651 mg, 3.0 mmol) and (6-hydrazineylpyridin-3-yl)(imino)(ethyl)-$\lambda^6$-sulfanone (600 mg, 3.0 mmol) in acetic acid (10.0 mL) was stirred at 120° C. for 1.0 h and concentrated. The resulting residue was purified by reverse prep-HPLC to give 4-(5-hydroxy-3-methyl-1-(5-(S-ethylsulfonimidoyl)pyridin-2-yl)-1H-pyrazol-4-yl)benzonitrile (Formate salt) (115.3 mg, 0.31 mmol, 10.5% yield) as white solid. LC-MS: m/z=368.1 $(M+H)^+$, retention time 3.36 min (Method A). $^1$HNMR (400 MHz, DMSO-$d_6$) δ 8.82 (s, 1H), 8.65-8.63 (m, 1H), 8.35-8.32 (m, 1H), 7.92-7.89 (m, 2H), 7.80-7.78 (m, 2H), 3.25-3.19 (m, 2H), 2.50 (s, 3H), 1.13-1.09 (m, 3H).

Example 22: Preparation of Compound 22

(S)-2-chloro-5-(methylsulfinyl)pyridine

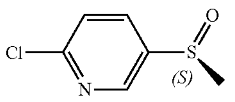

-continued

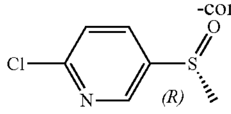

To a solution of 2-chloro-5-(methylthio)pyridine (2.5 g, 15.82 mmol) (Intermediate for Example 12) in dichloromethane (20.0 mL) was added 3-chloroperoxybenzoic acid (3.84 g, 19.0 mmol, 85%) at 0° C. The mixture was stirred at this temperature for 1 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-5-(methylsulfinyl)pyridine (1.6 g, 9.20 mmol, 58.1% yield) as white solid. LC-MS: m/z=176 $(M+H)^+$, retention time 0.55 min (Method A).

The two isomers were separated by chiral prep-HPLC as white solid.

(S)-2-chloro-5-(methylsulfinyl)pyridine (550 mg, 3.16 mmol).

(R)-2-chloro-5-(methylsulfinyl)pyridine (500 mg, 2.87 mmol).

(S)-2-hydrazineyl-5-(methylsulfinyl)pyridine

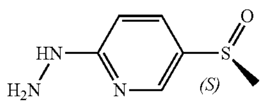

To a solution of (S)-2-chloro-5-(methylsulfinyl)pyridine (200 mg, 1.15 mmol) in ethanol (10.0 mL) was added hydrazine hydrate (350 mg, 5.74 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (S)-2-hydrazineyl-5-(methylsulfinyl)pyridine (130 mg, 0.76 mmol, 66.1% yield) as yellow solid. LC-MS: m/z=172.0 $(M+H)^+$, retention time 0.37 min (Method A).

(S)-4-(5-hydroxy-3-methyl-1-(5-(methylsulfinyl)pyridin-2-yl)-1H-pyrazol-4-yl)benzonitrile

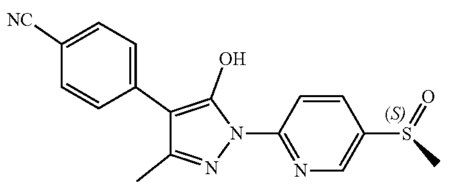

A mixture of methyl 2-(4-cyanophenyl)-3-oxobutanoate (165 mg, 0.76 mmol) and (S)-2-hydrazineyl-5-(methylsulfinyl)pyridine (130 mg, 0.76 mmol) in acetic acid (8.0 mL) was stirred at 120° C. for 1 h and evaporated to give dryness. The residue was purified by reverse prep-HPLC to give (S)-4-(5-hydroxy-3-methyl-1-(5-(methylsulfinyl)pyridin-2-yl)-1H-pyrazol-4-yl)benzonitrile (52 mg, 0.15 mmol, 20.2% yield) as white solid. LC-MS: m/z=339.0 $(M+H)^+$, retention time 3.23 min (Method A). $^{1}$HNMR (400 MHz, DMSO-$d_6$) δ 13.08 (s, 1H), 8.73 (s, 2H), 8.29-8.31 (d, J=8.6 Hz, 2H), 7.90-7.91 (d, J=8.5 Hz, 2H), 7.81-7.91 (d, J=8.5 Hz, 2H), 2.89 (s, 3H), 2.51 (s, 3H).

Example 23: Preparation of Compound 23

(R)-2-hydrazineyl-5-(methylsulfinyl)pyridine

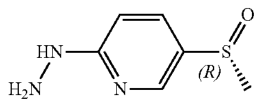

To a solution of (R)-2-chloro-5-(methylsulfinyl)pyridine (350 mg, 2.01 mmol) (Intermediate for Example 22) in ethanol (10.0 mL) was added hydrazine hydrate (610 mg, 10.05 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (R)-2-hydrazineyl-5-(methylsulfinyl)pyridine (150 mg, 0.88 mmol, 43.6% yield) as yellow solid. LC-MS: m/z=172.0 $(M+H)^+$, retention time 0.37 min (Method A).

(R)-4-(5-hydroxy-3-methyl-1-(5-(methylsulfinyl)pyridin-2-yl)-1H-pyrazol-4-yl)benzonitrile

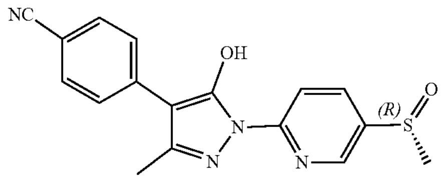

A mixture of methyl 2-(4-cyanophenyl)-3-oxobutanoate (190 mg, 0.88 mmol) and (R)-2-hydrazineyl-5-(methylsulfinyl)pyridine (150 mg, 0.88 mmol) in acetic acid (8.0 mL) was stirred at 120° C. for 1 h and evaporated to give dryness. The residue was purified by reverse prep-HPLC to give (R)-4-(5-hydroxy-3-methyl-1-(5-(methylsulfinyl)pyridin-2-yl)-1H-pyrazol-4-yl)benzonitrile (60 mg, 0.18 mmol, 20.1% yield) as white solid. LC-MS: m/z=339.0 $(M+H)^+$, retention time 3.24 min (Method A). $^{1}$HNMR (400 MHz, DMSO-$d_6$) δ 13.09 (s, 1H), 8.73 (s, 2H), 8.28-8.31 (d, J=8.6 Hz, 2H), 7.89-7.91 (d, J=8.3 Hz, 2H), 7.81-7.83 (d, J=8.3 Hz, 2H), 2.89 (s, 3H), 2.51 (s, 3H).

Example 24: Preparation of Compound 24

2-ethylhexyl 3-((6-chloropyridin-3-yl)thio)propanoate

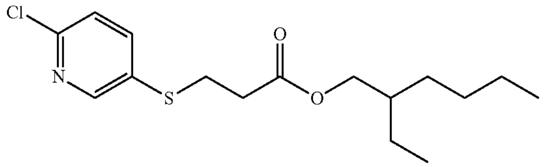 [SMILES: CCCCC(CC)COC(=O)CCSc1ccc(Cl)nc1]

A mixture of 5-bromo-2-chloropyridine (10.0 g, 52.1 mmol), 3-mercaptopropionic acid 2-ethylhexyl ester (13.6 g, 62.5 mmol), N,N-diisopropylethylamine (648 mg, 104.2 mmol), 4,5-bis(diphenylphosphino)-9,9-dimethylxanthene (6.02 g, 10.4 mmol) and tris(dibenzylideneacetone)dipalladium (4.76 g, 5.2 mmol) in N,N-dimethylformamide (60.0 mL) was stirred at 120° C. for 12.0 h under nitrogen and cooled. The reaction was diluted with ice-water and extracted with ethyl acetate twice. The organic layer was separated, washed with brine, dried over sodium sulfate and concentrated. The crude product was purified by flash chromatography (petroleum ether/ethyl acetate=3/1) to give 2-ethylhexyl 3-((6-chloropyridin-3-yl)thio)propanoate (11.2 g, 34.04 mmol, 65.3% yield) as yellow oil. LC-MS: m/z=330.1 $(M+H)^+$, retention time 2.31 min (Method A)

6-chloropyridine-3-thiol

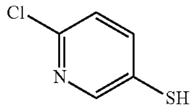

To a solution of 2-ethylhexyl 3-((6-chloropyridin-3-yl)thio)propanoate (11.2 g, 34.04 mmol) in anhydrous tetrahydrofuran (30.0 mL) was added potassium tert-butoxide (51.1 mL, 51.1 mmol, 1M in tetrahydrofuran) at −78° C. The mixture was allowed to warm up to 0° C. and left stirring for another 30 min. The reaction was quenched with saturated ammonium chloride solution and extracted twice with ethyl acetate. The organic layer was separated, washed with brine, dried over sodium sulfate and concentrated. The crude product was purified by flash chromatography (petroleum ether/ethyl acetate=5/1) to give 6-chloropyridine-3-thiol (3.5 g, 24.1 mmol, 70.9% yield) as yellow oil. LC-MS: m/z=289.1 $(M+H)^+$, retention time 2.1 min (Method A)

methyl 6-chloropyridine-3-sulfinate

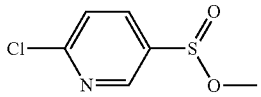

To a solution of 6-chloropyridine-3-thiol (3.5 g, 24.1 mmol) in methanol (30.0 mL) was added N-bromosuccinimide (9.0 g, 50.6 mmol). The mixture was stirred for 1.0 h at room temperature. The reaction was diluted with water and extracted twice with ethyl acetate. The organic layer was separated, washed with brine, dried over sodium sulfate and concentrated. The crude methyl 6-chloropyridine-3-sulfinate (4.0 g, 20.94 mmol, 86.9% yield) was obtained as yellow solid. LC-MS: m/z=192.1 $(M+H)^+$, retention time 1.64 min (Method A). The product was used to the next step without purification.

6-chloropyridine-3-sulfinamide

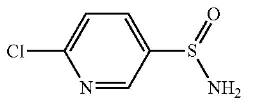

To a solution of methyl 6-chloropyridine-3-sulfinate (2.0 g, 10.47 mmol) in anhydrous tetrahydrofuran (15.0 mL) was added lithium bis(trimethylsilyl)amide (50.0 mL, 50.0 mmol, 1M in tetrahydrofuran) at −78° C. The mixture was stirred at −78° C. for 30 min, saturated aqueous ammonium chloride solution (10.0 mL) was added, and the mixture was stirred at room temperature for another 15 min. The reaction was extracted twice with ethyl acetate. The organic layer was separated, washed with brine, dried over sodium sulfate and concentrated. The residue was purified by flash chromatography (petroleum ether/ethyl acetate=5/1) to give 6-chloropyridine-3-sulfinamide (1.5 g, 8.52 mmol, 81.4% yield) as white solid. LC-MS: m/z=177.1 $(M+H)^+$, retention time 1.36 min (Method A)

tert-butyl ((6-chloropyridin-3-yl)sulfinyl)carbamate

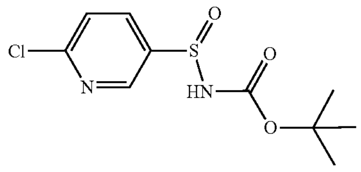 [SMILES: CC(C)(C)OC(=O)NS(=O)c1ccc(Cl)nc1]

To a solution of 6-chloropyridine-3-sulfinamide (620 mg, 3.52 mmol) in anhydrous tetrahydrofuran (8.0 mL) was added lithium diisopropylamide (2.64 mL, 5.28 mmol, 2M in tetrahydrofuran) at 0° C. The mixture was stirred at 0° C. for 1.0 h and di-tert-butyl dicarbonate (767 mg, 3.52 mmol) was added. The mixture was allowed to warm up to 20° C. and left stirring for another 2.0 h. The reaction was quenched with saturated ammonium chloride solution and extracted twice with ethyl acetate. The organic layer was separated, washed with brine, dried over sodium sulfate and concentrated under reduced pressure. The crude product was purified by flash chromatography (petroleum ether/ethyl acetate=3/1) to obtain tert-butyl ((6-chloropyridin-3-yl) sulfinyl)carbamate (600 mg, 2.17 mmol, 61.7% yield) as white solid. LC-MS: m/z=276.7 $(M+H)^+$, retention time 1.84 min (Method A).

tert-butyl (amino(6-chloropyridin-3-yl)(oxo)-$\lambda^6$-sulfaneylidene)carbamate

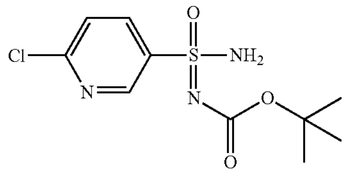 [SMILES: CC(C)(C)OC(=O)N=S(N)(=O)c1ccc(Cl)nc1]

To a solution of tert-butyl ((6-chloropyridin-3-yl)sulfinyl) carbamate (600 mg, 2.17 mmol) in acetonitrile (10.0 mL) was added N-chlorosuccinimide (344 mg, 2.59 mmol). The mixture was stirred at room temperature for 1.0 h and ammonia solution (5.0 mL, ca. 7M in methanol) was added dropwise. The mixture was stirred for another 2H. The reaction was concentrated to give dryness. The residue was purified by flash chromatography (petroleum ether/ethyl acetate=1/1) to obtain tert-butyl (amino(6-chloropyridin-3-yl)(oxo)-$\lambda^6$-sulfaneylidene)carbamate (500 mg, 1.72 mmol, 79.2% yield) as white solid. LC-MS: m/z=292.1 $(M+H)^+$, retention time 1.72 min (Method A).

tert-butyl (amino(6-hydrazineylpyridin-3-yl)(oxo)-$\lambda^6$-sulfaneylidene)carbamate

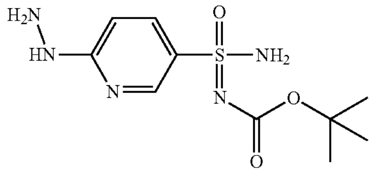 [SMILES: CC(C)(C)OC(=O)N=S(N)(=O)c1ccc(NN)nc1]

To a solution of tert-butyl (amino(6-chloropyridin-3-yl) (oxo)-$\lambda^6$-sulfaneylidene)carbamate (100 mg, 0.34 mmol) in ethanol (3.0 mL) was added hydrazine hydrate (100 mg, 1.7 mmol, 85% in water). The mixture was stirred at 85° C. for 45 min. The mixture was cooled and concentrated to give dryness. The crude tert-butyl (amino(6-hydrazineylpyridin-3-yl)(oxo)-$\lambda^6$-sulfaneylidene)carbamate (100 mg, crude) was obtained as yellow syrup. LC-MS: m/z=288.0 $(M+H)^+$, retention time 1.24 min (Method A). The crude product was used to the next step.

tert-butyl (amino(6-(4-(4-cyanophenyl)-5-hydroxy-3-methyl-1H-pyrazol-1-yl)pyridin-3-yl)(oxo)-$\lambda^6$-sulfaneylidene)carbamate

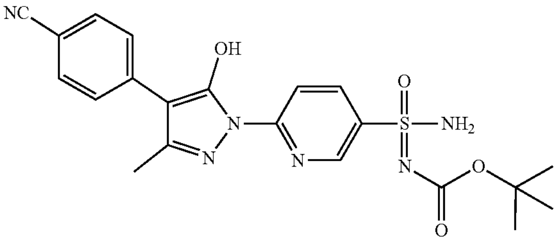 [SMILES: Cc1nn(-c2ccc(S(N)(=O)=NC(=O)OC(C)(C)C)cn2)c(O)c1-c1ccc(C#N)cc1]

To a solution of methyl 2-(4-cyanophenyl)-3-oxobutanoate (73.8 mg, 0.34 mmol) and tert-butyl (amino(6-hydrazineylpyridin-3-yl)(oxo)-$\lambda^6$-sulfaneylidene)carbamate (100 mg, crude) in ethanol (5.0 mL) was added p-toluenesulfonic acid monohydrate (13.3 mg, 0.07 mmol). The mixture was stirred at 90° C. in a sealed tube for 12.0 h and cooled to precipitate solid. The solid was filtered, washed with ethanol and dried to give tert-butyl (amino(6-(4-(4-cyanophenyl)-5-hydroxy-3-methyl-TH-pyrazol-1-yl)pyridin-3-yl)(oxo)-$\lambda^6$-sulfaneylidene)carbamate (50 mg, 0.11 mmol, 32.4% yield) as white solid. LC-MS: m/z=455.0 $(M+H)^+$, retention time 1.74 min (Method A).

6-(4-(4-cyanophenyl)-5-hydroxy-3-methyl-TH-pyrazol-1-yl)pyridine-3-sulfonimidamide

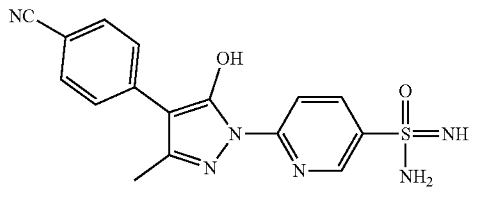 [SMILES: Cc1nn(-c2ccc(S(=N)(N)=O)cn2)c(O)c1-c1ccc(C#N)cc1]

To a solution of (4-(4-cyanophenyl)-5-hydroxy-3-methyl-TH-pyrazol-1-yl)pyridin-3-yl)(oxo)-λ$^6$-sulfaneylidene)carbamate (50 mg, 0.11 mmol) in dichloromethane (5.0 mL) was added trifluoroacetic acid (5.0 mL). The mixture was stirred at 40° C. for 2.0 h and concentrated. The residue was purified by reverse prep-HPLC to give 6-(4-(4-cyanophenyl)-5-hydroxy-3-methyl-TH-pyrazol-1-yl)pyridine-3-sulfonimidamide (4.0 mg, 0.011 mmol, 10.3% yield) as white solid. LC-MS: m/z=355.0 (M+H)$^+$, retention time 3.11 min (Method A). $^1$HNMR (400 MHz, DMSO-d$_6$) δ 8.93 (s, 1H), 8.22-8.33 (m, 3H), 7.97-7.98 (d, J=5.5 Hz, 2H), 7.53-7.55 (d, J=5.8 Hz, 2H), 3.82-4.61 (s, 3H), 2.34 (s, 3H).

Example 25: Preparation of Compound 25

Tert-butyl ((6-chloropyridin-3-yl)(dimethylamino)(oxo)-λ$^6$-sulfaneylidene)carbamate

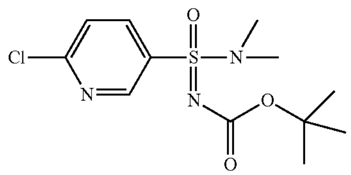 [SMILES: CN(C)S(=O)(=NC(=O)OC(C)(C)C)c1ccc(Cl)nc1]

To a solution of tert-butyl ((6-chloropyridin-3-yl)sulfinyl) carbamate (Intermediate for Example 24) (1.0 g, 3.82 mmol) in acetonitrile (20.0 mL) was added N-chlorosuccinimide (6.10 g, 4.58 mmol). The mixture was stirred at room temperature for 1.0 h and dimethylamine solution (5.0 mL, 2M in tetrahydrofuran) was added dropwise. The mixture was stirred at room temperature overnight. The reaction was concentrated to give dryness. The residue was purified by flash chromatography (petroleum ether/ethyl acetate=1/1) to obtain tert-butyl ((6-chloropyridin-3-yl)(dimethylamino)(oxo)-λ$^6$-sulfaneylidene)carbamate (800 mg, 2.51 mmol, 65.7% yield) as white solid. LC-MS: m/z=320.1 (M+H)$^+$, retention time 1.87 min (Method A).

tert-butyl ((dimethylamino)(6-hydrazineylpyridin-3-yl)(oxo)-λ$^6$-sulfaneylidene)carbamate

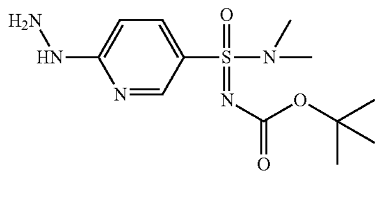 [SMILES: CN(C)S(=O)(=NC(=O)OC(C)(C)C)c1ccc(NN)nc1]

To a solution of tert-butyl ((6-chloropyridin-3-yl)(dimethylamino)(oxo)-λ$^6$-sulfaneylidene)carbamate (800 mg, 2.51 mmol) in ethanol (8.0 mL) was added hydrazine hydrate (740 mg, 12.6 mmol, 85% in water). The mixture was stirred at 85° C. overnight. The mixture was cooled and concentrated to give dryness. The crude tert-butyl ((dimethylamino)(6-hydrazineylpyridin-3-yl)(oxo)-λ$^6$-sulfaneylidene) carbamate (600 mg, 1.90 mmol, 75.9%) was obtained as yellow syrup. LC-MS: m/z=316.0 (M+H)$^+$, retention time 1.68 min (Method A). The crude product was used to the next step.

tert-butyl ((6-(4-(4-cyanophenyl)-5-hydroxy-3-methyl-1H-pyrazol-1-yl)pyridin-3-yl)(dimethylamino)(oxo)-λ$^6$-sulfaneylidene)carbamate

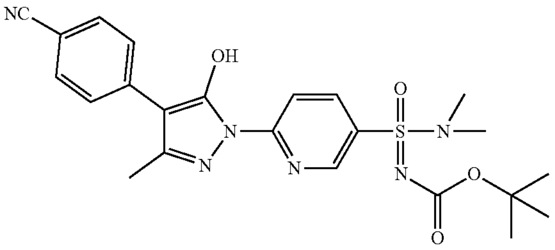

To a solution of methyl 2-(4-cyanophenyl)-3-oxobutanoate (412.3 mg, 1.90 mmol) and tert-butyl ((dimethylamino)(6-hydrazineylpyridin-3-yl)(oxo)-λ$^6$-sulfaneylidene)carbamate (600 mg, 1.90 mmol) in ethanol (10.0 mL) was added p-toluenesulfonic acid monohydrate (72.2 mg, 0.38 mmol). The mixture was stirred at 90° C. in a sealed tube for 12.0 h and cooled to precipitate solid. The solid was filtered, washed with ethanol and dried to give tert-butyl ((6-(4-(4-cyanophenyl)-5-hydroxy-3-methyl-1H-pyrazol-1-yl)pyridin-3-yl)(dimethylamino)(oxo)-λ$^6$-sulfaneylidene)-carbamate (400 mg, 0.83 mmol, 43.7% yield) as white solid. LC-MS: m/z=483.0 (M+H)$^+$, retention time 2.08 min (Method A).

6-(4-(4-cyanophenyl)-5-hydroxy-3-methyl-1H-pyrazol-1-yl)-N,N-dimethylpyridine-3-sulfonimidamide

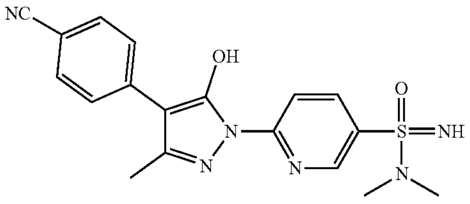 [SMILES: Cc1nn(-c2ccc(S(=N)(=O)N(C)C)cn2)c(O)c1-c1ccc(C#N)cc1]

To a solution of tert-butyl ((6-(4-(4-cyanophenyl)-5-hydroxy-3-methyl-1H-pyrazol-1-yl)pyridin-3-yl)(dimethylamino)(oxo)-λ$^6$-sulfaneylidene)carbamate (400 mg, 0.83 mmol) in dichloromethane (10.0 mL) was added trifluoroacetic acid (10.0 mL). The mixture was stirred at 40° C. for 2.0 h and concentrated. The residue was triturated with ethyl acetate and filtered to afford 6-(4-(4-cyanophenyl)-5-hydroxy-3-methyl-1H-pyrazol-1-yl)-N,N-dimethylpyridine-3-sulfonimidamide (170 mg, 0.45 mmol, 53.6% yield) as yellow solid. LC-MS: m/z=383.0 (M+H)$^+$, retention time 4.13 min (Method A). $^1$HNMR (400 MHz, DMSO-d$_6$) δ 13.16 (s, 1H), 8.77 (s, 1H), 8.66 (s, 1H), 8.30-8.32 (d, J=7.0 Hz, 1H), 7.89-7.91 (d, J=8.7 Hz, 2H), 7.81-7.83 (d, J=8.7 Hz, 2H), 2.62 (s, 6H), 2.49 (s, 3H).

Example 26: Preparation of Compound 26 tert-butyl ((6-chloropyridin-3-yl)(methylamino)(oxo)-$\lambda^6$-sulfaneylidene)carbamate

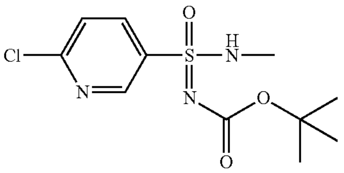 [SMILES: CNS(=O)(=NC(=O)OC(C)(C)C)c1ccc(Cl)nc1]

To a solution of tert-butyl ((6-chloropyridin-3-yl)sulfinyl) carbamate (Intermediate for Example 24) (500 mg, 1.81 mmol) in acetonitrile (10.0 mL) was added N-chlorosuccinimide (480 mg, 3.62 mmol). The mixture was stirred at room temperature for 1.0 h and methylamine solution (2.0 mL, 2M in tetrahydrofuran) was added dropwise. The mixture was stirred at room temperature overnight. The reaction was concentrated to give dryness. The residue was purified by flash chromatography (petroleum ether/ethyl acetate=1/1) to obtain tert-butyl ((6-chloropyridin-3-yl)(methylamino)(oxo)-$\lambda^6$-sulfaneylidene)carbamate (300 mg, 0.98 mmol, 54.3% yield) as white solid. LC-MS: m/z=305.8.0 $(M+H)^+$, retention time 1.73 min (Method A).

tert-butyl ((6-hydrazineylpyridin-3-yl)(methylamino)(oxo)-$\lambda^6$-sulfaneylidene)carbamate

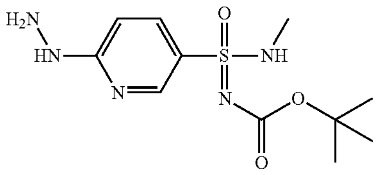 [SMILES: CNS(=O)(=NC(=O)OC(C)(C)C)c1ccc(NN)nc1]

To a solution of tert-butyl ((6-chloropyridin-3-yl)(methylamino)(oxo)-$\lambda^6$-sulfaneylidene)carbamate (300 mg, 0.98 mmol) in ethanol (5.0 mL) was added hydrazine hydrate (287 mg, 4.9 mmol, 85% in water). The mixture was stirred at 85° C. overnight. The mixture was cooled and concentrated to give dryness. The crude tert-butyl ((6-hydrazineylpyridin-3-yl)(methylamino)(oxo)-$\lambda^6$-sulfaneylidene)carbamate (300 mg, crude) was obtained as yellow syrup. LC-MS: m/z=302.0 $(M+H)^+$, retention time 1.3 min (Method A). The crude product was used to the next step.

tert-butyl ((6-(4-(4-cyanophenyl)-5-hydroxy-3-methyl-TH-pyrazol-1-yl)pyridin-3-yl)(methylamino)(oxo)-$\lambda^6$-sulfaneylidene)carbamate

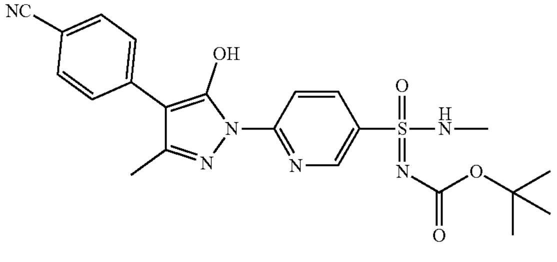 [SMILES: CNS(=O)(=NC(=O)OC(C)(C)C)c1ccc(-n2nc(C)c(-c3ccc(C#N)cc3)c2O)nc1]

To a solution of methyl 2-(4-cyanophenyl)-3-oxobutanoate (212 mg, 0.98 mmol) and tert-butyl ((6-hydrazineylpyridin-3-yl)(methylamino)(oxo)-$\lambda^6$-sulfaneylidene)carbamate (300 mg, crude) in ethanol (5.0 mL) was added p-toluenesulfonic acid monohydrate (38 mg, 0.20 mmol). The mixture was stirred at 90° C. in a sealed tube for 12.0 h and cooled to precipitate solid. The solid was filtered, washed with ethanol and dried to give tert-butyl ((6-(4-(4-cyanophenyl)-5-hydroxy-3-methyl-1H-pyrazol-1-yl)pyridin-3-yl)(methylamino)(oxo)-$\lambda^6$-sulfaneylidene)carbamate (50 mg, 0.11 mmol, 10.9% yield) as yellow solid. LC-MS: m/z=469.0 $(M+H)^+$, retention time 1.80 min (Method A).

6-(4-(4-cyanophenyl)-5-hydroxy-3-methyl-1H-pyrazol-1-yl)-N-methylpyridine-3-sulfonimidamide

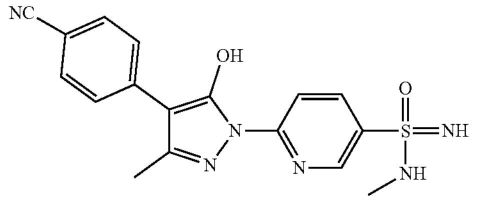 [SMILES: CNS(=N)(=O)c1ccc(-n2nc(C)c(-c3ccc(C#N)cc3)c2O)nc1]

To a solution of tert-butyl ((6-(4-(4-cyanophenyl)-5-hydroxy-3-methyl-1H-pyrazol-1-yl)pyridin-3-yl)(methylamino)(oxo)-$\lambda^6$-sulfaneylidene)carbamate (50 mg, 0.11 mmol) in dichloromethane (5.0 mL) was added trifluoroacetic acid (5.0 mL). The mixture was stirred at 40° C. for 2.0 h and concentrated. The residue was purified by reverse prep-HPLC to afford 6-(4-(4-cyanophenyl)-5-hydroxy-3-methyl-1H-pyrazol-1-yl)-N-methylpyridine-3-sulfonimidamide (Formate salt) (13.2 mg, 0.04 mmol, 32.6% yield) as yellow solid. LC-MS: m/z=369.0 $(M+H)^+$, retention time 3.37 min (Method A). $^1$HNMR (400 MHz, DMSO-$d_6$) δ 8.81 (s, 1H), 8.52 (s, 1H), 8.15 (s, 2H), 7.95-7.97 (d, J=7.2 Hz, 2H), 7.57-7.59 (d, J=7.3 Hz, 2H), 2.43 (s, 3H), 2.37 (s, 3H).

Example 27: Preparation of Compound 27

6-(4-(4-cyanophenyl)-5-hydroxy-3-methyl-1H-pyrazol-1-yl)-N-(methylsulfonyl)nicotinamide

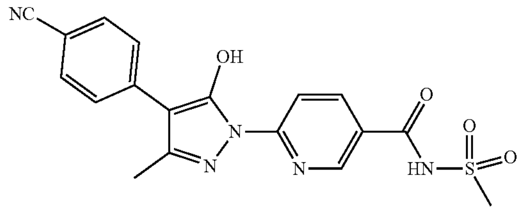 [SMILES: Cc1nn(-c2ccc(C(=O)NS(C)(=O)=O)cn2)c(O)c1-c1ccc(C#N)cc1]

A mixture of 6-(4-(4-cyanophenyl)-5-hydroxy-3-methyl-1H-pyrazol-1-yl)nicotinic acid (Intermediate for Example 10) (220.0 mg, 0.69 mmol), methanesulfonamide (72.1 mg, 0.76 mmol), benzotriazole-1-yl-oxytripyrrolidinophosphonium hexafluorophosphate (359 mg, 0.69 mmol) and triethylamine (140 mg, 1.37 mmol) in dichloromethane (10.0 mL) was stirred at room temperature overnight. The reaction was quenched with water and extracted with dichloromethane. The organic layer was separated, washed with brine, dried over sodium sulfate and concentrated under reduced pressure. The resulting residue was purified by reverse prep-HPLC to afford 6-(4-(4-cyanophenyl)-5-hydroxy-3-methyl-1H-pyrazol-1-yl)-N-(methylsulfonyl)nicotinamide (Formate salt) (130.8 mg, 0.30 mmol, 42.8% yield) as white solid. LC-MS: m/z=398.1 $(M+H)^+$, retention time 3.58 min (Method A). $^1$HNMR (400 MHz, DMSO-$d_6$) δ 8.98 (s, 1H), 8.56 (s, 1H), 8.46-8.44 (m, 1H), 7.90-7.88 (m, 2H), 7.82-7.80 (m, 2H), 3.39 (s, 3H), 2.50 (s, 3H).

Example 28: Preparation of Compound 28 tert-butyl 6-(4-(4-chlorophenyl)-5-hydroxy-3-methyl-1H-pyrazol-1-yl)nicotinate

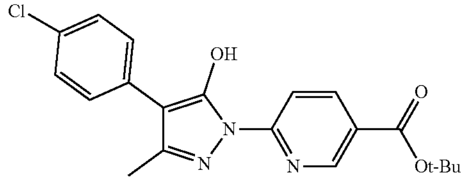 [SMILES: Cc1nn(-c2ccc(C(=O)OC(C)(C)C)cn2)c(O)c1-c1ccc(Cl)cc1]

A solution of ethyl 2-(4-chlorophenyl)-3-oxobutanoate (Intermediate for Example 1) (200 mg, 0.83 mmol) and tert-butyl 6-hydrazineylnicotinate (Intermediate for Example 10) (173 mg, 0.83 mmol) in acetic acid (5.0 mL) was stirred at 120° C. for 1.0 h and concentrated to give dryness. The residue was purified by flash chromatography (methanol/dichloromethane=1/10) to afford tert-butyl 6-(4-(4-chlorophenyl)-5-hydroxy-3-methyl-1H-pyrazol-1-yl) nicotinate (220 mg, 0.57 mmol, 68.8% yield) as yellow solid. LC-MS: m/z=386.1 $(M+H)^+$, retention time 2.41 min (Method A).

6-(4-(4-chlorophenyl)-5-hydroxy-3-methyl-1H-pyrazol-1-yl)nicotinic acid

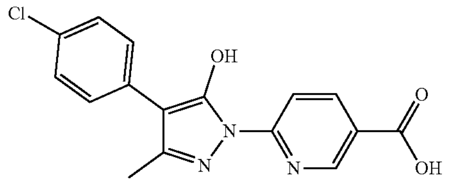 [SMILES: Cc1nn(-c2ccc(C(=O)O)cn2)c(O)c1-c1ccc(Cl)cc1]

To a solution of tert-butyl 6-(4-(4-chlorophenyl)-5-hydroxy-3-methyl-1H-pyrazol-1-yl)nicotinate (220 mg, 0.57 mmol) in dichloromethane (10.0 mL) was added trifluoroacetic acid (5.0 mL). The mixture was stirred at 40° C. for 2.0 h and concentrated. The residue was triturated with ethyl acetate and filtered to afford 6-(4-(4-chlorophenyl)-5-hydroxy-3-methyl-1H-pyrazol-1-yl)nicotinic acid (150 mg, 0.46 mmol, 80% yield) as yellow solid. LC-MS: m/z=330.1 $(M+H)^+$, retention time 1.94 min (Method A).

6-(4-(4-chlorophenyl)-5-hydroxy-3-methyl-1H-pyrazol-1-yl)-N-(methylsulfonyl)nicotinamide

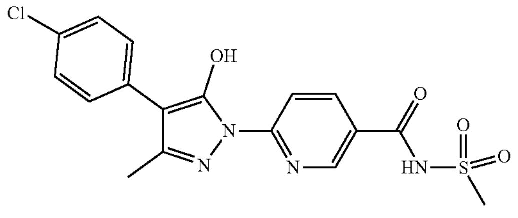 [SMILES: Cc1nn(-c2ccc(C(=O)NS(C)(=O)=O)cn2)c(O)c1-c1ccc(Cl)cc1]

A mixture of 6-(4-(4-chlorophenyl)-5-hydroxy-3-methyl-1H-pyrazol-1-yl)nicotinic acid (200 mg, 0.61 mmol), methanesulfonamide (69 mg, 0.73 mmol), benzotriazole-1-yl-oxytripyrrolidinophosphonium hexafluorophosphate (319 mg, 0.61 mmol) and triethylamine (308 mg, 3.06 mmol) in dichloromethane (5.0 mL) was stirred at room temperature overnight. The reaction was quenched with water and extracted with dichloromethane. The organic layer was separated, washed with brine, dried over sodium sulfate and concentrated under reduced pressure. The resulting residue was purified by reverse prep-HPLC to afford 6-(4-(4-chlorophenyl)-5-hydroxy-3-methyl-1H-pyrazol-1-yl)-N-(methylsulfonyl)nicotinamide (172.6 mg, 0.43 mmol, 70.5% yield) as white solid. LC-MS: m/z=407.1 $(M+H)^+$, retention time 4.55 min (Method A). $^1$HNMR (400 MHz, DMSO-$d_6$) δ 12.77-12.75 (m, 2H), 8.98 (s, 1H), 8.60-8.43 (m, 3H), 7.67-7.65 (m, 2H), 7.45-7.43 (m, 2H), 3.41 (s, 3H), 2.42 (s, 3H).

Example 29: Preparation of Compound 29

6-hydrazineylpyridine-3-sulfonamide

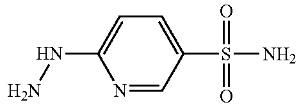 [SMILES: NNc1ccc(S(N)(=O)=O)cn1]

To a solution of 6-chloropyridine-3-sulfonamide (1.63 g, 8.5 mmol) in ethanol (5.0 mL) was added hydrazine hydrate (5.0 mL, 85% in water). The mixture was stirred at 100° C. for 4.0 h in a sealed tube. The mixture was cooled and concentrated to give dryness. The residue was partitioned between ethyl acetate and water. The organic phase was washed with brine, dried over sodium sulfate and concentrated. The residue was triturated with petroleum ether and filtered to afford 6-hydrazineylpyridine-3-sulfonamide (600 mg, 3.20 mmol, 37.7% yield) as yellow solid. LC-MS: m/z=189.0 $(M+H)^+$, retention time 0.32 min (Method A).

6-(4-(4-cyanophenyl)-5-hydroxy-3-methyl-1H-pyrazol-1-yl)pyridine-3-sulfonamide

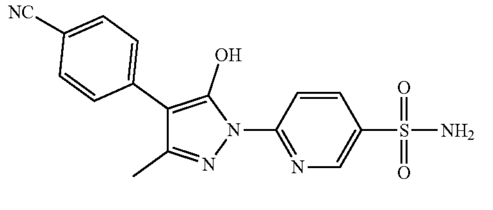 [SMILES: Cc1nn(-c2ccc(S(N)(=O)=O)cn2)c(O)c1-c1ccc(C#N)cc1]

A solution of methyl 2-(4-cyanophenyl)-3-oxobutanoate (500 mg, 2.30 mmol) and 6-hydrazineylpyridine-3-sulfonamide (432 mg, 2.30 mmol) (Intermediate for Example 11) in acetic acid (5.0 mL) was stirred at 120° C. for 1.0 h and concentrated to give dryness. The residue was triturated with ethyl acetate and filtered to afford 6-(4-(4-cyanophenyl)-5-hydroxy-3-methyl-1H-pyrazol-1-yl)pyridine-3-sulfonamide (450 mg, 1.27 mmol, 55.1% yield) as yellow solid. LC-MS: m/z=356.0 $(M+H)^+$, retention time 1.70 min (Method A).

6-(4-(4-Cyanophenyl)-5-methoxy-3-methyl-1H-pyrazol-1-yl)pyridine-3-sulfonamide & 6-(4-(4-Cyanophenyl)-2,3-dimethyl-5-oxo-2,5-dihydro-1H-pyrazol-1-yl)pyridine-3-sulfonamide

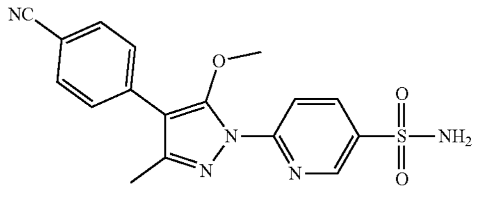

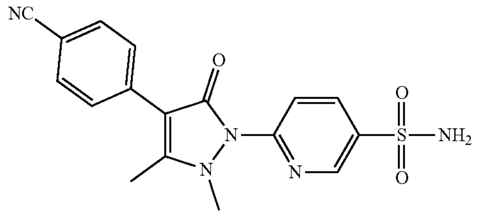

To a solution of 6-(4-(4-cyanophenyl)-5-hydroxy-3-methyl-1H-pyrazol-1-yl)pyridine-3-sulfonamide (450 mg, 1.27 mmol) in dichloromethane/methanol (10.0 mL/1.0 mL) was added (diazomethyl)trimethylsilane (0.76 mL, 1.52 mmol, 2M in hexane). The mixture was stirred at 25° C. overnight and concentrated to give dryness. The residue was purified by flash chromatography (dichloromethane/methanol=100/2) to obtain two isomers of 6-(4-(4-Cyanophenyl)-5-methoxy-3-methyl-1H-pyrazol-1-yl)pyridine-3-sulfonamide and 6-(4-(4-Cyanophenyl)-2,3-dimethyl-5-oxo-2,5-dihydro-1H-pyrazol-1-yl)pyridine-3-sulfonamide (234 mg, 0.63 mmol, 50% yield) as yellow solid. LC-MS: m/z=370.0 $[M+H]^+$, retention time 1.80 min (Method A). The two isomers were used directly to the next step without separation.

N-((6-(4-(4-cyanophenyl)-5-methoxy-3-methyl-1H-pyrazol-1-yl)pyridin-3-yl)sulfonyl)acetamide & N-((6-(4-(4-cyanophenyl)-2,3-dimethyl-5-oxo-2,5-dihydro-1H-pyrazol-1-yl)pyridin-3-yl)sulfonyl)acetamide

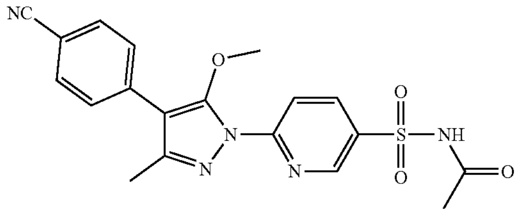

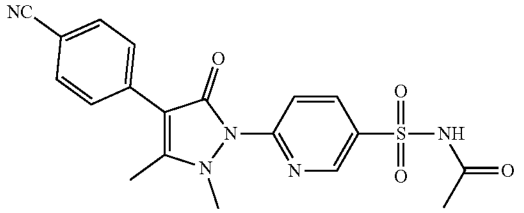

To a solution of 6-(4-(4-cyanophenyl)-5-methoxy-3-methyl-1H-pyrazol-1-yl)pyridine-3-sulfonamide and 6-(4-(4-cyanophenyl)-2,3-dimethyl-5-oxo-2,5-dihydro-1H-pyrazol-1-yl)pyridine-3-sulfonamide (234 mg, 0.63 mmol) in anhydrous tetrahydrofuran (10.0 mL) were added triethylamine (127 mg, 1.26 mmol) and acetyl chloride (60 mg, 0.76 mmol) at 0° C. The mixture was stirred at room temperature overnight and concentrated to give dryness. The residue was purified by flash chromatography (dichloromethane/methanol=20/1) to obtain two isomers of N-((6-(4-(4-cyanophenyl)-5-methoxy-3-methyl-1H-pyrazol-1-yl)pyridin-3-yl)sulfonyl)-acetamide and N-((6-(4-(4-cyanophenyl)-2,3-dimethyl-5-oxo-2,5-dihydro-1H-pyrazol-1-yl)pyridin-3-yl)sulfonyl)acetamide (200 mg, 0.49 mmol, 77.2% yield) as yellow solid. LC-MS: m/z=412.0 $[M+H]^+$, retention time 1.86 min (Method A). The two isomers were used to the next step without separation.

N-((6-(4-(4-cyanophenyl)-5-hydroxy-3-methyl-1H-pyrazol-1-yl)pyridin-3-yl)sulfonyl)acetamide

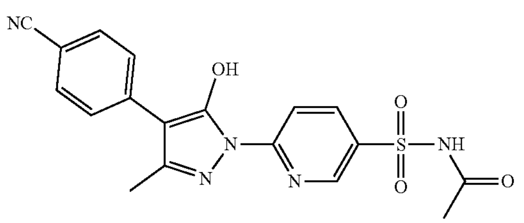 [SMILES: CC(=O)NS(=O)(=O)c1ccc(-n2nc(C)c(-c3ccc(C#N)cc3)c2O)nc1]

To a solution of N-((6-(4-(4-cyanophenyl)-5-methoxy-3-methyl-1H-pyrazol-1-yl)pyridin-3-yl)sulfonyl)acetamide and N-((6-(4-(4-cyanophenyl)-2,3-dimethyl-5-oxo-2,5-dihydro-1H-pyrazol-1-yl)pyridin-3-yl)sulfonyl)acetamide (200 mg, 0.49 mmol) in N,N-dimethylformamide (10.0 mL) was added lithium chloride (206 mg, 4.9 mmol). The mixture was stirred at 60° C. overnight. The solution was diluted with ethyl acetate and water. The organic layer was washed with brine, dried over sodium sulfate and evaporated to give dryness. The residue was purified by reverse prep-HPLC to give N-((6-(4-(4-cyanophenyl)-5-hydroxy-3-methyl-1H-pyrazol-1-yl)pyridin-3-yl)sulfonyl) acetamide (Formate salt) (29.8 mg, 0.07 mmol, 13.7% yield) as white solid. LC-MS: m/z=398.1 $(M+H)^+$, retention time 3.97 min (Method A). $^1$HNMR (400 MHz, DMSO-$d_6$) δ 12.72 (s, 2H), 8.89 (d, J=1.0 Hz, 1H), 8.63 (d, J=4.6 Hz, 1H), 8.38-8.35 (m, 1H), 8.14 (s, 1H), 7.92-7.90 (m, 2H), 7.80-7.78 (m, 2H), 2.48 (s, 3H), 1.93 (s, 3H).

Example 30: Preparation of Compound 30

6-(4-(4-chlorophenyl)-5-hydroxy-3-methyl-1H-pyrazol-1-yl)pyridine-3-sulfonamide

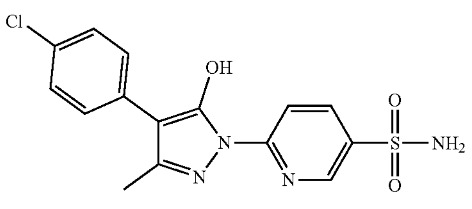 [SMILES: Cc1nn(-c2ccc(S(N)(=O)=O)cn2)c(O)c1-c1ccc(Cl)cc1]

A solution of ethyl 2-(4-chlorophenyl)-3-oxobutanoate (600 mg, 2.5 mmol) (Intermediate for Example 1) and 6-hydrazineylpyridine-3-sulfonamide (Intermediate for Example 11) (470 mg, 2.5 mmol) in acetic acid (8.0 mL) was stirred at 120° C. for 1.0 h and concentrated to give dryness. The residue was triturated with ethyl acetate and filtered to afford 6-(4-(4-chlorophenyl)-5-hydroxy-3-methyl-1H-pyrazol-1-yl)pyridine-3-sulfonamide (610 mg, 1.67 mmol, 67.03% yield) as yellow solid. LC-MS: m/z=365.0 $(M+H)^+$, retention time 1.89 min (Method A).

6-(4-(4-chlorophenyl)-5-methoxy-3-methyl-1H-pyrazol-1-yl)pyridine-3-sulfonamide & 6-(4-(4-Chlorophenyl)-2,3-dimethyl-5-oxo-2,5-dihydro-1H-pyrazol-1-yl)pyridine-3-sulfonamide

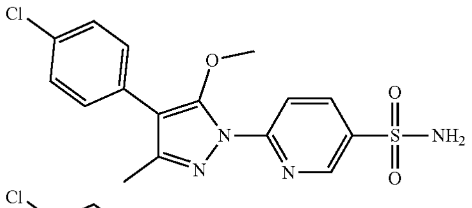

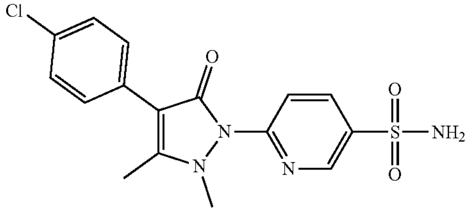

To a solution of 6-(4-(4-chlorophenyl)-5-hydroxy-3-methyl-1H-pyrazol-1-yl)pyridine-3-sulfonamide (610 mg, 1.67 mmol) in dichloromethane/methanol (10.0 mL/1.0 mL) was added (diazomethyl)trimethylsilane (1.0 mL, 2.0 mmol, 2M in hexane). The mixture was stirred at 25° C. overnight and concentrated to give dryness. The residue was purified by flash chromatography (dichloromethane/methanol=100/2) to obtain two isomers of 6-(4-(4-chlorophenyl)-5-methoxy-3-methyl-1H-pyrazol-1-yl)pyridine-3-sulfonamide and 6-(4-(4-chlorophenyl)-2,3-dimethyl-5-oxo-2,5-dihydro-1H-pyrazol-1-yl)pyridine-3-sulfonamide (550 mg, 1.46 mmol, 87.1% yield) as yellow solid. LC-MS: m/z=379.0 $[M+H]^+$, retention time 1.98 min (Method A). The two isomers were used directly to the next step without separation.

N-((6-(4-(4-chlorophenyl)-5-methoxy-3-methyl-1H-pyrazol-1-yl)pyridin-3-yl)sulfonyl)acetamide & N-((6-(4-(4-chlorophenyl)-2,3-dimethyl-5-oxo-2,5-dihydro-1H-pyrazol-1-yl)pyridin-3-yl)sulfonyl)acetamide

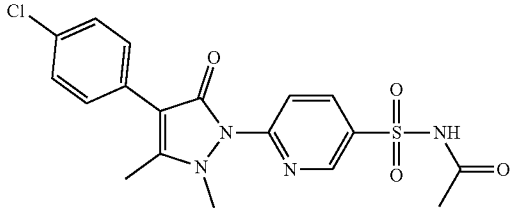

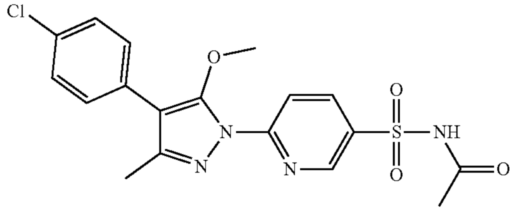

To a solution of 6-(4-(4-chlorophenyl)-5-methoxy-3-methyl-1H-pyrazol-1-yl)pyridine-3-sulfonamide and 6-(4-(4-chlorophenyl)-2,3-dimethyl-5-oxo-2,5-dihydro-1H-pyrazol-1-yl)pyridine-3-sulfonamide (550 mg, 1.46 mmol) in anhydrous tetrahydrofuran (10.0 mL) were added triethylamine (295 mg, 2.92 mmol) and acetyl chloride (136 mg, 1.75 mmol) at 0° C. The mixture was stirred at room temperature overnight and concentrated to give dryness. The residue was purified by flash chromatography (dichloromethane/methanol=20/1) to obtain two isomers of N-((6-(4-(4-chlorophenyl)-5-methoxy-3-methyl-1H-pyrazol-1-yl)pyridin-3-yl)sulfonyl)acetamide and N-((6-(4-(4-chlorophenyl)-2,3-dimethyl-5-oxo-2,5-dihydro-1H-pyrazol-1-yl)pyridin-3-yl)sulfonyl)acetamide (500 mg, 1.19 mmol, 81.5% yield) as yellow solid. LC-MS: m/z=421.0 $[M+H]^+$, retention time 2.05 min (Method A). The two isomers were used to the next step without separation.

N-((6-(4-(4-chlorophenyl)-5-hydroxy-3-methyl-1H-pyrazol-1-yl)pyridin-3-yl)sulfonyl)acetamide

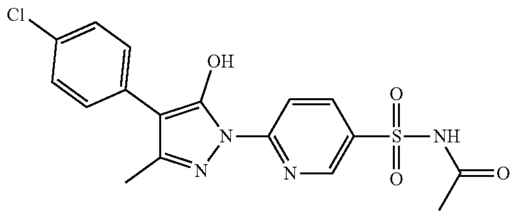 [SMILES: CC(=O)NS(=O)(=O)c1ccc(-n2nc(C)c(-c3ccc(Cl)cc3)c2O)nc1]

To a solution of N-((6-(4-(4-chlorophenyl)-5-methoxy-3-methyl-1H-pyrazol-1-yl)pyridin-3-yl)sulfonyl)acetamide and N-((6-(4-(4-chlorophenyl)-2,3-dimethyl-5-oxo-2,5-dihydro-1H-pyrazol-1-yl)pyridin-3-yl)sulfonyl)acetamide (500 mg, 1.19 mmol) in N,N-dimethylformamide (10.0 mL) was added lithium chloride (500 mg, 11.9 mmol). The mixture was stirred at 60° C. overnight. The solution was diluted with ethyl acetate and water. The organic layer was washed with brine, dried over sodium sulfate and evaporated to give dryness. The residue was purified by reverse prep-HPLC to give N-((6-(4-(4-chlorophenyl)-5-hydroxy-3-methyl-1H-pyrazol-1-yl)pyridin-3-yl)sulfonyl)acetamide (Formate salt) (78.9 mg, 0.17 mmol, 14.7% yield) as white solid. LC-MS: m/z=407.0 $(M+H)^+$, retention time 4.62 min (Method A). $^1$HNMR (400 MHz, DMSO-$d_6$) δ 12.61 (s, 2H), 8.87 (d, J=1.0 Hz, 1H), 8.62 (d, J=4.2 Hz, 1H), 8.38-8.35 (m, 1H), 8.14 (s, 1H), 7.68-7.66 (m, 2H), 7.46-7.44 (m, 2H), 2.42 (s, 3H), 1.91 (s, 3H).

Example 31: Preparation of Compound 31

4-(5-hydroxy-1-(5-isocyanatopyridin-2-yl)-3-methyl-1H-pyrazol-4-yl)benzonitrile

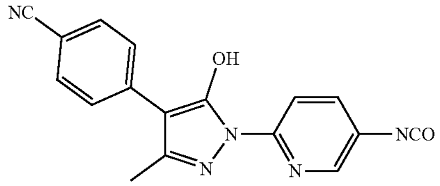

A mixture of 6-(4-(4-cyanophenyl)-5-hydroxy-3-methyl-1H-pyrazol-1-yl)nicotinic acid (Intermediate for Example 10) (150 mg, 0.47 mmol), diphenylphosphonic azide (194 mg, 0.71 mmol) and triethylamine (95 mg, 0.94 mmol) in toluene (5.0 mL) was stirred at 110° C. for 3H. The reaction was diluted with water and extracted with ethyl acetate. The organic layer was separated, washed with brine, dried over sodium sulfate and concentrated under reduced pressure. The crude 4-(5-hydroxy-1-(5-isocyanatopyridin-2-yl)-3-methyl-1H-pyrazol-4-yl)benzonitrile (150 mg, crude) was obtained as yellow syrup. LC-MS: m/z=318.0 $(M+H)^+$, retention time 1.27 min (Method A). The crude product was used to the next step.

N-(6-(4-(4-cyanophenyl)-5-hydroxy-3-methyl-1H-pyrazol-1-yl)pyridin-3-yl)morpholine-4-carboxamide

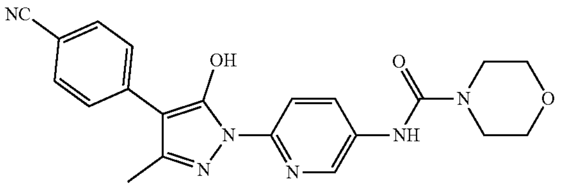 [SMILES: Cc1nn(-c2ccc(NC(=O)N3CCOCC3)cn2)c(O)c1-c1ccc(C#N)cc1]

A mixture of 4-(5-hydroxy-1-(5-isocyanatopyridin-2-yl)-3-methyl-1H-pyrazol-4-yl)benzonitrile (150 mg, crude), morpholine (87 mg, 1.0 mmol) in dichloromethane (5.0 mL) was stirred at room temperature overnight. The reaction was diluted with water and extracted with dichloromethane. The organic layer was separated, washed with brine, dried over sodium sulfate and concentrated under reduced pressure. The residue was purified by reverse prep-HPLC to give N-(6-(4-(4-cyanophenyl)-5-hydroxy-3-methyl-1H-pyrazol-1-yl)pyridin-3-yl)morpholine-4-carboxamide (Formate salt) (13.8 mg, 0.03 mmol, 7.26% yield) as white solid. LC-MS: m/z=405.0 $(M+H)^+$, retention time 3.89 min (Method A). $^1$HNMR (400 MHz, DMSO-$d_6$) δ 8.81 (s, 1H), 8.61 (s, 1H), 8.23 (d, J=0.6 Hz, 1H), 8.15 (s, 1H), 7.99-7.96 (m, 1H), 7.94-7.92 (m, 2H), 7.76-7.74 (m, 2H), 3.64-3.62 (m, 4H), 3.47-3.44 (m, 4H), 2.35 (s, 3H).

Example 32: Preparation of Compound 32 tert-butyl 6-(4-(4-cyanophenyl)-5-methoxy-3-methyl-1H-pyrazol-1-yl)nicotinate

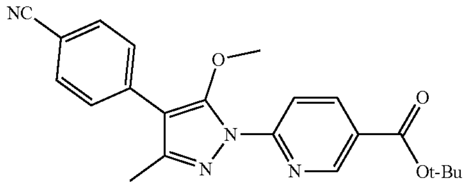 [SMILES: COc1c(-c2ccc(C#N)cc2)c(C)nn1-c1ccc(C(=O)OC(C)(C)C)cn1]

To a solution of tert-butyl 6-(4-(4-cyanophenyl)-5-hydroxy-3-methyl-1H-pyrazol-1-yl)nicotinate (1.0 g, 2.66 mmol) in dichloromethane/methanol (15.0 mL/2.0 mL) was added (diazomethyl)trimethylsilane (2.0 mL, 4.0 mmol, 2M in hexane). The mixture was stirred at 25° C. overnight and concentrated to give dryness. The residue was purified by flash chromatography (petroleum ether/ethyl acetate=3/1) to obtain tert-butyl 6-(4-(4-cyanophenyl)-5-methoxy-3-methyl-1H-pyrazol-1-yl)nicotinate (400 mg, 1.02 mmol, 38.5% yield) as yellow solid. LC-MS: m/z=391.0 $[M+H]^+$, retention time 2.29 min (Method A).

6-(4-(4-Cyanophenyl)-5-methoxy-3-methyl-1H-pyrazol-1-yl)nicotinic acid

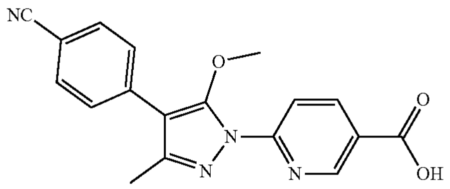 [SMILES: COc1c(-c2ccc(C#N)cc2)c(C)nn1-c1ccc(C(=O)O)cn1]

To a solution of tert-butyl 6-(4-(4-cyanophenyl)-5-methoxy-3-methyl-1H-pyrazol-1-yl)nicotinate (400 mg, 1.19 mmol) in dichloromethane (10.0 mL) was added trifluoroacetic acid (5.0 mL). The mixture was stirred at 40° C. for 2.0 h and concentrated. The residue was triturated with ethyl acetate and filtered to afford 6-(4-(4-cyanophenyl)-5-methoxy-3-methyl-1H-pyrazol-1-yl)nicotinic acid (290 mg, 0.87 mmol, 73.0% yield) as yellow solid. LC-MS: m/z=335.1 $(M+H)^+$, retention time 1.85 min (Method A).

4-(1-(5-isocyanatopyridin-2-yl)-5-methoxy-3-methyl-1H-pyrazol-4-yl)benzonitrile

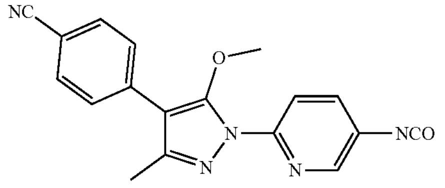

A mixture of 6-(4-(4-cyanophenyl)-5-methoxy-3-methyl-1H-pyrazol-1-yl)nicotinic acid (200 mg, 0.60 mmol), diphenylphosphonic azide (247 mg, 0.90 mmol) and triethylamine (121 mg, 1.2 mmol) in toluene (5.0 mL) was stirred at 110° C. for 3H. The reaction was diluted with water and extracted with ethyl acetate. The organic layer was separated, washed with brine, dried over sodium sulfate and concentrated under reduced pressure. The crude 4-(1-(5-isocyanatopyridin-2-yl)-5-methoxy-3-methyl-1H-pyrazol-4-yl)benzonitrile (200 mg, crude) was obtained as yellow syrup. LC-MS: m/z=332.0 $(M+H)^+$, retention time 1.85 min (Method A). The crude product was used to the next step.

tert-butyl 4-((6-(4-(4-cyanophenyl)-5-methoxy-3-methyl-1H-pyrazol-1-yl)pyridin-3-yl)carbamo-yl)piperazine-1-carboxylate

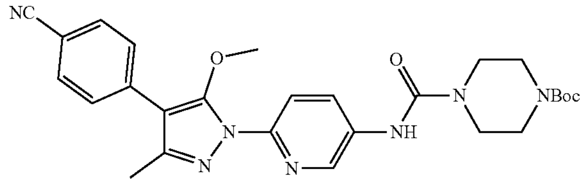 [SMILES: COc1c(-c2ccc(C#N)cc2)c(C)nn1-c1ccc(NC(=O)N2CCN(C(=O)OC(C)(C)C)CC2)cn1]

A mixture of 4-(1-(5-isocyanatopyridin-2-yl)-5-methoxy-3-methyl-1H-pyrazol-4-yl)benzonitrile (200 mg, crude) and tert-butyl piperazine-1-carboxylate (334 mg, 1.8 mmol) in dichloromethane (8.0 mL) was stirred at room temperature overnight. The reaction was diluted with water and extracted with dichloromethane. The organic layer was separated, washed with brine, dried over sodium sulfate and concentrated under reduced pressure. The residue was purified. The residue was purified by flash chromatography (petroleum ether/ethyl acetate=1/1) to obtain tert-butyl 4-((6-(4-(4-cyanophenyl)-5-methoxy-3-methyl-1H-pyrazol-1-yl)pyridin-3-yl)carbamoyl)piperazine-1-carboxylate (150 mg, 0.29 mmol, 48.3% yield) as yellow solid. LC-MS: m/z=517.9 $[M+H]^+$, retention time 1.93 min (Method A).

tert-butyl 4-((6-(4-(4-cyanophenyl)-5-hydroxy-3-methyl-1H-pyrazol-1-yl)pyridin-3-yl)carbamo-yl)piperazine-1-carboxylate

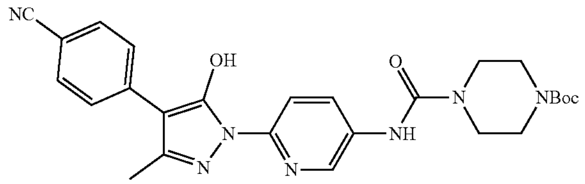 [SMILES: Cc1nn(-c2ccc(NC(=O)N3CCN(C(=O)OC(C)(C)C)CC3)cn2)c(O)c1-c1ccc(C#N)cc1]

To a solution of tert-butyl 4-((6-(4-(4-cyanophenyl)-5-methoxy-3-methyl-1H-pyrazol-1-yl)pyridin-3-yl)carbamoyl)piperazine-1-carboxylate (150 mg, 0.29 mmol) in N,N-dimethylformamide (6.0 mL) was added lithium chloride (121 mg, 2.9 mmol). The mixture was stirred at 60° C. overnight. The solution was diluted with ethyl acetate and water. The organic layer was washed with brine, dried over sodium sulfate and evaporated to give dryness. The residue was purified by reverse Prep-HPLC to give tert-butyl 4-((6-(4-(4-cyanophenyl)-5-hydroxy-3-methyl-1H-pyrazol-1-yl)pyridin-3-yl)carbamoyl)piperazine-1-carboxylate (90 mg, 0.18 mmol, 62.1% yield) as white solid. LC-MS: m/z=504.0 $(M+H)^+$, retention time 2.05 min (Method A).

N-(6-(4-(4-cyanophenyl)-5-hydroxy-3-methyl-1H-pyrazol-1-yl)pyridin-3-yl)piperazine-1-carboxamide hydrochloride

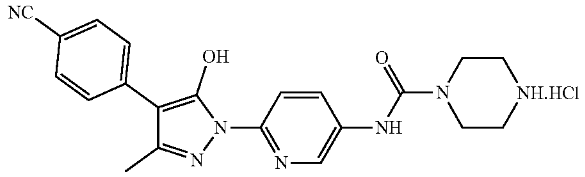

To a mixture of 4-((6-(4-(4-cyanophenyl)-5-hydroxy-3-methyl-1H-pyrazol-1-yl)pyridin-3-yl)carbamoyl)piperazine-1-carboxylate (90 mg, 0.18 mmol) in methanol (10.0 mL) was added hydrochloric acid solution (3.0 mL, 4M in 1,4-dioxane). The mixture was stirred at room temperature for 2.0 h and concentrated. The residue was triturated with diethyl ether and filtered to afford N-(6-(4-(4-cyanophenyl)-5-hydroxy-3-methyl-1H-pyrazol-1-yl)pyridin-3-yl)piperazine-1-carboxamide hydrochloride (61.5 mg, 0.14 mmol, 77.7% yield) as white solid. LC-MS: m/z=404.0 $(M+H)^+$, retention time 2.67 min (Method A). $^1$HNMR (400 MHz, $D_2O$) δ 7.80 (s, 1H), 7.56-7.52 (m, 2H), 7.38-7.32 (m, 4H), 3.62 (s, 4H), 3.21 (s, 4H), 2.18 (s, 3H).

Example 33: Preparation of Compound 33

2-chloro-5-(cyclopropylthio)pyridine

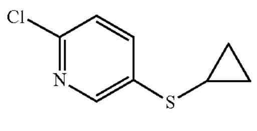 [SMILES: Clc1ccc(SC2CC2)cn1]

A mixture of 6-chloropyridine-3-thiol (Intermediate for Example 24) (350 mg, 2.41 mmol) and cyclopropyl bromide (430 mg, 3.62 mmol) in dimethyl sulfoxide (8.0 mL) was added sodium tert-butoxide (278 mg, 2.89 mmol). The mixture was stirred at 70° C. in a sealed tube overnight. The reaction was diluted with water and extracted with ethyl acetate. The organic layer was separated, washed with brine, dried over sodium sulfate and concentrated under reduced pressure. The residue was purified by flash chromatography (petroleum ether/ethyl acetate=10/1) to afford 2-chloro-5-(cyclopropylthio)pyridine (250 mg, 1.35 mmol, 56% yield) as yellow oil. LC-MS: m/z=186.0 $(M+H)^+$, retention time 1.97 min (Method A).

2-chloro-5-(cyclopropylsulfinyl)pyridine

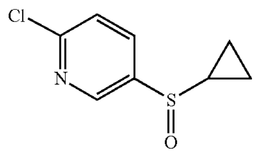 [SMILES: O=S(c1ccc(Cl)nc1)C1CC1]

To a solution of 2-chloro-5-(cyclopropylthio)pyridine (250 mg, 1.35 mmol) in dichloromethane (10.0 mL) was added 3-chloroperoxybenzoic acid (286 mg, 1.42 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-5-(cyclopropylsulfinyl)pyridine (130 mg, 0.65 mmol, 47.9% yield) as white solid. LC-MS: m/z=202.1 $(M+H)^+$, retention time 1.49 min (Method A).

(6-chloropyridin-3-yl)(cyclopropyl)(imino)-$\lambda^6$-sulfanone

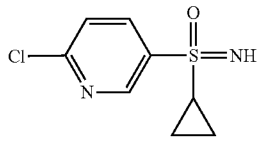 [SMILES: N=S(=O)(c1ccc(Cl)nc1)C1CC1]

To a mixture of 2-chloro-5-(cyclopropylsulfinyl)pyridine (130 mg, 0.65 mmol) and ammonium carbamate (202 mg, 2.6 mmol) in methanol (8.0 mL) was added (diacetoxyiodo) benzene (628 mg, 1.95 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-chloropyridin-3-yl)(cyclopropyl)(imino)-$\lambda^6$-sulfanone (100 mg, 0.46 mmol, 71.2% yield) as yellow solid. LC-MS: m/z=217.1 $(M+H)^+$, retention time 1.45 min (Method A).

cyclopropyl(6-hydrazineylpyridin-3-yl)(imino)-$\lambda^6$-sulfanone

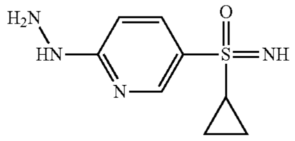 [SMILES: N=S(=O)(c1ccc(NN)nc1)C1CC1]

To a solution of (6-chloropyridin-3-yl)(cyclopropyl)(imino)-$\lambda^6$-sulfanone (100 mg, 0.46 mmol) in ethanol (5.0 mL) was added hydrazine hydrate (280 mg, 4.6 mmol, 85% in water). The mixture was stirred at 90° C. overnight. The mixture was cooled and concentrated to give dryness. The residue was partitioned between ethyl acetate and water. The organic phase was washed with brine, dried over sodium sulfate and concentrated. The crude cyclopropyl(6-hydrazineylpyridin-3-yl)(imino)-$\lambda^6$-sulfanone (90 mg, 0.42 mmol, 92.3% yield) was obtained as yellow syrup. LC-MS: m/z=213.0 $(M+H)^+$, retention time 0.35 min (Method A). The product was directly used to the next step.

4-(1-(5-(cyclopropanesulfonimidoyl)pyridin-2-yl)-5-hydroxy-3-methyl-1H-pyrazol-4-yl)benzonitrile

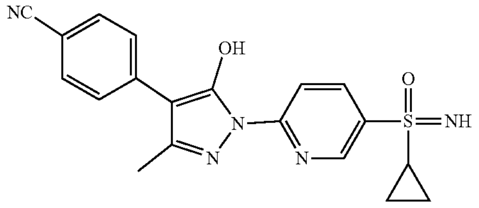 [SMILES: Cc1nn(-c2ccc(S(=N)(=O)C3CC3)cn2)c(O)c1-c1ccc(C#N)cc1]

A mixture of methyl 2-(4-cyanophenyl)-3-oxobutanoate (91 mg, 0.42 mmol) and cyclopropyl(6-hydrazineylpyridin-3-yl)(imino)-$\lambda^6$-sulfanone (90 mg, 0.42 mmol) in acetic acid (8.0 mL) was stirred at 120° C. for 1.0 h and evaporated to give dryness. The residue was purified by reverse prep-HPLC to give 4-(1-(5-(cyclopropanesulfonimidoyl)pyridin-2-yl)-5-hydroxy-3-methyl-1H-pyrazol-4-yl)benzonitrile (Formate salt) (10.6 mg, 0.024 mmol, 5.93% yield) as white solid. LC-MS: m/z=380.0 $(M+H)^+$, retention time 3.66 min (Method A). $^1$HNMR (400 MHz, DMSO-$d_6$) δ 8.82 (s, 1H), 8.57 (s, 1H), 8.24-8.26 (d, J=6.9 Hz, 1H), 8.14 (s, 1H), 7.94-7.96 (d, J=8.6 Hz, 2H), 7.65-7.67 (d, J=7.6 Hz, 2H), 4.44 (s, 1H), 2.71-2.72 (m, 1H), 2.40 (s, 3H), 1.12-1.14 (m, 1H), 0.90-1.00 (m, 3H).

Example 34: Preparation of Compound 34

2-chloro-5-(cyclobutylthio)pyridine

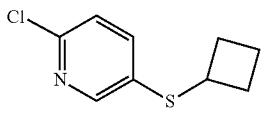 [SMILES: Clc1ccc(SC2CCC2)cn1]

A mixture of 6-chloropyridine-3-thiol (Intermediate for Example 24) (500 mg, 3.45 mmol) and cyclopropyl bromide (615 mg, 5.18 mmol) in dimethyl sulfoxide (10.0 mL) was added sodium tert-butoxide (398 mg, 4.13 mmol). The mixture was stirred at 70° C. in a sealed tube overnight. The reaction was diluted with water and extracted with ethyl acetate. The organic layer was separated, washed with brine, dried over sodium sulfate and concentrated under reduced pressure. The residue was purified by flash chromatography (petroleum ether/ethyl acetate=10/1) to afford 2-chloro-5-(cyclobutylthio)pyridine (400 mg, 2.01 mmol, 58.3% yield) as yellow oil. LC-MS: m/z=200.0 $(M+H)^+$, retention time 2.07 min (Method A).

2-chloro-5-(cyclobutylsulfinyl)pyridine

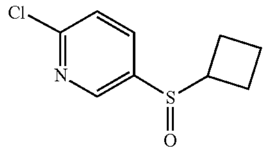 [SMILES: O=S(c1ccc(Cl)nc1)C1CCC1]

To a solution of 2-chloro-5-(cyclobutylthio)pyridine (400 mg, 2.01 mmol) in dichloromethane (10.0 mL) was added 3-chloroperoxybenzoic acid (427 mg, 2.11 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-5-(cyclobutylsulfinyl)pyridine (330 mg, 1.53 mmol, 76.4% yield) as white solid. LC-MS: m/z=216.0 $(M+H)^+$, retention time 1.60 min (Method A).

(6-chloropyridin-3-yl)(cyclobutyl)(imino)-$\lambda^6$-sulfanone

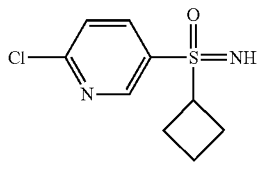 [SMILES: N=S(=O)(c1ccc(Cl)nc1)C1CCC1]

To a mixture of 2-chloro-5-(cyclobutylsulfinyl)pyridine (330 mg, 1.53 mmol) and ammonium carbamate (475 mg, 6.11 mmol) in methanol (12.0 mL) was added (diacetoxyiodo)benzene (1.48 g, 4.58 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-chloropyridin-3-yl)(cyclobutyl)(imino)-$\lambda^6$-sulfanone (250 mg, 1.09 mmol, 71.0% yield) as yellow solid. LC-MS: m/z=231.1 $(M+H)^+$, retention time 1.56 min (Method A).

cyclobutyl (6-hydrazineylpyridin-3-yl)(imino)-$\lambda^6$-sulfanone

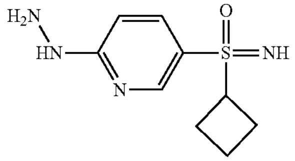 [SMILES: N=S(=O)(c1ccc(NN)nc1)C1CCC1]

To a solution of (6-chloropyridin-3-yl)(cyclobutyl)(imino)-$\lambda^6$-sulfanone (250 mg, 1.09 mmol) in ethanol (5.0 mL) was added hydrazine hydrate (332 mg, 5.45 mmol, 85% in water). The mixture was stirred at 90° C. overnight. The mixture was cooled and concentrated to give dryness. The residue was partitioned between ethyl acetate and water. The organic phase was washed with brine, dried over sodium sulfate and concentrated. The crude cyclobutyl(6-hydrazineylpyridin-3-yl)(imino)-$\lambda^6$-sulfanone (150 mg, 0.66 mmol, 60.9% yield) was obtained as yellow syrup. LC-MS: m/z=227.0 $(M+H)^+$, retention time 0.68 min (Method A). The product was directly used to the next step.

4-(1-(5-(cyclobutanesulfonimidoyl)pyridin-2-yl)-5-hydroxy-3-methyl-1H-pyrazol-4-yl)benzonitrile

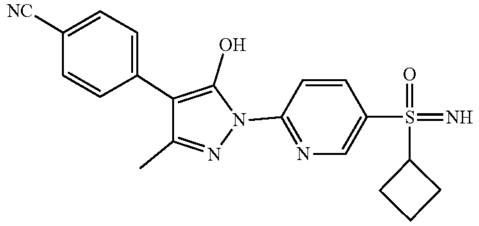 [SMILES: Cc1nn(-c2ccc(S(=N)(=O)C3CCC3)cn2)c(O)c1-c1ccc(C#N)cc1]

A mixture of methyl 2-(4-cyanophenyl)-3-oxobutanoate (143 mg, 0.66 mmol) and cyclobutyl(6-hydrazineylpyridin-3-yl)(imino)-$\lambda^6$-sulfanone (150 mg, 0.66 mmol) in acetic acid (8.0 mL) was stirred at 120° C. for 1.0 h and evaporated to give dryness. The residue was purified by reverse prep-HPLC to give 4-(1-(5-(cyclobutanesulfonimidoyl)pyridin-2-yl)-5-hydroxy-3-methyl-1H-pyrazol-4-yl)benzonitrile (Formate salt) (78 mg, 0.18 mmol, 26.9% yield) as white solid. LC-MS: m/z=394.1.0 $(M+H)^+$, retention time 3.85 min (Method A). $^1$HNMR (400 MHz, DMSO-$d_6$) δ 13.15 (s, 1H), 8.80 (s, 1H), 8.62-8.64 (d, J=9.1 Hz, 1H), 8.30-8.33 (d, J=9.1 Hz, 1H), 8.14 (s, 1H), 7.90-7.92 (d, J=7.8 Hz, 2H), 7.79-7.81 (d, J=7.7 Hz, 2H), 4.49 (s, 1H), 3.99-4.03 (m, 2H), 2.48 (s, 3H), 2.31-2.33 (m, 2H), 2.01-2.12 (m, 2H), 1.80-1.88 (m, 2H).

Example 35: Preparation of Compound 35

2-chloro-5-(cyclopentylthio)pyridine

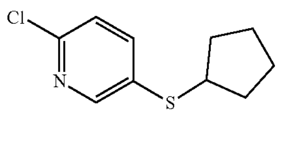 [SMILES: Clc1ccc(SC2CCCC2)cn1]

A mixture of 6-chloropyridine-3-thiol (Intermediate for Example 24) (500 mg, 3.45 mmol) and bromocyclopentane (770 mg, 5.18 mmol) in dimethyl sulfoxide (10.0 mL) was added sodium tert-butoxide (398 mg, 4.13 mmol). The mixture was stirred at 70° C. in a sealed tube overnight. The reaction was diluted with water and extracted with ethyl acetate. The organic layer was separated, washed with brine, dried over sodium sulfate and concentrated under reduced pressure. The residue was purified by flash chromatography (petroleum ether/ethyl acetate=10/1) to afford 2-chloro-5-(cyclopentylthio)pyridine (400 mg, 1.87 mmol, 54.4% yield) as yellow oil. LC-MS: m/z=214.0 $(M+H)^+$, retention time 2.13 min (Method A).

2-chloro-5-(cyclopentylsulfinyl)pyridine

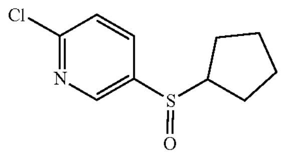 [SMILES: O=S(c1ccc(Cl)nc1)C1CCCC1]

To a solution of 2-chloro-5-(cyclopentylthio)pyridine (400 mg, 1.87 mmol) in dichloromethane (10.0 mL) was added 3-chloroperoxybenzoic acid (454 mg, 2.24 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-5-(cyclopentylsulfinyl)pyridine (350 mg, 1.43 mmol, 76.7% yield) as white solid. LC-MS: m/z=230.0 $(M+H)^+$, retention time 1.74 min (Method A).

(6-chloropyridin-3-yl)(cyclopentyl)(imino)-$\lambda^6$-sulfanone

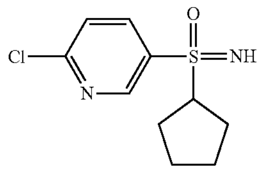 [SMILES: N=S(=O)(c1ccc(Cl)nc1)C1CCCC1]

To a mixture of 2-chloro-5-(cyclopentylsulfinyl)pyridine (350 mg, 1.43 mmol) and ammonium carbamate (446 mg, 5.72 mmol) in methanol (12.0 mL) was added (diacetoxyiodo)benzene (1.39 g, 4.30 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-chloropyridin-3-yl)(cyclopentyl)(imino)-$\lambda^6$-sulfanone (250 mg, 1.02 mmol, 71.6% yield) as yellow solid. LC-MS: m/z=245.1 $(M+H)^+$, retention time 1.59 min (Method A).

cyclopentyl(6-hydrazineylpyridin-3-yl)(imino)-$\lambda^6$-sulfanone

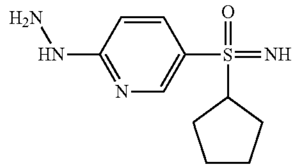 [SMILES: N=S(=O)(c1ccc(NN)nc1)C1CCCC1]

To a solution of (6-chloropyridin-3-yl)(cyclopentyl)(imino)-$\lambda^6$-sulfanone (250 mg, 1.02 mmol) in ethanol (5.0 mL) was added hydrazine hydrate (310 mg, 5.1 mmol, 85% in water). The mixture was stirred at 90° C. overnight. The mixture was cooled and concentrated to give dryness. The residue was partitioned between ethyl acetate and water. The organic phase was washed with brine, dried over sodium sulfate and concentrated. The crude cyclopentyl(6-hydrazineylpyridin-3-yl)(imino)-$\lambda^6$-sulfanone (200 mg, 0.83 mmol, 81.7% yield) was obtained as yellow syrup. LC-MS: m/z=241.0 $(M+H)^+$, retention time 0.96 min (Method A). The crude product was used to the next step.

4-(1-(5-(cyclopentanesulfonimidoyl)pyridin-2-yl)-5-hydroxy-3-methyl-1H-pyrazol-4-yl)benzonitrile

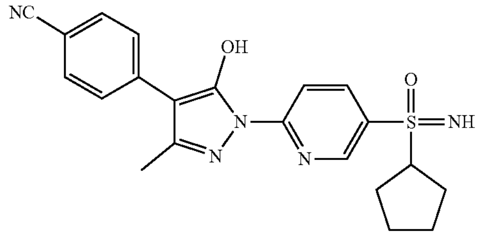 [SMILES: Cc1nn(-c2ccc(S(=N)(=O)C3CCCC3)cn2)c(O)c1-c1ccc(C#N)cc1]

A mixture of methyl 2-(4-cyanophenyl)-3-oxobutanoate (180 mg, 0.83 mmol) and cyclopentyl(6-hydrazineylpyridin-3-yl)(imino)-$\lambda^6$-sulfanone (200 mg, 0.83 mmol) in acetic acid (8.0 mL) was stirred at 120° C. for 1.0 h and evaporated to give dryness. The residue was purified by reverse prep-HPLC to give 4-(1-(5-(cyclopentanesulfonimidoyl)pyridin-2-yl)-5-hydroxy-3-methyl-1H-pyrazol-4-yl)benzonitrile (Formate salt) (118 mg, 0.26 mmol, 31.4% yield) as white solid. LC-MS: m/z=408.0 $(M+H)^+$, retention time 4.07 min (Method A). $^1$HNMR (400 MHz, DMSO-$d_6$) δ 13.15 (s, 1H), 8.83 (s, 1H), 8.63-8.65 (d, J=8.6 Hz, 1H), 8.33-8.36 (d, J=8.6 Hz, 1H), 8.14 (s, 1H), 7.90-7.92 (d, J=8.6 Hz, 2H), 7.78-7.80 (d, J=8.6 Hz, 2H), 4.43 (s, 2H), 3.67-3.71 (m, 1H), 2.48 (m, 3H), 1.75-1.92 (m, 4H), 1.52-1.62 (m, 4H).

Example 36: Preparation of Compound 36

(6-bromo-4-methylpyridin-3-yl)dimethylphosphine oxide

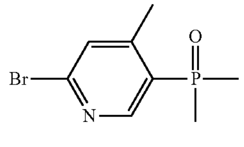

A mixture of 2-bromo-5-iodo-4-methylpyridine (800 mg, 2.69 mmol), dimethylphosphine oxide (314 mg 4.04 mmol), triethylamine (817 mg, 8.07 mmol), 4,5-bis(diphenylphosphino)-9,9-dimethylxanthene (310 mg, 0.54 mmol) and tris (dibenzylideneacetone)dipalladium (492 mg, 0.54 mmol) in 1,4-dioxane (15.0 mL) was stirred at 50° C. overnight under nitrogen. The reaction mixture was filtered with celite, and the filtrate was concentrated under reduced pressure. The obtained residue was purified by flash chromatography (petroleum ether/ethyl acetate=1/1) to afford (6-bromo-4-methylpyridin-3-yl)dimethylphosphine oxide (600 mg, 2.42 mmol, 89.9% yield) as yellow oil. LC-MS: m/z=247.9 $[M+H]^+$, retention time=1.44 min (Method A).

(6-hydrazineyl-4-methylpyridin-3-yl)dimethylphosphine oxide

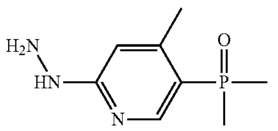

To a solution of (6-bromo-4-methylpyridin-3-yl)dimethylphosphine oxide (600 mg, 2.42 mmol) in ethanol (5.0 mL) was added hydrazine hydrate (760 mg, 12.1 mmol, 85% in water). The mixture was stirred at 90° C. overnight. The mixture was cooled and concentrated to give dryness. The residue was partitioned between ethyl acetate and water. The organic phase was washed with brine, dried over sodium sulfate and concentrated. The crude (6-hydrazineyl-4-methylpyridin-3-yl)dimethylphosphine oxide (600 mg, crude) was obtained as yellow syrup. LC-MS: m/z=200.0 (M+H)+, retention time 0.29 min (Method A).

4-(1-(5-(dimethylphosphoryl)-4-methylpyridin-2-yl)-5-hydroxy-3-methyl-1H-pyrazol-4-yl)benzonitrile

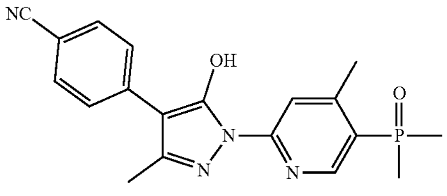 [SMILES: Cc1cc(-n2nc(C)c(-c3ccc(C#N)cc3)c2O)ncc1P(C)(C)=O]

A mixture of methyl 2-(4-cyanophenyl)-3-oxobutanoate (163 mg, 0.75 mmol) and (6-hydrazineyl-4-methylpyridin-3-yl)dimethylphosphine oxide (150 mg, 0.75) in acetic acid (5.0 mL) was stirred at 100° C. for 2.0 h and concentrated. The resulting residue was purified by reverse prep-HPLC to give 4-(1-(5-(dimethylphosphoryl)-4-methylpyridin-2-yl)-5-hydroxy-3-methyl-1H-pyrazol-4-yl)benzonitrile (Formate salt) (20.3 mg, 0.05 mmol, 6.57% yield) as white solid. LC-MS: m/z=367.1 $(M+H)^+$, retention time 3.54 min (Method A). $^1$HNMR (400 MHz, DMSO-$d_6$) δ 8.58-8.56 (m, 1H), 8.34 (s, 1H), 7.91-7.89 (m, 2H), 7.79-7.77 (m, 2H), 2.65 (s, 3H), 2.46 (s, 3H), 1.80-1.77 (m, 6H).

Example 37: Preparation of Compound 37

1-(6-chloro-4-methylpyridin-3-yl)pyrrolidin-2-one

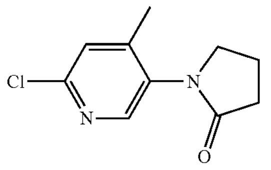

A mixture of 5-bromo-2-chloro-4-methylpyridine (1.0 g, 4.85 mmol), dimethylphosphine oxide (824 mg 9.7 mmol), cesium carbonate (2.62 g, 8.07 mmol), 4,5-bis(diphenylphosphino)-9,9-dimethylxanthene (560 mg, 0.97 mmol) and tris(dibenzylideneacetone)dipalladium (457 mg, 0.5 mmol) in 1,4-dioxane (20.0 mL) was stirred at 100° C. overnight under nitrogen. The reaction mixture was filtered with celite, and the filtrate was concentrated under reduced pressure. The obtained residue was purified by flash chromatography (petroleum ether/ethyl acetate=1/1) to afford 1-(6-chloro-4-methylpyridin-3-yl)pyrrolidin-2-one (150 mg, 0.71 mmol, 14.7% yield) as yellow oil. LC-MS: m/z=211.1 $[M+H]^+$, retention time=1.58 min (Method A).

1-(6-hydrazineyl-4-methylpyridin-3-yl)pyrrolidin-2-one

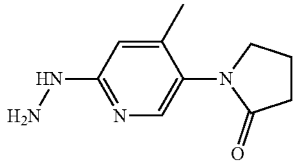

To a solution of 1-(6-chloro-4-methylpyridin-3-yl)pyrrolidin-2-one (150 mg, 0.71 mmol) in ethanol (4.0 mL) was added hydrazine hydrate (2.0 mL, 85% in water). The mixture was stirred at 130° C. for 18.0 h in a sealed tube. The mixture was cooled and concentrated to give dryness. The crude 1-(6-hydrazineyl-4-methylpyridin-3-yl)pyrrolidin-2-one (130 mg, crude) was obtained as yellow oil. LC-MS: m/z=207.1 $[M+H]^+$, retention time=0.43 min (Method A). The crude product was used to the next step.

4-(5-hydroxy-3-methyl-1-(4-methyl-5-(2-oxopyrrolidin-1-yl)pyridin-2-yl)-1H-pyrazol-4-yl)benzonitrile

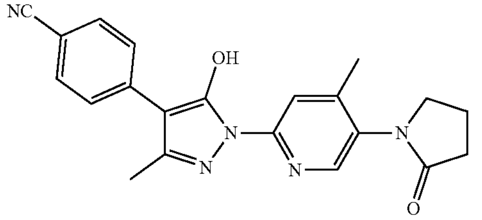 [SMILES: Cc1cc(-n2nc(C)c(-c3ccc(C#N)cc3)c2O)ncc1N1CCCC1=O]

To a solution of methyl 2-(4-cyanophenyl)-3-oxobutanoate (154 mg, 0.71 mmol) and 1-(6-hydrazineyl-4-methylpyridin-3-yl)pyrrolidin-2-one (130 mg, crude) in acetic acid (5.0 mL) was stirred at 100° C. for 2.0 h and concentrated. The resulting residue was purified by reverse prep-HPLC to afford 4-(5-hydroxy-3-methyl-1-(4-methyl-5-(2-oxopyrrolidin-1-yl)pyridin-2-yl)-1H-pyrazol-4-yl) benzonitrile (13.2 mg, 0.03 mmol, 3.53% yield) as white solid. LC-MS: m/z=374.1 $(M+H)^+$, retention time 4.15 min (Method A). $^1$HNMR (400 MHz, DMSO-$d_6$) δ 8.27 (s, 2H), 7.95-7.93 (m, 2H), 7.72-7.70 (m, 2H), 3.68 (s, 2H), 2.54-2.33 (m, 5H), 2.22 (s, 3H), 2.15-2.13 (m, 2H).

Example 38: Preparation of Compound 38

6-chloro-4-methylpyridine-3-sulfonyl chloride

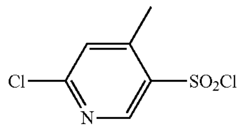

A solution of sulfur dioxide was prepared by adding thionyl chloride (2.42 mL) into stirring water (15.0 mL) containing copper (I) chloride (45 mg, 0.45 mmol). The solution was stirred at room temperature overnight. 6-Chloro-4-methylpyridin-3-amine (1.0 g, 7.04 mmol) was added into stirring concentrated hydrochloric acid solution (8.0 mL) portionwise. The mixture was stirred until all solid dissolved and was then cooled to −5° C. Into the mixture was added dropwise a solution of sodium nitrite (3.0 g, 42.8 mmol) dissolved in water (10.0 mL) while the temperature was kept between −5° C. and 0° C. The resulting mixture was stirred for 30 minutes after the completion of the addition and then added dropwise into the aqueous solution of sulfur dioxide. The temperature was kept below 0° C. during the addition. After the addition the mixture was stirred for 1.0 h below 0° C. and then filtered. The cake was washed with ice-cold water and extracted with dichloromethane. The organic layer was separated, washed with brine, dried over sodium sulfate and concentrated under reduced pressure to give 6-chloro-4-methylpyridine-3-sulfonyl chloride (350 mg, 1.55 mmol, 21.9% yield) as grey solid. LC-MS: m/z=226.0 $(M+H)^+$, retention time 2.00 min (Method A).

6-chloro-4-methylpyridine-3-sulfonamide

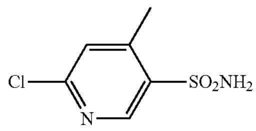

To a solution of 6-chloro-4-methylpyridine-3-sulfonyl chloride (350 mg, 1.55 mmol) in anhydrous tetrahydrofuran (10.0 mL) was added ammonia solution (2.0 mL, 0.5 M in 1,4-dioxane) at 0° C. The mixture was stirred at room temperature for 3.0 h and concentrated to give dryness. The residue was purified by flash chromatography (petroleum ether/ethyl acetate=1/1) to obtain 6-chloro-4-methylpyridine-3-sulfonamide (200 mg, 0.97 mmol, 62.6% yield) as white solid. LC-MS: m/z=207.1 $(M+H)^+$, retention time 1.39 min (Method A).

6-hydrazineyl-4-methylpyridine-3-sulfonamide

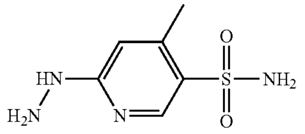

To a solution of 6-chloro-4-methylpyridine-3-sulfonamide (200 mg, 0.97 mmol) in ethanol (5.0 mL) was added hydrazine hydrate (5.0 mL, 85% in water). The mixture was stirred at 90° C. for 4.0 h in a sealed tube. The mixture was cooled and concentrated to give dryness. The residue was partitioned between ethyl acetate and water. The organic phase was washed with brine, dried over sodium sulfate and concentrated. The residue was triturated with petroleum ether and filtered to afford 6-hydrazineyl-4-methylpyridine-3-sulfonamide (180 mg, 0.89 mmol, 91.8% yield) as yellow solid. LC-MS: m/z=203.0 $(M+H)^+$, retention time 0.32 min (Method A).

6-(4-(4-cyanophenyl)-5-hydroxy-3-methyl-1H-pyrazol-1-yl)-4-methylpyridine-3-sulfonamide

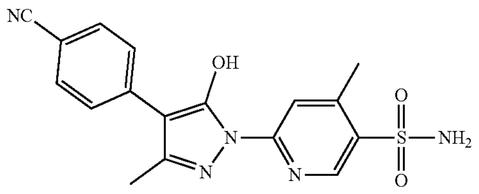 [SMILES: Cc1cc(-n2nc(C)c(-c3ccc(C#N)cc3)c2O)ncc1S(N)(=O)=O]

To a solution of methyl 2-(4-cyanophenyl)-3-oxobutanoate (193 mg, 0.89 mmol) and 6-hydrazineyl-4-methylpyridine-3-sulfonamide (180 mg, 0.89 mmol) in acetic acid (5.0 mL) was stirred at 100° C. for 2.0 h and concentrated. The resulting residue was purified by reverse prep-HPLC to afford 6-(4-(4-cyanophenyl)-5-hydroxy-3-methyl-1H-pyrazol-1-yl)-4-methylpyridine-3-sulfonamide (60 mg, 0.16 mmol, 18.3% yield) as white solid. LC-MS: m/z=370.0 $(M+H)^+$, retention time 4.02 min (Method A). $^1$HNMR (400 MHz, DMSO-$d_6$) δ 13.11 (s, 1H), 8.77 (s, 1H), 8.52 (s, 1H), 8.89-7.91 (d, J=7.4 Hz, 2H), 7.82-7.84 (d, J=7.9 Hz, 2H), 7.68 (s, 1H), 3.34 (s, 3H), 2.67 (s, 3H).

Example 39: Preparation of Compound 39

N-(6-chloro-4-methylpyridin-3-yl)methanesulfonamide

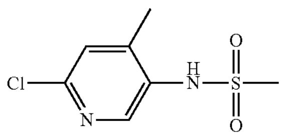

To a solution of 6-chloropyridin-3-amine (600 mg, 4.22 mmol) in pyridine (2.5 mL) was added methanesulfonyl chloride (2.5 mL) at 0° C. The mixture was allowed to warm up to room temperature and left stirring for another one hour.

The reaction was diluted with water and extracted twice with ethyl acetate. The organic layer was washed with brine, dried over sodium sulfate and concentrated to give N-(6-chloropyridin-3-yl)methanesulfonamide (900 mg, 4.09 mmol, 96.9% yield) as yellow solid. LC-MS: m/z=221.0 $[M+H]^+$, retention time 1.60 min (Method A).

N-(6-hydrazineyl-4-methylpyridin-3-yl)methane-sulfonamide

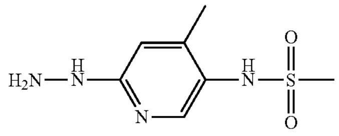

To a solution of N-(6-chloropyridin-3-yl)methanesulfonamide (900 mg, 4.09 mmol) in ethanol (4.0 mL) was added hydrazine hydrate (2.0 mL, 85% in water). The mixture was stirred at 130° C. in a sealed tube overnight. The mixture was cooled and concentrated to give dryness. The residue was partitioned between ethyl acetate and water. The organic layer was washed with brine, dried over sodium sulfate and concentrated to give N-(6-hydrazineyl-4-methylpyridin-3-yl)methanesulfonamide (600 mg, 2.77 mmol, 67.9% yield) as yellow oil. LC-MS: m/z=217.0 $[M+H]^+$, retention time 0.40 min (Method A). The crude product was used to the next step N-(6-(4-(4-cyanophenyl)-5-hydroxy-3-methyl-1H-pyrazol-1-yl)-4-methylpyridin-3-yl)methanesulfonamide

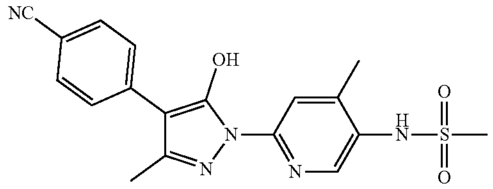 [SMILES: Cc1cc(-n2nc(C)c(-c3ccc(C#N)cc3)c2O)ncc1NS(C)(=O)=O]

To a solution of methyl 2-(4-cyanophenyl)-3-oxobutanoate (341 mg, 1.48 mmol) and N-(6-hydrazineyl-4-methylpyridin-3-yl)methanesulfonamide (600 mg, 2.77 mmol) in acetic acid (5.0 mL) was stirred at 100° C. for 2.0 h and concentrated. The resulting residue was purified by reverse prep-HPLC to afford N-(6-(4-(4-cyanophenyl)-5-hydroxy-3-methyl-1H-pyrazol-1-yl)-4-methylpyridin-3-yl)methanesulfonamide (Formate salt) (75.8 mg, 0.18 mmol, 11.9% yield) as white solid. LC-MS: m/z=384.0 $(M+H)^+$, retention time 4.17 min (Method A). $^1$HNMR (400 MHz, DMSO-$d_6$) δ 8.32-8.29 (m, 2H), 8.14 (s, 1H), 7.92-7.90 (m, 2H), 7.80-7.78 (m, 2H), 3.05 (s, 3H), 2.46 (s, 3H), 2.42 (s, 3H).

Example 40: Preparation of Compound 40

2-chloro-4-methyl-5-(methylthio)pyridine

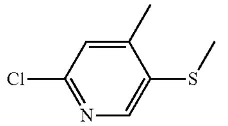

To a solution of 5-bromo-2-chloro-4-methylpyridine (800 mg, 3.88 mmol) and N,N,N',N'-tetramethylethylenediamine (0.59 g, 5.05 mmol) in anhydrous tetrahydrofuran (10.0 mL) was added n-butyllithium (2.91 mL, 4.66 mmol, 1.6M in hexane) at −78° C. under nitrogen. The mixture was stirred at −78° C. for 50 min and dimethyldisulfide (1.13 g, 4.66 mmol) was added. The mixture was allowed to warm up to 20° C. and left stirring for another one hour. The reaction was quenched with saturated ammonium chloride solution and extracted twice with ethyl acetate. The organic layer was separated, washed with brine, dried over sodium sulfate and concentrated under reduced pressure. The crude product was purified by flash chromatography (petroleum ether/ethyl acetate=50/1) to obtain 2-chloro-4-methyl-5-(methylthio)pyridine (600 mg, 3.47 mmol, 89.4% yield) as yellow oil. LC-MS: m/z=174.1 $(M+H)^+$, retention time 1.73 min (Method A).

2-chloro-4-methyl-5-(methylsulfinyl)pyridine

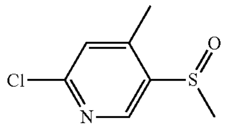

To a solution of 2-chloro-4-methyl-5-(methylthio)pyridine (600 mg, 3.47 mmol) in dichloromethane (10.0 mL) was added 3-chloroperoxybenzoic acid (772 mg, 3.82 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=2/1) to obtain 2-chloro-4-methyl-5-(methylsulfinyl)pyridine (500 mg, 2.65 mmol, 76.2% yield) as white solid. LC-MS: m/z=190.1 $(M+H)^+$, retention time 1.47 min (Method A).

(6-hydrazineyl-4-methylpyridin-3-yl)(imino)(methyl)-$\lambda^6$-sulfanone

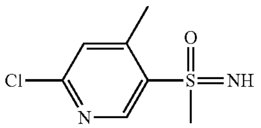

To a mixture of 2-chloro-4-methyl-5-(methylsulfinyl) pyridine (500 mg, 2.65 mmol) and ammonium carbamate (823 mg, 10.6 mmol) in methanol (15.0 mL) was added (diacetoxyiodo)benzene (2.56 g, 7.95 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-hydrazineyl-4-methylpyridin-3-yl)(imino)(methyl)-$\lambda^6$-sulfanone (350 mg, 1.72 mmol, 64.7% yield) as yellow solid. LC-MS: m/z=205.0 $(M+H)^+$, retention time 1.40 min (Method A).

(6-hydrazineyl-4-methylpyridin-3-yl)(imino)(methyl)-$\lambda^6$-sulfanone

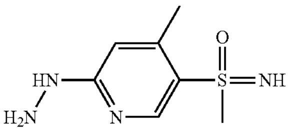

To a solution of (6-hydrazineyl-4-methylpyridin-3-yl)(imino)(methyl)-$\lambda^6$-sulfanone (350 mg, 1.72 mmol) in ethanol (5.0 mL) was added hydrazine hydrate (1.05 g, 17.2 mmol, 85% in water). The mixture was stirred at 90° C. overnight. The mixture was cooled and concentrated to give dryness. The residue was partitioned between ethyl acetate and water. The organic phase was washed with brine, dried over sodium sulfate and concentrated. The crude (6-hydrazineyl-4-methylpyridin-3-yl)(imino)(methyl)-$\lambda^6$-sulfanone (150 mg, 0.75 mmol, 43.6% yield) was obtained as yellow syrup. LC-MS: m/z=251.0 $(M+H)^+$, retention time 0.3 min (Method A). The crude product was used to the next step.

4-(5-hydroxy-3-methyl-1-(4-methyl-5-(S-methylsulfonimidoyl)pyridin-2-yl)-1H-pyrazol-4-yl)benzonitrile

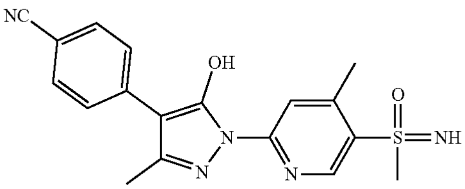 [SMILES: Cc1cc(-n2nc(C)c(-c3ccc(C#N)cc3)c2O)ncc1S(C)(=N)=O]

A mixture of methyl 2-(4-cyanophenyl)-3-oxobutanoate (162 mg, 0.75 mmol) and (6-hydrazineyl-4-methylpyridin-3-yl)(imino)(methyl)-$\lambda^6$-sulfanone (150 mg, 0.75 mmol) in acetic acid (8.0 mL) was stirred at 110° C. for 1.0 h and evaporated to give dryness. The residue was purified by reverse prep-HPLC to give 4-(5-hydroxy-3-methyl-1-(4-methyl-5-(S-methylsulfonimidoyl)pyridin-2-yl)-1H-pyrazol-4-yl)benzonitrile (Formate salt) (12.2 mg, 0.029 mmol, 3.93% yield) as white solid. LC-MS: m/z=368.0 $(M+H)^+$, retention time 3.61 min (Method A). $^1$HNMR (400 MHz, DMSO-$d_6$) δ 8.85 (s, 1H), 8.48 (s, 1H), 8.13 (s, 1H), 7.90-7.92 (d, J=8.3 Hz, 2H), 7.76-7.78 (d, J=7.9 Hz, 2H), 4.54 (s, 1H), 3.15 (s, 3H), 2.74 (s, 3H), 2.43 (s, 3H).

Example 41: Preparation of Compound 41

(S)-(6-chloropyridin-3-yl)(imino)(isopropyl)-$\lambda^6$-sulfanone & (R)-(6-chloropyridin-3-yl)(imino)-(isopropyl)-$\lambda^6$-sulfanone

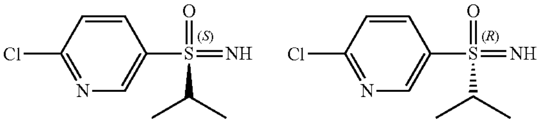

To a mixture of 2-chloro-5-(isopropylsulfinyl)pyridine (1.6 g, 7.28 mmol) and ammonium carbamate (2.29 g, 29.4 mmol) in methanol (20.0 mL) was added (diacetoxyiodo)benzene (7.04 g, 21.8 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-chloropyridin-3-yl)(imino)(isopropyl)-$\lambda^6$-sulfanone (1.27 g, 5.82 mmol, 80% yield) as yellow solid. LC-MS: m/z=218.1 $(M+H)^+$, retention time 0.55 min (Method A). The two chiral isomers were separated by Chiral prep-HPLC as white solid.

(S)-(6-chloropyridin-3-yl)(imino)(isopropyl)-$\lambda^6$-sulfanone (550 mg, 2.52 mmol).

(R)-(6-chloropyridin-3-yl)(imino)(isopropyl)-$\lambda^6$-sulfanone (600 mg, 2.75 mmol).

(S)-(6-hydrazineylpyridin-3-yl)(imino)(isopropyl)-$\lambda^6$-sulfanone

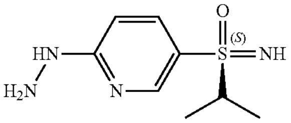

To a solution of (S)-(6-chloropyridin-3-yl)(imino)(isopropyl)-$\lambda^6$-sulfanone (150 mg, 0.69 mmol) in ethanol (5.0 mL) was added hydrazine hydrate (219 mg, 3.45 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (S)-(6-hydrazineylpyridin-3-yl)(imino)(isopropyl)-$\lambda^6$-sulfanone (100 mg, crude) as yellow syrup. LC-MS: m/z=215.0 $(M+H)^+$, retention time 0.34 min (Method A). The crude product was used to the next step.

(S)-4-(5-hydroxy-3-methyl-1-(5-(S-isopropylsulfonimidoyl)pyridin-2-yl)-1H-pyrazol-4-yl)benzonitrile

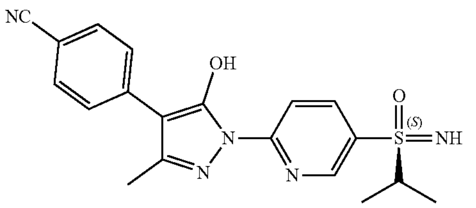

A mixture of methyl 2-(4-cyanophenyl)-3-oxobutanoate (150 mg, 0.69 mmol) and (S)-(6-hydrazineylpyridin-3-yl)(imino)(isopropyl)-$\lambda^6$-sulfanone (100 mg, crude) in acetic acid (8.0 mL) was stirred at 120° C. for 1.0 h and concentrated. The resulting residue was purified by reverse prep-HPLC to give (S)-4-(5-hydroxy-3-methyl-1-(5-(S-isopropylsulfonimidoyl)pyridin-2-yl)-1H-pyrazol-4-yl)benzonitrile (Formate salt) (30.1 mg, 0.07 mmol, 10.2% yield) as white solid. LC-MS: m/z=381.0 $(M+H)^+$, retention time 3.72 min (Method A). $^1$HNMR (400 MHz, DMSO-$d_6$) δ 13.02-13.13 (m, 1H), 8.79 (s, 1H), 8.63-8.85 (d, J=8.5 Hz, 1H), 8.31-8.33 (d, J=8.7 Hz, 1H), 8.13 (s, 1H), 7.89-7.91 (d, J=7.9 Hz, 2H), 7.79-7.81 (d, J=7.9 Hz, 2H), 4.48 (s, 1H), 2.48 (s, 3H), 1.16-1.19 (m, 6H).

Example 42: Preparation of Compound 42

(R)-(6-hydrazineylpyridin-3-yl)(imino)(isopropyl)-$\lambda^6$-sulfanone

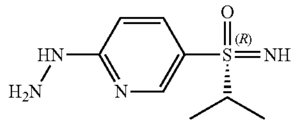

To a solution of (R)-(6-chloropyridin-3-yl)(imino)(isopropyl)-$\lambda^6$-sulfanone (150 mg, 0.69 mmol) (Intermediate for Example 41) in ethanol (5.0 mL) was added hydrazine hydrate (219 mg, 3.45 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (R)-(6-hydrazineylpyridin-3-yl)(imino)(isopropyl)-$\lambda^6$-sulfanone (100 mg, crude) as yellow syrup. LC-MS: m/z=215.0 $(M+H)^+$, retention time 0.34 min (Method A). The crude product was used to the next step.

(R)-4-(5-hydroxy-3-methyl-1-(5-(S-isopropylsulfonimidoyl)pyridin-2-yl)-1H-pyrazol-4-yl)benzonitrile

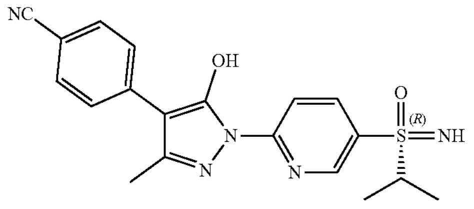

A mixture of methyl 2-(4-cyanophenyl)-3-oxobutanoate (150 mg, 0.69 mmol) and (R)-(6-hydrazineylpyridin-3-yl)(imino)(isopropyl)-$\lambda^6$-sulfanone (100 mg, crude) in acetic acid (8.0 mL) was stirred at 120° C. for 1.0 h and concentrated. The resulting residue was purified by reverse prep-HPLC to give (R)-4-(5-hydroxy-3-methyl-1-(5-(S-isopropylsulfonimidoyl)pyridin-2-yl)-1H-pyrazol-4-yl)benzonitrile (Formate salt) (30.9 mg, 0.07 mmol, 10.5% yield) as white solid. LC-MS: m/z=381.0 $(M+H)^+$, retention time 3.72 min (Method A). $^1$HNMR (400 MHz, DMSO-$d_6$) δ 13.11-13.19 (m, 1H), 8.79 (s, 1H), 8.64-8.66 (d, J=9.1 Hz, 1H), 8.28-8.32 (d, J=8.9 Hz, 1H), 8.14 (s, 1H), 7.90-7.92 (d, J=8.3 Hz, 2H), 7.78-7.80 (d, J=8.2 Hz, 2H), 4.51 (s, 1H), 2.47 (s, 3H), 1.16-1.19 (m, 6H).

Example 43: Preparation of Compound 43 tert-butyl 3-(2-chloropyridin-4-yl)azetidine-1-carboxylate

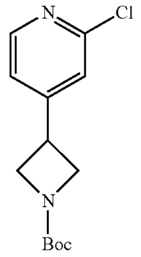 [SMILES: CC(C)(C)OC(=O)N1CC(c2ccnc(Cl)c2)C1]

To a solution of zinc powder (1.5 g, 6.26 mmol) in N,N-dimethylacetamide (5.0 mL) was added a solution of chlorotrimethylsilane and 1,2-dibromoethane (0.1 mL, 7:5 v/v ratio). The mixture was stirred at room temperature for 15 min and then tert-butyl 3-iodoazetidine-1-carboxylate (3.2 g, 11.3 mmol) was added. The mixture was stirred for 30 min. In a separate flask, [1,1'-dis(diphenylphosphino)ferrocene]dichloropalladium(II) (196 mg, 0.24 mmol) and then copper iodide (92 mg, 0.48 mmol) were added to a degassed solution of 2-chloro-4-iodopyridine in N,N-dimethylacetamide (20.0 mL). After stirring for 30 min, the zinc suspension above was added to the 2-chloro-4-iodopyridine solution and the reaction mixture was allowed to stir at room temperature for 2.0 h. The reaction solution was quenched by adding saturated ammonium chloride solution and extracted with ethyl acetate (×2). The organic layer was washed with brine, dried over sodium sulfate and concentrated under reduced pressure. The crude product was purified by flash chromatography (petroleum ether/ethyl acetate=4/1) to give tert-butyl 3-(2-chloropyridin-4-yl)azetidine-1-carboxylate (600 mg, 3.29 mmol, 62.6% yield) as white solid. LC-MS: m/z=269.1 $(M+H)^+$, retention time 1.98 min (Method A).

4-(azetidin-3-yl)-2-chloropyridine

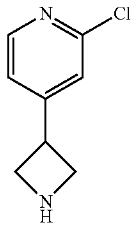 [SMILES: Clc1cc(C2CNC2)ccn1]

To a solution of tert-butyl 3-(2-chloropyridin-4-yl)azetidine-1-carboxylate (600 mg, 3.29 mmol) in dichloromethane (10.0 mL) was added trifluoroacetic acid (5.0 mL). The mixture was stirred at 40° C. for 2.0 h and concentrated. The residue was partitioned between dichloromethane and saturated sodium hydrocarbonate solution. The organic phase was washed with brine, dried over sodium sulfate and concentrated. 4-(Azetidin-3-yl)-2-chloropyridine (600 mg, 2.23 mmol, 68% yield) was obtained as yellow syrup. LC-MS: m/z=169.0 (M+H)+, retention time 0.33 min (Method A).

2-chloro-4-(1-(methylsulfonyl)azetidin-3-yl)pyridine

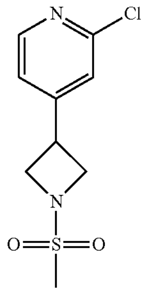

To a solution of 4-(azetidin-3-yl)-2-chloropyridine (600 mg, 2.23 mmol) in pyridine (2.5 mL) was added methanesulfonyl chloride (305 mg, 2.68 mmol) at 0° C. The mixture was allowed to warm up to room temperature and left stirring for another one hour. The reaction was diluted with water and extracted twice with ethyl acetate. The organic layer was washed with brine, dried over sodium sulfate and concentrated to give 2-chloro-4-(1-(methylsulfonyl)azetidin-3-yl)pyridine (400 mg, 1.63 mmol, 72.9% yield) as yellow solid. LC-MS: m/z=247 $[M+H]^+$, retention time 1.63 min (Method A).

2-hydrazineyl-4-(1-(methylsulfonyl)azetidin-3-yl) pyridine

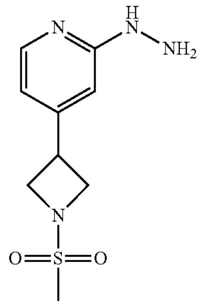 [SMILES: CS(=O)(=O)N1CC(c2ccnc(NN)c2)C1]

To a solution of 2-chloro-4-(1-(methylsulfonyl)azetidin-3-yl)pyridine (400 mg, 1.63 mmol) in ethanol (8.0 mL) was added hydrazine hydrate (4.0 mL). The mixture was stirred at 130° C. in a sealed tube overnight. The mixture was cooled and concentrated to give dryness. The residue was partitioned between ethyl acetate and water. The organic phase was washed with brine, dried over sodium sulfate and concentrated. The residue was triturated with petroleum ether and filtered to afford 2-hydrazineyl-4-(1-(methylsulfonyl)azetidin-3-yl)pyridine (300 mg, crude) as yellow syrup. The product was used directly to the next step. LC-MS: m/z=243.0 (M+H)+, retention time 0.3 min (Method A).

4-(5-hydroxy-3-methyl-1-(5-(1-(methylsulfonyl) azetidin-3-yl)pyridin-2-yl)-1H-pyrazol-4-yl)benzonitrile

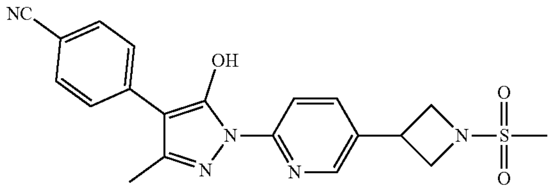 [SMILES: Cc1nn(-c2ccc(C3CN(S(C)(=O)=O)C3)cn2)c(O)c1-c1ccc(C#N)cc1]

A mixture of methyl 2-(4-cyanophenyl)-3-oxobutanoate (30 mg, 0.14 mmol) and 2-hydrazineyl-4-(1-(methylsulfonyl)azetidin-3-yl)pyridine (300 mg, crude) in acetic acid (5.0 mL) was stirred at 120° C. for 1.0 h and concentrated. The resulting residue was purified by reverse prep-HPLC to give 4-(5-hydroxy-3-methyl-1-(5-(1-(methylsulfonyl)azetidin-3-yl)pyridin-2-yl)-1H-pyrazol-4-yl)benzonitrile (Formate salt) (8.4 mg, 0.02 mmol, 13.2% yield) as white solid. LC-MS: m/z=409.0 $(M+H)^+$, retention time 5.10 min (Method A). $^1$HNMR (400 MHz, DMSO-$d_6$) δ 8.44-8.45 (d, J=5.5 Hz, 1H), 8.39 (s, 1H), 8.14 (s, 1H), 7.91-7.93 (d, J=8.9 Hz, 2H), 7.76-7.78 (d, J=8.1 Hz, 2H), 7.31 (s, 1H), 4.28-4.31 (m, 2H), 3.94-3.98 (m, 2H), 3.09 (s, 3H), 2.45 (s, 3H).

Example 44: Preparation of Compound 44 methyl 2-(5-bromopyridin-2-yl)acetate

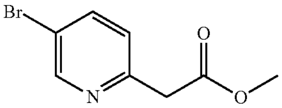

To a solution of 5-bromopyridine-2-acetic acid (3.00 g, 13.89 mmol) in MeOH (50 mL) at rt was added $SOCl_2$ (2 mL) dropwise over 5 min. The reaction was stirred at 60° C. for 2 hrs. After the reaction was completed by TLC analysis, the most of the solvent was evaporated in vacuum. The residue was quenched with an aqueous saturated $NaHCO_3$ solution (50 mL) and extracted with EtOAc (40 mL×3). The combined organic phase was dried with anhydrous $Na_2SO_4$ (20 g), filtered and concentrated in vacuo. The residue was purified by silica column chromatography (EtOAc:Hex=1:5) to give the title product (3.01 g) as yellow oil. LCMS (ESI+): m/z 230 $(M+H)^+$; $^1H$ NMR (300 MHz, $CDCl_3$) δ 8.61 (d, J=2.1 Hz, 1H), 7.78 (dd, J=2.4 Hz, 8.4 Hz, 1H), 7.21 (d, J=8.4 Hz, 1H), 3.81 (s, 2H), 3.72 (s, 3H).

methyl 2-(5-cyanopyridin-2-yl)acetate

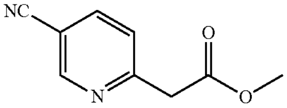

Under nitrogen atmosphere, to a solution of methyl 2-(5-bromopyridin-2-yl)acetate (2.84 g, 12.35 mmol) in anhydrous DMF (50 mL) was added $Zn(CN)_2$ (2.17 g, 18.52 mmol) and $Pd(PPh_3)_4$ (1.00 g, 0.86 mmol). The mixture was stirred at 120° C. for 1 hr. After the reaction was completed by TLC analysis, the mixture was cooled to rt and filtered through a pad of Celite. The filtrate was quenched with water (200 mL) and extracted with EtOAc (50 mL×3). The combined organic phases were dried with anhydrous $Na_2SO_4$ (30 g), filtered and concentrated in vacuo. The residue was purified by silica column chromatography (PE:EtOAc=8:1 to 5:1) to give 1.81 g of the title compound as yellow oil. LCMS (ESI+): m/z=177 $(M+H)^+$; $^1H$ NMR (300 MHz, $CDCl_3$) δ 8.84 (d, J=1.5 Hz, 1H), 7.95 (dd, J=2.1 Hz, 8.1 Hz, 1H), 7.47 (d, J=8.1 Hz, 1H), 3.94 (s, 2H), 3.75 (s, 3H).

methyl 2-(5-cyanopyridin-2-yl)-3-oxobutanoate

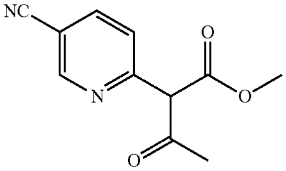 [SMILES: COC(=O)C(C(C)=O)c1ccc(C#N)cn1]

Under nitrogen atmosphere, to a solution of methyl 2-(5-cyanopyridin-2-yl)acetate (0.80 g, 4.52 mmol) in anhydrous THF (30 mL) at −30° C. was added LiHMDS (6.78 mL, 6.78 mmol) dropwise over 10 min. After the reaction was stirred at −30° C. for 30 min, a solution of acetyl chloride (0.53 g, 6.78 mmol) in anhydrous THF (5 mL) was added into dropwise over 5 min and the reaction was continued to stir at that same condition for 30 min. The reaction was allowed to warm to rt and stirred for additional 2 hrs. After the reaction was completed by TLC analysis, the mixture was quenched with a saturated ammonium chloride aqueous (30 mL) and extracted with EtOAc (20 mL×3). The combined organic phases were dried with anhydrous $Na_2SO_4$ (20 g), filtered and concentrated in vacuo. The residue was purified by silica column chromatography (PE:EtOAc=15:1 to 10:1) to give 250 mg of the title compound as yellow solid. LCMS (ESI+): m/z 219 $(M+H)^+$; $^1H$ NMR (300 MHz, $CDCl_3$) δ 8.43 (s, 1H), 7.89 (d, J=9.3 Hz, 1H), 7.81 (dd, J=9.0 Hz, 2.1 Hz, 1H), 3.86 (s, 3H), 3.73 (s, 1H), 2.40 (s, 3H).

6-(5-hydroxy-3-methyl-1-(5-(methylsulfonyl)pyridin-2-yl)-1H-pyrazol-4-yl)nicotinonitrile

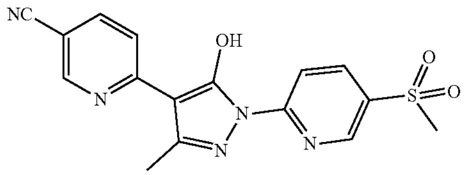 [SMILES: Cc1nn(-c2ccc(S(C)(=O)=O)cn2)c(O)c1-c1ccc(C#N)cn1]

To a solution of methyl 2-(5-cyanopyridin-2-yl)-3-oxobutanoate (72 mg, 0.33 mmol) in acetic acid (3 mL) was added 2-hydrazinyl-5-(methylsulfonyl)pyridine (93 mg, 0.49 mmol). After the reaction was stirred at 100° C. overnight, a large amount of solid was precipitated. The suspension was filtered by a funnel and the filtered cake was washed with acetic acid (1 mL). The solid was slurried in ethanol (3 mL) and filtrated to give 31 mg of the title compound as yellow solid. LCMS (ESI+): m/z 356 $(M+H)^+$; HPLC purity was 95.9%, $^1H$ NMR (300 MHz, DMSO-$d_6$) δ 13.92 (brs, 1H), 8.89 (dd, J=7.8 Hz, 2.4 Hz, 2H), 8.69 (d, J=9.0 Hz, 1H), 8.45 (dd, J=8.7 Hz, 2.1 Hz, 2H), 8.16 (dd, J=8.7 Hz, 2.1 Hz, 1H), 3.32 (s, 3H), 2.65 (s, 3H).

Example 45: Preparation of Compound 45

6-chloro-2-methyl-3-(methylthio)pyridine

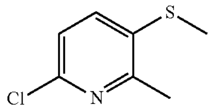

To a solution of 6-chloro-2-methylpyridin-3-amine (1 g, 7.01 mmol) in conc. HCl (5 mL) at 0° C. was added a solution of $NaNO_2$ (726 mg, 10.52 mmol) in water (5 mL) dropwise over 5 min. After the reaction was stirred at 0° C. for 1 hr, some solids were precipitated. The suspension was filtered quickly with the internal temperature kept below 5° C. The filtrate was added to a solution of $NaBF_4$ (8 mg, 0.07 mmol) and MeSNa (2.95 g, 8.42 mmol) in MeCN (10 mL) at 0° C. dropwise over 5 min. The resulting mixture was stirred at 0° C. for about 3 hr. After the reaction was completed as indicated by TLC analysis, the reaction was quenched with water (50 mL) and adjusted pH to 6-7 with a diluted NaOH solution (1N). The resulting mixture was extracted with EtOAc (30 mL×3). The combined organic phase was dried and concentrated to give 745 mg of crude product, which was used for next step without further purification. LC-MS (ESI+): m/z 174 $(M+H)^+$.

6-chloro-2-methyl-3-(methylsulfonyl)pyridine

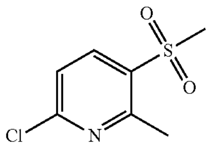

To a solution of crude 6-chloro-2-methyl-3-(methylthio) pyridine (745 mg, 4.29 mmol) in DCM (40 mL) at 0° C. was added m-CPBA (1.48 g, 8.58 mmol) portion wise over 5 min. The reaction was stirred in ice water bath for about 2 hr. After the reaction was completed as indicated by TLC analysis, the reaction was quenched with a saturated $NaHCO_3$ solution (20 mL) and extracted with DCM (30 mL×2). The combined organic phase was dried and concentrated to afford 1.03 g of the crude product. LC-MS (ESI+): m/z 206 $(M+H)^+$;

6-hydrazineyl-2-methyl-3-(methylsulfonyl)pyridine

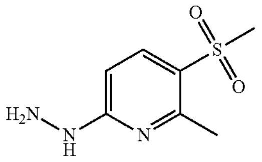

A solution of crude 6-chloro-2-methyl-3-(methylsulfonyl) pyridine (1.03 g, 5.01 mmol) and hydrazine hydrate (1.57 g, 25 mmol, 80% wt) in ethanol (50 mL) was stirred at 70° C. overnight. After the reaction was completed based on TLC analysis, the reaction was concentrated to dryness. After the residue was added ethanol (15 mL) and stirred at rt for 30 min, a large amount of solids were precipitated. The suspension was filtered and the filter cake was washed with cold ethanol (5 mL). The isolated solid was dried in high vacuum to afford 445 mg of the title compound. LC-MS (ESI+): m/z 202 $(M+H)^+$;

4-(5-hydroxy-3-methyl-1-(6-methyl-5-(methylsulfonyl)pyridin-2-yl)-1H-pyrazol-4-yl)benzonitrile

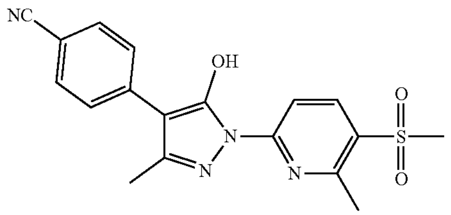 [SMILES: Cc1nc(-n2nc(C)c(-c3ccc(C#N)cc3)c2O)ccc1S(C)(=O)=O]

A solution of crude 6-hydrazinyl-2-methyl-3-(methylsulfonyl)pyridine (270 mg, 1.17 mmol) and methyl 2-(4-cyanophenyl)-3-oxobutanoate (235 mg, 1.17 mmol) in AcOH (6 mL) was stirred at 110° C. for 3 hrs. After the reaction was completed as indicated by TLC analysis, the reaction was cooled to rt and quenched with water (80 mL). A large amount of solids were precipitated. The suspension was filtered and the filter cake was slurried in methanol (30 mL) three times to afford 43 mg of the title compound. LC-MS (ESI+): m/z 369 $(M+H)^+$; $^1$H-NMR (300 MHz, $CD_3OD$) δ 8.43 (d, J=8.7 Hz, 1H), 8.25 (d, J=8.7 Hz, 1H), 7.89 (d, J=8.7 Hz, 2H), 7.60 (d, J=8.7 Hz, 2H), 3.19 (s, 3H), 2.88 (s, 3H), 2.42 (s, 3H).

Example 46: Preparation of Compound 46

2-chloro-4-methyl-5-(methylthio)pyridine

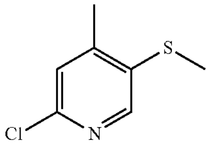

The compound was synthesized according to the procedure for the preparation of 6-chloro-2-methyl-3-(methylthio)pyridine (Intermediate for Example 45). LC-MS (ESI+): m/z 174 $(M+H)^+$;

2-chloro-4-methyl-5-(methylsulfonyl)pyridine

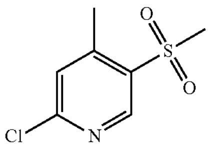

The compound was synthesized according to the procedure for the preparation of 6-chloro-2-methyl-3-(methylsulfonyl)pyridine (Intermediate for Example 45) using 2-chloro-4-methyl-5-(methylthio)pyridine. $^1$H-NMR (300 MHz, $CDCl_3$) δ 8.93 (s, 1H), 7.34 (s, 1H), 3.16 (s, 3H), 2.71 (s, 3H).

2-hydrazineyl-4-methyl-5-(methylsulfonyl)pyridine

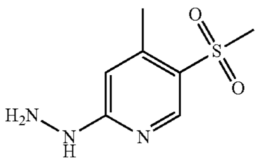

The compound was synthesized according to the procedure for the preparation of 6-hydrazineyl-2-methyl-3-(methylsulfonyl)pyridine (Intermediate for Example 45) using 2-chloro-4-methyl-5-(methylsulfonyl)pyridine. LC-MS (ESI+): m/z 202 $(M+H)^+$.

4-(5-hydroxy-3-methyl-1-(4-methyl-5-(methylsulfonyl)pyridin-2-yl)-1H-pyrazol-4-yl)benzonitrile

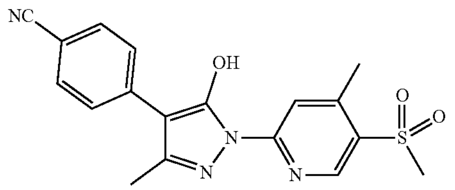 [SMILES: Cc1cc(-n2nc(C)c(-c3ccc(C#N)cc3)c2O)ncc1S(C)(=O)=O]

The compound was synthesized according to the procedure for the preparation of 4-(5-hydroxy-3-methyl-1-(6-methyl-5-(methylsulfonyl)pyridin-2-yl)-1H-pyrazol-4-yl) benzonitrile (Intermediate for Example 45) using 2-hydrazineyl-4-methyl-5-(methylsulfonyl)pyridine. LC-MS (ESI+): m/z 369 $(M+H)^+$; $^1H$-NMR (300 MHz, DMSO-$d_6$) δ 8.76 (s, 1H), 8.58 (s, 1H), 7.93 (d, J=8.7 Hz, 2H), 7.72 (d, J=8.7 Hz, 2H), 3.52 (s, 3H), 2.69 (s, 3H), 2.44 (s, 3H).

Example 47: Preparation of Compound 47

2-(6-hydrazineylpyridin-3-yl)acetic acid

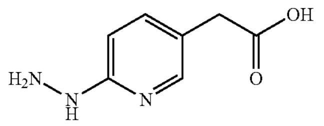 [SMILES: NNc1ccc(CC(=O)O)cn1]

A solution of 2-(6-bromopyridin-3-yl)acetic acid (420 mg, 1.94 mmol) and hydrazine hydrate (5 mL, 80 wt %, 80 mmol) in water (3 mL) was stirred at reflux condition overnight. After the reaction was completed as indicated by TLC analysis, the reaction was concentrated to dryness to afford 540 mg of the crude product, which was used for the next step without further purification. LC-MS (ESI+): m/z 168 $(M+H)^+$.

2-(6-(4-(4-cyanophenyl)-5-hydroxy-3-methyl-1H-pyrazol-1-yl)pyridin-3-yl)acetic acid

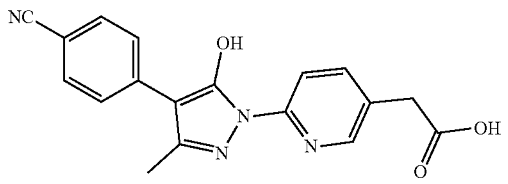 [SMILES: Cc1nn(-c2ccc(CC(=O)O)cn2)c(O)c1-c1ccc(C#N)cc1]

A solution of methyl 2-(4-cyanophenyl)-3-oxobutanoate (302 mg, 1.31 mmol) and crude 2-(6-hydrazinyl pyridin-3-yl)acetic acid (218 mg, 1.31 mmol) in AcOH (8 mL) was stirred under reflux for 3 hr. After the reaction was completed as indicated by TLC analysis, the reaction was cooled to rt and diluted with water (20 mL). A large amount of solid was precipitated. The solid was collected by filtration to give 192 mg of crude product. The crude product was purified by preparative HPLC to afford 10 mg of the title compound. LC-MS (ESI+): m/z 335 $(M+H)^+$; $^1H$-NMR (300 MHz, $CD_3OD$) δ8.35 (s, 1H), 8.20 (d, J=8.7 Hz, 1H), 7.90 (d, J=8.7 Hz, 1H), 7.82 (d, J=8.4 Hz, 2H), 7.72 (d, J=8.7 Hz, 2H), 3.60 (s, 3H), 2.46 (s, 3H).

Example 48: Preparation of Compound 48

2-bromo-5-(methylthio)pyridine

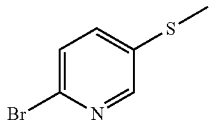

Under nitrogen protection, to a solution of 2,5-dibromopyridine (8.34 g, 35.2 mmol) in anhydrous $Et_2O$ (200 mL) at −78° C. was added n-BuLi (23.2 mL, 37 mmol) dropwise over 20 min. After the resulting mixture was stirred at −78° C. for 1 hr, dimethyl disulfide (3.65 g, 38.7 mmol) was added dropwise to the reaction over 10 min. The reaction was continued to stir at −78° C. for additional 1 hr. After the reaction was completed as indicated by TLC analysis, the reaction was warmed to 0° C. and quenched with a diluted HCl solution (40 mL, 1N) and extracted with MTBE (100 mL×2). The combined organic phase was washed with water (20 mL), dried and concentrated to afford 6.035 g of the crude product, which was used for the next step without further purification. LC-MS (ESI+): m/z 204, 206 $(M+H)^+$.

2-bromo-5-(methylsulfonyl)pyridine

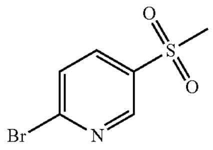

The compound was synthesized according to the procedure for the preparation of 6-chloro-2-methyl-3-(methylsulfonyl)pyridine (Intermediate for Example 45) using 2-bromo-5-(methylthio)pyridine. $^1H$-NMR (300 MHz, $CDCl_3$) δ 8.92 (d, J=1.8 Hz, 1H), 8.05 (dd, J=8.1, 1.8 Hz, 1H), 7.72 (d, J=8.1 Hz, 1H), 3.12 (s, 3H).

2-hydrazineyl-5-(methylsulfonyl)pyridine

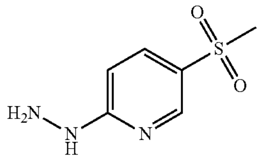

The compound was synthesized according to the procedure for the preparation of 6-hydrazineyl-2-methyl-3-(methylsulfonyl)pyridine (Intermediate for Example 45) using 2-bromo-5-(methylsulfonyl)pyridine. LC-MS (ESI+): m/z 188 $(M+H)^+$.

methyl 2-(4-hydroxy-3-methylphenyl)-3-oxobutanoate

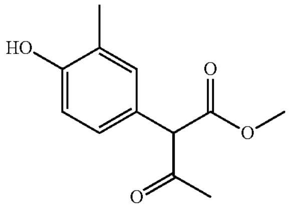 [SMILES: COC(=O)C(C(C)=O)c1ccc(O)c(C)c1]

Under nitrogen protection, to a solution of methyl 2-(4-hydroxy-3-methylphenyl)acetate (930 mg, 5.16 mmol) in anhydrous DMF (15 mL) at −78° C. was added LHMDS (12.9 mL, 12.9 mmol) dropwise over 15 min. After the reaction was stirred at −78° C. for 30 min, a solution of 1-acetylimidazole (1.25 g, 11.35 mmol) in DMF (15 mL) was added to the reaction dropwise over 15 min. The reaction was warmed to rt slowly over 2 hr. After the reaction was completed as indicated by TLC analysis, the reaction was quenched with a saturated $NH_4Cl$ solution (100 mL) and extracted with EtOAc (50 mL×3). The combined organic phase was washed with water (25 mL), dried and concentrated to afford 1.47 g of the crude title compound, which was used for the next step without further purification. LC-MS (ESI+): m/z 245 $(M+Na)^+$.

4-(4-hydroxy-3-methylphenyl)-3-methyl-1-(5-(methylsulfonyl)pyridin-2-yl)-1H-pyrazol-5-ol

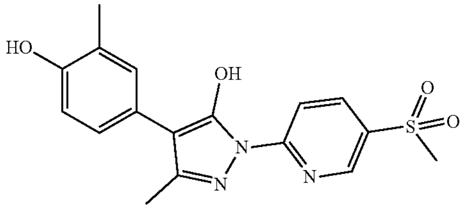 [SMILES: Cc1cc(-c2c(C)nn(-c3ccc(S(C)(=O)=O)cn3)c2O)ccc1O]

The compound was synthesized according to the procedure for the preparation of 4-(5-hydroxy-3-methyl-1-(6-methyl-5-(methylsulfonyl)pyridin-2-yl)-1H-pyrazol-4-yl) benzonitrile (Intermediate for Example 45) using methyl 2-(4-hydroxy-3-methylphenyl)-3-oxobutanoate. LC-MS (ESI+): m/z 358 $(M+H)^+$; $^1$H-NMR (300 MHz, $CD_3OD$) δ 8.92 (d, J=1.8 Hz, 1H), 8.69 (brs, 1H), 8.38 (dd, J=9.0, 2.4 Hz, 1H), 7.21 (s, 1H), 7.13 (d, J=8.4 Hz, 1H), 6.79 (d, J=8.4 Hz, 1H), 3.21 (s, 3H), 2.36 (s, 3H), 2.22 (s, 3H).

Example 49: Preparation of Compound 49 methyl 2-(4-methoxy-3-methylphenyl)acetate

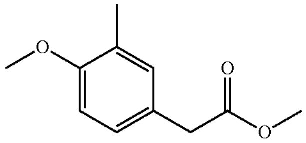

To a solution of 2-(4-methoxy-3-methylphenyl)acetic acid (2.15 g, 11.9 mmol) in methanol in an ice-water bath was added $SOCl_2$ (4 mL) dropwise over 5 min. The reaction was stirred at rt for about 1 hr. After the reaction was completed as indicated by TLC analysis, the reaction was concentrated to dryness. The residue was diluted with EtOAc (50 mL) and washed with a saturated $NaHCO_3$ solution (20 mL). The aqueous phase was extracted with EtOAc (20 mL). The combined organic phase was dried and concentrated to afford 2.14 g of the crude product. $^1$H-NMR (300 MHz, $CDCl_3$) δ 7.05-7.07 (m, 2H), 6.77 (d, J=8.1 Hz, 1H), 3.82 (s, 3H), 3.68 (s, 3H), 3.53 (s, 2H), 2.20 (s, 3H).

methyl 2-(4-methoxy-3-methylphenyl)-3-oxobutanoate

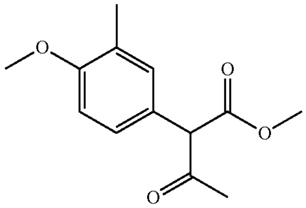

The compound was synthesized according to the procedure for the preparation of methyl 2-(4-hydroxy-3-methylphenyl)-3-oxobutanoate (Intermediate from Example 48) using methyl 2-(4-methoxy-3-methylphenyl)acetate. LC-MS (ESI+): m/z 259 $(M+Na)^+$.

4-(4-methoxy-3-methylphenyl)-3-methyl-1-(5-(methylsulfonyl)pyridin-2-yl)-1H-pyrazol-5-ol

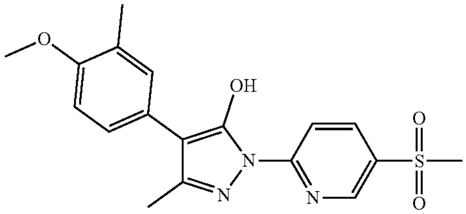

The compound was synthesized according to the procedure for the preparation of 4-(5-hydroxy-3-methyl-1-(6-methyl-5-(methylsulfonyl)pyridin-2-yl)-1H-pyrazol-4-yl) benzonitrile (Intermediate from Example 45) using methyl 2-(4-methoxy-3-methylphenyl)-3-oxobutanoate. LC-MS (ESI+): m/z 374 $(M+H)^+$; $^1$H-NMR (300 MHz, DMSO-$d_6$) δ 12.37 (s, 1H), 8.89 (s, 1H), 8.72 (s, 1H), 8.42 (dd, J=9.0, 2.1 Hz, 1H), 7.34-7.36 (m, 2H), 6.96 (d, J=9.0 Hz, 1H), 3.80 (s, 3H), 2.36 (s, 3H), 2.18 (s, 3H).

Example 50: Preparation of Compound 50

6-chloronicotinimidohydrazide

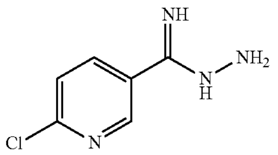 [SMILES: N=C(NN)c1ccc(Cl)nc1]

Under nitrogen protection, to a solution of 6-chloronicotinonitrile (1 g, 7.19 mmol) in methanol (2.5 mL) and dioxane (2.5 mL) in an ice-water bath was added MeONa (78 mg, 1.44 mmol) portionwise over 2 mins. After the reaction was stirred at rt for 2 hr, hydrazine hydrate (480 mg, 7.69 mmol) was added in one portion. The resulting mixture was stirred at 30° C. for 30 mins. A large amount of solids were precipitated. The suspension was diluted with MTBE (5 mL) and continued to stir for 30 min. After filtration, 764 mg of the crude product was obtained. $^1$H-NMR (300 MHz, DMSO-$d_6$) δ 8.67 (d, J=2.1 Hz, 1H), 8.06 (d, J=8.4, 2.1 Hz, 1H), 7.48 (d, J=8.4 Hz, 1H), 5.79 (brs, 2H), 5.33 (brs, 2H).

2-chloro-5-(2H-tetrazol-5-yl)pyridine

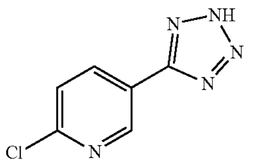 [SMILES: Clc1ccc(-c2nn[nH]n2)cn1]

A solution of 6-chloronicotinimidohydrazide (664 mg, 3.91 mmol) in AcOH (2 mL) and water (1.6 mL) at rt was added an aqueous $NaNO_2$ (323 mg, 4.69 mmol, in 0.6 mL water) solution dropwise over 5 mins. After the reaction was stirred at rt for 5 hrs, a large amount of solids were precipitated. The suspension was cooled to 0° C. with an ice-water bath and adjusted pH to 2 using a diluted HCl solution (1 N). The resulting suspension was filtered to afford 540 mg of the title compound. $^1$H-NMR (300 MHz, DMSO-$d_6$) δ 9.05 (d, J=2.4 Hz, 1H), 8.06 (d, J=8.4, 2.4 Hz, 1H), 7.80 (d, J=8.4 Hz, 1H).

2-hydrazineyl-5-(2H-tetrazol-5-yl)pyridine

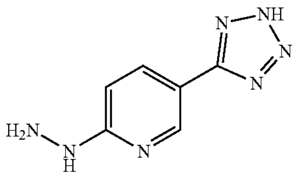 [SMILES: NNc1ccc(-c2nn[nH]n2)cn1]

The compound was synthesized according to the procedure for the preparation of 6-hydrazineyl-2-methyl-3-(methylsulfonyl)pyridine (Intermediate for Example 45) using 2-chloro-5-(2H-tetrazol-5-yl)pyridine. $^1$H-NMR (300 MHz, DMSO-$d_6$) δ 8.65 (d, J=2.1 Hz, 1H), 8.00 (d, J=8.4, 2.1 Hz, 1H), 6.95 (brs, 4H), 6.78 (d, J=8.4 Hz, 1H).

4-(1-(5-(2H-tetrazol-5-yl)pyridin-2-yl)-5-hydroxy-3-methyl-1H-pyrazol-4-yl)benzonitrile

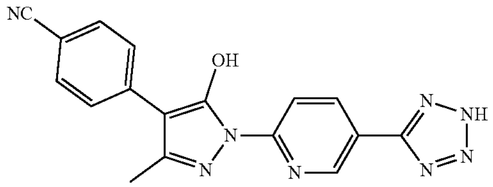 [SMILES: Cc1nn(-c2ccc(-c3nn[nH]n3)cn2)c(O)c1-c1ccc(C#N)cc1]

The compound was synthesized according to the procedure for the preparation of 4-(5-hydroxy-3-methyl-1-(6-methyl-5-(methylsulfonyl)pyridin-2-yl)-1H-pyrazol-4-yl) benzonitrile (Intermediate for Example 45) using 2-hydrazineyl-5-(2H-tetrazol-5-yl)pyridine. LC-MS (ESI+): m/z 345 $(M+H)^+$; $^1$H-NMR (300 MHz, DMSO-$d_6$) δ 9.01 (s, 1H), 8.37-8.47 (m, 2H), 7.95 (d, J=8.4 Hz, 2H), 7.75 (d, J=8.4 Hz, 2H), 2.45 (s, 3H).

Example 51: Preparation of Compound 51

N-(6-(4-(4-cyanophenyl)-5-hydroxy-3-methyl-1H-pyrazol-1-yl)pyridin-3-yl)-N'-methylsulfamide

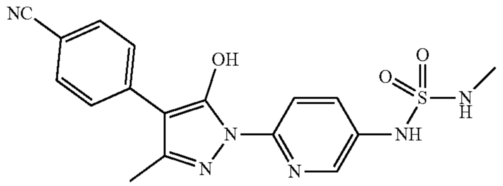 [SMILES: CNS(=O)(=O)Nc1ccc(-n2nc(C)c(-c3ccc(C#N)cc3)c2O)nc1]

The compound was synthesized according to the procedure for the preparation of N-(6-(4-(4-cyanophenyl)-5-hydroxy-3-methyl-1H-pyrazol-1-yl)pyridin-3-yl) methanesulfonamide (Example 6).

Example 52: Preparation of Compound 52

N-(6-(4-(4-cyanophenyl)-5-hydroxy-3-methyl-1H-pyrazol-1-yl)pyridin-3-yl)-N'-dimethylsulfamide

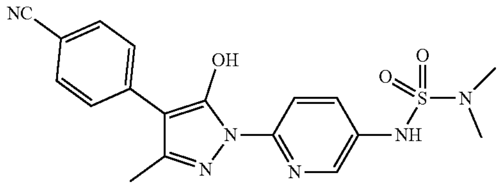 [SMILES: Cc1nn(-c2ccc(NS(=O)(=O)N(C)C)cn2)c(O)c1-c1ccc(C#N)cc1]

The compound was synthesized according to the procedure for the preparation of N-(6-(4-(4-cyanophenyl)-5-hydroxy-3-methyl-1H-pyrazol-1-yl)pyridin-3-yl) methanesulfonamide (Example 6).

Example 53: Preparation of Compound 53

4-(1-(4-cyclopropyl-5-(methylsulfonyl)pyridin-2-yl)-5-hydroxy-3-methyl-1H-pyrazol-4-yl)benzonitrile

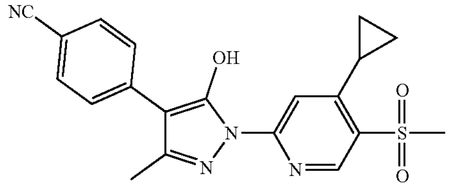 [SMILES: Cc1nn(-c2cc(C3CC3)c(S(C)(=O)=O)cn2)c(O)c1-c1ccc(C#N)cc1]

The compound was synthesized according to the procedure for the preparation of 4-(5-hydroxy-3-methyl-1-(6-methyl-5-(methylsulfonyl)pyridin-2-yl)-1H-pyrazol-4-yl) benzonitrile (Example 45).

Example 54: Preparation of Compound 54

4-(5-hydroxy-3-methyl-1-(5-(1-methyl-1H-1,2,3-triazol-4-yl)pyridin-2-yl)-1H-pyrazol-4-yl)benzonitrile

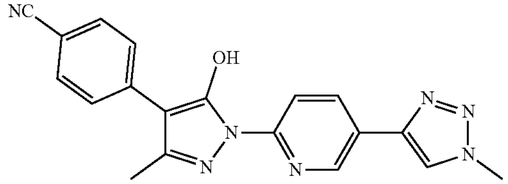 [SMILES: Cc1nn(-c2ccc(-c3cn(C)nn3)cn2)c(O)c1-c1ccc(C#N)cc1]

The compound was synthesized according to the procedure for the preparation of 4-(1-(5-(2H-tetrazol-5-yl)pyridin-2-yl)-5-hydroxy-3-methyl-1H-pyrazol-4-yl)benzonitrile (Example 50) using 2-hydrazineyl-5-(1-methyl-1H-1,2,3-triazol-4-yl)pyridine.

Example 55: Preparation of Compound 55

2-(N-(6-(4-(4-cyanophenyl)-5-hydroxy-3-methyl-1H-pyrazol-1-yl)pyridin-3-yl)sulfamoyl)acetic acid

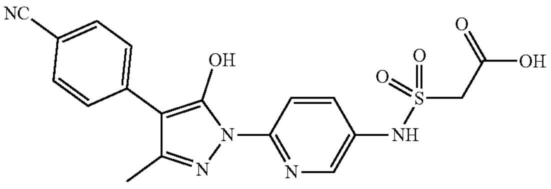 [SMILES: Cc1nn(-c2ccc(NS(=O)(=O)CC(=O)O)cn2)c(O)c1-c1ccc(C#N)cc1]

The compound was synthesized according to the procedure for the preparation of N-(6-(4-(4-cyanophenyl)-5-hydroxy-3-methyl-1H-pyrazol-1-yl)pyridin-3-yl) methanesulfonamide (Example 6).

Example 56: Preparation of Compound 56

(S)-4-(1-(5-(cyclopropanesulfonimidoyl)pyridin-2-yl)-5-hydroxy-3-methyl-1H-pyrazol-4-yl)benzonitrile

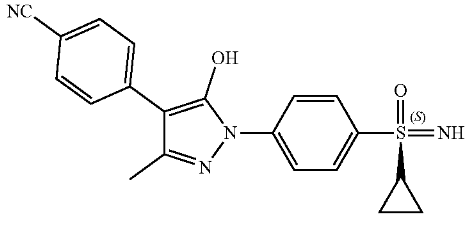

The compound was synthesized according to the procedure for the preparation of (S)-4-(5-hydroxy-3-methyl-1-(5-(S-isopropylsulfonimidoyl)pyridin-2-yl)-1H-pyrazol-4-yl) benzonitrile (Example 41).

Example 57: Preparation of Compound 57

(S)-4-(1-(5-(cyclopropanesulfonimidoyl)pyridin-2-yl)-5-hydroxy-3-methyl-1H-pyrazol-4-yl)benzonitrile

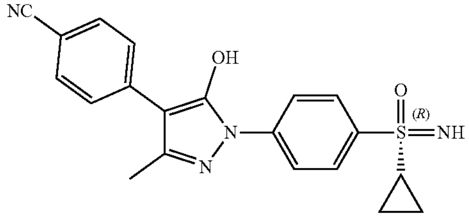

The compound was synthesized according to the procedure for the preparation of (S)-4-(5-hydroxy-3-methyl-1-(5-(S-isopropylsulfonimidoyl)pyridin-2-yl)-1H-pyrazol-4-yl) benzonitrile (Example 41).

Example 58: Preparation of Compound 58

(6-Chloropyridin-3-yl)(imino)(methyl)-$\lambda^6$-sulfanone

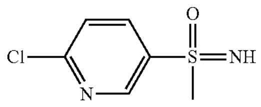

To a mixture of 2-chloro-5-(methylsulfinyl)pyridine (0.50 g, 2.8 mmol) (Intermediate for Example 12) and ammonium carbamate (0.88 g, 11.2 mmol) in methanol (25.0 mL) was added (diacetoxyiodo)benzene (2.7 g, 8.5 mmol). The mixture was stirred at 55° C. for 1.0 h and cooled. The reaction was diluted with ice-water and extracted twice with ethyl acetate. The organic layer was separated, washed with brine, dried over sodium sulfate and concentrated under reduced pressure. The crude product was purified by flash chromatography (dichloromethane/methanol=50/1) to afford (6-chloropyridin-3-yl)(imino)(methyl)-λ$^6$-sulfanone (300 mg, 1.58 mmol, 56.3% yield) as yellow syrup. LC-MS: m/z=191.0 $(M+H)^+$, retention time 1.22 min (Method A).

N-((6-chloropyridin-3-yl)(methyl)(oxo)-λ$^6$-sulfaneylidene)cyanamide

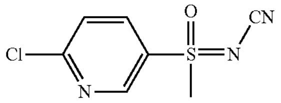

To a solution of (6-chloropyridin-3-yl)(imino)(methyl)-λ$^6$-sulfanone (190 mg, 1.0 mmol) in dichloromethane (10.0 mL) was added N,N-dimethylpyridin-4-amine (0.15 g, 1.2 mmol) and cyanic bromide (0.21 g, 2.0 mmol). The mixture was stirred at room temperature for 1.0 h. The reaction was partitioned between water and ethyl acetate. The organic layer was separated, washed with brine, dried over sodium sulfate and concentrated. The crude product was purified by flash chromatography (dichloromethane/methanol=50/1) to give N-((6-chloropyridin-3-yl)(methyl)(oxo)-λ$^6$-sulfaneylidene) cyanamide (100 mg, 0.46 mmol, 46.3% yield) as yellow oil. LC-MS: m/z=216.0 $(M+H)^+$, retention time 1.53 min (Method A).

N-((6-hydrazineylpyridin-3-yl)(methyl)(oxo)-λ$^6$-sulfaneylidene)cyanamide

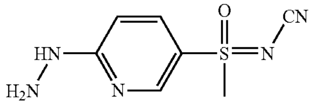

To a solution of N-((6-chloropyridin-3-yl)(methyl)(oxo)-λ$^6$-sulfaneylidene)cyanamide (100 mg, 0.46 mmol) in ethanol (3.0 mL) was added hydrazine hydrate (115 mg, 1.8 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford N-((6-hydrazineylpyridin-3-yl)(methyl)(oxo)-λ$^6$-sulfaneylidene) cyanamide (70 mg, 0.33 mmol, 72.1% yield) as yellow solid. LC-MS: m/z=212.0 $(M+H)^+$, retention time 0.32 min (Method A).

N-((6-(4-(4-cyanophenyl)-5-hydroxy-3-methyl-1H-pyrazol-1-yl)pyridin-3-yl)(methyl)(oxo)-λ$^6$-sulfaneylidene)cyanamide

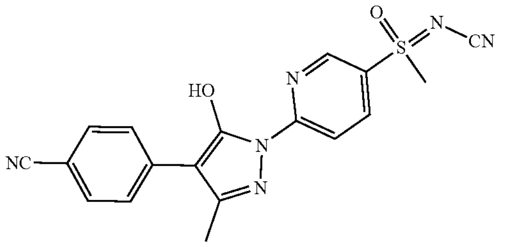 [SMILES: Cc1nn(-c2ccc(S(C)(=O)=NC#N)cn2)c(O)c1-c1ccc(C#N)cc1]

A mixture of N-((6-hydrazineylpyridin-3-yl)(methyl)(oxo)-λ$^6$-sulfaneylidene)cyanamide (70 mg, 0.33 mmol) and methyl 2-(4-cyanophenyl)-3-oxobutanoate (0.09 g, 0.39 mmol) in acetic acid (3.0 mL) was stirred at 100° C. for 1.0 h and concentrated. The resulting residue was purified by reverse prep-HPLC to afford N-((6-(4-(4-cyanophenyl)-5-hydroxy-3-methyl-1H-pyrazol-1-yl)pyridin-3-yl)(methyl)(oxo)-λ$^6$-sulfaneylidene)cyanamide (20.8 mg, 0.06 mmol, 16.7% yield) as white solid. LC-MS: m/z=379.0 $(M+H)^+$, retention time 4.49 min (Method A). $^1$HNMR (400 MHz, DMSO-$d_6$) δ 8.99 (d, J=2.3 Hz, 1H), 8.80 (d, J=9.1 Hz, 1H), 8.53 (dd, J=9.1, 2.5 Hz, 1H), 7.92 (d, J=8.4 Hz, 2H), 7.79 (d, J=8.4 Hz, 2H), 3.83 (s, 3H).

Example 59: Preparation of Compound 59

2-(6-Bromopyridin-3-yl)oxazole

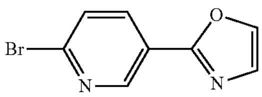 [SMILES: Brc1ccc(-c2ncco2)cn1]

n-Butyllithium (2.4 mL, 5.99 mmol, 2.5 M) was added dropwise to a stirred solution of oxazole (340.57 mg, 4.93 mmol) in tetrahydrofuran (50 mL) under nitrogen atmosphere at −78° C. The reaction mixture was stirred for 10 min and then zinc chloride (1 M in tetrahydrofuran, 10.6 mL, 10.57 mmol) was added portion wise to the above mixture. The mixture was warmed to room temperature. Then tetrakis(triphenylphosphine)palladium (203.53 mg, 0.18 mmol) and 2-bromo-5-iodopyridine (1000.00 mg, 3.52 mmol) were added to the reaction mixture, the mixture was stirred at 60° C. for 4 h. The reaction mixture was quenched with saturated ammonium chloride solution and extracted with ethyl acetate (50 mL×3). The organic phase was washed with saturated brine solution (50 mL), dried over sodium sulfate, filtered and concentrated. The residue was purified by flash chromatography (Biotage, 40 g normal phase silica gel, UV 254, petroleum ether/ethyl acetate=5/1) to give the 2-(6-bromopyridin-3-yl)oxazole (420 mg, 1.87 mmol, 53% yield). LC-MS: m/z=225 $(M+H)^+$, retention time 1.838 min (Method A).

2-(6-Hydrazineylpyridin-3-yl)oxazole

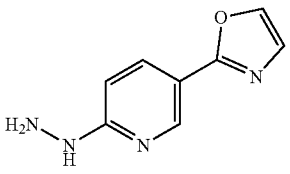

To a solution of 2-(6-bromopyridin-3-yl)oxazole (150.00 mg, 0.67 mmol) in ethanol (3 mL) was added hydrazine hydrate (2 mL), the reaction was stirred at 110° C. for 3 h in a sealed tube. The mixture was treated with water and white solid precipitated. Then it was filtered and dried to give the title compound (crude, 82 mg). LC-MS: m/z=177 $(M+H)^+$, retention time 1.186 min (Method A). The crude product was used to the next step.

4-(5-Hydroxy-3-methyl-1-(5-(oxazol-2-yl)pyridin-2-yl)-1H-pyrazol-4-yl)benzonitrile

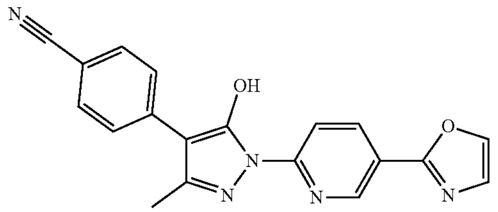

In a sealed tube equipped with a magnetic stirring bar were suspended methyl 2-(4-cyanophenyl)-3-oxobutanoate (90.00 mg, 0.41 mmol) and 2-(6-hydrazineylpyridin-3-yl) oxazole (73.00 mg, 0.41 mmol) in acetic acid (2 mL). The reaction mixture was heated to 120° C. for 1 h. The reaction was concentrated under reduced pressure and the residue was purified by slurrying in ethyl acetate to give the 4-(5-hydroxy-3-methyl-1-(5-(oxazol-2-yl)pyridin-2-yl)-1H-pyrazol-4-yl)benzonitrile (66.9 mg, 0.20 mmol, 47% yield) as yellow solid. LC-MS: m/z=344 $(M+H)^+$, retention time 4.750 min (Method A). $^1$HNMR (400 MHz, DMSO-$d_6$) δ 13.13 (s, 1H), 9.03 (s, 1H), 8.68-8.64 (m, 1H), 8.52-8.47 (m, 1H), 8.31 (s, 1H), 7.93-7.90 (m, 2H), 7.85-7.80 (m, 2H), 7.45 (s, 1H), 2.50 (s, 3H).

Example 60: Preparation of Compound 60

2-(6-chloropyridin-3-yl)thiazole

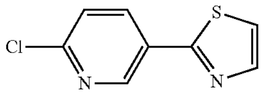

To a solution of 5-bromo-2-chloropyridine (500.0 mg, 2.60 mmol) and 2-(tributylstannyl) thiazole (1458.2 mg, 3.90 mmol) in N,N-dimethylformamide (10.0 mL) was added bis(triphenylphosphine)palladium(II) dichloride (182.37 mg, 0.26 mmol). The reaction was stirred at 100° C. for 3 hr in a sealed tube. The mixture was cooled to room temperature and concentrated to dryness. The residue was purified by flash chromatography (petroleum ether/ethyl acetate=20/1) to give 2-(6-chloropyridin-3-yl)thiazole (350 mg, 1.77 mmol, 68% yield). LCMS: m/z=197.0 $[M+H]^+$, retention time 1.719 min (Method A).

2-(6-hydrazineylpyridin-3-yl)thiazole

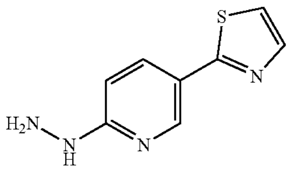 [SMILES: NNc1ccc(-c2ncco2)cn1]

A mixture of 2-(6-chloropyridin-3-yl)thiazole (300.0 mg, 1.53 mmol) in ethanol (3.0 mL) and hydrazine hydrate (3.0 mL, 85% in water) was stirred at 110° C. for 3 hr in a sealed tube. The mixture was cooled and concentrated to dryness. The residue was partitioned between ethyl acetate and water. The organic phase was washed with brine, dried over sodium sulfate and concentrated. The residue was triturated with petroleum ether and filtered to afford 2-(6-hydrazineylpyridin-3-yl)thiazole (185 mg, 0.96 mmol, 63% yield). LCMS: m/z=193.0 $[M+H]^+$, retention time 1.120 min (Method B). The product was pure enough and used directly to the next step.

4-(5-Hydroxy-3-methyl-1-(5-(thiazol-2-yl)pyridin-2-yl)-1H-pyrazol-4-yl)benzonitrile

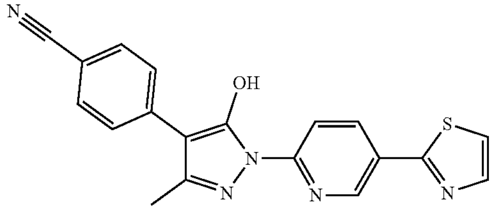 [SMILES: Cc1nn(-c2ccc(-c3ncco3)cn2)c(O)c1-c1ccc(C#N)cc1]

In a sealed tube equipped with a magnetic stirring bar were suspended methyl 2-(4-cyanophenyl)-3-oxobutanoate (180.00 mg, 0.83 mmol) and 2-(6-hydrazineylpyridin-3-yl) thiazole (159.30 mg, 0.83 mmol) in acetic acid (3 mL). The reaction mixture was heated to 120° C. for 1 h. The reaction was concentrated under reduced pressure and the residue was purified by slurrying in ethyl acetate to give the 4-(5-hydroxy-3-methyl-1-(5-(thiazol-2-yl)pyridin-2-yl)-1H-pyrazol-4-yl)benzonitrile (214.2 mg, 0.60 mmol, 72% yield) as yellow solid. LC-MS: m/z=360 $(M+H)^+$, retention time 5.064 min (Method A). $^1$HNMR (400 MHz, DMSO-$d_6$) δ 13.13 (br, 1H), 9.03 (d, J=2.0 Hz, 1H), 8.67-8.58 (m, 1H), 8.52-8.46 (m, 1H), 8.00 (d, J=3.6 Hz, 1H), 7.93-7.87 (m, 3H), 7.84-7.81 (m, 2H), 2.50 (s, 3H).

Example 61: Preparation of Compound 61

2-Bromo-5-phenylthiazole

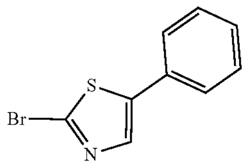 [SMILES: Brc1ncc(-c2ccccc2)s1]

To a solution of 5-phenylthiazol-2-amine (2.0 g, 11.40 mmol) in acetonitrile (50.0 mL) was added copper bromide (1.96 g, 13.60 mmol) and tert-butyl nitrite (14.0 g, 13.60 mmol). The mixture was stirred at 60° C. for 0.5 h under nitrogen. The reaction solution was cooled and diluted with ethyl acetate and water. The organic layer was washed with brine, dried over sodium sulfate and concentrated. The residue was purified by flash chromatography (petroleum ether/ethyl acetate=10/1) to afford 2-bromo-5-phenylthiazole (780 mg, 11.40 mmol, 28.9% yield) as white solid. LC-MS: m/z=239.9 $(M+H)^+$, retention time 2.202 min (Method A).

2-(6-Chloropyridin-3-yl)-5-phenylthiazole

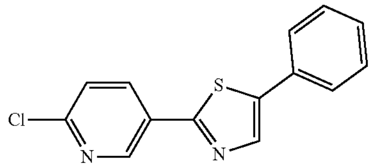 [SMILES: Clc1ccc(-c2ncc(-c3ccccc3)s2)cn1]

To a solution of 2-bromo-5-phenylthiazole (510 mg, 2.10 mmol), 2-chloro-5-(4,4,5,5-tetramethyl-1,3,2-dioxaborolan-2-yl)pyridine (750.0 mg, 3.14 mmol) and potassium carbonate (869.4 mg, 6.30 mmol) was added tetrakis(triphenylphosphine)palladium (127.0 mg, 0.11 mmol) in 1,4-dioxane/water (10.0 mL/2.5 mL). The mixture was stirred at 120° C. for 16.0 h under nitrogen and cooled to room temperature. Ethyl acetate and water were added to the solution, and the layers were separated. The organic layer was washed with brine, dried over sodium sulfate and concentrated to dryness. The residue was purified by flash chromatography (petroleum ether/ethyl acetate=10/1) to afford 2-(6-chloropyridin-3-yl)-5-phenylthiazole (200.0 mg, 2.10 mmol, 34.6% yield) as white solid. LC-MS: m/z=273.0 $(M+H)^+$, retention time 2.223 min (Method A).

2-(6-Hydrazineylpyridin-3-yl)-5-phenylthiazole

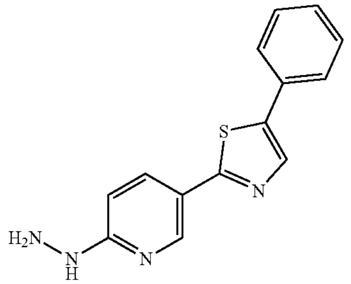 [SMILES: NNc1ccc(-c2ncc(-c3ccccc3)s2)cn1]

To a solution of 2-(6-chloropyridin-3-yl)-5-phenylthiazole (400 mg, 1.5 mmol) in ethanol (10.0 mL) was added hydrazine hydrate (4.0 mL, 85% in water). The mixture was stirred at 110° C. in a sealed tube for 2.0 h. The mixture was cooled and concentrated to dryness. The residue was partitioned between ethyl acetate and water. The organic phase was washed with brine, dried over sodium sulfate and concentrated. The residue was triturated with petroleum ether and filtered to afford 2-(6-hydrazineylpyridin-3-yl)-5-phenylthiazole (150.0 mg, 1.50 mmol, 38.1% yield) as yellow solid. LC-MS: m/z=269.1 $(M+H)^+$, retention time 1.538 min (Method A).

4-(5-Hydroxy-3-methyl-1-(5-(5-phenylthiazol-2-yl)pyridin-2-yl)-1H-pyrazol-4-yl)benzonitrile

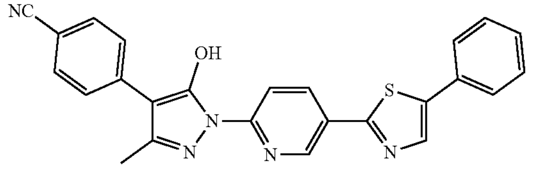 [SMILES: Cc1nn(-c2ccc(-c3ncc(-c4ccccc4)s3)cn2)c(O)c1-c1ccc(C#N)cc1]

A mixture of methyl 2-(4-cyanophenyl)-3-oxobutanoate (108.5 mg, 0.50 mmol) and 2-(6-hydrazineylpyridin-3-yl)-5-phenylthiazole (134.0 mg, 0.50 mmol) in acetic acid (3.0 mL) was stirred at 120° C. for 1.0 h and concentrated. The resulting residue was purified by reverse prep-HPLC to afford 4-(5-hydroxy-3-methyl-1-(5-(5-phenylthiazol-2-yl)pyridin-2-yl)-1H-pyrazol-4-yl)benzonitrile (76.4 mg, 0.50 mmol, 35.5% yield) as white solid. LC-MS: m/z=435.9 $(M+H)^+$, retention time 6.278 min (Method A). $^1$HNMR (400 MHz, DMSO-$d_6$) δ 13.13 (s, 1H), 9.08 (s, 1H), 8.60 (m, 2H), 8.27 (s, 1H), 8.08 (d, J=8.0 Hz, 2H), 7.92 (d, J=8.0 Hz, 2H), 7.83 (d, J=8.0 Hz, 2H), 7.50 (t, J=8.0 Hz, 2H), 7.40 (t, J=8.0 Hz, 1H), 2.56-2.49 (m, 3H).

Example 62: Preparation of Compound 62

2-Bromo-4-phenylthiazole

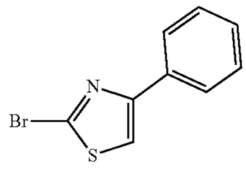 [SMILES: Brc1nc(-c2ccccc2)cs1]

To a solution of 4-phenylthiazol-2-amin (2.0 g, 11.40 mmol) in acetonitrile (50.0 mL) was added copper bromide (1.96 g, 13.60 mmol) and tert-butyl nitrite (14.0 g, 13.60 mmol). The mixture was stirred at 60° C. for 0.5 h under nitrogen. The reaction solution was cooled and diluted with ethyl acetate and water. The organic layer was washed with brine, dried over sodium sulfate and concentrated. The residue was purified by flash chromatography (petroleum ether/ethyl acetate=10/1) to afford 2-bromo-4-phenylthiazole (900 mg, 11.40 mmol, 33.3% yield) as white solid. LC-MS: m/z=239.9 $(M+H)^+$, retention time 2.204 min (Method A).

2-(6-Chloropyridin-3-yl)-4-phenylthiazole

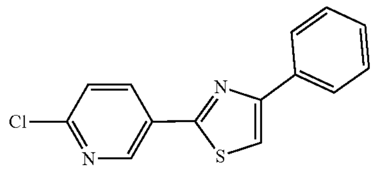 [SMILES: Clc1ccc(-c2nc(-c3ccccc3)cs2)cn1]

To a solution of 2-bromo-4-phenylthiazole (450 mg, 1.90 mmol), 2-chloro-5-(4,4,5,5-tetramethyl-1,3,2-dioxaborolan-2-yl)pyridine (675.0 mg, 2.80 mmol) and potassium carbonate (786.60 mg, 5.70 mmol) was added tetrakis(triphenylphosphine)palladium (440.0 mg, 0.38 mmol) in 1,4-dioxane/water (20.0 mL/5.0 mL). The mixture was stirred at 120° C. for 16.0 h under nitrogen and cooled to room temperature. Ethyl acetate and water were added to the solution, and the layers were separated. The organic layer was washed with brine, dried over sodium sulfate and concentrated to dryness. The residue was purified by flash chromatography (petroleum ether/ethyl acetate=10/1) to afford 2-(6-chloropyridin-3-yl)-4-phenylthiazole (220.0 mg, 1.90 mmol, 43.1% yield) as white solid. LC-MS: m/z=273.0 $(M+H)^+$, retention time 2.288 min (Method A).

2-(6-Hydrazineylpyridin-3-yl)-4-phenylthiazole

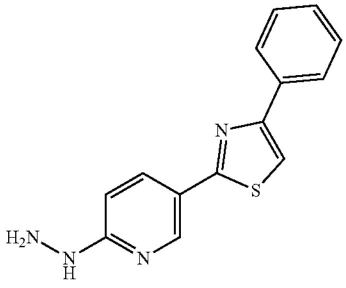 [SMILES: NNc1ccc(-c2nc(-c3ccccc3)cs2)cn1]

To a solution of 2-(6-chloropyridin-3-yl)-4-phenylthiazole (400 mg, 1.5 mmol) in ethanol (10.0 mL) was added hydrazine hydrate (4.0 mL, 85% in water). The mixture was stirred at 110° C. in a sealed tube for 2.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford 2-(6-hydrazineylpyridin-3-yl)-4-phenylthiazole (140.0 mg, 1.50 mmol, 36.10% yield) as white solid. LC-MS: m/z=269.1 $(M+H)^+$, retention time 1.552 min (Method A).

4-(5-Hydroxy-3-methyl-1-(5-(4-phenylthiazol-2-yl)pyridin-2-yl)-1H-pyrazol-4-yl)benzonitrile

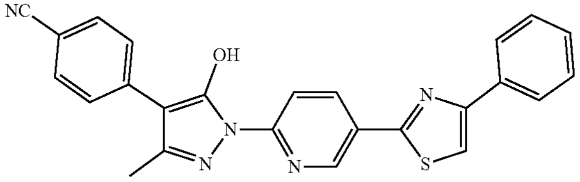 [SMILES: Cc1nn(-c2ccc(-c3nc(-c4ccccc4)cs3)cn2)c(O)c1-c1ccc(C#N)cc1]

A mixture of methyl 2-(4-cyanophenyl)-3-oxobutanoate (81.0 mg 0.37 mmol) and 2-(6-hydrazineylpyridin-3-yl)-4-phenylthiazole (100.0 mg, 0.37 mmol) in acetic acid (3.0 mL) was stirred at 120° C. for 1.0 h and concentrated. The resulting residue was purified by reverse prep-HPLC to afford 4-(5-hydroxy-3-methyl-1-(5-(4-phenylthiazol-2-yl)pyridin-2-yl)-1H-pyrazol-4-yl)benzonitrile (97.5 mg, 0.37 mmol, 59.9% yield) as white solid. LC-MS: m/z=435.9 $(M+H)^+$, retention time 6.385 min (Method A). $^1$HNMR (400 MHz, DMSO-$d_6$) δ 13.15 (s, 1H), 9.04 (d, J=4 Hz, 1H), 8.64 (s, 1H), 8.51 (d, J=8.0 Hz, 1H), 8.41 (s, 1H), 7.92 (d, J=8.0 Hz, 2H), 7.83 (d, J=8.0 Hz, 2H), 7.76 (d, J=8.0 Hz, 2H), 7.50 (t, J=8.0 Hz, 2H), 7.41 (t, J=8.0 Hz, 1H), 2.52 (m, 3H).

Example 63: Preparation of Compound 63

2-bromo-5-(1H-pyrazol-1-yl)pyridine

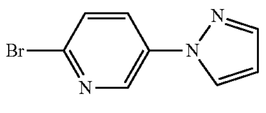 [SMILES: Brc1ccc(-n2cccn2)cn1]

A mixture of 2-bromo-5-iodopyridine (1.00 g, 3.52 mmol), 1H-pyrazole (239.8 mg, 3.52 mmol), cuprous iodide (67.09 mg, 0.35 mmol), potassium phosphate (1.87 g, 8.81 mmol) and (1R,2R)-cyclohexane-1,2-diamine (45.6 mg, 0.4 mmol) in 1,4-dioxane (10.0 mL) was stirred at room temperature for 12 h. The reaction solution was diluted with ethyl acetate and water. The organic layer was washed with brine, dried over sodium sulfate and concentrated. The residue was purified by flash chromatography (petroleum ether/ethyl acetate=6/1) to afford 2-bromo-5-(1H-pyrazol-1-yl)pyridine (220 mg, 2.85 mmol, 81.12% yield) as yellow oil. LCMS: m/z=224.1 (M+H)+, retention time 1.55 min (Method A).

2-hydrazineyl-5-(1H-pyrazol-1-yl)pyridine

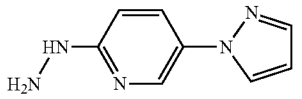

To a solution of 2-bromo-5-(1H-pyrazol-1-yl)pyridine (200 mg, 0.89 mmol) in ethanol (2.0 mL) was added hydrazine hydrate (223.2 mg, 4.46 mmol, 85% in water). The mixture was stirred at 100° C. for 2 hr in a sealed tube. The mixture was cooled and concentrated to dryness. The residue was partitioned between ethyl acetate and water. The organic layer was separated, washed with brine, dried over sodium sulfate and concentrated. The residue was triturated with petroleum ether and filtered to afford 2-hydrazineyl-5-(1H-pyrazol-1-yl)pyridine (140 mg, 0.80 mmol, 90.32% yield) as yellow solid. LCMS: m/z=176.1 (M+H)+, retention time 1.01 min (Method B).

4-(1-(5-(1H-pyrazol-1-yl)pyridin-2-yl)-5-hydroxy-3-methyl-1H-pyrazol-4-yl)benzonitrile

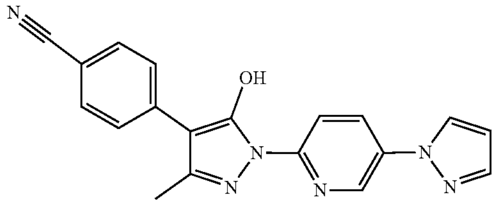 [SMILES: Cc1nn(-c2ccc(-n3cccn3)cn2)c(O)c1-c1ccc(C#N)cc1]

A mixture of methyl (E)-2-(4-cyanophenyl)-3-(dimethylamino)acrylate (210.3 mg, 0.91 mmol) and 2-hydrazineyl-5-(1H-pyrazol-1-yl)pyridine (0.14 g, 0.8 mmol) in acetic acid (5.0 mL) was stirred at 120° C. for 1.0 h and concentrated. The resulting residue was purified by reverse prep-HPLC to afford 4-(1-(5-(1H-pyrazol-1-yl)pyridin-2-yl)-5-hydroxy-3-methyl-1H-pyrazol-4-yl)benzonitrile (47.5 mg, 0.14 mmol, 17.3% yield) as white solid. LC-MS: m/z=343.0 $(M+H)^+$, retention time 4.72 min (Method A). $^1$HNMR (400 MHz, DMSO-$d_6$) δ 13.01 (s, 1H), 8.96 (d, J=2.6 Hz, 1H), 8.61 (d, J=2.4 Hz, 2H), 8.50-8.27 (m, 1H), 7.97-7.88 (m, 2H), 7.86-7.75 (m, 3H), 6.76-6.46 (m, 1H), 2.51 (s, 3H).

Example 64: Preparation of Compound 64

4-(4,4,5,5-Tetramethyl-1,3,2-dioxaborolan-2-yl)-1H-pyrazole

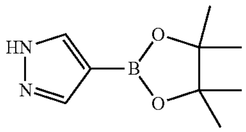

To a solution of 4-bromo-1H-pyrazole (2.9 g, 20.0 mmol), bis(pinacolato)diboron (7.68 g, 30.0 mmol) and potassium acetate (3.8 g, 40.0 mmol) in 1,4-dioxane (100.0 mL) was added [1,1'-bis(diphenylphosphino)ferrocene]dichloropalladium(II) (1.5 g, 2.0 mmol). The mixture was stirred at 100° C. under nitrogen for 8.0 h and cooled to room temperature. Ethyl acetate and water were added to the solution, and the layers were separated. The organic layer was washed with brine, dried over sodium sulfate and concentrated to dryness. Crude 4-(4,4,5,5-tetramethyl-1,3,2-dioxaborolan-2-yl)-1H-pyrazol (1.1 g, 5.64 mmol, 28.2% yield) was obtained. LC-MS: m/z=195.0 $(M+H)^+$, retention time 1.70 min (Method A). The product was used directly to the next step.

4-Phenyl-1H-pyrazole

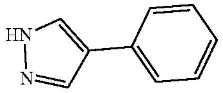 [SMILES: c1ccc(-c2cn[nH]c2)cc1]

To a solution of bromobenzene (1.32 g, 8.5 mmol), 4-(4,4,5,5-tetramethyl-1,3,2-dioxaborolan-2-yl)-1H-pyrazol (1.1 g, 5.6 mmol) and potassium carbonate (2.35 g, 17.0 mmol) was added [1,1'-bis(diphenylphosphino)ferrocene] dichloropalladium(II) (580 mg, 0.8 mmol) in N,N-dimethylformamide/water (15.0 mL/3.0 mL). The mixture was stirred at 100° C. for 4.0 h under nitrogen and cooled to room temperature. Ethyl acetate and water were added to the solution, and the layers were separated. The organic layer was washed with brine, dried over sodium sulfate and concentrated to dryness. The residue was purified by flash chromatography (petroleum ether/ethyl acetate=3/1) to afford 4-phenyl-1H-pyrazole (600 mg, 6.32 mmol, 74.4% yield) as yellow solid. LC-MS: m/z=145.0 $(M+H)^+$, retention time 1.65 min (Method A).

2-Bromo-5-(4-phenyl-1H-pyrazol-1-yl)pyridine

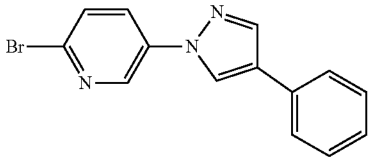 [SMILES: Brc1ccc(-n2cc(-c3ccccc3)cn2)cn1]

A mixture of 2-bromo-5-iodopyridine (1.0 g, 3.52 mmol), 4-phenyl-1H-pyrazole (500 mg, 3.5 mmol), cuprous iodide (67.09 mg, 0.35 mmol), potassium phosphate (1.87 g, 8.81 mmol), (1R,2R)-cyclohexane-1,2-diamine (45.6 mg, 0.4 mmol) in 1,4-dioxane (10.0 mL) was stirred at 100° C. for 4.0 h. The reaction solution was diluted with ethyl acetate and water. The organic layer was washed with brine, dried over sodium sulfate and concentrated. The residue was purified by flash chromatography (petroleum ether/ethyl acetate=3/1) to afford 2-bromo-5-(4-phenyl-1H-pyrazol-1-yl)pyridine (520 mg, 1.74 mmol, 49.5% yield) as yellow oil. LC-MS: m/z=300.0 $(M+H)^+$, retention time 2.05 min (Method A).

2-Hydrazineyl-5-(4-phenyl-1H-pyrazol-1-yl)pyridine

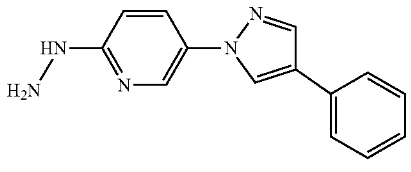 [SMILES: NNc1ccc(-n2cc(-c3ccccc3)cn2)cn1]

To a solution of 2-bromo-5-(4-phenyl-1H-pyrazol-1-yl) pyridine (480 mg, 1.6 mmol) in ethanol (5.0 mL) was added hydrazine hydrate (400 mg, 8.0 mmol, 85% in water). The mixture was stirred at 110° C. in a sealed tube for 2.0 h. The mixture was cooled and concentrated to dryness. The residue was partitioned between ethyl acetate and water. The organic phase was washed with brine, dried over sodium sulfate and concentrated. The residue was triturated with petroleum ether and filtered to afford (2-Hydrazineyl-5-(4-phenyl-1H-pyrazol-1-yl)pyridine (160 mg, 0.64 mmol, 39.9% yield) as yellow solid. LC-MS: m/z=252.0 $(M+H)^+$, retention time 1.65 min (Method A).

4-(5-Hydroxy-3-methyl-1-(5-(4-phenyl-1H-pyrazol-1-yl)pyridin-2-yl)-1H-pyrazol-4-yl)benzonitrile

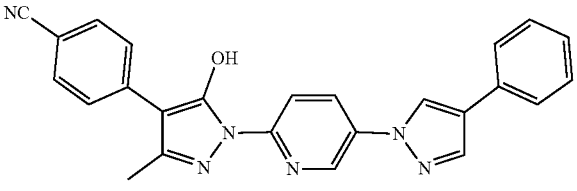 [SMILES: Cc1nn(-c2ccc(-n3cc(-c4ccccc4)cn3)cn2)c(O)c1-c1ccc(C#N)cc1]

A mixture of methyl 2-(4-cyanophenyl)-3-oxobutanoate (0.1 g, 0.48 mmol) and 2-hydrazineyl-5-(4-phenyl-1H-pyrazol-1-yl)pyridine (0.1 g, 0.4 mmol) in acetic acid (10.0 mL) was stirred at 120° C. for 0.5 h and concentrated. The resulting residue was purified by reverse prep-HPLC to afford 4-(5-hydroxy-3-methyl-1-(5-(4-phenyl-1H-pyrazol-1-yl)pyridin-2-yl)-1H-pyrazol-4-yl)benzonitrile (42.8 mg, 0.43 mmol, 25.6% yield) as white solid. LC-MS: m/z=419.0 $(M+H)^+$, retention time 3.52 min (Method A). $^1$HNMR (400 MHz, DMSO-$d_6$) δ 13.04 (s, 1H), 9.09 (s, 1H), 9.01 (s, 1H), 8.73-8.58 (m, 1H), 8.54-8.40 (m, 1H), 8.31 (s, 1H), 8.01-7.87 (m, 2H), 7.87-7.78 (m, 2H), 7.79-7.67 (m, 2H), 7.52-7.36 (m, 2H), 7.35-7.20 (m, 1H), 2.51 (s, 3H).

Example 65: Preparation of Compound 65

2-Chloro-5-(cyclopropylthio)pyridine

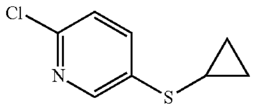 [SMILES: Clc1ccc(SC2CC2)cn1]

A mixture of 6-chloropyridine-3-thiol (1.0 g, 6.90 mmol) (Intermediate for Example 24), cyclopropylboronic acid (2.97 g, 34.48 mmol), cupric acetate (2.48 g, 13.8 mmol) and triethylamine (4.19 g, 41.4 mmol) in dichloromethane (50.0 mL) was stirred at 40° C. for 12.0 h under oxygen. The reaction mixture was then filtered and the filtrate was concentrated to give a residue. The residue was purified by flash chromatography (petroleum ether/ethyl acetate=10/1) to to afford 2-chloro-5-(cyclopropylthio)pyridine (900 mg, 4.86 mmol, 70.9% yield) as yellow oil. LC-MS: m/z=186.1 $(M+H)^+$, retention time 2.04 min (Method A)

2-Chloro-5-(cyclopropylsulfinyl)pyridine

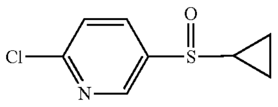 [SMILES: O=S(c1ccc(Cl)nc1)C1CC1]

To a solution of 2-chloro-5-(cyclopropylthio)pyridine (900 mg, 4.86 mmol) in dichloromethane (10.0 mL) was added 3-chloroperoxybenzoic acid (1.08 g, 5.35 mmol, 85%) at 0° C. The mixture was stirred at this temperature for 1.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=5/1) to obtain 2-chloro-5-(cyclopropylsulfinyl)pyridine (900 mg, 4.47 mmol, 92.1% yield) as yellow solid. LC-MS: m/z=202.1 $(M+H)^+$, retention time 1.49 min (Method A).

(S)-(6-Chloropyridin-3-yl)(cyclopropyl)(imino)-$\lambda^6$-sulfanone and (R)-(6-Chloropyridin-3-yl)(cyclopropyl)(imino)-$\lambda^6$-sulfanone

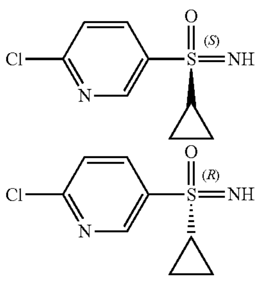

To a mixture of 2-chloro-5-(cyclopropylsulfinyl)pyridine (900 mg, 4.47 mmol) and ammonium carbamate (1.39 g, 17.9 mmol) in methanol (25.0 mL) was added (diacetoxyiodo)benzene (4.30 g, 13.4 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-chloropyridin-3-yl)(cyclopropyl)(imino)-$\lambda^6$-sulfanone (1.2 g, crude) as yellow syrup. LC-MS: m/z=217.0 $(M+H)^+$, retention time 0.55 min (Method A).

It was separated by chiral prep-HPLC to give both isomers as yellow solids: (S)-(6-chloropyridin-3-yl)(cyclopropyl)(imino)-$\lambda^6$-sulfanone (400 mg, 1.85 mmol) and (R)-(6-chloropyridin-3-yl)(cyclopropyl)(imino)-$\lambda^6$-sulfanone (430 mg, 1.99 mmol).

(S)-cyclopropyl(6-hydrazineylpyridin-3-yl)(imino)-$\lambda^6$-sulfanone

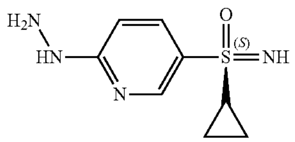

To a solution of (S)-(6-chloropyridin-3-yl)(cyclopropyl)(imino)-$\lambda^6$-sulfanone (120 mg, 0.56 mmol) in ethanol (10.0 mL) was added hydrazine hydrate (180 mg, 2.87 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (S)-cyclopropyl(6-hydrazineylpyridin-3-yl)(imino)-$\lambda^6$-sulfanone (120 mg, crude) as yellow solid. LC-MS: m/z=213.0 $(M+H)^+$, retention time 0.35 min (Method A).

(R)-cyclopropyl(6-hydrazineylpyridin-3-yl)(imino)-$\lambda^6$-sulfanone

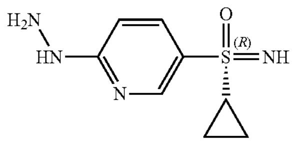

To a solution of (R)-(6-chloropyridin-3-yl)(cyclopropyl)(imino)-$\lambda^6$-sulfanone (120 mg, 0.56 mmol) in ethanol (10.0 mL) was added hydrazine hydrate (180 mg, 2.87 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (R)-cyclopropyl(6-hydrazineylpyridin-3-yl)(imino)-$\lambda^6$-sulfanone (130 mg, crude) as yellow solid. LC-MS: m/z=213.0 $(M+H)^+$, retention time 0.35 min (Method A).

(S)-(6-(4-(4-chlorophenyl)-5-hydroxy-3-methyl-1H-pyrazol-1-yl)pyridin-3-yl)(cyclopropyl)(imino)-$\lambda^6$-sulfanone

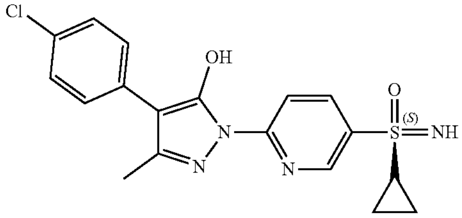

A mixture of ethyl 2-(4-chlorophenyl)-3-oxobutanoate (130 mg, 0.56 mmol) (Intermediate for Example 1) and (S)-cyclopropyl(6-hydrazineylpyridin-3-yl)(imino)-$\lambda^6$-sulfanone (100 mg, 0.47 mmol) in acetic acid (5.0 mL) was stirred at 120° C. for 1.0 h and concentrated. The resulting residue was purified by reverse prep-HPLC to give (S)-(6-(4-(4-chlorophenyl)-5-hydroxy-3-methyl-1H-pyrazol-1-yl)pyridin-3-yl)(cyclopropyl)(imino)-$\lambda^6$-sulfanone (37.95 mg, 0.10 mmol, 20.8% yield) as white solid. LC-MS: m/z=389.0 $(M+H)^+$, retention time 7.68 min (Method A). $^1$HNMR (400 MHz, DMSO-$d_6$) δ 12.73 (s, 1H), 8.85 (d, J=2.0 Hz, 1H), 8.69-8.51 (m, 1H), 8.37 (dd, J=8.9, 2.3 Hz, 1H), 7.68 (d, J=8.6 Hz, 2H), 7.43 (d, J=8.5 Hz, 2H), 4.55 (s, 1H), 2.87-2.71 (m, 1H), 2.41 (s, 3H), 1.28-1.10 (m, 1H), 1.07-0.85 (m, 3H).

Example 66: Preparation of Compound 66

(R)-(6-(4-(4-chlorophenyl)-5-hydroxy-3-methyl-1H-pyrazol-1-yl)pyridin-3-yl)(cyclopropyl)(imino)-$\lambda^6$-sulfanone

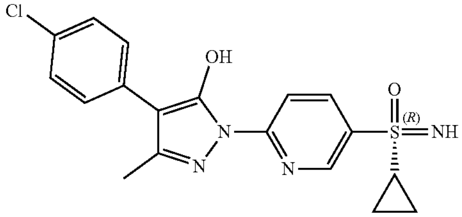

A mixture of ethyl 2-(4-chlorophenyl)-3-oxobutanoate (130 mg, 0.56 mmol) (Intermediate for Example 1) and (R)-cyclopropyl(6-hydrazineylpyridin-3-yl)(imino)-$\lambda^6$-sulfanone (100 mg, 0.47 mmol) in acetic acid (5.0 mL) was stirred at 120° C. for 1.0 h and concentrated. The resulting residue was purified by reverse prep-HPLC to give (R)-(6-(4-(4-chlorophenyl)-5-hydroxy-3-methyl-1H-pyrazol-1-yl)pyridin-3-yl)(cyclopropyl)(imino)-$\lambda^6$-sulfanone (49.9 mg, 0.13 mmol, 27.4% yield) as white solid. LC-MS: m/z=389.0 $(M+H)^+$, retention time 7.68 min (Method A). $^1$HNMR (400 MHz, DMSO-$d_6$) δ 12.74 (s, 1H), 8.85 (d, J=2.1 Hz, 1H), 8.63 (d, J=8.6 Hz, 1H), 8.38 (dd, J=8.9, 2.4 Hz, 1H), 7.67 (d, J=8.6 Hz, 2H), 7.44 (d, J=8.6 Hz, 2H), 4.56 (s, 1H), 2.85-2.72 (m, 1H), 2.42 (s, 3H), 1.21-1.12 (m, 1H), 1.09-0.84 (m, 3H).

Example 67: Preparation of Compound 67

N-(6-(4-(4-chlorophenyl)-5-hydroxy-3-methyl-1H-pyrazol-1-yl)pyridin-3-yl)methanesulfonamide

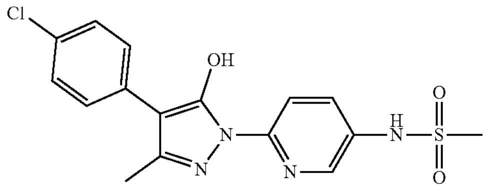 [SMILES: Cc1nn(-c2ccc(NS(C)(=O)=O)cn2)c(O)c1-c1ccc(Cl)cc1]

A solution of methyl 2-(4-chlorophenyl)-3-oxobutanoate (258.00 mg 1.07 mmol) and N-(6-hydrazineylpyridin-3-yl)methanesulfonamide (217.0 mg, 1.07 mmol) (Intermediate for Example 6) in acetic acid (5.0 mL) was stirred at 120° C. for 1.0 h and concentrated to dryness. The residue was triturated with ethyl acetate and filtered to afford N-(6-(4-(4-chlorophenyl)-5-hydroxy-3-methyl-1H-pyrazol-1-yl)pyridin-3-yl)methanesulfonamide (210 mg, 1.07 mmol, 53.4% yield) as white solid. LC-MS: m/z=378.9 $(M+H)^+$, retention time 4.70 min (Method A). $^1$HNMR (400 MHz, DMSO-$d_6$) δ 12.52 (s, 1H), 9.92 (s, 1H), 8.47 (s, 1H), 8.31 (m, 1H), 7.76 (m, 1H), 7.67 (m, 1H), 7.43 (d, J=8.0 Hz, 1H), 3.06 (s, 3H), 2.40 (s, 3H).

Example 68: Preparation of Compound 68

2-Ethylhexyl 3-((6-chloro-4-methylpyridin-3-yl)thio)propanoate

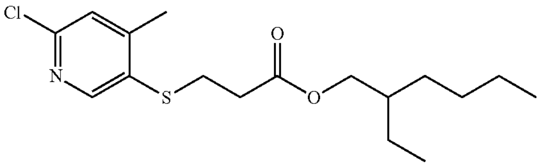 [SMILES: CCCCC(CC)COC(=O)CCSc1cnc(Cl)cc1C]

A mixture of 5-bromo-2-chloro-4-methylpyridine (4.3 g, 20.9 mmol), 3-mercapto propionic acid 2-ethylhexyl ester (4.5 g, 20.9 mmol), N,N-diisopropylethylamine (5.4 g, 41.8 mmol), 4,5-bis(diphenylphosphino)-9,9-dimethylxanthene (1.3 g, 2.1 mmol) and tris(dibenzylideneacetone)dipalladium (0.96 g, 1.1 mmol) in toluene (100.0 mL) was stirred at 120° C. for 12 h under nitrogen and cooled. The reaction was diluted with ice-water and extracted with ethyl acetate twice. The organic layer was separated, washed with brine, dried over sodium sulfate and concentrated. The crude product was purified by flash chromatography (petroleum ether/ethyl acetate=3/1) to give 2-ethylhexyl 3-((6-chloro-4-methylpyridin-3-yl)thio)propanoate (3.2 g, 9.32 mmol, 44.6% yield) as brown oil. LC-MS: m/z=344.0 $(M+H)^+$, retention time 2.50 min (Method A).

6-Chloro-4-methylpyridine-3-thiol

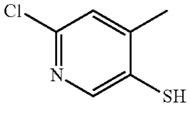

To a solution of 2-ethylhexyl 3-((6-chloro-4-methylpyridin-3-yl)thio)propanoate 3.4 g, 10 mmol) in anhydrous tetrahydrofuran (100.0 mL) was added potassium tert-butoxide (15.0 mL, 15.0 mmol, 1M in tetrahydrofuran) at −78° C. The mixture was allowed to warm up to 0° C. and left stirring for another 30 min. The reaction was quenched with saturated ammonium chloride solution and extracted twice with ethyl acetate. The organic layer was separated, washed with brine, dried over sodium sulfate and concentrated. The crude product was purified by flash chromatography (petroleum ether/ethyl acetate=5/1) to give 6-chloro-4-methylpyridine-3-thiol (1.0 g, 6.25 mmol, 62.5% yield) as yellow oil. LC-MS: m/z=160.0 $(M+H)^+$, retention time 1.82 min (Method A).

2-Chloro-5-(cyclopropylthio)-4-methylpyridine

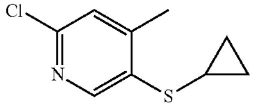

A mixture of 6-chloro-4-methylpyridine-3-thiol (1.59 g, 10.0 mmol), cyclopropylboronic acid (0.43 g, 50.0 mmol), cupric acetate (3.5 g, 20.0 mmol) and triethylamine (6.07 g, 60.0 mmol) in dichloromethane (100.0 mL) was stirred at 40° C. for 12.0 h under oxygen. The reaction mixture was then filtered and the filtrate was concentrated to give a residue. The residue was purified by flash chromatography (petroleum ether/ethyl acetate=10/1) to afford 2-chloro-5-(cyclopropylthio)-4-methylpyridine (200 mg, 1.0 mmol, 10% yield) as yellow oil. LC-MS: m/z=200.0 $(M+H)^+$, retention time 2.06 min (Method A).

2-Chloro-5-(cyclopropylsulfinyl)-4-methylpyridine

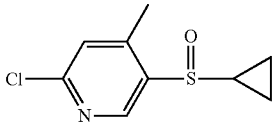

To a solution of 2-chloro-5-(cyclopropylthio)-4-methylpyridine (200 mg, 1.0 mmol) in dichloromethane (20.0 mL) was added 3-chloroperoxybenzoic acid (200 mg, 1.0 mmol, 85%) at 0° C. The mixture was stirred at this temperature for 2.0 h. The reaction was basified with 10% sodium hydroxide solution and extracted twice with dichloromethane. The organic layer was separated, washed with brine, dried over sodium sulfate and concentrated under reduced pressure. The crude product was purified by flash chromatography (petroleum ether/ethyl acetate=5/1) to obtain 2-chloro-5-(cyclopropylsulfinyl)-4-methylpyridine (200 mg, 0.92 mmol, 92.5% yield) as yellow solid. LC-MS: m/z=216.0 $(M+H)^+$, retention time 1.55 min (Method A).

(S)-(6-chloro-4-methylpyridin-3-yl)(cyclopropyl)(imino)-$\lambda^6$-sulfanone and (R)-(6-chloro-4-methylpyridin-3-yl)(cyclopropyl)(imino)-$\lambda^6$-sulfanone

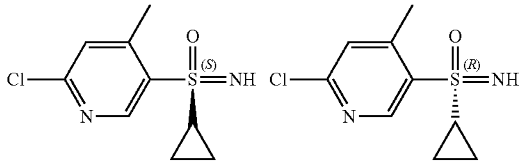

To a mixture of 2-chloro-5-(cyclopropylsulfinyl)-4-methylpyridine (200 mg, 1.0 mmol) and ammonium carbamate (300 mg, 4.0 mmol) in methanol (20.0 mL) was added (diacetoxyiodo)benzene (1.0 g, 3.0 mmol). The mixture was stirred at room temperature for 30 min and cooled. The reaction was diluted with ice-water and extracted twice with ethyl acetate. The organic layer was separated, washed with brine, dried over sodium sulfate and concentrated under reduced pressure. The crude product was purified by flash chromatography (petroleum ether/ethyl acetate=2/1) to obtain (6-chloro-4-methylpyridin-3-yl)(cyclopropyl)(imino)-$\lambda^6$-sulfanone (200 mg, crude) as yellow syrup. LC-MS: m/z=231.0 $(M+H)^+$, retention time 0.55 min (Method A).

It was separated by chiral prep-HPLC to afford both isomers as yellow solid: (S)-(6-chloro-4-methylpyridin-3-yl)(cyclopropyl)(imino)-$\lambda^6$-sulfanone (80 mg, 0.35 mmol); and (R)-(6-chloro-4-methylpyridin-3-yl)(cyclopropyl)(imino)-$\lambda^6$-sulfanone (80 mg, 0.35 mmol).

(S)-cyclopropyl(6-hydrazineyl-4-methylpyridin-3-yl)(imino)-$\lambda^6$-sulfanone

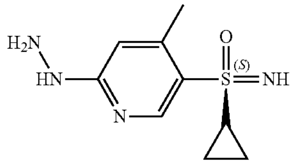

To a solution of (S)-(6-chloro-4-methylpyridin-3-yl)(cyclopropyl)(imino)-$\lambda^6$-sulfanone (80 mg, 0.34 mmol) in ethanol (5.0 mL) was added hydrazine hydrate (73 mg, 1.15 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (S)-cyclopropyl(6-hydrazineyl-4-methylpyridin-3-yl)(imino)-$\lambda^6$-sulfanone (64 mg, crude) as yellow solid. LC-MS: m/z=227.0 $(M+H)^+$, retention time 0.34 min (Method A).

(R)-cyclopropyl(6-hydrazineyl-4-methylpyridin-3-yl)(imino)-$\lambda^6$-sulfanone

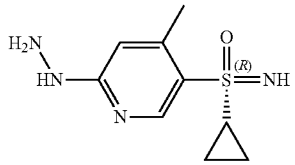

To a solution of (R)-(6-chloro-4-methylpyridin-3-yl)(cyclopropyl)(imino)-$\lambda^6$-sulfanone (80 mg, 0.34 mmol) in ethanol (5.0 mL) was added hydrazine hydrate (73 mg, 1.15 mmol, 85% in water). The mixture was stirred at 80° C. for 4.0 h. The mixture was cooled and concentrated to give dryness. The residue was partitioned between ethyl acetate and water. The organic phase was washed with brine, dried over sodium sulfate and concentrated. The residue was triturated with petroleum ether and filtered to afford (R)-cyclopropyl(6-hydrazineyl-4-methylpyridin-3-yl)(imino)-$\lambda^6$-sulfanone (66 mg, crude) as yellow solid. LC-MS: m/z=227.0 $(M+H)^+$, retention time 0.34 min (Method A).

(S)-4-(1-(5-(cyclopropanesulfonimidoyl)-4-methylpyridin-2-yl)-5-hydroxy-3-methyl-1H-pyrazol-4-yl)benzonitrile

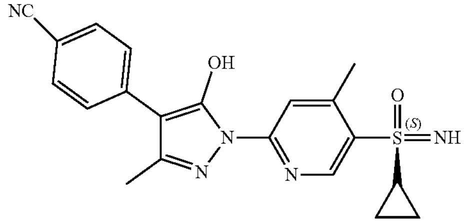

A mixture of methyl 2-(4-cyanophenyl)-3-oxobutanoate (70 mg, 0.31 mmol) and (S)-cyclopropyl(6-hydrazineyl-4-methylpyridin-3-yl)(imino)-$\lambda^6$-sulfanone (60 mg, crude) in acetic acid (8.0 mL) was stirred at 120° C. for 1.0 h and concentrated. The resulting residue was purified by reverse prep-HPLC to afford (S)-4-(1-(5-(cyclopropanesulfonimidoyl)-4-methylpyridin-2-yl)-5-hydroxy-3-methyl-1H-pyrazol-4-yl)benzonitrile (30.5 mg, 0.08 mmol, 29.8% yield) as white solid. LC-MS: m/z=394.0 $(M+H)^+$, retention time 3.68 min (Method A). $^1$HNMR (400 MHz, DMSO-$d_6$) δ 13.16 (s, 1H), 8.78 (s, 1H), 7.96-7.87 (m, 2H), 7.86-7.78 (m, 2H), 3.00-2.86 (m, 1H), 2.80 (s, 3H), 2.52 (s, 3H), 1.20-0.77 (m, 4H).

Example 69: Preparation of Compound 69

1 (R)-4-(1-(5-(cyclopropanesulfonimidoyl)-4-methylpyridin-2-yl)-5-hydroxy-3-methyl-1H-pyrazol-4-yl)benzonitrile

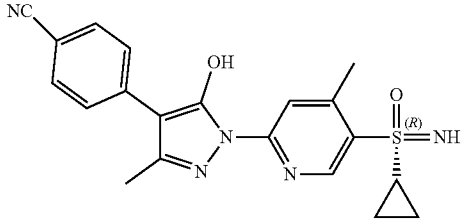

A mixture of methyl 2-(4-cyanophenyl)-3-oxobutanoate (70 mg, 0.31 mmol) and (S)-cyclopropyl(6-hydrazineyl-4-methylpyridin-3-yl)(imino)-$\lambda^6$-sulfanone (66 mg, crude) in acetic acid (5.0 mL) was stirred at 120° C. for 1.0 h and concentrated. The resulting residue was purified by reverse prep-HPLC to give (R)-4-(1-(5-(cyclopropanesulfonimidoyl)-4-methylpyridin-2-yl)-5-hydroxy-3-methyl-1H-pyrazol-4-yl)benzonitrile (31.5 mg, 0.08 mmol, 25.9% yield) as white solid. LC-MS: m/z=394.0 $(M+H)^+$, retention time 3.69 min (Method A). $^1$HNMR (400 MHz, DMSO-$d_6$) δ 13.17 (s, 1H), 8.78 (s, 1H), 8.14-7.69 (m, 4H), 3.00-2.86 (m, 1H), 2.80 (s, 3H), 2.50 (s, 3H), 1.13-0.82 (m, 4H).

Example 70: Preparation of Compound 70

6-chloro-4-methyl-N-phenylpyridine-3-sulfonamide

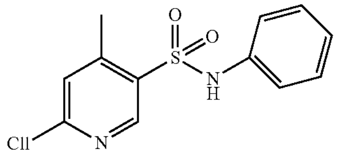

To a solution of 6-chloro-4-methylpyridine-3-sulfonyl chloride (200 mg, 0.88 mmol) in DCM (3 mL) was added aniline (206 mg, 2.21 mmol). The reaction was stirred at RT for about 0.5 hr. After the reaction was completed as indicated by TLC, the resulting mixture was concentrated, the crude solid was washed with water and a diluted HCl solution (2N, 10 mL). After filtration, 225 mg of the desired product was obtained. $^1$H-NMR (300 MHz, $CDCl_3$) δ 8.82 (s, 1H), 7.31-7.28 (m, 2H), 7.20-7.11 (m, 1H), 7.09-7.01 (m, 2H), 6.67 (s, 1H), 2.59 (s, 3H).

6-hydrazinyl-4-methyl-N-phenylpyridine-3-sulfonamide

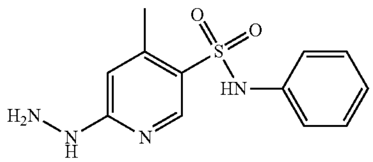 [SMILES: Cc1cc(NN)ncc1S(=O)(=O)Nc1ccccc1]

A mixture of 6-chloro-4-methyl-N-phenylpyridine-3-sulfonamide (205 mg, 0.73 mmol) in water (1 mL) and EtOH (5 mL) was added Hydrazine hydrate (2 mL). The reaction was stirred at 100° C. overnight. After the reaction was completed as indicated by TLC analysis, the reaction mixture was concentrated directly. 250 mg of the crude solid was obtained, which was used for the next step without further purification. LC-MS (ESI+): m/z 279 $(M+H)^+$.

6-(4-(4-cyanophenyl)-5-hydroxy-3-methyl-1H-pyrazol-1-yl)-4-methyl-N-phenylpyridine-3-sulfonamide

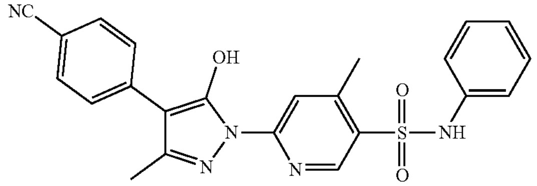 [SMILES: Cc1cc(-n2nc(C)c(-c3ccc(C#N)cc3)c2O)ncc1S(=O)(=O)Nc1ccccc1]

To a mixture of 6-hydrazinyl-4-methyl-N-phenylpyridine-3-sulfonamide (200 mg, 0.72 mmol) in AcOH (5 ml) was added ethyl 2-(4-cyanophenyl)-3-oxobutanoate (499 mg, 2.16 mmol). The reaction was stirred at 100° C. for 3 hrs. After the reaction was completed as indicated by TLC analysis, the reaction was concentrated to dryness. The crude product was purified by preparative HPLC. 35.1 mg of the desired product was obtained. LC-MS (ESI−): m/z 444 $(M-H)^-$; HPLC purity: 98.6%; $^1$H-NMR (300 MHz, $CDCl_3$) δ 8.74 (s, 1H), 7.83 (s, 1H), 7.75-7.66 (m, 4H), 7.31-7.30 (m, 1H), 7.20-7.18 (m, 1H), 7.10-7.01 (m, 2H), 6.47 (s, 1H), 2.72 (s, 3H), 2.43 (s, 3H).

Example 71: Preparation of Compound 71

6-(4-(4-cyanophenyl)-5-hydroxy-3-methyl-1H-pyrazol-1-yl)-N-cyclopropyl-4-methylpyridine-3-sulfonamide

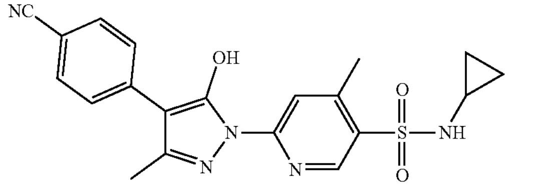 [SMILES: Cc1cc(-n2nc(C)c(-c3ccc(C#N)cc3)c2O)ncc1S(=O)(=O)NC1CC1]

The compound was synthesized according to the procedure used in the preparation of 6-(4-(4-cyanophenyl)-5-hydroxy-3-methyl-1H-pyrazol-1-yl)-4-methyl-N-phenylpyridine-3-sulfonamide using N-cyclopropyl-6-hydrazineyl-4-methylpyridine-3-sulfonamide. LC-MS (ESI−): m/z 408 $(M-H)^-$; HPLC purity was 98.5%; $^1$H-NMR (300 MHz, $CDCl_3$) δ 8.89 (s, 1H), 7.88 (s, 1H), 7.70 (s, 4H), 5.03 (s, 1H), 2.73 (s, 3H), 2.50-2.41 (m, 4H), 0.69-0.60 (m, 2H), 0.52-0.44 (m, 2H).

Example 72: Preparation of Compound 72

4-(5-hydroxy-3-methyl-1-(4-methyl-5-(pyrrolidin-1-ylsulfonyl)pyridin-2-yl)-1H-pyrazol-4-yl)benzonitrile

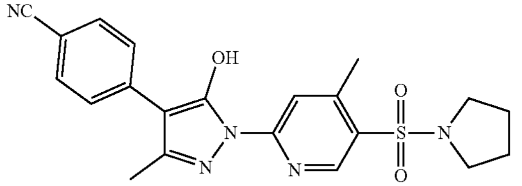 [SMILES: Cc1cc(-n2nc(C)c(-c3ccc(C#N)cc3)c2O)ncc1S(=O)(=O)N1CCCC1]

The compound was synthesized according to the procedure used in the preparation of 6-(4-(4-cyanophenyl)-5-hydroxy-3-methyl-1H-pyrazol-1-yl)-4-methyl-N-phenylpyridine-3-sulfonamide using 2-hydrazineyl-4-methyl-5-(pyrrolidin-1-ylsulfonyl)pyridine. LC-MS (ESI+): m/z 424 $(M+H)^+$; HPLC purity was 99.3%; $^1$H-NMR (300 MHz, $CDCl_3$) δ 12.80 (brs, 1H), 8.76 (s, 1H), 7.87 (s, 1H), 7.69 (s, 4H), 3.37 (t, J=6.6 Hz, 4H), 2.74 (s, 3H), 2.45 (s, 3H), 1.94-1.99 (m, 4H).

Example 73: Preparation of Compound 73

4-(1-(5-(N,S-dimethylsulfonimidoyl)pyridin-2-yl)-5-hydroxy-3-methyl-1H-pyrazol-4-yl)benzonitrile

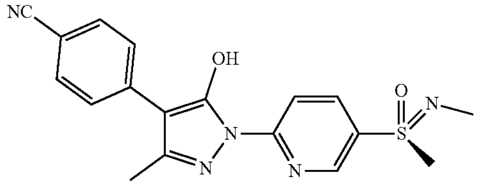 [SMILES: CN=[S@@](C)(=O)c1ccc(-n2nc(C)c(-c3ccc(C#N)cc3)c2O)nc1]

The compound is synthesized according to the procedure for the preparation of Example 15. The racemic mixture of (6-hydrazineylpyridin-3-yl)(methyl)(methylimino)-$\lambda^6$-sulfanone is separated by Chiral prep-HPLC.

Example 74: Preparation of Compound 74

4-(1-(5-(N,R-dimethylsulfonimidoyl)pyridin-2-yl)-5-hydroxy-3-methyl-1H-pyrazol-4-yl)benzonitrile

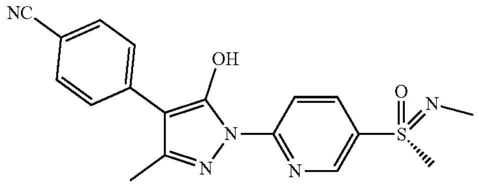 [SMILES: CN=[S@](C)(=O)c1ccc(-n2nc(C)c(-c3ccc(C#N)cc3)c2O)nc1]

The compound is synthesized according to the procedure for the preparation of Example 15. The racemic mixture of (6-hydrazineylpyridin-3-yl)(methyl)(methylimino)-$\lambda^6$-sulfanone is separated by Chiral prep-HPLC.

Example 75: Preparation of Compound 75

4-(5-hydroxy-3-methyl-1-(5-(phenylsulfonimidoyl)pyridin-2-yl)-1H-pyrazol-4-yl)benzonitrile

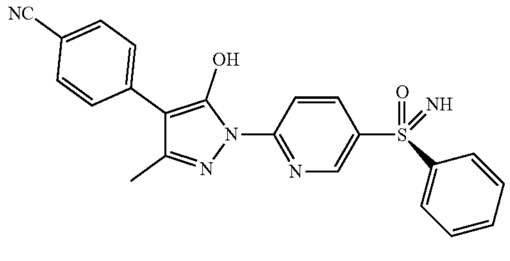 [SMILES: Cc1nn(-c2ccc([S@@](=N)(=O)c3ccccc3)cn2)c(O)c1-c1ccc(C#N)cc1]

The compound is synthesized according to the procedure for the preparation of Example 20. The racemic mixture of (6-hydrazineylpyridin-3-yl)(imino)(phenyl)-λ6-sulfanone is separated by Chiral prep-HPLC.

Example 76: Preparation of Compound 76

4-(5-hydroxy-3-methyl-1-(5-(phenylsulfonimidoyl)pyridin-2-yl)-1H-pyrazol-4-yl)benzonitrile

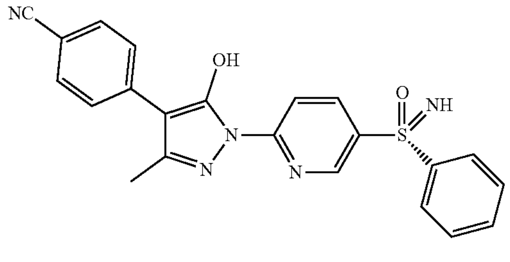 [SMILES: Cc1nn(-c2ccc([S@](=N)(=O)c3ccccc3)cn2)c(O)c1-c1ccc(C#N)cc1]

The compound is synthesized according to the procedure for the preparation of Example 20. The racemic mixture of (6-hydrazineylpyridin-3-yl)(imino)(phenyl)-λ6-sulfanone is separated by Chiral prep-HPLC.

Example 77: Preparation of Compound 77

6-(4-(4-cyanophenyl)-5-hydroxy-3-methyl-1H-pyrazol-1-yl)-N,N-dimethylpyridine-3-sulfonimidamide

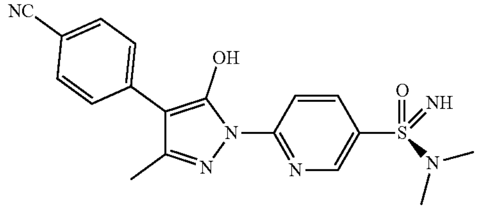 [SMILES: Cc1nn(-c2ccc([S@@](=N)(=O)N(C)C)cn2)c(O)c1-c1ccc(C#N)cc1]

The compound is synthesized according to the procedure for the preparation of Example 25. The racemic mixture of tert-butyl ((dimethylamino)(6-hydrazineylpyridin-3-yl)(oxo)-λ6-sulfaneylidene)carbamate is separated by Chiral prep-HPLC.

Example 78: Preparation of Compound 78

6-(4-(4-cyanophenyl)-5-hydroxy-3-methyl-1H-pyrazol-1-yl)-N,N-dimethylpyridine-3-sulfonimidamide

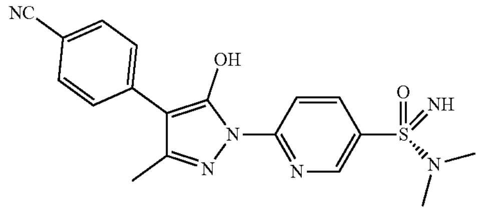 [SMILES: Cc1nn(-c2ccc([S@](=N)(=O)N(C)C)cn2)c(O)c1-c1ccc(C#N)cc1]

The compound is synthesized according to the procedure for the preparation of Example 25. The racemic mixture of tert-butyl ((dimethylamino)(6-hydrazineylpyridin-3-yl)(oxo)-λ6-sulfaneylidene)carbamate is separated by Chiral prep-HPLC.

Example 79: Preparation of Compound 79

4-(5-hydroxy-3-methyl-1-(5-(N-methylcyclopropanesulfonimidoyl)pyridin-2-yl)-1H-pyrazol-4-yl)benzonitrile

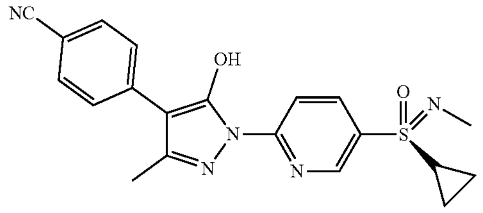 [SMILES: CN=[S@@](=O)(c1ccc(-n2nc(C)c(-c3ccc(C#N)cc3)c2O)nc1)C1CC1]

The compound is synthesized according to a procedure similar to the preparation of Example 15. The racemic mixture of (6-hydrazineylpyridin-3-yl)(methyl)(cycloproyplimino)-$\lambda^6$-sulfanone is separated by Chiral prep-HPLC.

Example 80: Preparation of Compound 80

4-(5-hydroxy-3-methyl-1-(5-(N-methylcyclopropanesulfonimidoyl)pyridin-2-yl)-1H-pyrazol-4-yl)benzonitrile

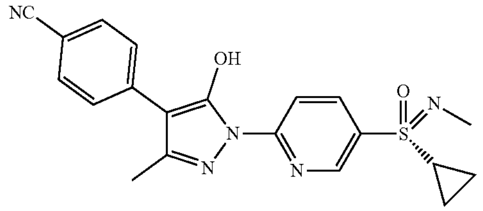 [SMILES: CN=[S@](=O)(c1ccc(-n2nc(C)c(-c3ccc(C#N)cc3)c2O)nc1)C1CC1]

The compound was synthesized according to a procedure similar to the preparation of Example 15. The racemic mixture of (6-hydrazineylpyridin-3-yl)(methyl)(cycloproyplimino)-$\lambda^6$-sulfanone was separated by Chiral prep-HPLC.

Example 81: Preparation of Compound 81

6-(4-(4-cyanophenyl)-5-hydroxy-3-methyl-1H-pyrazol-1-yl)-N,N,N'-trimethylpyridine-3-sulfonimidamide

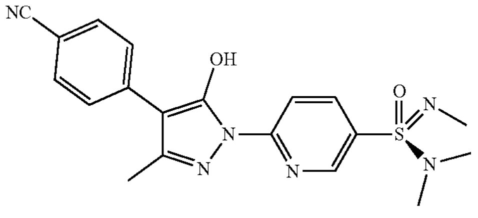 [SMILES: CN=[S@@](=O)(c1ccc(-n2nc(C)c(-c3ccc(C#N)cc3)c2O)nc1)N(C)C]

The compound is synthesized according to a procedure similar to the preparation of Example 25. The racemic mixture of 6-hydrazineyl-N,N,N'-trimethylpyridine-3-sulfonimidamide is separated by Chiral prep-HPLC.

Example 82: Preparation of Compound 82

6-(4-(4-cyanophenyl)-5-hydroxy-3-methyl-1H-pyrazol-1-yl)-N,N,N'-trimethylpyridine-3-sulfonimidamide

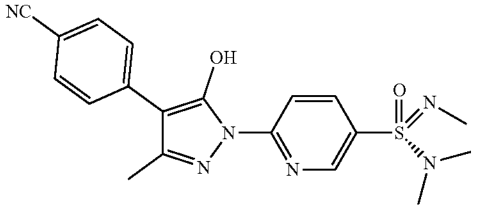 [SMILES: CN=[S@](=O)(c1ccc(-n2nc(C)c(-c3ccc(C#N)cc3)c2O)nc1)N(C)C]

The compound is synthesized according to a procedure similar to the preparation of Example 25. The racemic mixture of 6-hydrazineyl-N,N,N'-trimethylpyridine-3-sulfonimidamide is separated by Chiral prep-HPLC.

Example 83: Preparation of Compound 83

4-(5-hydroxy-3-methyl-1-(5-(5-phenyl-1,3,4-thiadiazol-2-yl)pyridin-2-yl)-1H-pyrazol-4-yl)benzonitrile

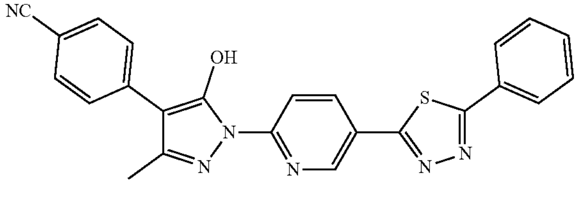

The compound is synthesized according to a procedure similar to the preparation of Example 61.

Vitro Assays Demonstrate PHD Inhibition

Enzymatic half maximal inhibitory concentration ($IC_{50}$) values were determined on selected compounds of the invention.

Time-resolved fluorescence resonance energy transfer (TR-FRET) assay was utilized to determine the enzymatic half maximal inhibitory concentration ($IC_{50}$) value of PHD inhibitors against the full-length human prolyl-4-hydroxylase domain (PHD) enzymes, PHD1, PHD2, and PHD3. The TR-FRET assay was developed based on the specific binding of hydroxylated HIF-1α peptide with the complex formed by VHL, EloB and EloC (VBC), to generate a fluorescent signal. Terbium (Tb)-Donor (monoclonal antibody anti-6His-Tb-cryptate Gold) and D2-acceptor (streptavidin [SA]-D2) of TR-FRET are linked to the VBC complex and to HIF-1α peptide, respectively. The VBC complex binds specifically to the HIF-1α peptide when it is hydroxylated, allowing energy transfer from TR-FRET donor to acceptor (FIG. 1).

Materials and Methods

All chemicals and materials unless otherwise noted were of standard laboratory grade and were purchased from Sigma-Aldrich (St. Louis, MO, USA).

Reagents

TR-FRET Reagents

Monoclonal antibody anti-6His-Tb-cryptate Gold (catalog #61HI2TLA) and streptavidin (SA)-D2 (catalog #610SADLA) were purchased from CisBio International (Bedford, MA, USA).

N-terminus biotinylated HIF-1α C35 synthetic peptide representing amino acids 547 to 581 and including the proline 564 PHD2 hydroxylation site was purchased from California Peptide Research (Salt Lake City, UT, USA).

Recombinant Proteins

VBC Complex

His-tagged recombinant VHL protein, EloB, EloC complex (His-VBC) was supplied by Axxam (Milan, Italy). Recombinant human VHL (National Center for Biotechnology Information [NCBI] accession number NP_00542.1) contained a His tag at the C-terminus of amino acids 55 to 213 and is referred to as VHL-His. VHL-His was co-expressed in *E. coli* with full-length human EloB (NCBI accession number Q15370.1) and full-length human EloC (NCBI accession number Q15369.1) and purified by affinity chromatography on a nickel-nitrilotriacetic acid (Ni-NTA) column as the His-VBC complex. Purity (~80%) was assessed by sodium dodecyl sulfate polyacrylamide gel electrophoresis (SDS-PAGE).

PHD1

Recombinant human PHD1 protein (catalog #81064, Lot #24717001) was purchased from Active Motif (Carlsbad, CA, USA). PHD1 was expressed in a baculovirus expression system as the full-length protein (NCBI accession number NP_542770.2) with an N-terminal FLAG tag (molecular weight 44.9 kDa). Purity (>90%) was assessed by SDS-PAGE.

PHD2

The full-length human PHD2 enzyme was produced with a baculovirus infected insect cell (BIIC) expression system by Beryllium (Bedford, MA, USA). The PHD2 construct contained amino acids 1 to 426 of PHD2 (UniProt Knowledgebase[UniProtKB]/Swiss-Prot accession number Q9GZT9.1), and a His tag and a Tobacco Etch Virus (TEV) protease cleavage site at the N-terminus. The construct was expressed in Sf9 insect cells, purified by Ni-NTA column and digested with TEV protease to remove the His tag. The purity of final cleaved protein was assessed by SDS-PAGE and was found to be >94% pure.

PHD3

Recombinant human PHD3 protein (molecular weight 31.1 kDa) was purchased from Active Motif (Carlsbad, CA, USA). It was expressed in *E. coli* as the full-length protein (NCBI accession number NP_071356.1) with an N-terminal 6-His tag (catalog #81033, Lot #24417001). Purity was assessed by SDS-PAGE and was found to be >75% pure.

PHD Inhibitors.

Small molecule PHD inhibitors were synthesized and their identities were confirmed as described herein.

TR-FRET Assay Procedure

PHD inhibitor compound was preincubated with PHD enzyme in a 10 μL reaction volume in white 384-well Optiplate microplates (catalog #6007290, Perkin Elmer, Waltham, MA, USA). For this, 5 μL PHD inhibitor compound was serially diluted with dilution buffer (50 mM HEPES [4-(2-hydroxyethyl)-1-piperazineethanesulfonic acid] pH 7.5, 50 mM sodium chloride [NaCl], 0.01% Tween-20, 0.01% purified bovine serum albumin [BSA]) and mixed with 5 μL PHD enzyme mix prepared as a 4× concentrate in the dilution buffer containing PHD enzyme (60 nM PHD1, 20 nM PHD2, 140 nM PHD3), 40 μM ferrous ammonium sulfate (FAS), 4 mM sodium (Na) ascorbate. The plates were incubated for 30 minutes at room temperature without rotation.

Five microliters of the VBC/anti-6His-Tb-cryptate Gold mix prepared as a 4× concentrate in dilution buffer containing 20 nM His-VBC, 1.32 nM monoclonal antibody anti-6His-Tb-cryptate Gold was then added. This step was followed immediately by the addition of 5 μL of the HIF-1α C35 substrate mix prepared as a 4× concentrate in the dilution buffer containing 120 nM biotin-labeled HIF-1α C35, 132 nM SA-D2, 4 μM 2-oxoglutarate (2-OG) to reach a final reaction volume of 20 μL.

The final assay reaction contained 50 mM HEPES, pH 7.5, 50 mM NaCl, 1 μM 2-OG, 10 μM FAS, 1 mM Na ascorbate, 0.01% Tween-20, 0.01% purified BSA, 30 nM biotin-labeled HIF-1α C35, 5 nM His-VBC, 0.33 nM monoclonal antibody anti-6His-Tb-cryptate Gold, 33 nM SA-D2 and PHD enzyme (15 nM PHD1, 5 nM PHD2, or 35 nM PHD3) with the diluted compound.

For the measurement of the $IC_{50}$ of PHD inhibitor compound, reactions were incubated for 10 minutes at room temperature and then read on a Perkin Elmer EnVision (Waltham, MA, USA) at an excitation wavelength of 340 nm and at emission wavelengths of 615 nm and 665 nm. The data represent the quotient of the signal intensity at 665 nm and 615 nm, automatically calculated by Envision Manager software (Perkin Elmer, Waltham, MA, USA). The $IC_{50}$ values (mean, standard deviation, standard error of the mean, geometric mean and 95% confidence interval) were determined using a four-parameter curve-fit using GraphPad Prism 7.0 (GraphPad, La Jolla, CA, USA) and represent the compound concentration plotted against the calculated ratio of 665 nm and 615 nm. TR-FRET assays were performed in triplicate at each concentration of compound and the assays were repeated independently three times.

Kis were calculated from $IC_{50}$s based on the Cheng Prussoff equation:

$$Ki=IC50=(1+[2\text{-}OG]/Km)$$

The final concentration of 2-OG in both the PHD1 and PHD2 assays is 1 uM. The Km of 2-OG for PHD1 was determined to be 12.7 nM, while the Km of 2-OG for PHD2 was determined to be 22.6 nM.

Exemplary Compounds

| Cmpd. No. | Structure | PHD1 $IC_{50}$ (nM) | PHD2 $IC_{50}$(nM) | PHD3 $IC_{50}$(nM) |
|---|---|---|---|---|
| 1. | 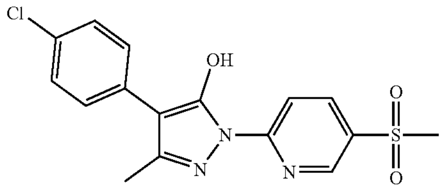 [SMILES: Cc1nn(-c2ccc(S(C)(=O)=O)cn2)c(O)c1-c1ccc(Cl)cc1] | A | A | B |
| 2. | 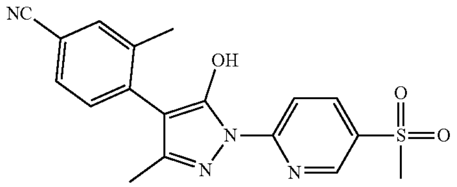 [SMILES: Cc1cc(C#N)ccc1-c1c(C)nn(-c2ccc(S(C)(=O)=O)cn2)c1O] | A | A | A |
| 3. | 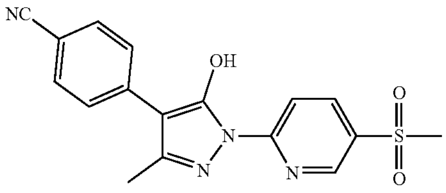 [SMILES: Cc1nn(-c2ccc(S(C)(=O)=O)cn2)c(O)c1-c1ccc(C#N)cc1] | A | A | A |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 4. | 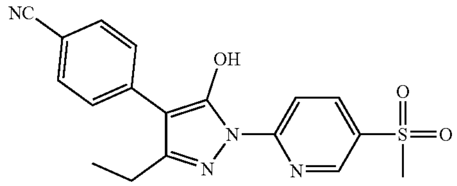 [SMILES: CCc1nn(-c2ccc(S(C)(=O)=O)cn2)c(O)c1-c1ccc(C#N)cc1] | A | A | C |
| 5. | 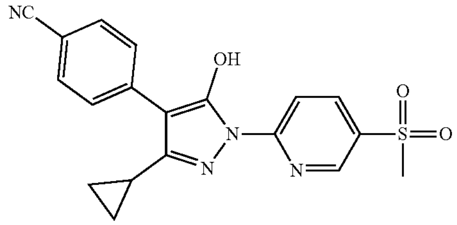 [SMILES: CS(=O)(=O)c1ccc(-n2nc(C3CC3)c(-c3ccc(C#N)cc3)c2O)nc1] | B | C | D |
| 6. | 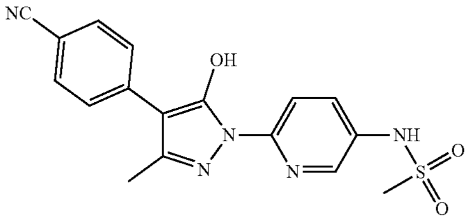 [SMILES: Cc1nn(-c2ccc(NS(C)(=O)=O)cn2)c(O)c1-c1ccc(C#N)cc1] | A | A | A |
| 7. | 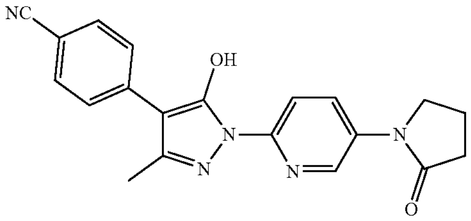 [SMILES: Cc1nn(-c2ccc(N3CCCC3=O)cn2)c(O)c1-c1ccc(C#N)cc1] | A | A | B |
| 8. | 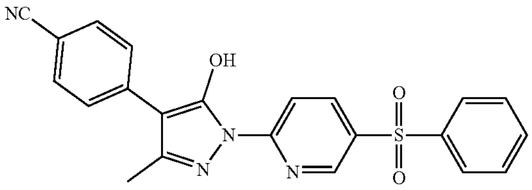 [SMILES: Cc1nn(-c2ccc(S(=O)(=O)c3ccccc3)cn2)c(O)c1-c1ccc(C#N)cc1] | A | A | B |
| 9. | 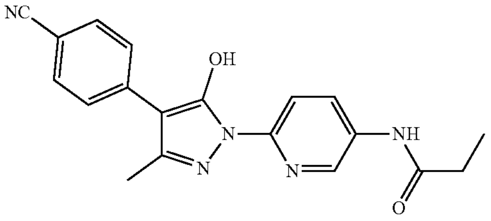 [SMILES: CCC(=O)Nc1ccc(-n2nc(C)c(-c3ccc(C#N)cc3)c2O)nc1] | A | A | B |
| 10. | 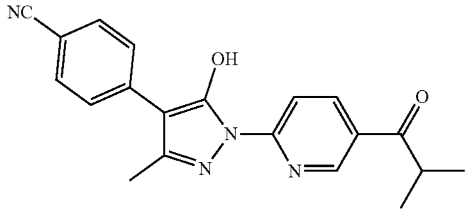 [SMILES: Cc1nn(-c2ccc(C(=O)C(C)C)cn2)c(O)c1-c1ccc(C#N)cc1] | A | A | B |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 11. | 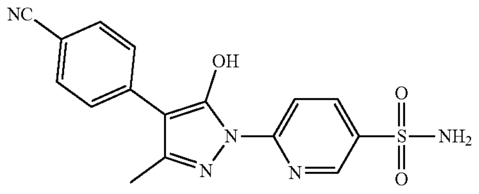 [SMILES: Cc1nn(-c2ccc(S(N)(=O)=O)cn2)c(O)c1-c1ccc(C#N)cc1] | A | A | A |
| 12. | 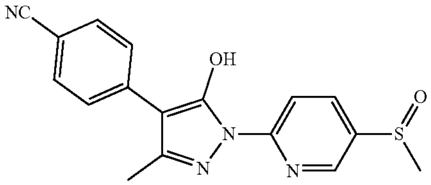 | A | A | A |
| 13. | 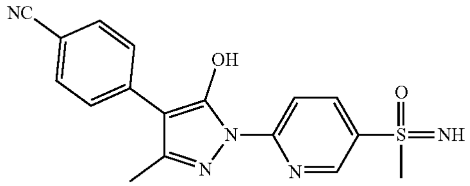 | A | A | B |
| 14. | 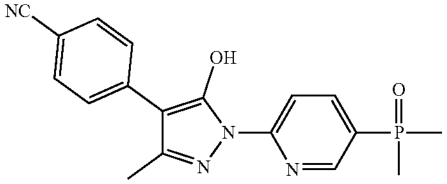 [SMILES: Cc1nn(-c2ccc(P(C)(C)=O)cn2)c(O)c1-c1ccc(C#N)cc1] | A | A | — |
| 15. | 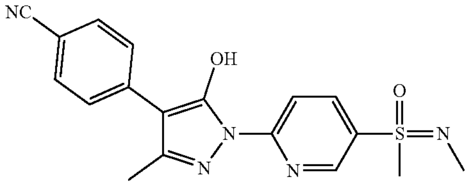 [SMILES: CN=S(C)(=O)c1ccc(-n2nc(C)c(-c3ccc(C#N)cc3)c2O)nc1] | A | A | A |
| 16. | 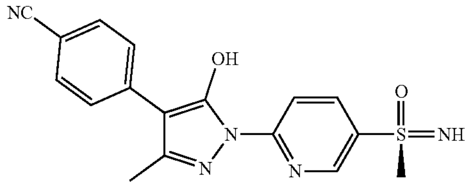 | A | A | — |
| 17. | 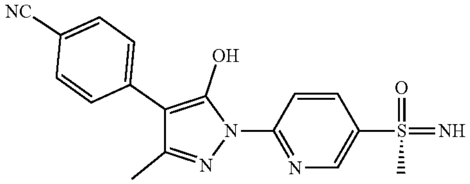 [SMILES: Cc1nn(-c2ccc([S@](C)(=N)=O)cn2)c(O)c1-c1ccc(C#N)cc1] | A | A | — |
| 18. | 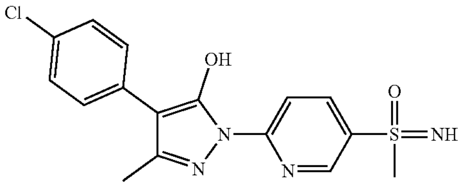 | A | A | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 19. | 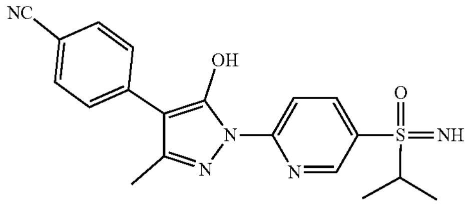 [SMILES: Cc1nn(-c2ccc(S(=N)(=O)C(C)C)cn2)c(O)c1-c1ccc(C#N)cc1] | A | A | — |
| 20. | 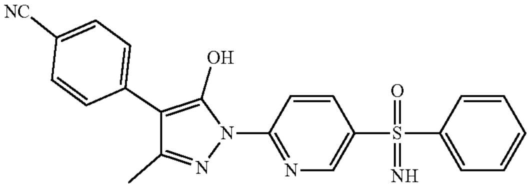 [SMILES: Cc1nn(-c2ccc(S(=N)(=O)c3ccccc3)cn2)c(O)c1-c1ccc(C#N)cc1] | A | A | — |
| 21. | 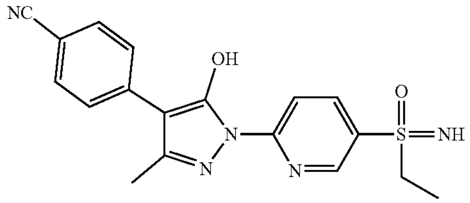 [SMILES: CCS(=N)(=O)c1ccc(-n2nc(C)c(-c3ccc(C#N)cc3)c2O)nc1] | A | A | — |
| 22. | 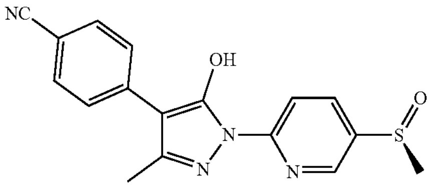 [SMILES: Cc1nn(-c2ccc([S@](C)=O)cn2)c(O)c1-c1ccc(C#N)cc1] | A | A | — |
| 23. | 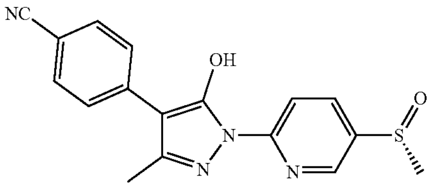 [SMILES: Cc1nn(-c2ccc([S@@](C)=O)cn2)c(O)c1-c1ccc(C#N)cc1] | A | A | — |
| 24. | 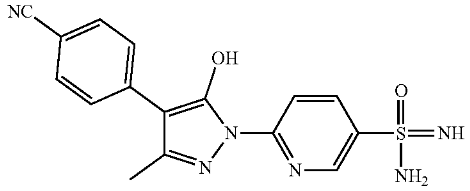 [SMILES: Cc1nn(-c2ccc(S(=N)(N)=O)cn2)c(O)c1-c1ccc(C#N)cc1] | A | A | — |
| 25. | 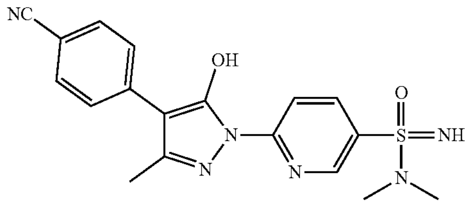 | A | A | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 26. | 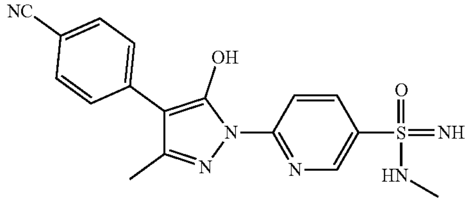 [SMILES: CNS(=N)(=O)c1ccc(-n2nc(C)c(-c3ccc(C#N)cc3)c2O)nc1] | A | A | — |
| 27. | 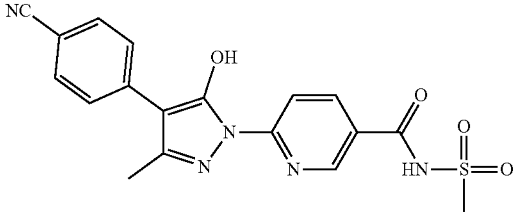 [SMILES: Cc1nn(-c2ccc(C(=O)NS(C)(=O)=O)cn2)c(O)c1-c1ccc(C#N)cc1] | A | A | A |
| 28. | 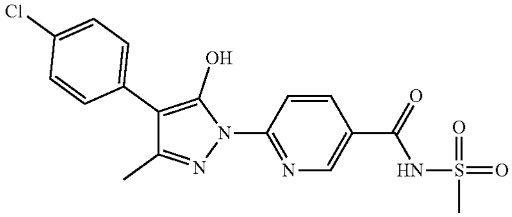 [SMILES: Cc1nn(-c2ccc(C(=O)NS(C)(=O)=O)cn2)c(O)c1-c1ccc(Cl)cc1] | A | B | — |
| 29. | 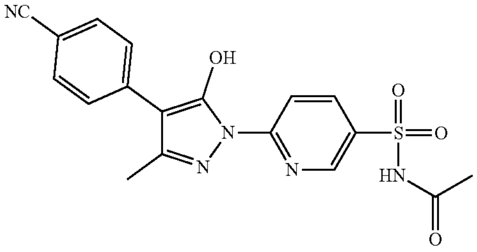 [SMILES: CC(=O)NS(=O)(=O)c1ccc(-n2nc(C)c(-c3ccc(C#N)cc3)c2O)nc1] | A | A | — |
| 30. | 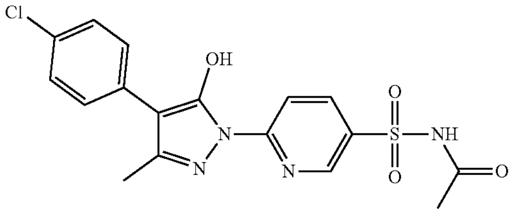 [SMILES: CC(=O)NS(=O)(=O)c1ccc(-n2nc(C)c(-c3ccc(Cl)cc3)c2O)nc1] | A | A | — |
| 31. | 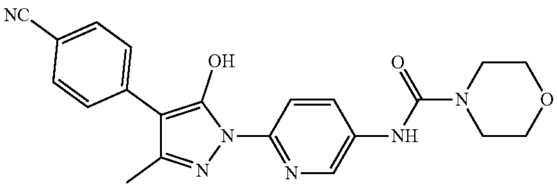 [SMILES: Cc1nn(-c2ccc(NC(=O)N3CCOCC3)cn2)c(O)c1-c1ccc(C#N)cc1] | A | B | — |
| 32. | 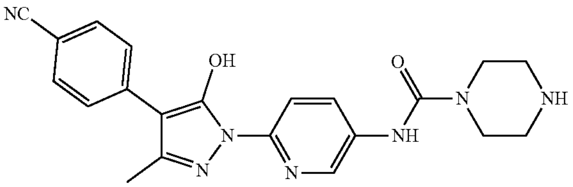 [SMILES: Cc1nn(-c2ccc(NC(=O)N3CCNCC3)cn2)c(O)c1-c1ccc(C#N)cc1] | B | B | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 33. | 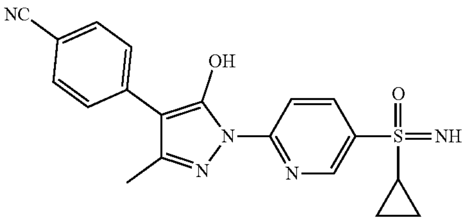 [SMILES: Cc1nn(-c2ccc(S(=N)(=O)C3CC3)cn2)c(O)c1-c1ccc(C#N)cc1] | A | A | — |
| 34. | 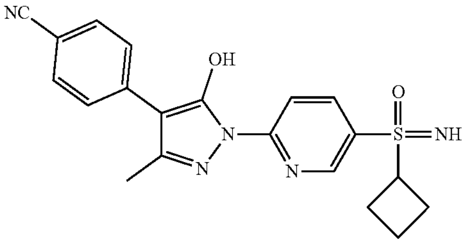 [SMILES: Cc1nn(-c2ccc(S(=N)(=O)C3CCC3)cn2)c(O)c1-c1ccc(C#N)cc1] | A | A | A |
| 35. | 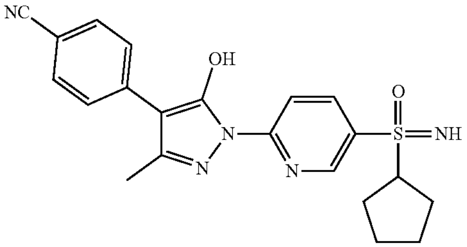 [SMILES: Cc1nn(-c2ccc(S(=N)(=O)C3CCCC3)cn2)c(O)c1-c1ccc(C#N)cc1] | A | A | A |
| 36. | 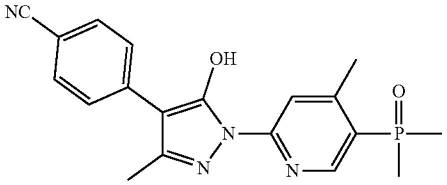 [SMILES: Cc1cc(-n2nc(C)c(-c3ccc(C#N)cc3)c2O)ncc1P(C)(C)=O] | A | A | B |
| 37. | 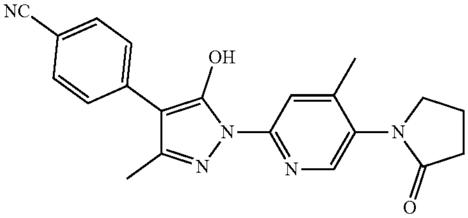 [SMILES: Cc1cc(-n2nc(C)c(-c3ccc(C#N)cc3)c2O)ncc1N1CCCC1=O] | A | A | — |
| 38. | 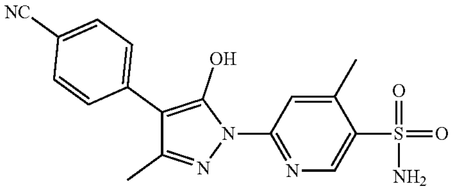 | A | A | — |
| 39. | 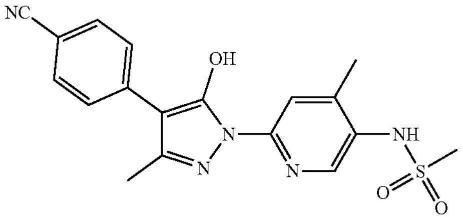 [SMILES: Cc1cc(-n2nc(C)c(-c3ccc(C#N)cc3)c2O)ncc1NS(C)(=O)=O] | A | A | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 40. | 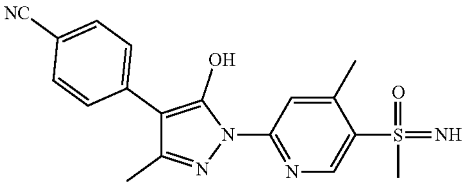 [SMILES: Cc1cc(-n2nc(C)c(-c3ccc(C#N)cc3)c2O)ncc1S(C)(=N)=O] | A | A | — |
| 41. | 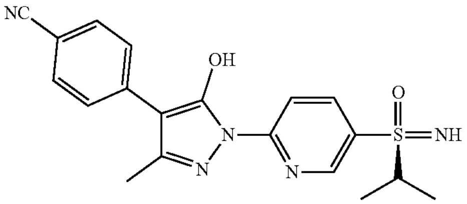 | A | A | — |
| 42. | 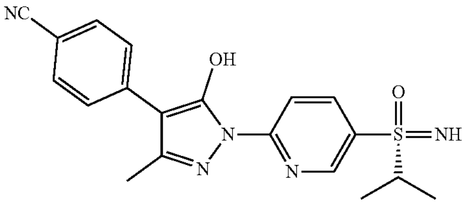 | A | A | — |
| 43. | 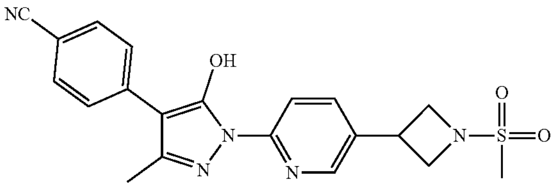 [SMILES: Cc1nn(-c2ccc(C3CN(S(C)(=O)=O)C3)cn2)c(O)c1-c1ccc(C#N)cc1] | A | A | — |
| 44. | 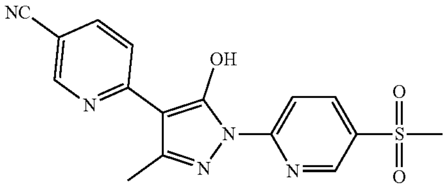 [SMILES: Cc1nn(-c2ccc(S(C)(=O)=O)cn2)c(O)c1-c1ccc(C#N)cn1] | B | B | C |
| 45. | 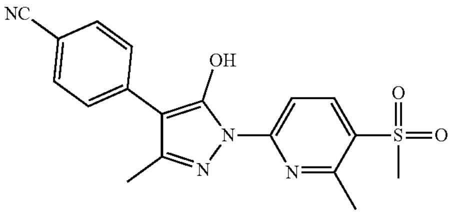 [SMILES: Cc1nc(-n2nc(C)c(-c3ccc(C#N)cc3)c2O)ccc1S(C)(=O)=O] | C | C | — |
| 46. | 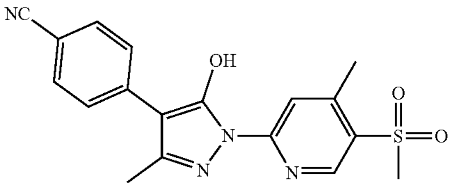 [SMILES: Cc1cc(-n2nc(C)c(-c3ccc(C#N)cc3)c2O)ncc1S(C)(=O)=O] | A | A | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 47. | 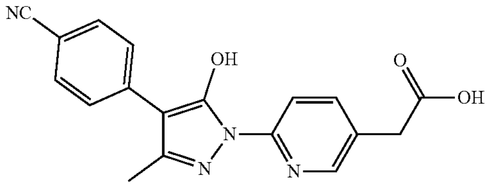 [SMILES: Cc1nn(-c2ccc(CC(=O)O)cn2)c(O)c1-c1ccc(C#N)cc1] | A | A | — |
| 48. | 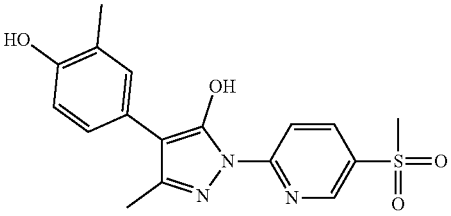 [SMILES: Cc1cc(-c2c(C)nn(-c3ccc(S(C)(=O)=O)cn3)c2O)ccc1O] | B | B | — |
| 49. | 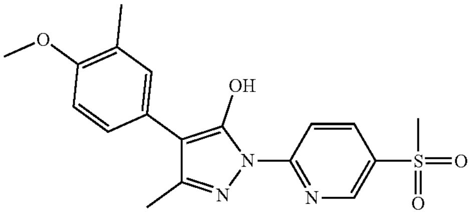 [SMILES: COc1ccc(-c2c(C)nn(-c3ccc(S(C)(=O)=O)cn3)c2O)cc1C] | B | B | — |
| 50. | 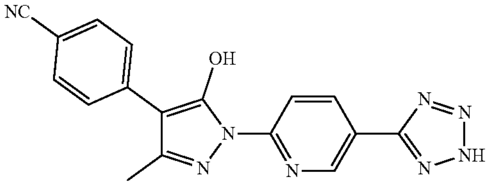 [SMILES: Cc1nn(-c2ccc(-c3nn[nH]n3)cn2)c(O)c1-c1ccc(C#N)cc1] | A | A | — |
| 51. | 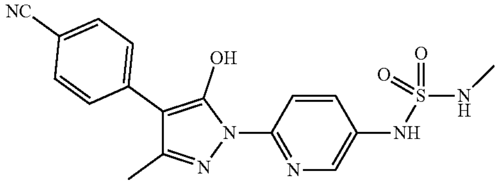 [SMILES: CNS(=O)(=O)Nc1ccc(-n2nc(C)c(-c3ccc(C#N)cc3)c2O)nc1] | A | A | — |
| 52. | 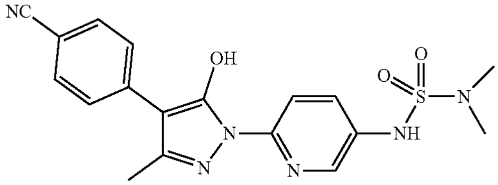 [SMILES: Cc1nn(-c2ccc(NS(=O)(=O)N(C)C)cn2)c(O)c1-c1ccc(C#N)cc1] | A | A | — |
| 53. | 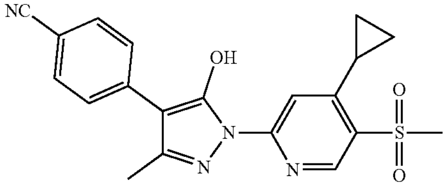 [SMILES: Cc1nn(-c2cc(C3CC3)c(S(C)(=O)=O)cn2)c(O)c1-c1ccc(C#N)cc1] | A | A | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 54. | 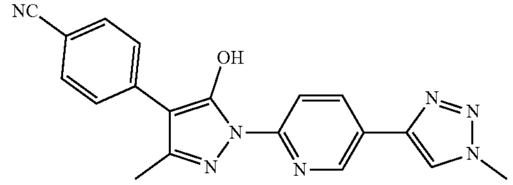 [SMILES: Cc1nn(-c2ccc(-c3cn(C)nn3)cn2)c(O)c1-c1ccc(C#N)cc1] | A | A | — |
| 55. | 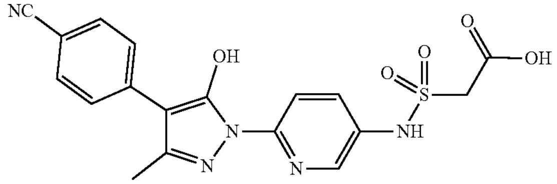 [SMILES: Cc1nn(-c2ccc(NS(=O)(=O)CC(=O)O)cn2)c(O)c1-c1ccc(C#N)cc1] | A | A | A |
| 56. | 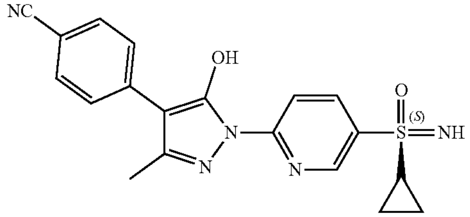 | A | A | A |
| 57. | 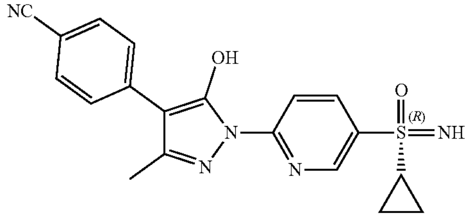 | A | A | — |
| 58. | 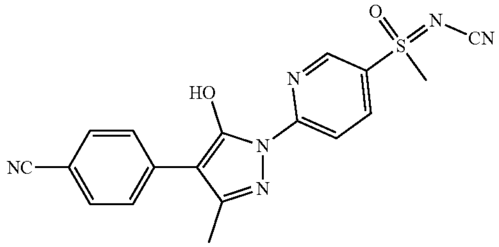 [SMILES: Cc1nn(-c2ccc(S(C)(=O)=NC#N)cn2)c(O)c1-c1ccc(C#N)cc1] | A | A | B |
| 59. | 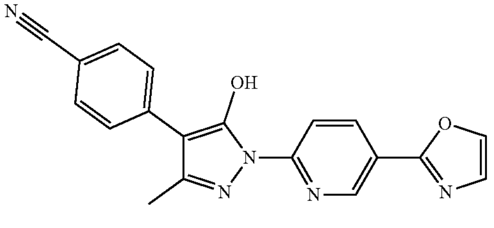 | A | A | — |
| 60. | 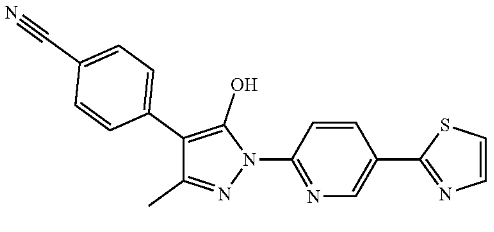 | A | B | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 61. | 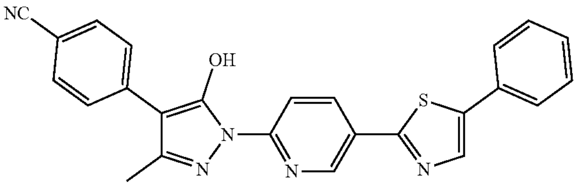 | A | D | — |
| 62. | 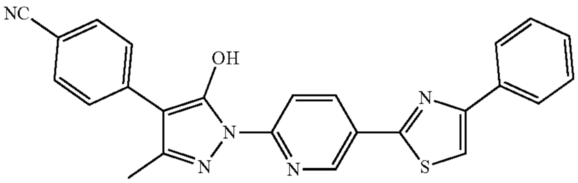 [SMILES: Cc1nn(-c2ccc(-c3nc(-c4ccccc4)cs3)cn2)c(O)c1-c1ccc(C#N)cc1] | B | D | — |
| 63. | 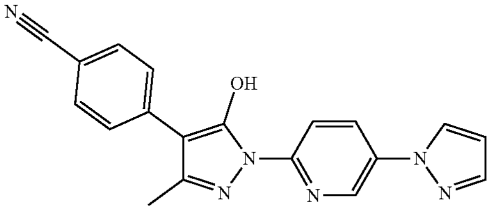 [SMILES: Cc1nn(-c2ccc(-n3cccn3)cn2)c(O)c1-c1ccc(C#N)cc1] | A | B | — |
| 64. | 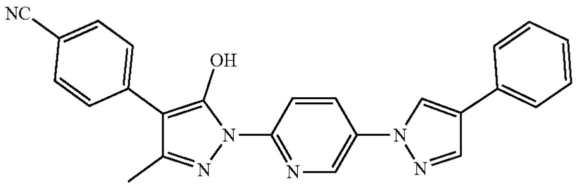 | A | B | — |
| 65. | 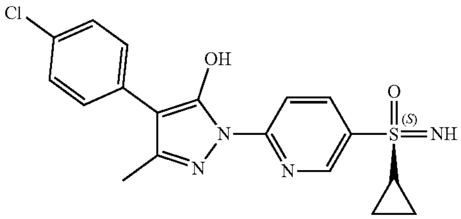 | A | A | — |
| 66. | 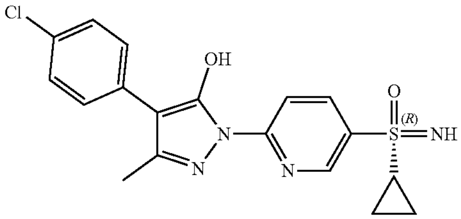 | A | A | — |
| 67. | 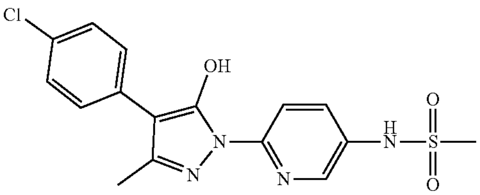 [SMILES: Cc1nn(-c2ccc(NS(C)(=O)=O)cn2)c(O)c1-c1ccc(Cl)cc1] | A | A | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 68. | 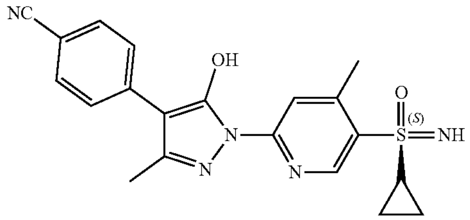 | A | A | — |
| 69. | 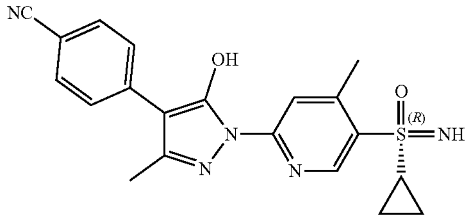 | A | A | — |
| 70. | 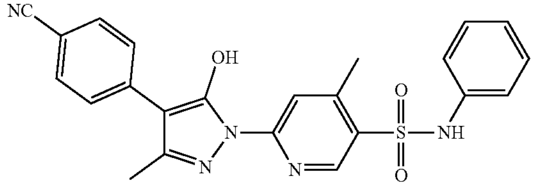 [SMILES: Cc1cc(-n2nc(C)c(-c3ccc(C#N)cc3)c2O)ncc1S(=O)(=O)Nc1ccccc1] | A | B | — |
| 71. | 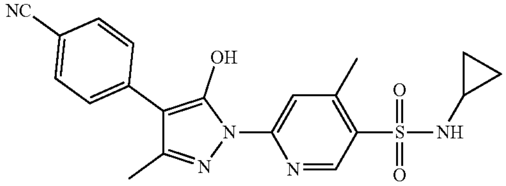 [SMILES: Cc1cc(-n2nc(C)c(-c3ccc(C#N)cc3)c2O)ncc1S(=O)(=O)NC1CC1] | A | A | — |
| 72. | 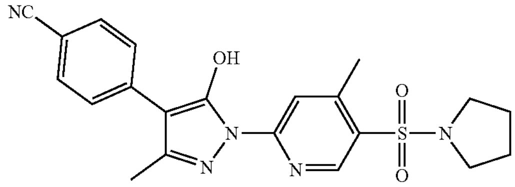 [SMILES: Cc1cc(-n2nc(C)c(-c3ccc(C#N)cc3)c2O)ncc1S(=O)(=O)N1CCCC1] | A | A | — |
| 73. | 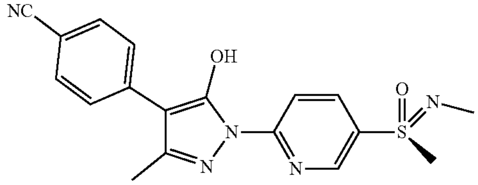 [SMILES: CN=[S@@](C)(=O)c1ccc(-n2nc(C)c(-c3ccc(C#N)cc3)c2O)nc1] | — | — | — |
| 74. | 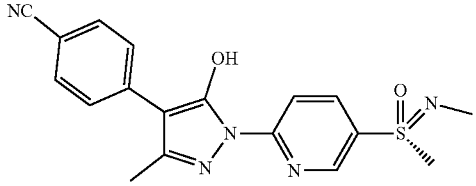 [SMILES: CN=[S@](C)(=O)c1ccc(-n2nc(C)c(-c3ccc(C#N)cc3)c2O)nc1] | — | — | — |

-continued
| Cmpd. No. | Structure | PHD1 $IC_{50}$ (nM) | PHD2 $IC_{50}$(nM) | PHD3 $IC_{50}$(nM) |
|---|---|---|---|---|
| 75. | 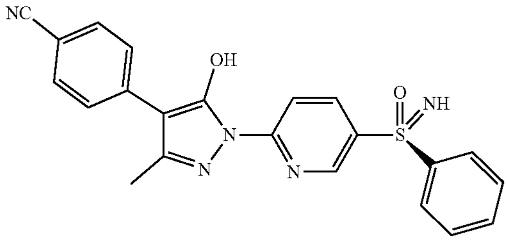 [SMILES: Cc1nn(-c2ccc([S@@](=N)(=O)c3ccccc3)cn2)c(O)c1-c1ccc(C#N)cc1] | — | — | — |
| 76. | 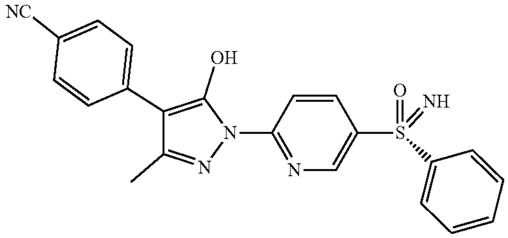 [SMILES: Cc1nn(-c2ccc([S@](=N)(=O)c3ccccc3)cn2)c(O)c1-c1ccc(C#N)cc1] | — | — | — |
| 77. | 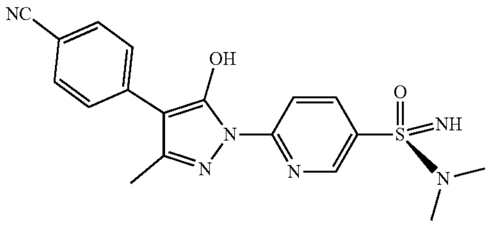 [SMILES: Cc1nn(-c2ccc([S@@](=N)(=O)N(C)C)cn2)c(O)c1-c1ccc(C#N)cc1] | — | — | — |
| 78. | 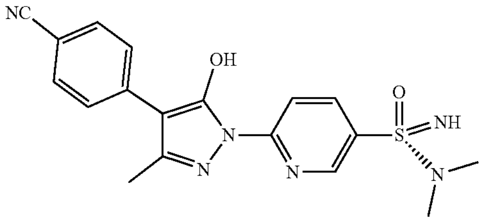 [SMILES: Cc1nn(-c2ccc([S@](=N)(=O)N(C)C)cn2)c(O)c1-c1ccc(C#N)cc1] | — | — | — |
| 79. | 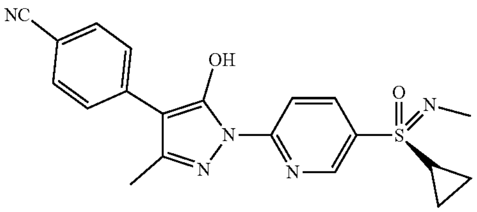 [SMILES: CN=[S@@](=O)(c1ccc(-n2nc(C)c(-c3ccc(C#N)cc3)c2O)nc1)C1CC1] | — | — | — |
| 80. | 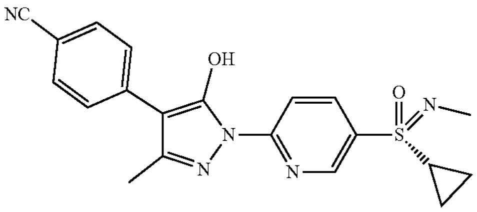 [SMILES: CN=[S@](=O)(c1ccc(-n2nc(C)c(-c3ccc(C#N)cc3)c2O)nc1)C1CC1] | — | — | — |

-continued

| Cmpd. No. | Structure | PHD1 $IC_{50}$ (nM) | PHD2 $IC_{50}$(nM) | PHD3 $IC_{50}$(nM) |
|---|---|---|---|---|
| 81. | 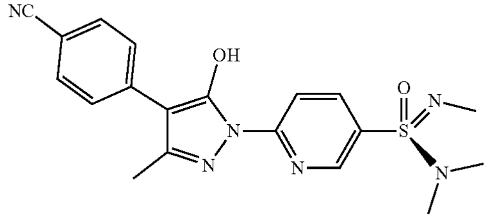 [SMILES: CN=[S@@](=O)(c1ccc(-n2nc(C)c(-c3ccc(C#N)cc3)c2O)nc1)N(C)C] | — | — | — |
| 82. | 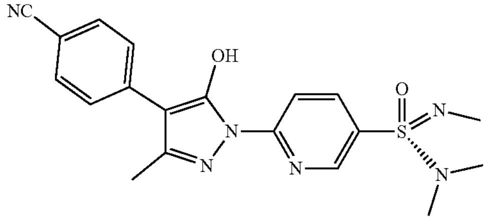 [SMILES: CN=[S@](=O)(c1ccc(-n2nc(C)c(-c3ccc(C#N)cc3)c2O)nc1)N(C)C] | — | — | — |
| 83. | 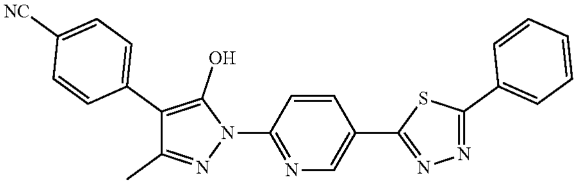 | — | — | — |

Legend: A = IC50 < 100nM
B = 100 nM ≤ IC50 < 1000 nM
C = 1000 nM ≤ IC50 < 10000 nM
D = IC50 ≥ 10000 nM From the ongoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

The invention claimed is:

1. A compound of Formula I:

(I)

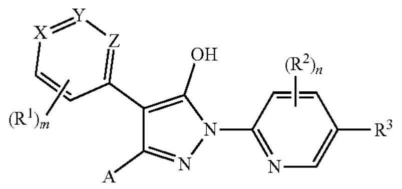

or a pharmaceutically acceptable salt thereof, wherein:

X is N or $CR^{1a}$;

Y and Z are independently CH or N;

A is $C_{1-3}$ alkyl or $C_{3-6}$ cycloalkyl;

$R^1$, each time taken, is independently selected from the group consisting of hydrogen, halogen, CN, OH, $C_{1-3}$ alkyl optionally substituted one or more halogens, and $C_{1-3}$ alkoxy;

$R^{1a}$ is H, CN, halogen, $C_{1-3}$ alkoxy, OH, or $C_{1-3}$ alkyl optionally substituted with CN;

$R^2$, each time taken, is independently selected from the group consisting of hydrogen, halogen, $NR^4R^5$, OH, $C_{1-3}$ alkyl, and $C_{3-6}$ cycloalkyl;

$R^3$ is $SO_2R^6$, $SOR^7R^8$, $SOR^9$, $NHR^{11}$, or $POR^{12}R^{13}$;

$R^4$ and $R^5$ are each independently H or $C_{1-3}$ alkyl;

$R^6$ is $C_{1-3}$ alkyl, $NHCOR^{15}$, $NR^{16}R^{17}$, or phenyl;

$R^7$ is $C_{1-3}$ alkyl, $C_{3-5}$ cycloalkyl, phenyl, or $NR^{18}R^{19}$;

$R^8$ is NH, NCN, or $NCH_3$;

$R^9$ is $C_{1-3}$ alkyl;

$R^{11}$ is $COR^{21}$ or $SO_2R^{22}$;

$R^{12}$ and $R^{13}$ are each independently $C_{1-3}$ alkyl;

$R^{15}$ is $C_{1-3}$ alkyl;

$R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl;

$R^{18}$ and $R^{19}$ are each independently H or $C_{1-3}$ alkyl;

$R^{21}$ is heterocycloalkyl, cycloalkyl, or $C_{1-3}$ alkyl;

$R^{22}$ is $NR^{23}R^{24}$ or $C_{1-3}$ alkyl optionally substituted with carboxyl;

$R^{23}$ and $R^{24}$ are each independently H or $C_{1-3}$ alkyl;

m is 1, 2, 3, or 4; and n is 0, 1, 2 or 3.

2. The compound of claim 1, having a structure according to Formula II:

(II)

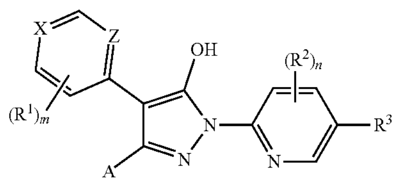

or a pharmaceutically acceptable salt thereof, wherein:

X is N or $CR^{1a}$;

Z is CH or N;

A is $C_{1-3}$ alkyl or $C_{3-6}$ cycloalkyl;

$R^1$, each time taken, is independently selected from the group consisting of hydrogen, halogen, CN, OH, $C_{1-3}$ alkyl optionally substituted one or more halogens, and $C_{1-3}$ alkoxy;

$R^{1a}$ is H, CN, halogen, $C_{1-3}$ alkoxy, OH, or $C_{1-3}$ alkyl optionally substituted with CN;

$R^2$, each time taken, is independently selected from the group consisting of hydrogen, halogen, $NR^4R^5$, OH, $C_{1-3}$ alkyl, and $C_{3-6}$ cycloalkyl;

$R^3$ is $SO_2R^6$, $SOR^7R^8$, $SOR^9$, $NHR^{11}$, or $POR^{12}R^{13}$;

$R^4$ and $R^5$ are each independently H or $C_{1-3}$ alkyl;

$R^6$ is $C_{1-3}$ alkyl, $NHCOR^{15}$, $NR^{16}R^{17}$, or phenyl;

$R^7$ is $C_{1-3}$ alkyl, $C_{3-5}$ cycloalkyl, phenyl, or $NR^{18}R^{19}$;

$R^8$ is NH, NCN, or $NCH_3$;

$R^9$ is $C_{1-3}$ alkyl;

$R^{11}$ is $COR^{21}$ or $SO_2R^{22}$;

$R^{12}$ and $R^{13}$ are each independently $C_{1-3}$ alkyl;

$R^{15}$ is $C_{1-3}$ alkyl;

$R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl;

$R^{18}$ and $R^{19}$ are independently H or $C_{1-3}$ alkyl;

$R^{21}$ is heterocycloalkyl, cycloalkyl, or $C_{1-3}$ alkyl;

$R^{22}$ is $NR^{23}R^{24}$ or $C_{1-3}$ alkyl optionally substituted with carboxyl;

$R^{23}$ and $R^{24}$ are independently H or $C_{1-3}$ alkyl;

m is 1, 2, 3, or 4; and n is 0, 1, 2 or 3.

3. The compound of claim 1, having a structure according to Formula III:

(III)

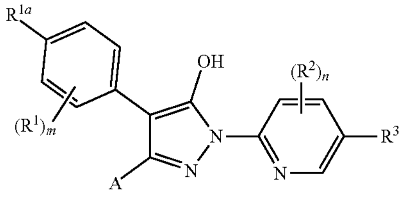

or a pharmaceutically acceptable salt thereof, wherein:

A is $C_{1-3}$ alkyl or $C_{3-6}$ cycloalkyl;

$R^1$, each time taken, is independently selected from the group consisting of hydrogen, halogen, CN, OH, $C_{1-3}$ alkyl optionally substituted one or more halogens, and $C_{1-3}$ alkoxy;

$R^{1a}$ is H, CN, halogen, $C_{1-3}$ alkoxy, OH, or $C_{1-3}$ alkyl optionally substituted with CN;

$R^2$, each time taken, is independently selected from the group consisting of hydrogen, halogen, $NR^4R^5$, OH, $C_{1-3}$ alkyl, and $C_{3-6}$ cycloalkyl;

$R^3$ is $SO_2R^6$, $SOR^7R^8$, $SOR^9$, $NHR^{11}$, or $POR^{12}R^{13}$;

$R^4$ and $R^5$ are each independently H or $C_{1-3}$ alkyl;

$R^6$ is $C_{1-3}$ alkyl, $NHCOR^{15}$, $NR^{16}R^{17}$, or phenyl;

$R^7$ is $C_{1-3}$ alkyl, $C_{3-5}$ cycloalkyl, phenyl, or $NR^{18}R^{19}$;

$R^8$ is NH, NCN, or $NCH_3$;

$R^9$ is $C_{1-3}$ alkyl;

$R^{11}$ is $COR^{21}$ or $SO_2R^{22}$;

$R^{12}$ and $R^{13}$ are each independently $C_{1-3}$ alkyl;

$R^{15}$ is $C_{1-3}$ alkyl;

$R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl;

$R^{18}$ and $R^{19}$ are independently H or $C_{1-3}$ alkyl;

$R^{21}$ is heterocycloalkyl, cycloalkyl, or $C_{1-3}$ alkyl;

$R^{22}$ is $NR^{23}R^{24}$ or $C_{1-3}$ alkyl optionally substituted with carboxyl;

$R^{23}$ and $R^{24}$ are independently H or $C_{1-3}$ alkyl;

m is 1, 2, 3, or 4; and n is 0, 1, 2 or 3.

4. The compound of claim 1, having a structure according to Formula IV:

(IV)

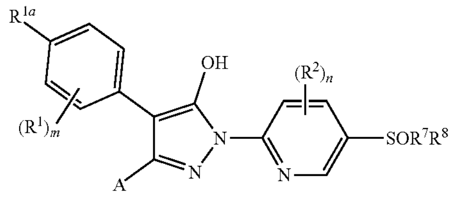

or a pharmaceutically acceptable salt thereof, wherein:

A is $C_{1-3}$ alkyl or $C_{3-6}$ cycloalkyl;

$R^1$, each time taken, is independently selected from the group consisting of hydrogen, halogen, CN, OH, $C_{1-3}$ alkyl optionally substituted one or more halogens, and $C_{1-3}$ alkoxy;

$R^{1a}$ is H, CN, halogen, $C_{1-3}$ alkoxy, OH, or $C_{1-3}$ alkyl optionally substituted with CN;

$R^2$, each time taken, is independently selected from the group consisting of hydrogen, halogen, $NR^4R^5$, OH, $C_{1-3}$ alkyl, and $C_{3-6}$ cycloalkyl;

$R^4$ and $R^5$ are each independently H or $C_{1-3}$ alkyl;

$R^7$ is $C_{1-3}$ alkyl, $C_{3-5}$ cycloalkyl, phenyl, or $NR^{18}R^{19}$;

$R^8$ is NH, NCN, or $NCH_3$;

$R^{18}$ and $R^{19}$ are each independently H or $C_{1-3}$ alkyl;

m is 1, 2, 3, or 4; and n is 0, 1, 2 or 3.

5. The compound of claim 1 having a structure of Formula IVa:

(IVa)

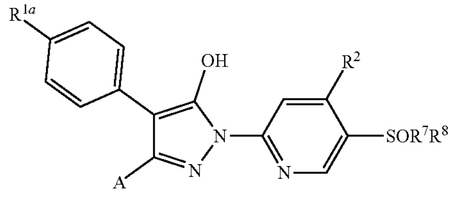

or a pharmaceutically acceptable salt thereof, wherein:
A is $C_{1-3}$ alkyl;
$R^{1a}$ is CN or halogen;
$R^2$ is selected from the group consisting of hydrogen or $C_{1-3}$ alkyl;
$R^7$ is $C_{1-3}$ alkyl, $C_{3-5}$ cycloalkyl, phenyl, or $NR^{18}R^{19}$;
$R^8$ is NH, NCN, or $NCH_3$; and
$R^{18}$ and $R^{19}$ are each independently H or $C_{1-3}$ alkyl.

6. The compound of claim 4, wherein:
$R^{1a}$ is CN; and/or
A is $CH_3$; and/or
$R^2$ is $CH_3$; and/or
$R^7$ is $CH_3$, $CH(CH_3)_2$, $CH_2CH_3$, cyclopropyl, cyclopentyl, or phenyl.

7. The compound of claim 1, having a structure according to Formula V:

(V)

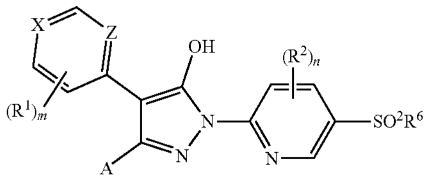

or a pharmaceutically acceptable salt thereof, wherein:
X is N or $CR^{1a}$;
Z is N or CH;
A is $C_{1-3}$ alkyl or $C_{3-6}$ cycloalkyl;
$R^1$, each time taken, is independently selected from the group consisting of hydrogen, halogen, CN, OH, $C_{1-3}$ alkyl optionally substituted one or more halogens, and $C_{1-3}$ alkoxy;
$R^{1a}$ is H, CN, halogen, $C_{1-3}$ alkoxy, OH, or $C_{1-3}$ alkyl optionally substituted with CN;
$R^2$, each time taken, is independently selected from the group consisting of hydrogen, halogen, $NR^4R^5$, OH, $C_{1-3}$ alkyl, and $C_{3-6}$ cycloalkyl;
$R^4$ and $R^5$ are each independently H or $C_{1-3}$ alkyl;
$R^6$ is $C_{1-3}$ alkyl, $NHCOR^{15}$, $NR^{16}R^{17}$, or phenyl; and
$R^{15}$ is $C_{1-3}$ alkyl;
$R^{16}$ and $R^{17}$ are each independently H, $C_{1-3}$ alkyl, aryl, cycloalkyl, or wherein $R^{16}$ and $R^{17}$ together with the carbon to which they are attached form a heterocycloalkyl;
m is 1, 2, 3, or 4; and
n is 0, 1, 2 or 3.

8. The compound of claim 1, having a structure according to Formula VII:

(VII)

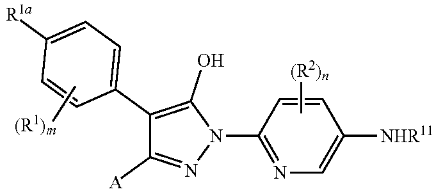

or a pharmaceutically acceptable salt thereof, wherein:
A is $C_{1-3}$ alkyl or $C_{3-6}$ cycloalkyl;
$R^1$, each time taken, is independently selected from the group consisting of hydrogen, halogen, CN, OH, $C_{1-3}$ alkyl optionally substituted one or more halogens, and $C_{1-3}$ alkoxy;
$R^{1a}$ is H, CN, halogen, $C_{1-3}$ alkoxy, OH, or $C_{1-3}$ alkyl optionally substituted with CN;
$R^2$, each time taken, is independently selected from the group consisting of hydrogen, halogen, $NR^4R^5$, OH, $C_{1-3}$ alkyl, and $C_{3-6}$ cycloalkyl;
$R^4$ and $R^5$ are each independently H or $C_{1-3}$ alkyl;
$R^{11}$ is $COR^{21}$ or $SO_2R^{22}$;
$R^{21}$ is heterocycloalkyl, cycloalkyl, or $C_{1-3}$ alkyl;
$R^{22}$ is $NR^{23}R^{24}$ or $C_{1-3}$ alkyl optionally substituted with carboxyl;
$R^{23}$ and $R^{24}$ are independently H or $C_{1-3}$ alkyl;
m is 1, 2, 3, or 4; and
n is 0, 1, 2 or 3.

9. The compound of claim 8 having a structure of Formula VIIa:

(VIIa)

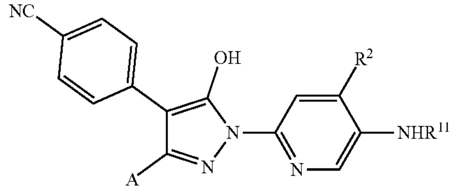

or a pharmaceutically acceptable salt thereof, wherein:
A is $C_{1-3}$ alkyl or $C_{3-6}$ cycloalkyl;
$R^2$ is hydrogen, $C_{1-3}$ alkyl or $C_{3-6}$ cycloalkyl;
$R^{11}$ is $COR^{21}$ or $SO_2R^{22}$;
$R^{21}$ is heterocycloalkyl, cycloalkyl, or $C_{1-3}$ alkyl;
$R^{22}$ is $NR^{23}R^{24}$ or $C_{1-3}$ alkyl optionally substituted with carboxyl; and
$R^{23}$ and $R^{24}$ are independently H or $C_{1-3}$ alkyl.

10. The compound of claim 9, wherein
A is $C_{1-3}$ alkyl; and
$R^2$ is hydrogen or $C_{1-3}$ alkyl.

11. The compound of claim 1, having a structure according to Formula X:

(X)

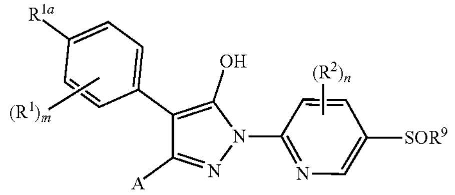

or a pharmaceutically acceptable salt thereof, wherein:
A is $C_{1-3}$ alkyl or $C_{3-6}$ cycloalkyl;
$R^1$, each time taken, is independently selected from the group consisting of hydrogen, halogen, CN, OH, $C_{1-3}$ alkyl optionally substituted one or more halogens, and $C_{1-3}$ alkoxy;
$R^{1a}$ is H, CN, halogen, $C_{1-3}$ alkoxy, OH, or $C_{1-3}$ alkyl optionally substituted with CN;
$R^2$, each time taken, is independently selected from the group consisting of hydrogen, halogen, $NR^4R^5$, OH, $C_{1-3}$ alkyl, and $C_{3-6}$ cycloalkyl;
$R^4$ and $R^5$ are each independently H or $C_{1-3}$ alkyl;
$R^9$ is $C_{1-3}$ alkyl;
m is 1, 2, 3, or 4; and
n is 0, 1, 2 or 3.

12. The compound of claim 1, having a structure according to Formula XIII:

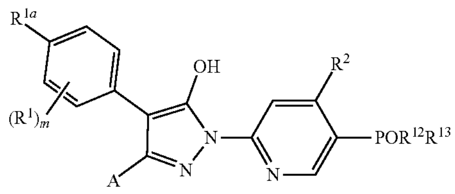

(XIII)

or a pharmaceutically acceptable salt thereof, wherein:

A is $C_{1-3}$ alkyl or $C_{3-6}$ cycloalkyl;

$R^1$, each time taken, is independently selected from the group consisting of hydrogen, halogen, CN, OH, $C_{1-3}$ alkyl optionally substituted one or more halogens, and $C_{1-3}$ alkoxy;

$R^{1a}$ is H, CN, halogen, $C_{1-3}$ alkoxy, OH, or $C_{1-3}$ alkyl optionally substituted with CN;

$R^2$, each time taken, is independently selected from the group consisting of hydrogen, halogen, $NR^4R^5$, OH, $C_{1-3}$ alkyl, and $C_{3-6}$ cycloalkyl;

$R^4$ and $R^5$ are each independently H or $C_{1-3}$ alkyl;

$R^{12}$ is $C_{1-3}$ alkyl;

$R^{13}$ is $C_{1-3}$ alkyl; and m is 1, 2, 3, or 4.

13. The compound of claim 1, wherein the compound is selected from the group consisting of:

| Cmpd No. | Structure |
|---|---|
| 1 | 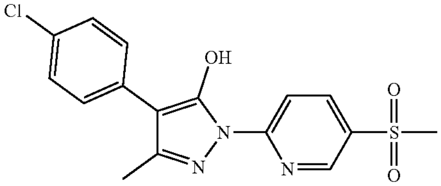 [SMILES: Cc1nn(-c2ccc(S(C)(=O)=O)cn2)c(O)c1-c1ccc(Cl)cc1] |
| 3 | 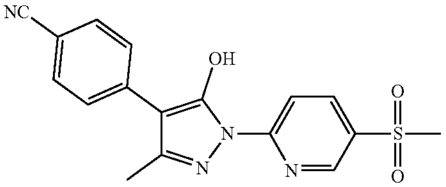 [SMILES: Cc1nn(-c2ccc(S(C)(=O)=O)cn2)c(O)c1-c1ccc(C#N)cc1] |
| 4 | 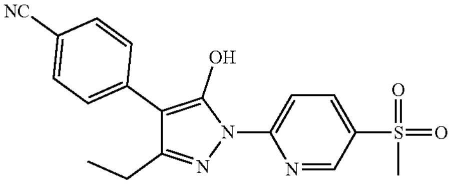 [SMILES: CCc1nn(-c2ccc(S(C)(=O)=O)cn2)c(O)c1-c1ccc(C#N)cc1] |
| 5 | 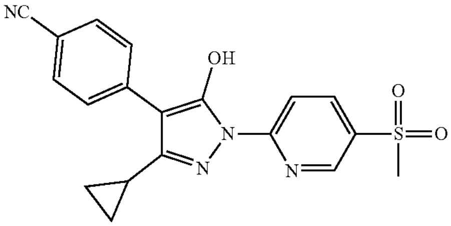 [SMILES: CS(=O)(=O)c1ccc(-n2nc(C3CC3)c(-c3ccc(C#N)cc3)c2O)nc1] |
| 6 | 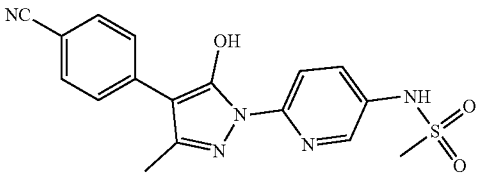 [SMILES: Cc1nn(-c2ccc(NS(C)(=O)=O)cn2)c(O)c1-c1ccc(C#N)cc1] |
| 8 | 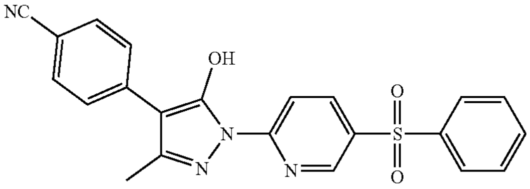 [SMILES: Cc1nn(-c2ccc(S(=O)(=O)c3ccccc3)cn2)c(O)c1-c1ccc(C#N)cc1] |

-continued
| Cmpd No. | Structure |
|---|---|
| 9 | 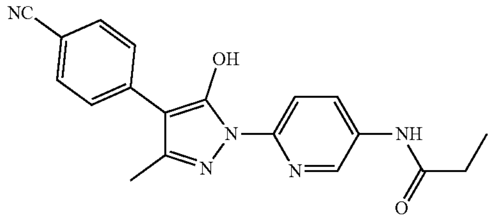 [SMILES: CCC(=O)Nc1ccc(-n2nc(C)c(-c3ccc(C#N)cc3)c2O)nc1] |
| 11 | 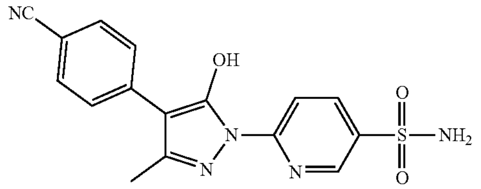 [SMILES: Cc1nn(-c2ccc(S(N)(=O)=O)cn2)c(O)c1-c1ccc(C#N)cc1] |
| 12 | 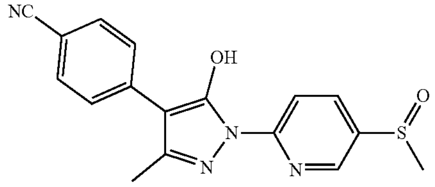 [SMILES: Cc1nn(-c2ccc(S(C)=O)cn2)c(O)c1-c1ccc(C#N)cc1] |
| 13 | 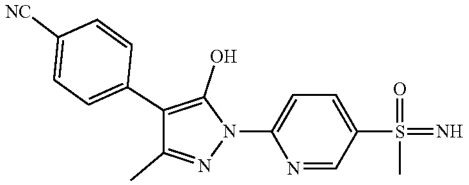 [SMILES: Cc1nn(-c2ccc(S(C)(=N)=O)cn2)c(O)c1-c1ccc(C#N)cc1] |
| 14 | 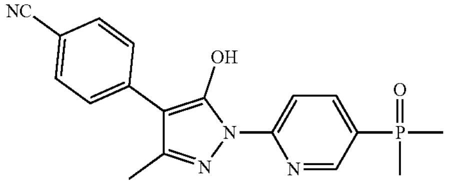 |
| 15 | 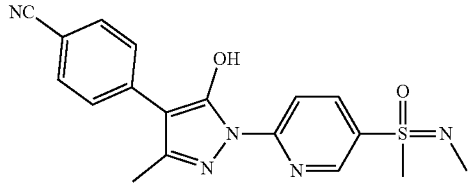 [SMILES: CN=S(C)(=O)c1ccc(-n2nc(C)c(-c3ccc(C#N)cc3)c2O)nc1] |
| 16 | 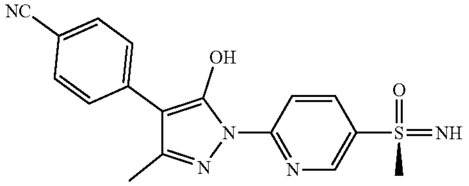 [SMILES: Cc1nn(-c2ccc([S@@](C)(=N)=O)cn2)c(O)c1-c1ccc(C#N)cc1] |

-continued
| Cmpd No. | Structure |
|---|---|
| 17 | 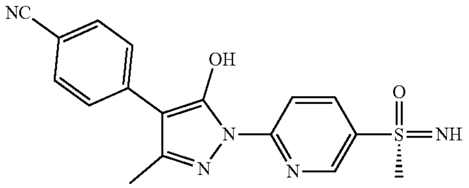 [SMILES: Cc1nn(-c2ccc([S@](C)(=N)=O)cn2)c(O)c1-c1ccc(C#N)cc1] |
| 18 | 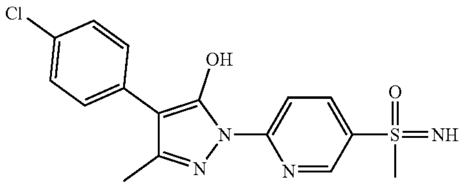 [SMILES: Cc1nn(-c2ccc(S(C)(=N)=O)cn2)c(O)c1-c1ccc(Cl)cc1] |
| 19 | 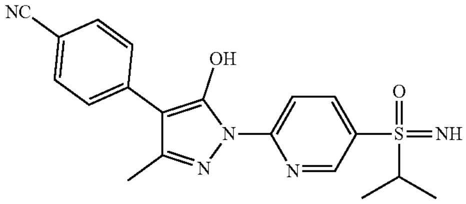 [SMILES: Cc1nn(-c2ccc(S(=N)(=O)C(C)C)cn2)c(O)c1-c1ccc(C#N)cc1] |
| 20 | 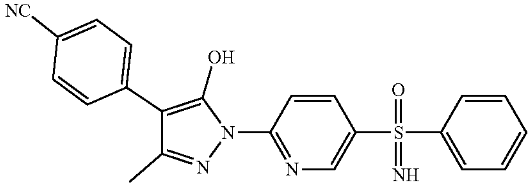 [SMILES: Cc1nn(-c2ccc(S(=N)(=O)c3ccccc3)cn2)c(O)c1-c1ccc(C#N)cc1] |
| 21 | 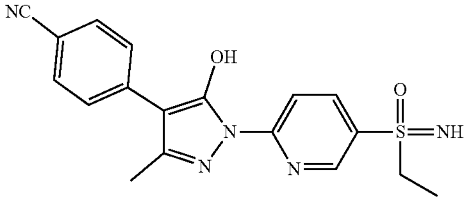 [SMILES: CCS(=N)(=O)c1ccc(-n2nc(C)c(-c3ccc(C#N)cc3)c2O)nc1] |
| 22 | 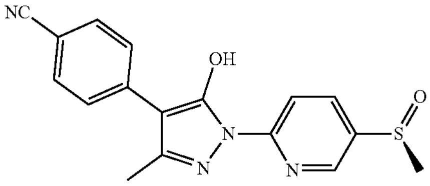 [SMILES: Cc1nn(-c2ccc([S@](C)=O)cn2)c(O)c1-c1ccc(C#N)cc1] |
| 23 | 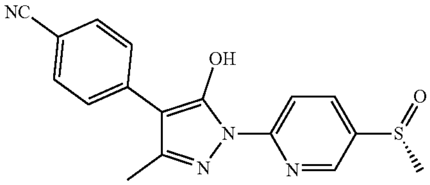 [SMILES: Cc1nn(-c2ccc([S@@](C)=O)cn2)c(O)c1-c1ccc(C#N)cc1] |
| 24 | 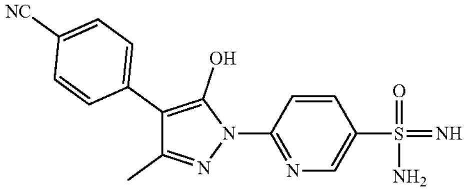 [SMILES: Cc1nn(-c2ccc(S(=N)(N)=O)cn2)c(O)c1-c1ccc(C#N)cc1] |

-continued
| Cmpd No. | Structure |
|---|---|
| 25 | 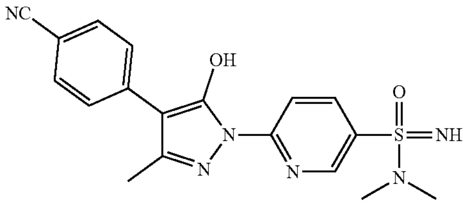 [SMILES: Cc1nn(-c2ccc(S(=N)(=O)N(C)C)cn2)c(O)c1-c1ccc(C#N)cc1] |
| 26 | 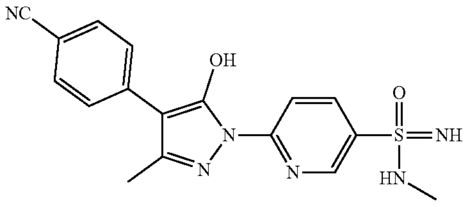 [SMILES: CNS(=N)(=O)c1ccc(-n2nc(C)c(-c3ccc(C#N)cc3)c2O)nc1] |
| 29 | 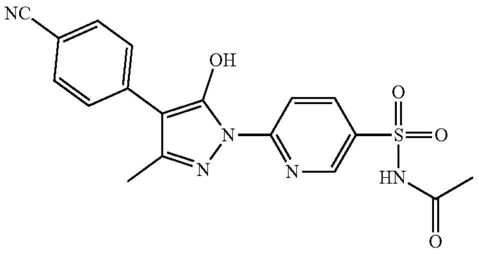 [SMILES: CC(=O)NS(=O)(=O)c1ccc(-n2nc(C)c(-c3ccc(C#N)cc3)c2O)nc1] |
| 30 | 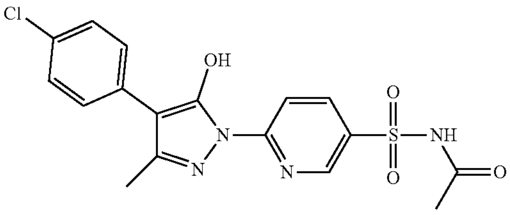 [SMILES: CC(=O)NS(=O)(=O)c1ccc(-n2nc(C)c(-c3ccc(Cl)cc3)c2O)nc1] |
| 31 | 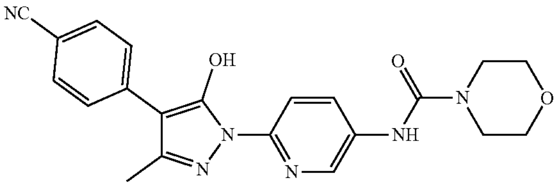 [SMILES: Cc1nn(-c2ccc(NC(=O)N3CCOCC3)cn2)c(O)c1-c1ccc(C#N)cc1] |
| 32 | 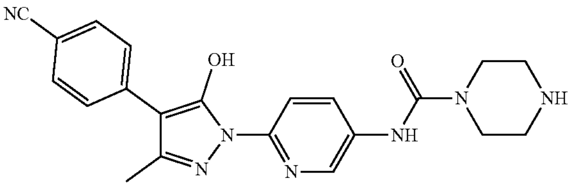 |
| 33 | 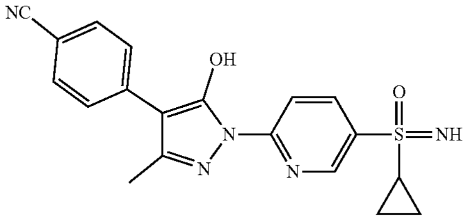 [SMILES: Cc1nn(-c2ccc(S(=N)(=O)C3CC3)cn2)c(O)c1-c1ccc(C#N)cc1] |

-continued
| Cmpd No. | Structure |
| --- | --- |
| 34 | 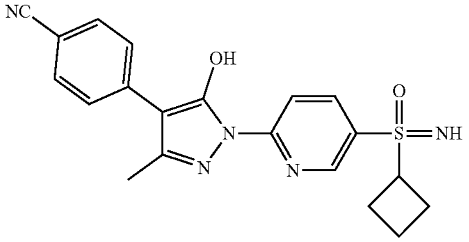 [SMILES: Cc1nn(-c2ccc(S(=N)(=O)C3CCC3)cn2)c(O)c1-c1ccc(C#N)cc1] |
| 35 | 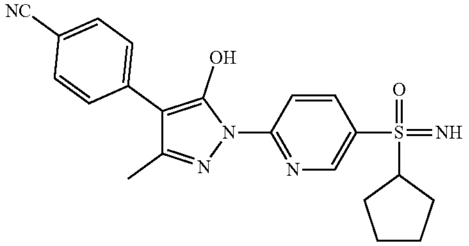 [SMILES: Cc1nn(-c2ccc(S(=N)(=O)C3CCCC3)cn2)c(O)c1-c1ccc(C#N)cc1] |
| 36 | 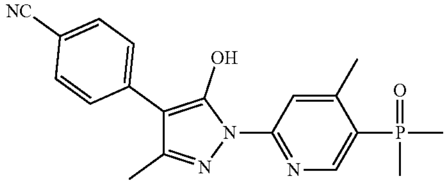 [SMILES: Cc1cc(-n2nc(C)c(-c3ccc(C#N)cc3)c2O)ncc1P(C)(C)=O] |
| 38 | 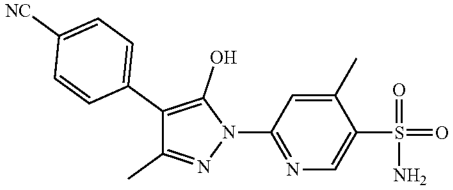 [SMILES: Cc1cc(-n2nc(C)c(-c3ccc(C#N)cc3)c2O)ncc1S(N)(=O)=O] |
| 39 | 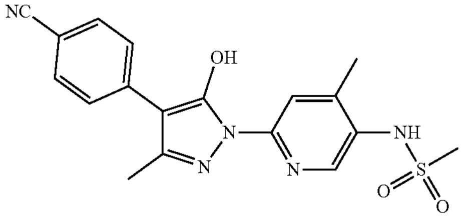 [SMILES: Cc1cc(-n2nc(C)c(-c3ccc(C#N)cc3)c2O)ncc1NS(C)(=O)=O] |
| 40 | 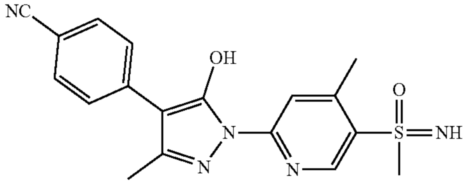 [SMILES: Cc1cc(-n2nc(C)c(-c3ccc(C#N)cc3)c2O)ncc1S(C)(=N)=O] |
| 41 | 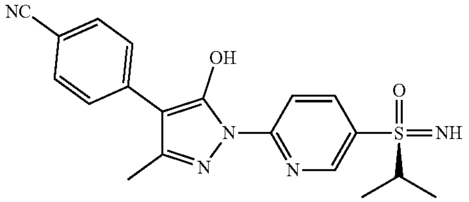 [SMILES: Cc1nn(-c2ccc([S@@](=N)(=O)C(C)C)cn2)c(O)c1-c1ccc(C#N)cc1] |

-continued
| Cmpd No. | Structure |
| --- | --- |
| 42 | 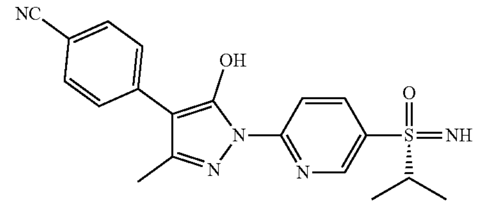 [SMILES: Cc1nn(-c2ccc([S@](=N)(=O)C(C)C)cn2)c(O)c1-c1ccc(C#N)cc1] |
| 44 | 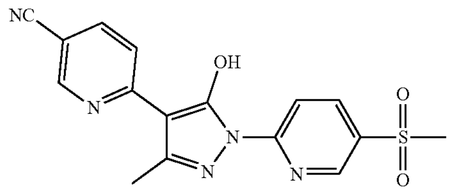 |
| 45 | 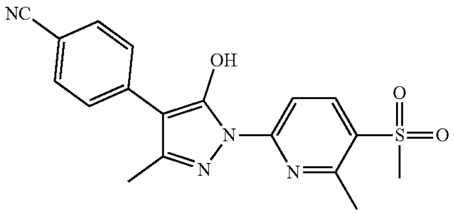 [SMILES: Cc1nc(-n2nc(C)c(-c3ccc(C#N)cc3)c2O)ccc1S(C)(=O)=O] |
| 46 | 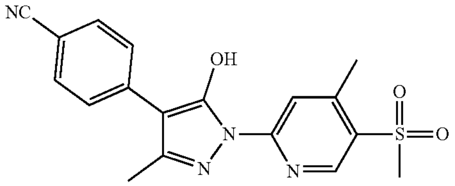 [SMILES: Cc1cc(-n2nc(C)c(-c3ccc(C#N)cc3)c2O)ncc1S(C)(=O)=O] |
| 48 | 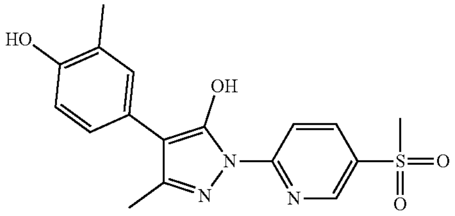 [SMILES: Cc1cc(-c2c(C)nn(-c3ccc(S(C)(=O)=O)cn3)c2O)ccc1O] |
| 49 | 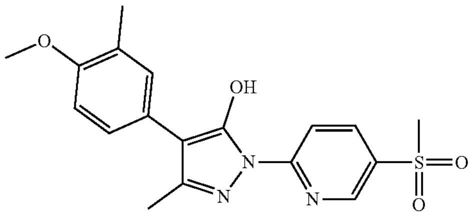 [SMILES: COc1ccc(-c2c(C)nn(-c3ccc(S(C)(=O)=O)cn3)c2O)cc1C] |
| 51 | 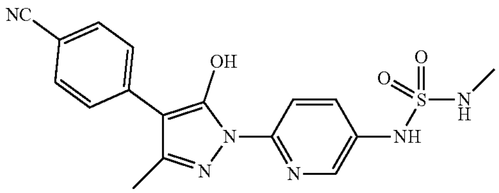 [SMILES: CNS(=O)(=O)Nc1ccc(-n2nc(C)c(-c3ccc(C#N)cc3)c2O)nc1] |

-continued
| Cmpd No. | Structure |
| --- | --- |
| 52 | 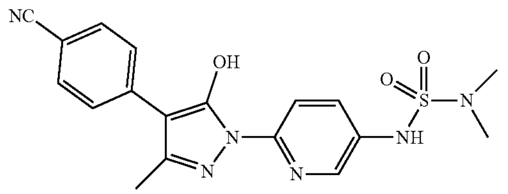 [SMILES: Cc1nn(-c2ccc(NS(=O)(=O)N(C)C)cn2)c(O)c1-c1ccc(C#N)cc1] |
| 53 | 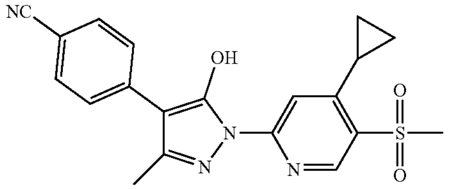 [SMILES: Cc1nn(-c2cc(C3CC3)c(S(C)(=O)=O)cn2)c(O)c1-c1ccc(C#N)cc1] |
| 55 | 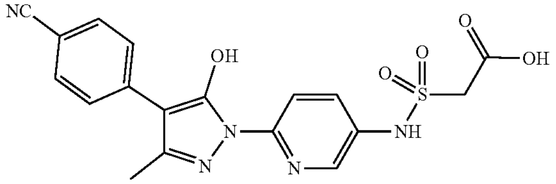 [SMILES: Cc1nn(-c2ccc(NS(=O)(=O)CC(=O)O)cn2)c(O)c1-c1ccc(C#N)cc1] |
| 56 | 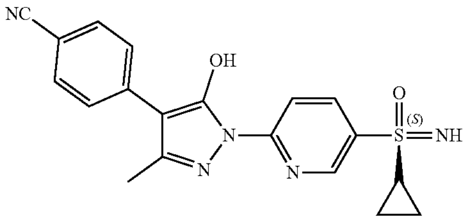 |
| 57 | 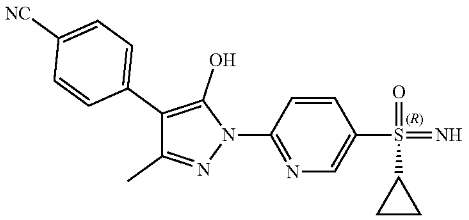 |
| 58 | 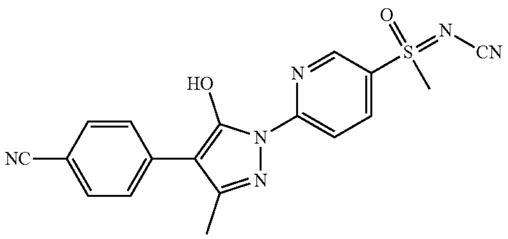 [SMILES: Cc1nn(-c2ccc(S(C)(=O)=NC#N)cn2)c(O)c1-c1ccc(C#N)cc1] |
| 65 | 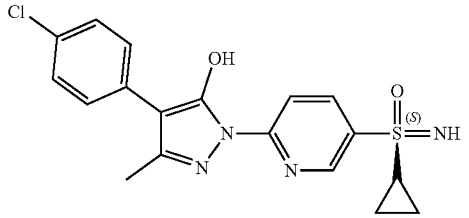 |

-continued
| Cmpd No. | Structure |
|---|---|
| 66 | 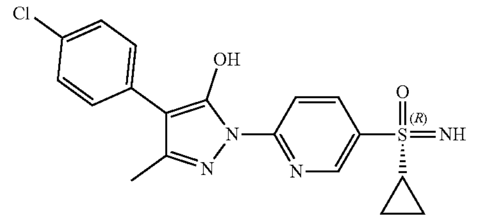 |
| 67 | 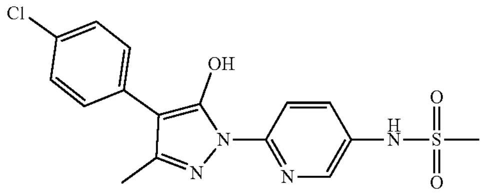 |
| 68 | 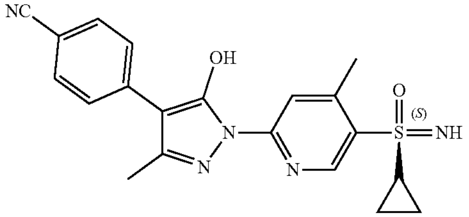 |
| 69 | 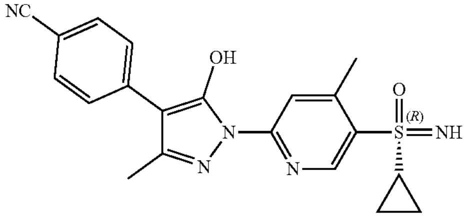 |
| 70 | 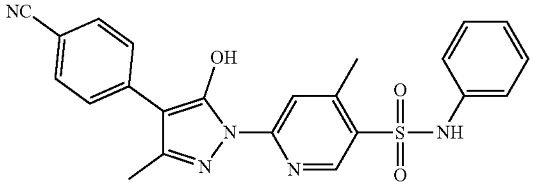 [SMILES: Cc1cc(-n2nc(C)c(-c3ccc(C#N)cc3)c2O)ncc1S(=O)(=O)Nc1ccccc1] |
| 71 | 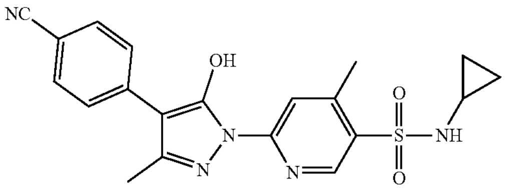 [SMILES: Cc1cc(-n2nc(C)c(-c3ccc(C#N)cc3)c2O)ncc1S(=O)(=O)NC1CC1] |
| 72 | 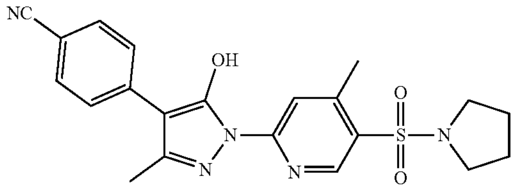 [SMILES: Cc1cc(-n2nc(C)c(-c3ccc(C#N)cc3)c2O)ncc1S(=O)(=O)N1CCCC1] |
or a pharmaceutically acceptable salt thereof.

14. A pharmaceutical composition comprising the compound of claim 1, or a pharmaceutically acceptable salt thereof, and a pharmaceutically acceptable excipient.

15. The compound of claim 13, wherein the compound is (3)

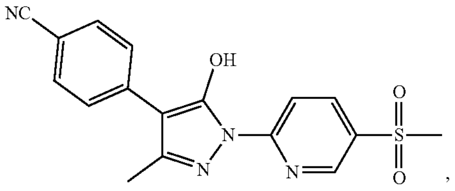

or a pharmaceutically acceptable salt thereof.

16. The compound of claim 13, wherein the compound is (6)

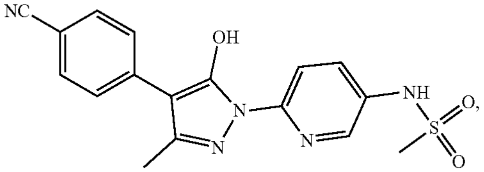

or a pharmaceutically acceptable salt thereof.

17. The compound of claim 13, wherein the compound is (11)

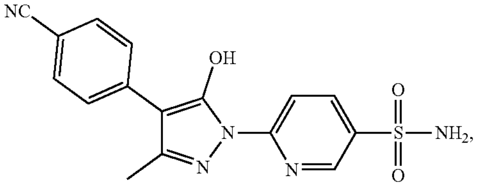

or a pharmaceutically acceptable salt thereof.

18. The compound of claim 13, wherein the compound is (12)

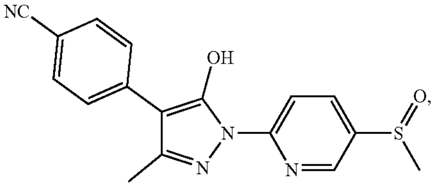

or a pharmaceutically acceptable salt thereof.

19. The compound of claim 13, wherein the compound is (15)

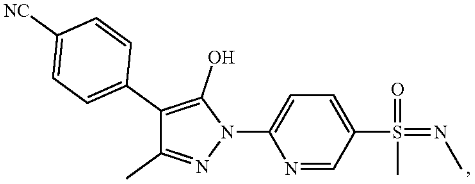

or a pharmaceutically acceptable salt thereof.

20. The compound of claim 13, wherein the compound is (34)

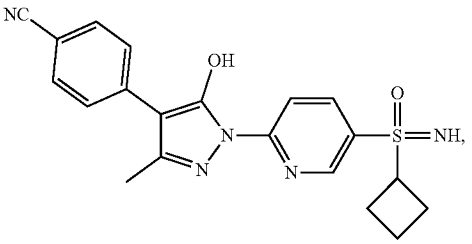

or a pharmaceutically acceptable salt thereof.

21. The compound of claim 13, wherein the compound is (56)

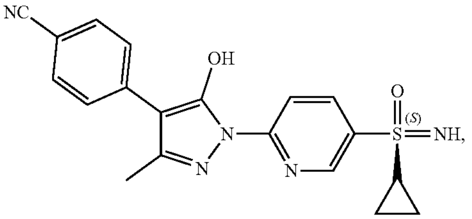

or a pharmaceutically acceptable salt thereof.

* * * * *